United States Patent
Stavenhagen et al.

(10) Patent No.: US 12,269,894 B2
(45) Date of Patent: *Apr. 8, 2025

(54) ANTIBODIES WHICH BIND HUMAN FIBRIN OR FIBRINOGEN γC DOMAIN AND METHODS OF USE

(71) Applicant: Therini Bio, Inc., Sacramento, CA (US)

(72) Inventors: Jeffrey Stavenhagen, San Mateo, CA (US); Olga Gasiorowska, Sacramento, CA (US); Mathias Rickert, Hayward, CA (US); Paul Fredrick Widboom, Lebanon, NH (US); Joseph Robert Warfield, Lebanon, NH (US)

(73) Assignee: Therini Bio, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/601,952

(22) Filed: Mar. 11, 2024

(65) Prior Publication Data

US 2024/0228661 A1  Jul. 11, 2024

Related U.S. Application Data

(63) Continuation of application No. 18/571,096, filed as application No. PCT/US2022/034189 on Jun. 20, 2022.

(60) Provisional application No. 63/212,414, filed on Jun. 18, 2021.

(51) Int. Cl.
| | |
|---|---|
| C07K 16/36 | (2006.01) |
| A61P 1/00 | (2006.01) |
| A61P 25/28 | (2006.01) |
| A61P 27/02 | (2006.01) |
| C07K 16/18 | (2006.01) |
| C12N 15/63 | (2006.01) |
| A61K 39/00 | (2006.01) |

(52) U.S. Cl.
CPC ............ *C07K 16/36* (2013.01); *A61P 1/00* (2018.01); *A61P 25/28* (2018.01); *A61P 27/02* (2018.01); *C07K 16/18* (2013.01); *C12N 15/63* (2013.01); *A61K 2039/505* (2013.01); *C07K 2317/24* (2013.01); *C07K 2317/34* (2013.01); *C07K 2317/52* (2013.01); *C07K 2317/55* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,571,894 A | 11/1996 | Wels et al. | |
| 5,587,458 A | 12/1996 | King et al. | |
| 5,648,237 A | 7/1997 | Carter | |
| 5,789,199 A | 8/1998 | Joly et al. | |
| 5,821,337 A | 10/1998 | Carter et al. | |
| 5,840,523 A | 11/1998 | Simmons et al. | |
| 5,877,293 A | 3/1999 | Adair et al. | |
| 5,886,152 A | 3/1999 | Nakatani et al. | |
| 5,959,177 A | 9/1999 | Hein et al. | |
| 6,040,498 A | 3/2000 | Stomp et al. | |
| 6,054,297 A | 4/2000 | Carter et al. | |
| 6,180,370 B1* | 1/2001 | Queen | A61P 19/02 435/69.6 |
| 6,194,551 B1 | 2/2001 | Idusogie et al. | |
| 6,417,429 B1 | 7/2002 | Hein et al. | |
| 6,420,548 B1 | 7/2002 | Vezina et al. | |
| 6,982,321 B2 | 1/2006 | Winter | |
| 7,087,409 B2 | 8/2006 | Barbas, III et al. | |
| 7,125,978 B1 | 10/2006 | Vezina et al. | |
| 7,527,791 B2 | 5/2009 | Adams et al. | |
| 8,409,572 B2 | 4/2013 | Beliard et al. | |
| 8,877,195 B2* | 11/2014 | Akassoglou | A61P 25/00 530/382 |
| 2002/0164328 A1 | 11/2002 | Shinkawa et al. | |
| 2003/0115614 A1 | 6/2003 | Kanda et al. | |
| 2003/0157108 A1 | 8/2003 | Presta | |

(Continued)

FOREIGN PATENT DOCUMENTS

| | | |
|---|---|---|
| WO | WO-1993/016185 A2 | 8/1993 |
| WO | WO-1997/30087 A1 | 8/1997 |

(Continued)

OTHER PUBLICATIONS

Ryu, Jae Kyu et al. "Fibrin-targeting immunotherapy protects against neuroinflammation and neurodegeneration." Nature immunology vol. 19,11 (2018): 1212-1223. doi:10.1038/s41590-018-0232-x (Year: 2018).*

(Continued)

*Primary Examiner* — Michael Szperka
*Assistant Examiner* — Lia E Taylor
(74) *Attorney, Agent, or Firm* — Goodwin Procter LLP

(57) ABSTRACT

Described herein are novel and improved antibodies that bind human fibrin or fibrinogen γC domain and methods of use thereof. In certain aspects, described herein are methods of inhibiting microglial activation. In certain aspects, described herein are pharmaceutical compositions comprising the antibodies that bind fibrin or fibrinogen γC domain. In certain aspects, the antibodies and methods described herein are used for treatment of degenerative neuronal disorders that involve inflammatory demyelination.

21 Claims, 37 Drawing Sheets

Specification includes a Sequence Listing.

(56) References Cited

U.S. PATENT DOCUMENTS

| | | |
|---|---|---|
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2011/0212087 A1 | 9/2011 | Strohl et al. |
| 2012/0183560 A1* | 7/2012 | Akassoglou ............ A61P 37/06 530/389.3 |
| 2012/0225058 A1 | 9/2012 | Lazar et al. |
| 2012/0251531 A1 | 10/2012 | Baehner et al. |
| 2018/0118836 A1 | 5/2018 | Bernett et al. |
| 2018/0355061 A1 | 12/2018 | Chen et al. |

FOREIGN PATENT DOCUMENTS

| | | |
|---|---|---|
| WO | WO-1998/58964 A1 | 12/1998 |
| WO | WO-1999/22764 A1 | 5/1999 |
| WO | WO-2000/61739 A1 | 10/2000 |
| WO | WO-2001/29246 A1 | 4/2001 |
| WO | WO-2003/084570 A1 | 10/2003 |
| WO | WO-2003/085107 A1 | 10/2003 |
| WO | WO-2003/085119 A1 | 10/2003 |
| WO | WO-2004/056312 A2 | 7/2004 |
| WO | WO-2005/035586 A1 | 4/2005 |
| WO | WO-2006/105338 A2 | 10/2006 |
| WO | WO-2008/077546 A1 | 7/2008 |
| WO | WO-2011120134 A1 | 10/2011 |
| WO | WO-2011120135 A1 | 10/2011 |

OTHER PUBLICATIONS

Gray, Madison T., and John M. Woulfe. "Striatal blood-brain barrier permeability in Parkinson's disease." Journal of Cerebral Blood Flow & Metabolism 35.5 (2015): 747-750 (Year: 2015).*

Winkler, Ethan A., et al. "Blood-spinal cord barrier breakdown and pericyte reductions in amyotrophic lateral sclerosis." Acta neuropathologica 125 (2013): 111-120 (Year: 2013).*

Drouin-Ouellet, Janelle, et al. "Cerebrovascular and blood-brain barrier impairments in Huntington's disease: potential implications for its pathophysiology." Annals of neurology 78.2 (2015): 160-177 (Year: 2015).*

Sun, Yanan, et al. "Relationship between fibrinogen level and its regulatory gene with Alzheimer's disease and vascular dementia." Journal of International Medical Research 48.2 (2020): 0300060520902578. (Year: 2020).*

Lull, Melinda E., and Michelle L. Block. "Microglial activation and chronic neurodegeneration." Neurotherapeutics 7.4 (2010): 354-365 (Year: 2010).*

Wang, Xinhua et al. "IgG Fc engineering to modulate antibody effector functions." Protein & cell vol. 9,1 (2018): 63-73. doi: 10.1007/s13238-017-0473-8 (Year: 2018).*

Peyman, Gholam A et al. "Intravitreal injection of therapeutic agents." Retina (Philadelphia, Pa.) vol. 29,7 (2009): 875-912. doi: 10.1097/IAE.0b013e3181a94f01 (Year: 2009).*

Janeway, Charles A. "Immunobiology: The Immune System in Health and Disease." 2001 (Year: 2001).*

Kipriyanov, Sergey M., and Fabrice Le Gall. "Generation and production of engineered antibodies." Molecular biotechnology 26.1 (2004): 39-60.(Year: 2004).*

Adams et al. The fibrin-derived gamma377-395 peptide inhibits microglia activation and suppresses relapsing paralysis in central nervous system autoimmune disease. J Exp Med. Mar. 19, 2007 vol. 204 No. 3 pp. 571-582. Especially abstract.

International Search Report and Written Opinion issued Dec. 20, 2022 in International Application No. PCT/US2022/034189.

Arbabi Ghahroudi, M. et al., "Selection and identification of single domain antibody fragments from camel heavy-chain antibodies", FEBS Letters 414 (1997) 521-526.

Muyldermans S, Cambillau C, Wyns L. Recognition of antigens by single-domain antibody fragments: the superfluous luxury of paired domains. Trends Biochem Sci. Apr. 2001;26(4):230-5. doi: 10.1016/s0968-0004(01)01790-x. PMID: 11295555.

Harmsen MM, De Haard HJ. Properties, production, and applications of camelid single-domain antibody fragments. Appl Microbiol Biotechnol. Nov. 2007;77(1):13-22. doi: 10.1007/s00253-007-1142-2. Epub Aug. 18, 2007. PMID: 17704915; PMCID: PMC2039825.

Smith, Temple F. and Waterman, Michael S., "Comparisons of Biosequences", Advances in Applied Mathematics 2, 482-489 (1981).

Needleman SB, Wunsch CD. A general method applicable to the search for similarities in the amino acid sequence of two proteins. J Mol Biol. Mar. 1970;48(3):443-53. doi: 10.1016/0022-2836(70)90057-4. PMID: 5420325.

Pearson WR, Lipman DJ. Improved tools for biological sequence comparison. Proc Natl Acad Sci USA. Apr. 1988; 85(8):2444-8. doi: 10.1073/pnas.85.8.2444. PMID: 3162770; PMCID: PMC280013.

Al-Lazikani B, Lesk AM, Chothia C. Standard conformations for the canonical structures of immunoglobulins. J Mol Biol. Nov. 7, 1997;273(4):927-48. doi: 10.1006/jmbi.1997.1354. PMID: 9367782.

MacCallum RM, Martin AC, Thornton JM. Antibody-antigen interactions: contact analysis and binding site topography. J Mol Biol. Oct. 11, 1996;262(5):732-45. doi: 10.1006/jmbi.1996.0548. PMID: 8876650.

Lefranc MP, Pommié C, Ruiz M, Giudicelli V, Foulquier E, Truong L, Thouvenin-Contet V, Lefranc G. IMGT unique numbering for immunoglobulin and T cell receptor variable domains and Ig superfamily V-like domains. Dev Comp Immunol. Jan. 2003;27(1):55-77. doi: 10.1016/s0145-305x(02)00039-3. PMID: 12477501.

Jones PT, Dear PH, Foote J, Neuberger MS, Winter G. Replacing the complementarity-determining regions in a human antibody with those from a mouse. Nature. May 29-Jun 4, 1986;321(6069):522-5. doi: 10.1038/321522a0. PMID: 3713831.

Riechmann L, Clark M, Waldmann H, Winter G. Reshaping human antibodies for therapy. Nature. Mar. 24, 1988;332(6162):323-7. doi: 10.1038/332323a0. PMID: 3127726.

Presta LG. Antibody engineering. Curr Opin Biotechnol. Aug. 1992;3(4):394-8. doi: 10.1016/0958-1669(92)90168-i. PMID: 1368441.

Altschul SF, Gish W, Miller W, Myers EW, Lipman DJ. Basic local alignment search tool. J Mol Biol. Oct. 5, 1990;215(3):403-10. doi: 10.1016/S0022-2836(05)80360-2. PMID: 2231712.

Schroeder HW Jr, Cavacini L. Structure and function of immunoglobulins. J Allergy Clin Immunol. Feb. 2010;125(2 Suppl 2):S41-52. doi: 10.1016/j.jaci.2009.09.046. PMID: 20176268; PMCID: PMC3670108.

Ruth L. Guyer, Marian E. Koshland, Paul M. Knopf; Immunoglobulin Binding by Mouse Intestinal Epithelial Cell Receptors1. JImmunol Aug. 1, 1976; 117 (2): 587-593. https://doi.org/10.4049/jimmunol.117.2.587.

Lu, Y. et al., "Identification of IgG1 variants with increased affinity to FcγRIIIa and unaltered affinity to FcγRI and FcRn: Comparison of soluble receptor-based and cell-based binding assays", Journal of Immunological Methods 365 (2011) 132-141.

Stavenhagen JB, Gorlatov S, Tuaillon N, Rankin CT, Li H, Burke S, Huang L, Vijh S, Johnson S, Bonvini E, Koenig S. Fc optimization of therapeutic antibodies enhances their ability to kill tumor cells in vitro and controls tumor expansion in vivo via low-affinity activating Fcgamma receptors. Cancer Res. Sep. 15, 2007;67(18):8882-90. doi: 10.1158/0008-5472.CAN-07-0696. Erratum in: Cancer Res. Sep. 15, 2008;68(18):7692. Vijh, Sujata [added]. PMID: 17875730.

Nordstrom JL, Gorlatov S, Zhang W, Yang Y, Huang L, Burke S, Li H, Ciccarone V, Zhang T, Stavenhagen J, Koenig S, Stewart SJ, Moore PA, Johnson S, Bonvini E. Anti-tumor activity and toxicokinetics analysis of MGAH22, an anti-HER2 monoclonal antibody with enhanced Fc? receptor binding properties. Breast Cancer Res. 2011;13(6):R123. doi: 10.1186/bcr3069. Epub Nov. 30, 2011. PMID: 22129105; PMCID: PMC3326565.

Stewart, R, Thom, G, Levens, M et al. A variant human IgG1-Fc mediates improved ADCC. Protein Eng Des Sel 2011; 24: 671-8.

Shields RL, Namenuk AK, Hong K, Meng YG, Rae J, Briggs J, Xie D, Lai J, Stadlen A, Li B, Fox JA, Presta LG. High resolution mapping of the binding site on human IgG1 for Fc gamma RI, Fc gamma RII, Fc gamma RIII, and FcRn and design of IgG1 variants

(56) References Cited

OTHER PUBLICATIONS with improved binding to the Fc gamma R. J Biol Chem. Mar. 2, 2001;276(9):6591-604. doi: 10.1074/jbc.M009483200. Epub Nov. 28, 2000. PMID: 11096108.
Lazar GA, Dang W, Karki S, Vafa O, Peng JS, Hyun L, Chan C, Chung HS, Eivazi A, Yoder SC, Vielmetter J, Carmichael DF, Hayes RJ, Dahiyat BI. Engineered antibody Fc variants with enhanced effector function. Proc Natl Acad Sci U S A. Mar. 14, 2006;103(11):4005-10. doi: 10.1073/pnas.0508123103. Epub Mar. 6, 2006. PMID: 16537476; PMCID: PMC1389705.
Strohl, William R. and Strohl, Lila M., Therapeutic Antibody Engineering: Current and Future Advances Driving the Strongest Growth Area in the Pharmaceutical Industry, 2012, pp. 225-249, 283.
Von Horsten HH, Ogorek C, Blanchard V, Demmler C, Giese C, Winkler K, Kaup M, Berger M, Jordan I, Sandig V. Production of non-fucosylated antibodies by co-expression of heterologous GDP-6-deoxy-D-lyxo-4-hexulose reductase. Glycobiology. Dec. 2010;20(12):1607-18. doi: 10.1093/glycob/cwq109. Epub Jul. 15, 2010. PMID: 20639190.
Strohl WR. Optimization of Fc-mediated effector functions of monoclonal antibodies. Curr Opin Biotechnol. Dec. 2009;20(6):685-91. doi: 10.1016/j.copbio.2009.10.011. Epub Nov. 4, 2009. PMID: 19896358.
Strop P, Ho WH, Boustany LM, Abdiche YN, Lindquist KC, Farias SE, Rickert M, Appah CT, Pascua E, Radcliffe T, Sutton J, Chaparro-Riggers J, Chen W, Casas MG, Chin SM, Wong OK, Liu SH, Vergara G, Shelton D, Rajpal A, Pons J. Generating bispecific human IgG1 and IgG2 antibodies from any antibody pair. J Mol Biol. Jul. 13, 2012;420(3):204-19. doi: 10.1016/j.jmb.2012.04.020. Epub Apr. 25, 2012. PMID: 22543237.
Capel PJ, van de Winkel JG, van den Herik-Oudijk IE, Verbeek JS. Heterogeneity of human IgG Fc receptors. Immunomethods. Feb. 1994;4(1):25-34. doi: 10.1006/immu.1994.1004. PMID: 8069524.
Yamane-Ohnuki N, Kinoshita S, Inoue-Urakubo M, Kusunoki M, Iida S, Nakano R, Wakitani M, Niwa R, Sakurada M, Uchida K, Shitara K, Satoh M. Establishment of FUT8 knockout Chinese hamster ovary cells: an ideal host cell line for producing completely defucosylated antibodies with enhanced antibody-dependent cellular cytotoxicity. Biotechnol Bioeng. Sep. 5, 2004;87(5):614-22. doi: 10.1002/bit.20151. PMID: 15352059.
Idusogie EE, Presta LG, Gazzano-Santoro H, Totpal K, Wong PY, Ultsch M, Meng YG, Mulkerrin MG. Mapping of the C1q binding site on rituxan, a chimeric antibody with a human IgG1 Fc. J Immunol. Apr. 15, 2000;164(8):4178-84. doi: 10.4049/jimmunol. 164.8.4178. PMID: 10754313.
Cox KL, Devanarayan V, Kriauciunas A, Manetta J, Montrose C, Sittampalam S. Immunoassay Methods. May 1, 2012 [updated Jul. 8, 2019]. In: Markossian S, Grossman A, Arkin M, Auld D, Austin C, Baell J, Brimacombe K, Chung TDY, Coussens NP, Dahlin JL, Devanarayan V, Foley TL, Glicksman M, Gorshkov K, Haas JV, Hall MD, Hoare S, Inglese J, Iversen PW, Lal-Nag M, Li Z, Manro JR, McGee J, McManus O, Pearson M, Riss T, Saradjian P, Sittampalam GS, Tarselli M, Trask OJ Jr, Weidner JR, Wildey MJ, Wilson K, Xia M, Xu X, editors. Assay Guidance Manual [Internet]. Bethesda (MD): Eli Lilly & Company and the National Center for Advancing Translational Sciences; 2004—. PMID: 22553884.
Graham FL, Smiley J, Russell WC, Nairn R. Characteristics of a human cell line transformed by DNA from human adenovirus type 5. J Gen Virol. Jul. 1977;36(1):59-74. doi: 10.1099/0022-1317-36-1-59. PMID: 886304.
Mather JP. Establishment and characterization of two distinct mouse testicular epithelial cell lines. Biol Reprod. Aug. 1980;23(1):243-52. doi: 10.1095/biolreprod23.1.243. PMID: 6774781.

Urlaub G, Chasin LA. Isolation of Chinese hamster cell mutants deficient in dihydrofolate reductase activity. Proc Natl Acad Sci U S A. Jul. 1980;77(7):4216-20. doi: 10.1073/pnas.77.7.4216. PMID: 6933469; PMCID: PMC349802.
Almagro JC, Fransson J. Humanization of antibodies. Front Biosci. Jan. 1, 2008;13:1619-33. doi: 10.2741/2786. PMID: 17981654.
Queen C, Schneider WP, Selick HE, Payne PW, Landolfi NF, Duncan JF, Avdalovic NM, Levitt M, Junghans RP, Waldmann TA. A humanized antibody that binds to the interleukin 2 receptor. Proc Natl Acad Sci U S A. Dec. 1989;86(24):10029-33. doi: 10.1073/pnas.86.24.10029. PMID: 2513570; PMCID: PMC298637.
Kashmiri SV, De Pascalis R, Gonzales NR, Schlom J. Sdr grafting—a new approach to antibody humanization. Methods. May 2005;36(1):25-34. doi: 10.1016/j.ymeth.2005.01.003. PMID: 15848072.
Padlan EA. A possible procedure for reducing the immunogenicity of antibody variable domains while preserving their ligand-binding properties. Mol Immunol. Apr.-May 1991;28(4-5):489-98. doi: 10.1016/0161-5890(91)90163-e. PMID: 1905784.
Dall'Acqua WF, Damschroder MM, Zhang J, Woods RM, Widjaja L, Yu J, Wu H. Antibody humanization by framework shuffling. Methods. May 2005;36(1):43-60. doi: 10.1016/j.ymeth.2005.01.005. PMID: 15848074.
Osbourn J, Groves M, Vaughan T. From rodent reagents to human therapeutics using antibody guided selection. Methods. May 2005;36(1):61-8. doi: 10.1016/j.ymeth.2005.01.006. PMID: 15848075.
Klimka A, Matthey B, Roovers RC, Barth S, Arends JW, Engert A, Hoogenboom HR. Human anti-CD30 recombinant antibodies by guided phage antibody selection using cell panning. Br J Cancer. Jul. 2000;83(2):252-60. doi: 10.1054/bjoc.2000.1226. PMID: 10901379; PMCID: PMC2363493.
Sims MJ, Hassal DG, Brett S, Rowan W, Lockyer MJ, Angel A, Lewis AP, Hale G, Waldmann H, Crowe JS. A humanized CD18 antibody can block function without cell destruction. J Immunol. Aug. 15, 1993;151(4):2296-308. PMID: 7688398.
Carter P, Presta L, Gorman CM, Ridgway JB, Henner D, Wong WL, Rowland AM, Kotts C, Carver ME, Shepard HM. Humanization of an anti-p185HER2 antibody for human cancer therapy. Proc Natl Acad Sci U S A. May 15, 1992;89(10):4285-9. doi: 10.1073/pnas. 89. 10.4285. PMID: 1350088; PMCID: PMC49066.
Presta LG, Lahr SJ, Shields RL, Porter JP, Gorman CM, Fendly BM, Jardieu PM. Humanization of an antibody directed against IgE. J Immunol. Sep. 1, 1993;151(5):2623-32. PMID: 8360482.
Baca M, Presta LG, O'Connor SJ, Wells JA. Antibody humanization using monovalent phage display. J Biol Chem. Apr. 18, 1997;272(16):10678-84. doi: 10.1074/jbc.272.16.10678. PMID: 9099717.
Rosok MJ, Yelton DE, Harris LJ, Bajorath J, Hellstrom KE, Hellström I, Cruz GA, Kristensson K, Lin H, Huse WD, Glaser SM. A combinatorial library strategy for the rapid humanization of anticarcinoma BR96 Fab. J Biol Chem. Sep. 13, 1996;271(37):22611-8. doi: 10.1074/jbc.271.37.22611. PMID: 8798431.
Xu Y, Roach W, Sun T, Jain T, Prinz B, Yu TY, Torrey J, Thomas J, Bobrowicz P, Vásquez M, Wittrup KD, Krauland E. Addressing polyspecificity of antibodies selected from an in vitro yeast presentation system: a FACS-based, high-throughput selection and analytical tool. Protein Eng Des Sel. Oct. 2013;26(10):663-70. doi: 10.1093/protein/gzt047. Epub Sep. 17, 2013. PMID: 24046438.
Estep, P., Reid, F., Nauman, C., Liu, Y., Sun, T., Sun, J., & Xu, Y. (2013). High throughput solution-based measurement of antibody-antigen affinity and epitope binning. mAbs, 5(2), 270-278. https://doi.org/10.4161/mabs.23049.
Liu Y, Caffry I, Wu J, Geng SB, Jain T, Sun T, Reid F, Cao Y, Estep P, Yu Y, Vásquez M, Tessier PM, Xu Y. High-throughput screening for developability during early-stage antibody discovery using self-interaction nanoparticle spectroscopy. MAbs. Mar.-Apr. 2014;6(2):483-92. doi: 10.4161/mabs.27431. Epub Dec. 6, 2013. PMID: 24492294; PMCID: PMC3984336.
Estep P, Caffry I, Yu Y, Sun T, Cao Y, Lynaugh H, Jain T, Vasquez M, Tessier PM, Xu Y. An alternative assay to hydrophobic interaction chromatography for high-throughput characterization of monoclonal antibodies. MAbs. 2015;7(3):553-61. doi: 10.1080/19420862.2015.1016694. PMID: 25790175; PMCID: PMC4622688.

\* cited by examiner

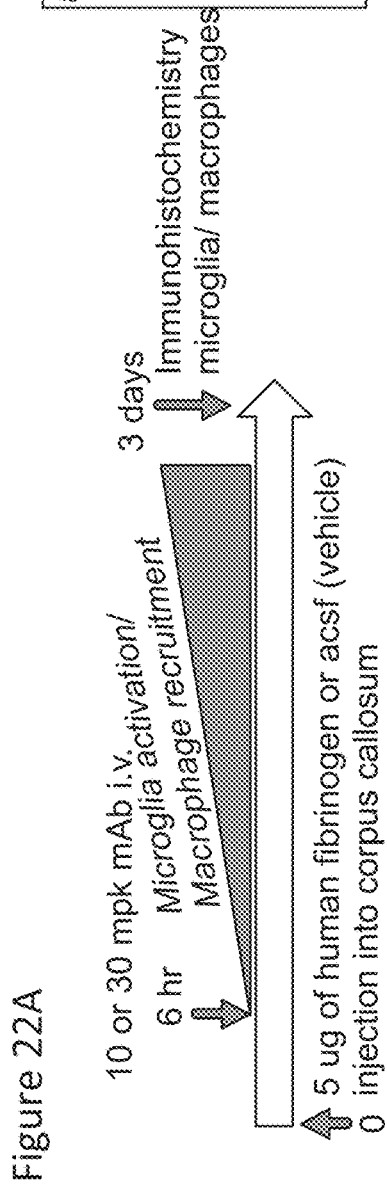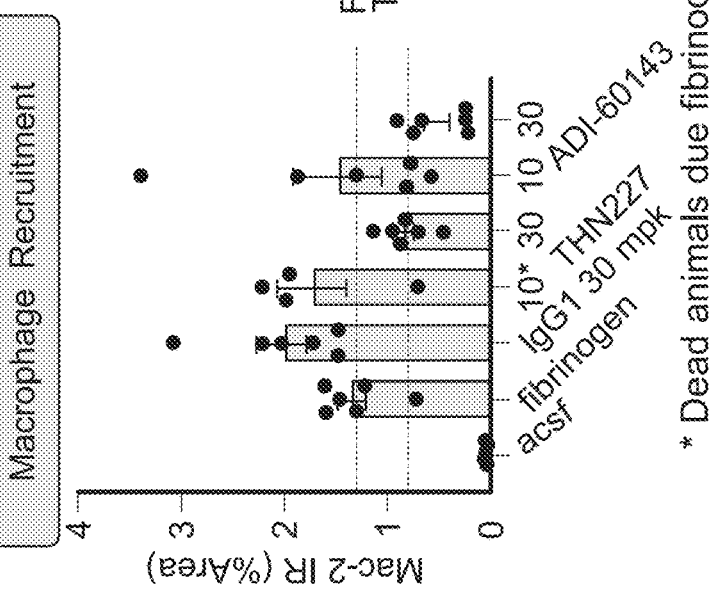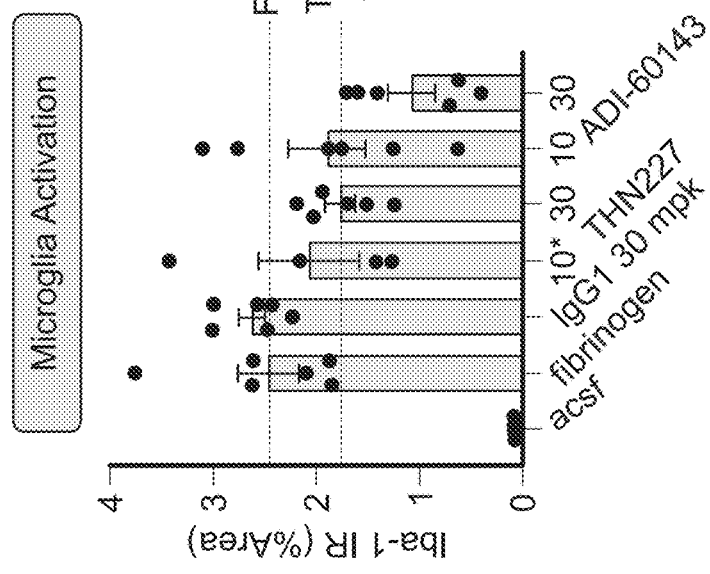
Figure 22A
Figure 22B
Figure 22C

ANTIBODIES WHICH BIND HUMAN FIBRIN OR FIBRINOGEN γC DOMAIN AND METHODS OF USE

CROSS REFERENCE TO RELATED APPLICATIONS

This application is a continuation of U.S. application Ser. No. 18/571,096, filed on Dec. 15, 2023, which is the National Stage Entry of International Application No. PCT/US2022/034189, filed Jun. 20, 2022, which claims the benefit of and priority to U.S. Provisional Application No. 63/212,414, filed Jun. 18, 2021, each of which are hereby incorporated by reference in their entireties.

SEQUENCE LISTING

The contents of the electronic sequence listing (THB-006C1_SL.xml; Size: 361,152 bytes; and Date of Creation: Mar. 6, 2024) is herein incorporated by reference in its entirety.

BACKGROUND

Degenerative neuronal disorders such as multiple sclerosis (MS) can involve inflammatory demyelination and autoimmune responses. Microglia, in particular perivascular microglia, are believed to be necessary not only for the maintenance, but also for the onset of inflammatory demyelination in central nervous system (CNS) autoimmune disease. Activation of microglia contributes to both neuronal and oligodendrocyte death via release of cytokines and nitric oxide. In MS, inflammatory processes are associated with destruction of myelin sheaths, and can also involve axonal damage that can lead to permanent functional deficits, such as paralysis and loss of vision. Resident microglia are responsible for demyelination, via their ability to phagocytose myelin and secrete proinflammatory cytokines.

In MS lesions, perivascular activation of microglia colocalizes with areas of blood brain barrier (BBB) disruption, and in vivo imaging studies have shown that BBB disruption provokes the immediate and focal activation of microglia. One of the earliest events coupled to BBB disruption in MS is leakage of the blood protein fibrinogen in the nervous system that results in perivascular deposition of fibrin. Fibrinogen is not present in the healthy CNS, but only leaks in the brain after BBB disruption, thus serving as an environmental "danger" signal. Upon conversion of fibrinogen to fibrin, the CD11b/CD18 integrin receptor (also referred to as: Mac-1, aMfl 2, Complement Receptor 3) binds to the fibrin and induces microglial activation leading to inflammatory demyelination. CD11b is the alpha chain of the receptor that regulates phagocytosis of myelin during inflammatory demyelination. Immobilized fibrinogen and insoluble fibrin, but not soluble fibrinogen, have been identified as physiological, high-affinity ligands for Mac-1.

The γ377-395 epitope of the fibrin or fibrinogen γC domain is the binding epitope of fibrin to CDIIb. The fibrin γ377-395 peptide functions as an inhibitor of microglia activation by blocking fibrin binding to Mac-1. Because fibrin mediates blood coagulation by binding via a distinct epitope to the platelet integrin $\alpha_{IIb}\beta_3$ receptor, therapeutic agents (including antibodies), that block CD11b binding epitope to fibrin can reduce the damaging effects of fibrin in the nervous system without affecting its beneficial effects in blood coagulation. Therefore, safe, effective antibodies that inhibit fibrin induced microglial activation without affecting its beneficial effects in blood coagulation are needed as therapeutics for degenerative neuronal disorders that involve inflammatory demyelination.

SUMMARY

In certain aspects, described herein are isolated antibodies that binds human fibrin or fibrinogen γC domain, comprising a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein: CDR-H1 comprises the sequence set forth in SEQ ID NO: 1, 13, 25, 37, 49, 61, 73, 85, 97, 109, 121, 133, 145, 157, 169, 181, 193, 205, 217, or 229; CDR-H2 comprises the sequence set forth in SEQ ID NO: 2, 14, 26, 38, 50, 62, 74, 86, 98, 110, 122, 134, 146, 158, 170, 182, 194, 206, 218, or 230; CDR-H3 comprises the sequence set forth in SEQ ID NO: 3, 15, 27, 39, 51, 63, 75, 87, 99, 111, 123, 135, 147, 159, 171, 183, 195, 207, 219, or 231; CDR-L1 comprises the sequence set forth in SEQ ID NO: 4, 16, 28, 40, 52, 64, 76, 88, 100, 112, 124, 136, 148, 160, 172, 184, 196, 208, 220, or 232; CDR-L2 comprises the sequence set forth in SEQ ID NO: 5, 17, 29, 41, 53, 65, 77, 89, 101, 113, 125, 137, 149, 161, 173, 185, 197, 209, 221, or 233; and CDR-L3 comprises the sequence set forth in SEQ ID NO: 6, 18, 30, 42, 54, 66, 78, 90, 102, 114, 126, 138, 150, 162, 174, 186, 198, 210, 222, or 234.

In certain embodiments, the antibody comprises a VH sequence selected from a sequence set forth in one of SEQ ID NOs: 7, 19, 31, 43, 55, 67, 79, 91, 103, 115, 127, 139, 151, 163, 175, 187, 199, 211, 223, or 235. In certain embodiments, the antibody comprises a VL sequence selected from a sequence set forth in SEQ ID NO 10, 22, 34, 46, 58, 70, 82, 94, 106, 118, 130, 142, 154, 166, 178, 190, 202, 214, 226, or 238.

In certain embodiments, the antibody comprises a VH sequence selected from a sequence set forth in one of SEQ ID Nos: 7, and the VL sequence set for in SEQ ID NO: 10. In certain embodiments, the antibody comprises a VH sequence set forth in SEQ ID NO: 19 and a VL sequence set forth in SEQ ID NO: 22. In certain embodiments, the antibody comprises a VH sequence set forth in SEQ ID NO: 31 and a VL sequence set forth in SEQ ID NO: 34. In certain embodiments, the antibody comprises a VH sequence set forth in SEQ ID NO: 43 and a VL sequence set forth in SEQ ID NO: 46. In certain embodiments, the antibody comprises a VH sequence set forth in SEQ ID NO: 55 and a VL sequence set forth in SEQ ID NO: 58. In certain embodiments, the antibody comprises a VH sequence set forth in SEQ ID NO: 67 and a VL sequence set forth in SEQ ID NO: 70. In certain embodiments, the antibody comprises a VH sequence set forth in SEQ ID NO: 79 and a VL sequence set forth in SEQ ID NO: 82. In certain embodiments, the antibody comprises a VH sequence set forth in SEQ ID NO: 91 and a VL sequence set forth in SEQ ID NO: 94. In certain embodiments, the antibody comprises a VH sequence set forth in SEQ ID NO: 103 and a VL sequence set forth in SEQ ID NO: 106. In certain embodiments, the antibody comprises a VH sequence set forth in SEQ ID NO: 115 and a VL sequence set forth in SEQ ID NO: 118. In certain embodiments, the antibody comprises a VH sequence set forth in SEQ ID NO: 127 and a VL sequence set forth in SEQ ID NO: 130. In certain embodiments, the antibody comprises a VH sequence set forth in SEQ ID NO: 139 and a VL sequence set forth in SEQ ID NO: 142. In certain embodiments, the antibody comprises a VH sequence set forth in SEQ ID NO: 151 and a VL sequence set forth in SEQ ID NO: 154. In certain embodiments, the antibody comprises a VH sequence set forth in SEQ ID NO: 163 and a VL sequence set forth in SEQ ID NO: 166. In certain embodiments, the antibody comprises a VH sequence set forth in SEQ ID NO: 175 and a VL sequence set forth in SEQ ID NO: 178. In certain embodiments, the antibody comprises a VH sequence set forth in SEQ ID NO: 187 and a VL sequence set forth in SEQ ID NO: 190. In certain embodiments, the antibody comprises a VH sequence set forth in SEQ ID NO: 199 and a VL sequence set forth in SEQ ID NO: 202. In certain embodiments, the antibody comprises a VH sequence set forth in SEQ ID NO: 211 and a VL sequence set forth in SEQ ID NO: 214. In certain embodiments, the antibody comprises a VH sequence set forth in SEQ ID NO: 223 and a VL sequence set forth in SEQ ID NO: 226. In certain embodiments, the antibody comprises a VH sequence set forth in SEQ ID NO: 235 and a VL sequence set forth in SEQ ID NO: 238.

In certain embodiments, the antibody comprises a humanized, human or chimeric antibody. In certain embodiments, the antibody comprises a humanized antibody. In certain embodiments, the antibody comprises a heavy chain human constant region of a class selected from IgG, IgA, IgD, IgE, and IgM. In certain embodiments, the human Fc region comprises a human heavy chain constant region of the class IgG and a subclass selected from IgG1, IgG2, IgG3, and IgG4. In certain embodiments, the human Fc region comprises wild-type, human IgG1 Fc. In certain embodiments, the human Fc domain comprises a sequence set forth in SEQ ID NO: 8, 20, 32, 44, 56, 68, 80, 92, 104, 116, 128, 140, 152, 164, 176, 188, 200, 212, 224, or 236.

In certain embodiments, the heavy chain comprises a constant heavy chain sequence set forth by SEQ ID NO: 8, 20, 32, 44, 56, 68, 80, 92, 104, 116, 128, 140, 152, 164, 176, 188, 200, 212, 224, or 236. In certain embodiments, the light chain comprises a constant light chain sequence set forth by SEQ ID NO: 9, 21, 33, 45, 57, 69, 81, 93, 105, 117, 129, 141, 153, 165, 177, 189, 201, 213, 225, or 237.

In certain embodiments, the antibody comprises the VH sequence set forth in SEQ ID NO: 7, and the VL sequence set forth in SEQ ID NO: 10; and the human Fc region comprises wild-type, human IgG1 Fc. In certain embodiments, the antibody comprises the VH sequence set forth in SEQ ID NO: 19, and the VL sequence set forth in SEQ ID NO: 22; and the human Fc region comprises wild-type, human IgG1 Fc. In certain embodiments, the antibody comprises the VH sequence set forth in SEQ ID NO: 31, and the VL sequence set forth in SEQ ID NO: 34; and the human Fc region comprises wild-type, human IgG1 Fc. In certain embodiments, the antibody comprises the VH sequence set forth in SEQ ID NO: 43, and the VL sequence set forth in SEQ ID NO: 46; and the human Fc region comprises wild-type, human IgG1 Fc. In certain embodiments, the antibody comprises the VH sequence set forth in SEQ ID NO: 55, and the VL sequence set forth in SEQ ID NO: 58; and the human Fc region comprises wild-type, human IgG1 Fc. In certain embodiments, the antibody comprises the VH sequence set forth in SEQ ID NO: 67, and the VL sequence set forth in SEQ ID NO: 70; and the human Fc region comprises wild-type, human IgG1 Fc. In certain embodiments, the antibody comprises the VH sequence set forth in SEQ ID NO: 79, and the VL sequence set forth in SEQ ID NO: 82; and the human Fc region comprises wild-type, human IgG1 Fc. In certain embodiments, the antibody comprises the VH sequence set forth in SEQ ID NO: 91, and the VL sequence set forth in SEQ ID NO: 94; and the human Fc region comprises wild-type, human IgG1 Fc. In certain embodiments, the antibody comprises the VH sequence set forth in SEQ ID NO: 103, and the VL sequence set forth in SEQ ID NO: 106; and the human Fc region comprises wild-type, human IgG1 Fc. In certain embodiments, the antibody comprises the VH sequence set forth in SEQ ID NO: 115, and the VL sequence set forth in SEQ ID NO: 118; and the human Fc region comprises wild-type, human IgG1 Fc. In certain embodiments, the antibody comprises the VH sequence set forth in SEQ ID NO: 127, and the VL sequence set forth in SEQ ID NO: 130; and the human Fc region comprises wild-type, human IgG1 Fc. In certain embodiments, the antibody comprises the VH sequence set forth in SEQ ID NO: 139, and the VL sequence set forth in SEQ ID NO: 142; and the human Fc region comprises wild-type, human IgG1 Fc. In certain embodiments, the antibody comprises the VH sequence set forth in SEQ ID NO: 151, and the VL sequence set forth in SEQ ID NO: 154; and the human Fc region comprises wild-type, human IgG1 Fc. In certain embodiments, the antibody comprises the VH sequence set forth in SEQ ID NO: 163, and the VL sequence set forth in SEQ ID NO: 166; and the human Fc region comprises wild-type, human IgG1 Fc. In certain embodiments, the antibody comprises the VH sequence set forth in SEQ ID NO: 175, and the VL sequence set forth in SEQ ID NO: 178; and the human Fc region comprises wild-type, human IgG1 Fc. In certain embodiments, the antibody comprises the VH sequence set forth in SEQ ID NO: 187, and the VL sequence set forth in SEQ ID NO: 190; and the human Fc region comprises wild-type, human IgG1 Fc. In certain embodiments, the antibody comprises the VH sequence set forth in SEQ ID NO: 199, and the VL sequence set forth in SEQ ID NO: 202; and the human Fc region comprises wild-type, human IgG1 Fc. In certain embodiments, the antibody comprises the VH sequence set forth in SEQ ID NO: 211, and the VL sequence set forth in SEQ ID NO: 214; and the human Fc region comprises wild-type, human IgG1 Fc. In certain embodiments, the antibody comprises the VH sequence set forth in SEQ ID NO: 223, and the VL sequence set forth in SEQ ID NO: 226; and the human Fc region comprises wild-type, human IgG1 Fc. In certain embodiments, the antibody comprises the VH sequence set forth in SEQ ID NO: 235, and the VL sequence set forth in SEQ ID NO: 238; and the human Fc region comprises wild-type, human IgG1 Fc.

In certain embodiments, the Fc region comprises one or more amino acid substitutions, wherein the one or more substitutions result in increased antibody half-life, increased ADCC activity, increased ADCP activity, or increased CDC activity compared with the Fc without the one or more substitutions. In certain embodiments, the Fc region binds an Fcγ Receptor selected from the group consisting of: FcγRI, FcγRIIa, FcγRIIb, FcγRIIc, FcγRIIIa, and FcγRIIIb.

In certain embodiments, the antibody is a monoclonal antibody. In certain embodiments, the antibody binds an γ377-395 epitope of the fibrin or fibrinogen γC domain. In certain embodiments, the antibody binds to a peptide comprising an amino acid sequence set forth in at least one of SEQ ID NOs: 241, and 249-253 with a $K_D$ of less than or equal to about 1, 2, 3, 4, 5, 6, 7, or $8 \times 10^{-5}$ M, as measured by surface plasmon resonance (SPR) single cycle kinetics (SCK) assay. In certain embodiments, the antibody binds to a peptide comprising the sequence of the 7377-395 epitope of the human fibrin or fibrinogen γC domain with a $K_D$ of less than or equal to about $8 \times 10^{-5}$ M, as measured by surface plasmon resonance (SPR) single cycle kinetics (SCK) assay. In certain embodiments, the antibody inhibits Mac-1 binding to fibrin or fibrinogen TC domain. In certain embodiments, the antibody exhibits inhibition of microglial adhesion to the fibrin or fibrinogen γC domain.

In certain aspects, described herein are the isolated antibodies of any one of the above claims for use in the treatment of a degenerative disorder of the nervous system.

In certain aspects, described herein are isolated polynucleotides or sets of polynucleotides encoding the antibody of any of the above claims, a VH thereof, a VL thereof, a light chain thereof, a heavy chain thereof, or an antigen-binding portion thereof, optionally cDNA.

In certain aspects, described herein are vectors or sets of vectors comprising the polynucleotide or set of polynucleotides described herein.

In certain embodiments, described herein is a host cell comprising the polynucleotide or set of polynucleotides, or the vector or set of vectors described herein.

In certain aspects, described herein are methods of producing an antibody, the method comprising expressing the antibody with the host cell described herein and isolating the expressed antibody.

In certain aspects, described herein are pharmaceutical compositions comprising an antibody described herein and a pharmaceutically acceptable excipient.

In certain aspects, described herein are kits comprising the described herein or a pharmaceutical composition described herein and instructions for use In certain aspects, described herein are methods for treating a degenerative disorder of the nervous system, the method comprising administering to a mammalian subject a therapeutically effective amount an antibody described herein or a pharmaceutical composition described herein. In certain embodiments, the degenerative disorder of the nervous system is selected from the group consisting of: multiple sclerosis, spinal cord injury, stroke, and Alzheimer's Disease.

In certain aspects, described herein are methods for treating a pathology associated with Mac-1 binding to fibrin or Mac-1 binding with fibrinogen, the method comprising administering to a mammalian subject a therapeutically effective amount an antibody or a pharmaceutical composition described herein.

In certain aspects, described herein are methods of inhibiting microglia activation, the method comprising administering to a mammalian subject a therapeutically effective amount an antibody or a pharmaceutical composition described herein.

In certain aspects, described herein are methods of preventing a degenerative disorder of the nervous system, the method comprising administering to a mammalian subject a therapeutically effective amount an antibody or a pharmaceutical composition described herein.

In certain aspects, described herein are methods of treating colitis in a subject in need thereof, the method comprising administering to a mammalian subject a therapeutically effective amount an antibody or a pharmaceutical composition described herein. In certain aspects, described herein are methods of preventing colitis in a subject in need thereof, the method comprising administering to a mammalian subject a therapeutically effective amount an antibody or a pharmaceutical composition described herein. In certain aspects, described herein are methods of treating a inflammatory condition of the eye in a subject in need thereof, the method comprising administering to a mammalian subject a therapeutically effective amount an antibody or a pharmaceutical composition described herein. In certain aspects, described herein are methods of preventing an inflammatory condition of the eye in a subject in need thereof, the method comprising administering to a mammalian subject a therapeutically effective amount an antibody or a pharmaceutical composition described herein. In certain embodiments, the inflammatory condition of the eye is uveitis.

In certain aspects, described herein are isolated antibodies that bind human fibrin or fibrinogen γC domain, wherein the antibody binds human fibrin at any one of amino acid residues Lys 411, Ile 412, Ile 413, Phe 415, Asn 416, Arg 417, Leu 418, Thr 419, Ile 420, and Gly 421. In certain embodiments, wherein the antibody binds human fibrin at least two, three, four, five, six, seven, eight, nine, or all ten of amino acid residues Lys 411, Ile 412, Ile 413, Phe 415, Asn 416, Arg 417, Leu 418, Thr 419, Ile 420, and Gly 421.

In certain embodiments, described herein are antibodies comprising a VH region comprising a paratope that comprises any one of amino acid residues Ser 31, Tyr 32, Trp 33, His 35, Trp 47, Leu 50, Asp 52, Asp 54, Tyr 56, Ala 93, Ser 94, Ser 95, Lys 96 or Asp 96, Pro 97 or Ala 97, Gly 101, Gly102, and Trp 103. In certain embodiments, the antibody comprises a VH region comprising a paratope that comprises at least two, three, four, five, six, seven, eight, nine, ten, eleven, twelve, thirteen, fourteen, fifteen, sixteen, or all seventeen of amino acid residues Ser 31, Tyr 32, Trp 33, His 35, Trp 47, Leu 50, Asp 52, Asp 54, Tyr 56, Ala 93, Ser 94, Ser 95, Lys 96 or Asp 96, Pro 97 or Ala 97, Gly 101, Gly102, and Trp 103. In certain embodiments, the antibody comprises a VH region comprising a paratope that comprises amino acid residues Ser 31, Trp 33, His 35, Asp 52, Asp 54, Tyr 56, Ser 94, Gly 101, Gly102, and Trp 103. In certain embodiments, the antibody comprises a VH region comprising a paratope that comprises amino acid residues Ser 31, Trp 33, His 35, Asp 52, Asp 54, Tyr 56, Ala 93, Ser 94, Lys 96, Pro 97, Gly 101, Gly102, and Trp 103. In certain embodiments, the antibody comprises a VH region comprising a paratope that comprises amino acid residues Ser 31, Tyr 32, Trp 33, His 35, Trp 47, Asp 52, Asp 54, Tyr 56, Ser 94, Ser 95, Asp 96, Ala 97, Gly 101, Gly102, and Trp 103.

In certain embodiments, described herein are isolated antibodies, wherein the antibody comprises a VL region comprising a paratope that comprises any one of amino acid residues His 27, Tyr 32, Tyr 36, Leu 46, Tyr 49, Gln 50, Ala 91 or Asn 91, Leu 92, Leu 94, and Leu 96. In certain embodiments, the antibody comprises a VL region comprising a paratope that comprises at least two, three, four, five, six, seven, eight, nine or all ten amino acid residues His 27, Tyr 32, Tyr 36, Leu 46, Tyr 49, Gln 50, Ala 91 or Asn 91, Leu 92, Leu 94, and Leu 96. In certain embodiments, the antibody comprises a VL region comprising a paratope that comprises the amino acid residues His 27, Tyr 32, Tyr 36, Leu 46, Gln 50, Leu 92, Leu 94, and Leu 96. In certain embodiments, the antibody comprises a VL region comprising a paratope that comprises the amino acid residues His 27, Tyr 32, Tyr 36, Leu 46, Gln 50, Asn 91, Leu 92, Leu 94, and Leu 96. In certain embodiments, the antibody comprises a VL region comprising a paratope that comprises the amino acid residues His 27, Tyr 32, Tyr 36, Leu 46, Tyr 49, Gln 50, Ala 91, Leu 92, Leu 94, and Leu 96.

BRIEF DESCRIPTION OF THE SEVERAL VIEWS OF THE DRAWINGS

These and other features, aspects, and advantages of the present invention will become better understood with regard to the following description, and accompanying drawings, where:

(FIGS. 21 and 22), and similar binding profiles were observed for the three P2 peptides from the different species. However, the extended P2 peptide of the three species, did not bind well to ADI-60143 Fab (FIG. 22).

FIG. 21 are graphs depicting Binding of ADI-60143 IgG to rat, mouse or human extended P2 peptide determined by ELISA.

FIG. 22A is a diagram depicting the experimental protocol performed for determining microglial activation and macrophage recruitment in the Fibrin induced encephalitis (FIE) mouse model.

FIG. 22B is a graph depicting percent area of Iba-1 positive staining for determining microglial activation in brain tissue sections from FIE mice administered aCSF (artificial cerebral spinal fluid), fibrinogen, IgG isotype control (30 mg/Kg), parental humanized antibody clone THN227 (not affinity matured) (10 or 30 mg/Kg), and affinity matured antibody clone ADI-60143 (10 or 30 mg/Kg).

FIG. 22C is a graph depicting percent area of Mac-2 positive staining for determining macrophage infiltration in brain tissue sections from FE mice administered aCSF (artificial cerebral spinal fluid), fibrinogen, IgG isotype control (30 mg/Kg), parental humanized antibody clone THN227 (not affinity matured) (10 or 30 mg/Kg), and affinity matured antibody clone ADI-60143 (10 or 30 mg/Kg).

DETAILED DESCRIPTION

Definitions

Figure 1:
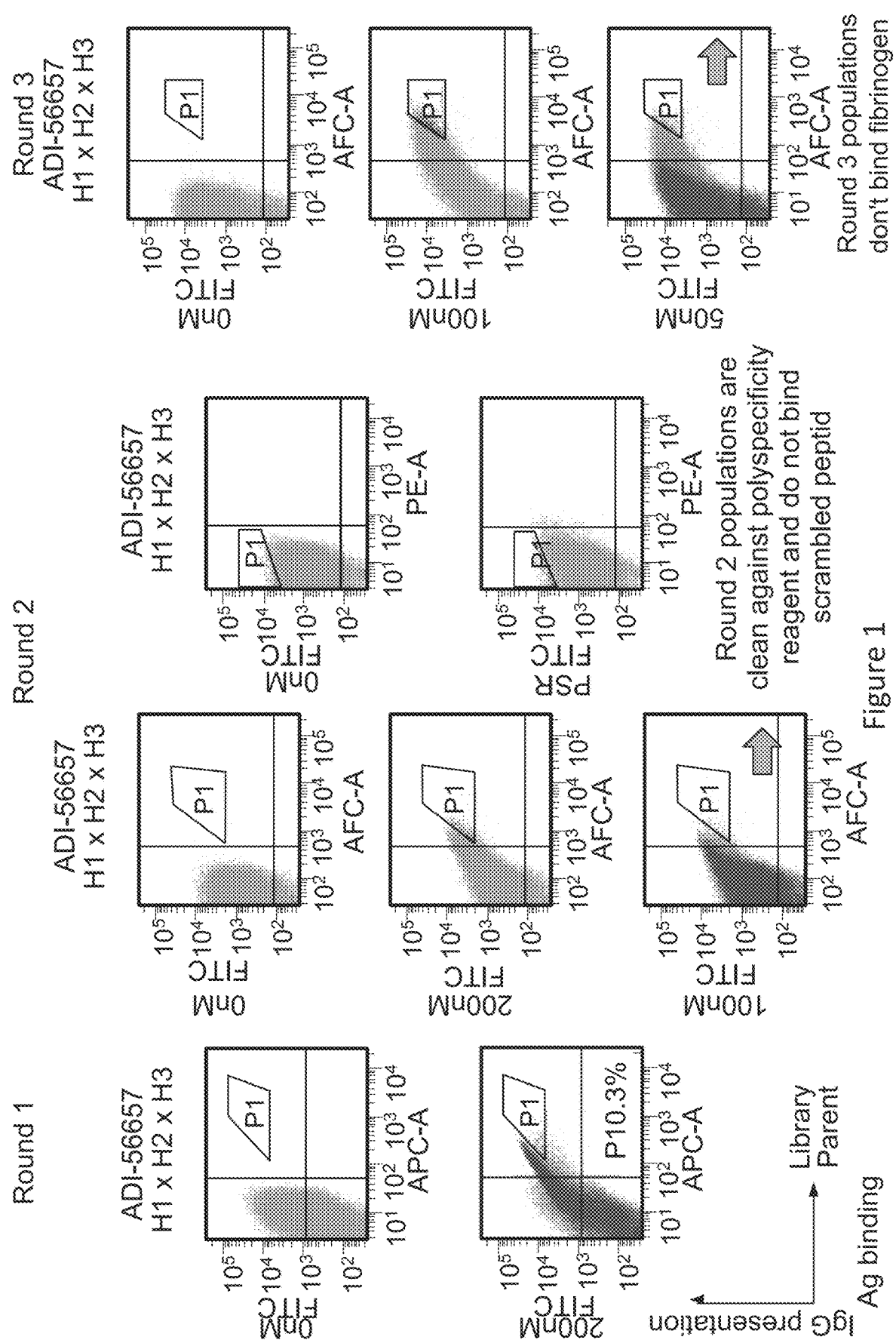
FIG. 1 are plots from FACS analysis of antibody library binding to N-terminally biotinylated fibrin P2 gamma peptide showing results of three rounds of antibody affinity maturation with one library produced from one of the three parental humanized antibodies (clone 56657).

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular form "a", "an", and "the" includes plural references unless indicated otherwise.

It is understood that aspects and embodiments of the invention described herein include "comprising," "consisting," and "consisting essentially of" aspects and embodiments.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations. A "recombinant host cell" or "host cell" refers to a cell that includes an exogenous polynucleotide, regardless of the method used for insertion, for example, direct uptake, transduction, f-mating, or other methods known in the art to create recombinant host cells.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, *flagellates*, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the *Archaea* (including but not limited to, *Methanococcus jannaschii, Methanobacterium* thermoautotrophicum*, Halobacterium* such as *Haloferax volcanii* and *Halobacterium* species NRC-1*, Archaeoglobus fulgidus, Pyrococcus furiosus, Pyrococcus horikoshii, Aeuropyrum pernix*, etc.) phylogenetic domain.

An "effective amount" or "therapeutically effective amount" as used herein refers to an amount of therapeutic compound, such as an anti-FIBRIN antibody, administered to an individual, either as a single dose or as part of a series of doses, which is effective to produce or contribute to a desired therapeutic effect, either alone or in combination with another therapeutic modality. Examples of a desired therapeutic effect is enhancing an immune response, slowing or delaying tumor development; stabilization of disease; amelioration of one or more symptoms. An effective amount may be given in one or more dosages.

The term "treating" (and variations thereof such as "treat" or "treatment") refers to clinical intervention in an attempt to alter the natural course of a disease or condition in a subject in need thereof. Treatment can be performed during the course of clinical pathology. Desirable effects of treatment include preventing recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "sufficient amount" means an amount sufficient to produce a desired effect, e.g., an amount sufficient to modulate an immune response in a subject.

As used herein, the term "subject" or "individual" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an antibody provided herein. In some aspects, the disease or condition is a cancer. In some aspects, the disease or condition is a viral infection.

The term "in vitro" refers to processes that occur in a living cell growing separate from a living organism, e.g., growing in tissue culture.

The term "in vivo" refers to processes that occur in a living organism.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "co-administration", "co-administer", and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to the administration of a second therapeutic agent.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "about" indicates and encompasses an indicated value and a range above and below that value. In certain embodiments, the term "about" indicates the designated value ±10%, +5%, or +1%. In certain embodiments, where applicable, the term "about" indicates the designated value(s)±one standard deviation of that value(s).

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

For any of the structural and functional characteristics described herein, methods of determining these characteristics are known in the art.

The term "optionally" is meant, when used sequentially, to include from one to all of the enumerated combinations and contemplates all sub-combinations.

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope).

The term "$k_d$" (sec$^{-1}$), as used herein, refers to the dissociation rate constant of a particular antibody-antigen interaction. This value is also referred to as the $k_{off}$ value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" (M$^{-1}$), as used herein, refers to the association equilibrium constant of a particular antibody-antigen interaction. $K_A = k_a/k_d$.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

A "Fibrin antibody," "anti-Fibrin antibody," or "Fibrin-specific antibody" is an antibody, as provided herein, which specifically binds to the antigen Fibrin. In some embodiments, the antibody binds the extracellular domain of Fibrin. In certain embodiments, a Fibrin antibody provided herein binds to an epitope of Fibrin that is conserved between or among Fibrin proteins from different species.

The term "epitope" means a portion of an antigen that specifically binds to an antibody.

The term "hypervariable region" or "HVR", as used herein, refers to each of the regions of an antibody variable domain which are hypervariable in sequence and/or form structurally defined loops ("hypervariable loops").

The term "antigen-binding domain" means the portion of an antibody that is capable of specifically binding to an antigen or epitope.

The term "chimeric antibody" refers to an antibody in which a portion of the heavy and/or light chain is derived from a particular source or species, while the remainder of the heavy and/or light chain is derived from a different source or species.

The term "human antibody" refers to an antibody which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

The term "humanized antibody" refers to a protein having a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject.

The term "multispecific antibody" refers to an antibody that comprises two or more different antigen-binding domains that collectively specifically bind two or more different epitopes.

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')2" fragments contain two Fab' fragments joined, near the hinge region, by disulfide bonds. F(ab')2 fragments may be generated, for example, by recombinant methods or by pepsin digestion of an intact antibody. The F(ab') fragments can be dissociated, for example, by treatment with ß-mercaptoethanol.

"Fv" fragments comprise a non-covalently-linked dimer of one heavy chain variable domain and one light chain variable domain.

"Single-chain Fv" or "sFv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

"scFv-Fc" fragments comprise an scFv attached to an Fc domain. For example, an Fc domain may be attached to the C-terminal of the scFv. The Fc domain may follow the VH or VL, depending on the orientation of the variable domains in the scFv (i.e., VH-VL or VL-VH). Any suitable Fc domain known in the art or described herein may be used. In some cases, the Fc domain comprises an IgG4 Fc domain.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22).

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "antibody fragment" refers to an antibody that comprises a portion of an intact antibody, such as the antigen-binding or variable region of an intact antibody. Antibody fragments include, for example, Fv fragments, Fab fragments, F(ab')2 fragments, Fab' fragments, scFv (sFv) fragments, and scFv-Fc fragments.

The term "Fc domain" or "Fc region" herein is used to define a C-terminal region of an immunoglobulin heavy chain that contains at least a portion of the constant region. The term includes native sequence Fc regions and variant Fc regions.

The term "substantially purified" refers to a construct described herein, or variant thereof that may be substantially or essentially free of components that normally accompany or interact with the protein as found in its naturally occurring environment, i.e. a native cell, or host cell in the case of recombinantly produced heteromultimer that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., using publicly available computer software such as BLAST, BLASTP, BLASTN, BLAST-2, ALIGN, MEGALIGN (DNASTAR), CLUSTALW, CLUSTAL OMEGA, or MUSCLE software or other algorithms available to persons of skill) or by visual inspection. Software for performing BLAST analyses is publicly available through the National Center for Biotechnology Information (ncbi.nlm.nih.gov). Those skilled in the art can determine appropriate parameters for aligning sequences, including any algorithms needed to achieve maximal alignment over the full length of the sequences being compared. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

It must be noted that, as used in the specification and the appended claims, the singular forms "a," "an" and "the" include plural referents unless the context clearly dictates otherwise.

Anti-Fibrin Antibodies
Antibody Structure

The present application provides antibodies and compositions comprising an antibody which binds a fibrin protein.

The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG1, $IgG_2$, $IgG_3$, $IgG_4$, IgA1, and $IgA_2$. The heavy chain constant domains that correspond to the different classes of immunoglobulins are called α, δ, ε, γ, and μ, respectively.

An exemplary immunoglobulin (antibody) structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

In some embodiments, the antibodies provided herein comprise a heavy chain. In one embodiment, the heavy chain is an IgA. In one embodiment, the heavy chain is an IgD. In one embodiment, the heavy chain is an IgE. In one embodiment, the heavy chain is an IgG. In one embodiment, the heavy chain is an IgM. In one embodiment, the heavy chain is an IgG1. In one embodiment, the heavy chain is an IgG2. In one embodiment, the heavy chain is an IgG3. In one embodiment, the heavy chain is an IgG4. In one embodiment, the heavy chain is an IgA1. In one embodiment, the heavy chain is an IgA2.

In some embodiments, an antibody is an IgG1 antibody. In some embodiments, an antibody is an IgG3 antibody. In some embodiments, an antibody is an IgG2 antibody. In some embodiments, an antibody is an IgG4 antibody.

Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); A1-Lazikani et al., 1997, J. Mol. Biol., 273:927-948 ("Chothia" numbering scheme); MacCallum et al., 1996, J. Mol. Biol. 262:732-745 ("Contact" numbering scheme); Lefranc et al., Dev. Comp. Immunol., 2003, 27:55-77 ("IMGT" numbering scheme); and Honegge and Plückthun, J. Mol. Biol., 2001, 309:657-70 ("AHo" numbering scheme); each of which is incorporated by reference in its entirety.

Table A provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at www.bioinforg.uk/abs/abnum/, and described in Abhinandan and Martin, Immunology, 2008, 45:3832-3839, incorporated by reference in its entirety.

TABLE A

Table A. Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

One example of an antigen-binding domain is an antigen-binding domain formed by a VH-VL dimer of an antibody. Another example of an antigen-binding domain is an antigen-binding domain formed by diversification of certain loops from the tenth fibronectin type III domain of an Adnectin. An antigen-binding domain can include CDRs 1, 2, and 3 from a heavy chain in that order; and CDRs 1, 2, and 3 from a light chain in that order.

Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to Fibrin variants with different point-mutations, or to chimeric Fibrin variants.

To screen for antibodies which bind to an epitope on a target antigen bound by an antibody of interest (e.g., Fibrin), a routine cross-blocking assay such as that described in Antibodies, A Laboratory Manual, Cold Spring Harbor Laboratory, Ed Harlow and David Lane (1988), can be performed. Alternatively, or additionally, epitope mapping can be performed by methods known in the art.

Chimeric antibodies are antibodies in which a portion of the heavy and/or light chain is derived from a particular source or species, while the remainder of the heavy and/or light chain is derived from a different source or species.

Human antibodies are antibodies which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies can be found in U.S. Pat. Nos. 6,054,297, 5,886,152 and 5,877,293. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

The two or more different epitopes may be epitopes on the same antigen (e.g., a single Fibrin molecule expressed by a cell) or on different antigens (e.g., different Fibrin molecules expressed by the same cell, or a Fibrin molecule and a non-Fibrin molecule). In some aspects, a multi-specific antibody binds two different epitopes (i.e., a "bispecific antibody"). In some aspects, a multi-specific antibody binds three different epitopes (i.e., a "trispecific antibody").

Anti-Fibrin antibodies can include those described herein such as the clones set forth in the drawings and/or tables. In some embodiments, the antibody comprises an alternative scaffold. In some embodiments, the antibody consists of an alternative scaffold. In some embodiments, the antibody consists essentially of an alternative scaffold. In some embodiments, the antibody comprises an antibody fragment. In some embodiments, the antibody consists of an antibody fragment. In some embodiments, the antibody consists essentially of an antibody fragment.

In some embodiments the antibodies are monoclonal antibodies.

In some embodiments the antibodies are polyclonal antibodies.

In some embodiments the antibodies are produced by hybridomas. In other embodiments, the antibodies are produced by recombinant cells engineered to express the desired variable and constant domains.

In some embodiments the antibodies may be single chain antibodies or other antibody derivatives retaining the antigen specificity and the lower hinge region or a variant thereof.

In some embodiments the antibodies may be polyfunctional antibodies, recombinant antibodies, human antibodies, humanized antibodies, fragments or variants thereof. In particular embodiments, the antibody fragment or a derivative thereof is selected from a Fab fragment, a Fab'2 fragment, a CDR and ScFv.

In some embodiments, the antibodies are capable of forming an immune complex. For example, an immune complex can be a tumor cell covered by antibodies.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

Sequences of Fibrin Antibodies $V_H$ Domains

In some embodiments, an antibody provided herein comprises a $V_H$ sequence selected from SEQ ID NOs: 7, 8, 9, 10, 11, 12, 13, 14, 15, 16, 17, 18, 19, and 20. In some embodiments, an antibody provided herein comprises a VH sequence of SEQ ID NO: 7. In some embodiments, an antibody provided herein comprises a VH sequence of SEQ ID NO: 8. In some embodiments, an antibody provided herein comprises a VH sequence of SEQ ID NO: 9. In some embodiments, an antibody provided herein comprises a VH sequence of SEQ ID NO: 10. In some embodiments, an antibody provided herein comprises a VH sequence of SEQ ID NO: 11. In some embodiments, an antibody provided herein comprises a VH sequence of SEQ ID NO: 12. In some embodiments, an antibody provided herein comprises a $V_H$ sequence of SEQ ID NO: 13. In some embodiments, an antibody provided herein comprises a VH sequence of SEQ ID NO: 14. In some embodiments, an antibody provided herein comprises a VH sequence of SEQ ID NO: 15. In some embodiments, an antibody provided herein comprises a VH sequence of SEQ ID NO: 16. In some embodiments, an antibody provided herein comprises a $V_H$ sequence of SEQ ID NO: 17. In some embodiments, an antibody provided herein comprises a VH sequence of SEQ ID NO: 18. In some embodiments, an antibody provided herein comprises a VH sequence of SEQ ID NO: 19. In some embodiments, an antibody provided herein comprises a VH sequence of SEQ ID NO: 20.

In some embodiments, an antibody provided herein comprises a VH sequence having at least about 50%, 60%, 70%, 80%, 90%, 95%, or 99% identity to an illustrative VH sequence provided in SEQ ID NOs: 7, 8, 9, 10, 11, 12, 13, 14, 15, 16, 17, 18, 19, and 20. In some embodiments, an antibody provided herein comprises a VH sequence provided in SEQ ID NOs: 7, 8, 9, 10, 11, 12, 13, 14, 15, 16, 17, 18, 19, and 20, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

$V_L$ Domains

In some embodiments, an antibody provided herein comprises a VL sequence selected from SEQ ID NO: 21.

In some embodiments, an antibody provided herein comprises a VL sequence having at least about 50%, 60%, 70%, 80%, 90%, 95%, or 99% identity to an illustrative VL sequence provided in SEQ ID NO: 21. In some embodiments, an antibody provided herein comprises a VL sequence provided in SEQ ID NO: 21 with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

VH-VL Combinations

In some embodiments, an antibody provided herein comprises a $V_H$ sequence selected from SEQ ID NOs: 7, 8, 9, 10, 11, 12, 13, 14, 15, 16, 17, 18, 19, and 20; and a $V_L$ sequence selected from SEQ ID NO: 21.

In some embodiments, an antibody provided herein comprises a VH sequence of SEQ ID NO: 7 and a $V_L$ sequence of SEQ ID NO: 21. In some embodiments, an antibody provided herein comprises a $V_H$ sequence of SEQ ID NO: 8 and a $V_L$ sequence of SEQ ID NO:21. In some embodiments, an antibody provided herein comprises a $V_H$ sequence of SEQ ID NO: 9 and a $V_L$ sequence of SEQ ID NO:21. In some embodiments, an antibody provided herein comprises a $V_H$ sequence of SEQ ID NO: 10 and a $V_L$ sequence of SEQ ID NO: 21. In some embodiments, an antibody provided herein comprises a $V_H$ sequence of SEQ ID NO: 11 and a $V_L$ sequence of SEQ ID NO: 21. In some embodiments, an antibody provided herein comprises a VH sequence of SEQ ID NO: 12 and a $V_L$ sequence of SEQ ID NO: 21. In some embodiments, an antibody provided herein comprises a $V_H$ sequence of SEQ ID NO: 13 and a $V_L$ sequence of SEQ ID NO: 21. In some embodiments, an antibody provided herein comprises a VH sequence of SEQ ID NO: 14 and a $V_L$ sequence of SEQ ID NO: 21. In some embodiments, an antibody provided herein comprises a $V_H$ sequence of SEQ ID NO: 15 and a $V_L$ sequence of SEQ ID NO: 21. In some embodiments, an antibody provided herein comprises a VH sequence of SEQ ID NO: 16 and a $V_L$ sequence of SEQ ID NO: 21. In some embodiments, an antibody provided herein comprises a $V_H$ sequence of SEQ ID NO: 17 and a $V_L$ sequence of SEQ ID NO: 21. In some embodiments, an antibody provided herein comprises a $V_H$ sequence of SEQ ID NO: 18 and a $V_L$ sequence of SEQ ID NO: 21. In some embodiments, an antibody provided herein comprises a $V_H$ sequence of SEQ ID NO:19 and a $V_L$ sequence of SEQ ID NO:21. In some embodiments, an antibody provided herein comprises a $V_H$ sequence of SEQ ID NO:20 and a $V_L$ sequence of SEQ ID NO:21.

In certain aspects, any of SEQ ID NOs: 7, 8, 9, 10, 11, 12, 13, 14, 15, 16, 17, 18, 19, and 20 can be combined with any of SEQ ID NO: 21.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 7, 8, 9, 10, 11, 12, 13, 14, 15, 16, 17, 18, 19, and 20; and a $V_L$ sequence having at least about 50%, 60%, 70%, 80%, 90%, 95%, or 99% identity to an illustrative VL sequence provided in SEQ ID NO: 21. In some embodiments, an antibody provided herein comprises a $V_H$ sequence provided in SEQ ID NOs: 7, 8, 9, 10, 11, 12, 13, 14, 15, 16, 17, 18, 19, and 20, with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a VL sequence provided in SEQ ID NO: 21, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

CDRs

In some embodiments, an antibody provided herein comprises one to three CDRs of a $V_H$ domain selected from SEQ ID NOs: 7, 8, 9, 10, 11, 12, 13, 14, 15, 16, 17, 18, 19, and 20. In some embodiments, an antibody provided herein comprises two to three CDRs of a $V_H$ domain selected from SEQ ID NOs: 7, 8, 9, 10, 11, 12, 13, 14, 15, 16, 17, 18, 19, and 20. In some embodiments, an antibody provided herein comprises three CDRs of a VH domain selected from SEQ ID NOs: 37, 8, 9, 10, 11, 12, 13, 14, 15, 16, 17, 18, 19, and 20. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 7, 8, 9, 10, 11, 12, 13, 14, 15, 16, 17, 18, 19, and 20. In some embodiments, the CDR-H1 is a CDR-H1 of a VH domain selected from SEQ ID NOs: 7, 8, 9, 10, 11, 12, 13, 14, 15, 16, 17, 18, 19, and 20, with up to 1, 2, 3, 4, or 5 amino acid substitutions. In some embodiments, the CDR-H2 is a CDR-H2 of a VH domain selected from SEQ ID NOs: 7, 8, 9, 10, 11, 12, 13, 14, 15, 16, 17, 18, 19, and 20, with up to 1, 2, 3, 4, 5, 6, 7, or 8 amino acid substitutions. In some embodiments, the CDR-H3 is a CDR-H3 of a VH domain selected from SEQ ID NOs: 7, 8, 9, 10, 11, 12, 13, 14, 15, 16, 17, 18, 19, and 20, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VL domain of SEQ ID NO: 21. In some embodiments, an antibody provided herein comprises two to three CDRs of a VL domain of SEQ ID NO: 21. In some embodiments, an antibody provided herein comprises three CDRs of a VL domain of SEQ ID NO: 21. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-L1, CDR-L2, or CDR-L3 of SEQ ID NO: 21. In some embodiments, the CDR-L1 is a CDR-L1 of a VL domain of SEQ ID NO: 21, with up to 1, 2, 3, 4, or 5 amino acid substitutions. In some embodiments, the CDR-L2 is a CDR-L2 of a VL domain of SEQ ID NO: 21, with up to 1, 2, 3, 4, 5, 6, 7, or 8 amino acid substitutions. In some embodiments, the CDR-L3 is a CDR-L3 of a VL domain of SEQ ID NO: 21, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VH domain selected from SEQ ID NOs: 7, 8, 9, 10, 11, 12, 13, 14, 15, 16, 17, 18, 19, and 20 and one to three CDRs of a VL domain of SEQ ID NO: 21. In some embodiments, an antibody provided herein comprises two to three CDRs of a VH domain selected from SEQ ID NOs: 7, 8, 9, 10, 11, 12, 13, 14, 15, 16, 17, 18, 19, and 20 and two to three CDRs of a VL domain of SEQ ID NO: 21. In some embodiments, an antibody provided herein comprises three CDRs of a VH domain selected from SEQ ID NOs: 7, 8, 9, 10, 11, 12, 13, 14, 15, 16, 17, 18, 19, and 20 and three CDRs of a VL domain of SEQ ID NO: 21. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an antibody provided herein comprises a CDR-H3 selected of SEQ ID NOs: 24, 25, 26, 27, 28, 29 and 30. In some aspects, the CDR-H3 has at least about 50%, 75%, 80%, 85%, 90%, or 95% identity with a CDR-H3 of SEQ ID NOs: 24, 25, 26, 27, 28, 29 and 30. In some embodiments, the CDR-H3 is a CDR-H3 selected of SEQ ID NO: 24, 25, 26, 27, 28, 29 and 30, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 24. In some aspects, the CDR-H3 has at least about 50%, 75%, 80%, 85%, 90%, or 95% identity with a CDR-H3 of SEQ ID NO: 24. In some embodiments, the CDR-H3 is a CDR-H3 selected of SEQ ID NO: 24, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 25. In some aspects, the CDR-H3 has at least about 50%, 75%, 80%, 85%, 90%, or 95% identity with a CDR-H3 of SEQ ID NO: 25. In some embodiments, the CDR-H3 is a CDR-H3 selected of SEQ ID NO: 25, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 26. In some aspects, the CDR-H3 has at least about 50%, 75%, 80%, 85%, 90%, or 95% identity with a CDR-H3 of SEQ ID NO: 26. In some embodiments, the CDR-H3 is a CDR-H3 selected of SEQ ID NO: 26, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 27. In some aspects, the CDR-H3 has at least about 50%, 75%, 80%, 85%, 90%, or 95% identity with a CDR-H3 of SEQ ID NO: 27. In some embodiments, the CDR-H3 is a CDR-H3 selected of SEQ ID NO: 27, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 28. In some aspects, the CDR-H3 has at least about 50%, 75%, 80%, 85%, 90%, or 95% identity with a CDR-H3 of SEQ ID NO: 28. In some embodiments, the CDR-H3 is a CDR-H3 selected of SEQ ID NO: 28, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 29. In some aspects, the CDR-H3 has at least about 50%, 75%, 80%, 85%, 90%, or 95% identity with a CDR-H3 of SEQ ID NO: 29. In some embodiments, the CDR-H3 is a CDR-H3 selected of SEQ ID NO: 29, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 30. In some aspects, the CDR-H3 has at least about 50%, 75%, 80%, 85%, 90%, or 95% identity with a CDR-H3 of SEQ ID NO: 30. In some embodiments, the CDR-H3 is a CDR-H3 selected of SEQ ID NO: 30, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 3. In some aspects, the CDR-H3 has at least about 50%, 75%, 80%, 85%, 90%, or 95% identity with a CDR-H3 of SEQ ID NO: 3. In some embodiments, the CDR-H3 is a CDR-H3 selected of SEQ ID NO: 3, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO: 1. In some aspects, the CDR-H1 has at least about 50%, 75%, 80%, 85%, 90%, or 95% identity with a CDR-H1 of SEQ ID NO: 1. In some embodiments, the CDR-H1 is a CDR-H1 of SEQ ID NO: 1, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H2 selected of SEQ ID NO: 2. In some aspects, the CDR-H2 has at least about 50%, 75%, 80%, 85%, 90%, or 95% identity with a CDR-H2 of SEQ ID NO: 2. In some embodiments, the CDR-H2 is a CDR-H2 selected of SEQ ID NO: 2, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 24 and a CDR-H2 of SEQ ID NO: 2. In some embodiments, an antibody provided herein comprises a CDR-H3 of SEQ ID NO: 25, a CDR-H2 of SEQ ID NO: 2, and a CDR-H1 of SEQ ID NO: 1. In some embodiments, the CDR-H3 has at least about 50%, 75%, 80%, 85%, 90%, or 95% identity with a CDR-H3 of SEQ ID NO: 24, the CDR-H2 has at least about 50%, 75%, 80%, 85%, 90%, or 95% identity with a CDR-H2 of SEQ ID NO: 2, and the CDR-H1 has at least about 50%, 75%, 80%, 85%, 90%, or 95% identity with a CDR-H1 of SEQ ID NO: 1. In some embodiments, the CDR-H3 is a CDR-H3 of SEQ ID NO: 24, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; and the CDR-H1 is a CDR-H1 of SEQ ID NO: 1, with up to 1, 2, 3, 4, or 5 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 25 and a CDR-H2 of SEQ ID NO: 2. In some embodiments, an antibody provided herein comprises a CDR-H3 of SEQ ID NO: 25, a CDR-H2 of SEQ ID NO: 2, and a CDR-H1 of SEQ ID NO: 1. In some embodiments, the CDR-H3 has at least about 50%, 75%, 80%, 85%, 90%, or 95% identity with a CDR-H3 of SEQ ID NO: 25, the CDR-H2 has at least about 50%, 75%, 80%, 85%, 90%, or 95% identity with a CDR-H2 of SEQ ID NO: 2, and the CDR-H1 has at least about 50%, 75%, 80%, 85%, 90%, or 95% identity with a CDR-H1 of SEQ ID NO: 1. In some embodiments, the CDR-H3 is a CDR-H3 of SEQ ID NO: 25, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; and the CDR-H1 is a CDR-H1 of SEQ ID NO: 1, with up to 1, 2, 3, 4, or 5 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 26 and a CDR-H2 of SEQ ID NO: 2. In some embodiments, an antibody provided herein comprises a CDR-H3 of SEQ ID NO: 26, a CDR-H2 of SEQ ID NO: 2, and a CDR-H1 of SEQ ID NO: 1. In some embodiments, the CDR-H3 has at least about 50%, 75%, 80%, 85%, 90%, or 95% identity with a CDR-H3 of SEQ ID NO: 26, the CDR-H2 has at least about 50%, 75%, 80%, 85%, 90%, or 95% identity with a CDR-H2 of SEQ ID NO: 2, and the CDR-H1 has at least about 50%, 75%, 80%, 85%, 90%, or 95% identity with a CDR-H1 of SEQ ID NO: 1. In some embodiments, the CDR-H3 is a CDR-H3 of SEQ ID NO: 26, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; and the CDR-H1 is a CDR-H1 of SEQ ID NO: 1, with up to 1, 2, 3, 4, or 5 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 27 and a CDR-H2 of SEQ ID NO: 2. In some embodiments, an antibody provided herein comprises a CDR-H3 of SEQ ID NO: 27, a CDR-H2 of SEQ ID NO: 2, and a CDR-H1 of SEQ ID NO: 1. In some embodiments, the CDR-H3 has at least about 50%, 75%, 80%, 85%, 90%, or 95% identity with a CDR-H3 of SEQ ID NO: 27, the CDR-H2 has at least about 50%, 75%, 80%, 85%, 90%, or 95% identity with a CDR-H2 of SEQ ID NO: 2, and the CDR-H1 has at least about 50%, 75%, 80%, 85%, 90%, or 95% identity with a CDR-H1 of SEQ ID NO: 1. In some embodiments, the CDR-H3 is a CDR-H3 of SEQ ID NO: 27, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; and the CDR-H1 is a CDR-H1 of SEQ ID NO: 1, with up to 1, 2, 3, 4, or 5 amino acid substitutions. In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 28 and a CDR-H2 of SEQ ID NO: 2. In some embodiments, an antibody provided herein comprises a CDR-H3 of SEQ ID NO: 28, a CDR-H2 of SEQ ID NO: 2, and a CDR-H1 of SEQ ID NO: 1. In some embodiments, the CDR-H3 has at least about 50%, 75%, 80%, 85%, 90%, or 95% identity with a CDR-H3 of SEQ ID NO: 28, the CDR-H2 has at least about 50%, 75%, 80%, 85%, 90%, or 95% identity with a CDR-H2 of SEQ ID NO: 2, and the CDR-H1 has at least about 50%, 75%, 80%, 85%, 90%, or 95% identity with a CDR-H1 of SEQ ID NO: 1. In some embodiments, the CDR-H3 is a CDR-H3 of SEQ ID NO: 28, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; and the CDR-H1 is a CDR-H1 of SEQ ID NO: 1, with up to 1, 2, 3, 4, or 5 amino acid substitutions. In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 29 and a CDR-H2 of SEQ ID NO: 2. In some embodiments, an antibody provided herein comprises a CDR-H3 of SEQ ID NO: 29, a CDR-H2 of SEQ ID NO: 2, and a CDR-H1 of SEQ ID NO: 1. In some embodiments, the CDR-H3 has at least about 50%, 75%, 80%, 85%, 90%, or 95% identity with a CDR-H3 of SEQ ID NO: 29, the CDR-H2 has at least about 50%, 75%, 80%, 85%, 90%, or 95% identity with a CDR-H2 of SEQ ID NO: 2, and the CDR-H1 has at least about 50%, 75%, 80%, 85%, 90%, or 95% identity with a CDR-H1 of SEQ ID NO: 1. In some embodiments, the CDR-H3 is a CDR-H3 of SEQ ID NO: 29, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; and the CDR-H1 is a CDR-H1 of SEQ ID NO: 1, with up to 1, 2, 3, 4, or 5 amino acid substitutions. In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 30 and a CDR-H2 of SEQ ID NO: 2. In some embodiments, an antibody provided herein comprises a CDR-H3 of SEQ ID NO: 30, a CDR-H2 of SEQ ID NO: 2, and a CDR-H1 of SEQ ID NO: 1. In some embodiments, the CDR-H3 has at least about 50%, 75%, 80%, 85%, 90%, or 95% identity with a CDR-H3 of SEQ ID NO: 30, the CDR-H2 has at least about 50%, 75%, 80%, 85%, 90%, or 95% identity with a CDR-H2 of SEQ ID NO: 2, and the CDR-H1 has at least about 50%, 75%, 80%, 85%, 90%, or 95% identity with a CDR-H1 of SEQ ID NO: 1. In some embodiments, the CDR-H3 is a CDR-H3 of SEQ ID NO: 30, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; and the CDR-H1 is a CDR-H1 of SEQ ID NO: 1, with up to 1, 2, 3, 4, or 5 amino acid substitutions. In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 of SEQ ID NO: 6. In some aspects, the CDR-L3 has at least about 50%, 75%, 80%, 85%, 90%, or 95% identity with a CDR-L3 of SEQ ID NO: 6. In some embodiments, the CDR-L3 is a CDR-L3 of SEQ ID NO: 6, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L2 of SEQ ID NO: 5. In some aspects, the CDR-L2 has at least about 50%, 75%, 80%, 85%, 90%, or 95% identity with a CDR-L2 of SEQ ID NO: 5. In some embodiments, the CDR-L2 is a CDR-L2 of SEQ ID NO: 5, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L1 of SEQ ID NO: 4. In some aspects, the CDR-L1 has at least about 50%, 75%, 80%, 85%, 90%, or 95% identity with a CDR-L1 of SEQ ID NO: 4. In some embodiments, the CDR-L1 is a CDR-L1 of SEQ ID NO: 4, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 of SEQ ID NO: 6 and a CDR-L2 of SEQ ID NO: 5. In some embodiments, an antibody provided herein comprises a CDR-L3 of SEQ ID NO: 6, a CDR-L2 of SEQ ID NO: 5, and a CDR-L1 of SEQ ID NO: 4. In some embodiments, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described herein are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 24, a CDR-H2 of SEQ ID NO: 2, a CDR-H1 of SEQ ID NO: 1, a CDR-L3 of SEQ ID NO: 6, a CDR-L2 of SEQ ID NO: 5, and a CDR-L1 of SEQ ID NO: 4. In some embodiments, the CDR-H3 has at least about 50%, 75%, 80%, 85%, 90%, or 95% identity with a CDR-H3 of SEQ ID NO: 24, the CDR-H2 has at least about 50%, 75%, 80%, 85%, 90%, or 95% identity with a CDR-H2 of SEQ ID NO: 2, the CDR-H1 has at least about 50%, 75%, 80%, 85%, 90%, or 95% identity with a CDR-H1 of SEQ ID NO: 1, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-H3 is a CDR-H3 of SEQ ID NO: 24, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; the CDR-H1 is a CDR-H1 of SEQ ID NO: 1, with up to 1, 2, 3, 4, or 5 amino acid substitutions; the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 25, a CDR-H2 of SEQ ID NO: 2, a CDR-H1 of SEQ ID NO: 1, a CDR-L3 of SEQ ID NO: 6, a CDR-L2 of SEQ ID NO: 5, and a CDR-L1 of SEQ ID NO: 4. In some embodiments, the CDR-H3 has at least about 50%, 75%, 80%, 85%, 90%, or 95% identity with a CDR-H3 of SEQ ID NO: 25, the CDR-H2 has at least about 50%, 75%, 80%, 85%, 90%, or 95% identity with a CDR-H2 of SEQ ID NO: 2, the CDR-H1 has at least about 50%, 75%, 80%, 85%, 90%, or 95% identity with a CDR-H1 of SEQ ID NO: 1, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-H3 is a CDR-H3 of SEQ ID NO: 25, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; the CDR-H1 is a CDR-H1 of SEQ ID NO: 1, with up to 1, 2, 3, 4, or 5 amino acid substitutions; the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 26, a CDR-H2 of SEQ ID NO: 2, a CDR-H1 of SEQ ID NO: 1, a CDR-L3 of SEQ ID NO: 6, a CDR-L2 of SEQ ID NO: 5, and a CDR-L1 of SEQ ID NO: 4. In some embodiments, the CDR-H3 has at least about 50%, 75%, 80%, 85%, 90%, or 95% identity with a CDR-H3 of SEQ ID NO: 26, the CDR-H2 has at least about 50%, 75%, 80%, 85%, 90%, or 95% identity with a CDR-H2 of SEQ ID NO: 2, the CDR-H1 has at least about 50%, 75%, 80%, 85%, 90%, or 95% identity with a CDR-H1 of SEQ ID NO: 1, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-H3 is a CDR-H3 of SEQ ID NO: 26, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; the CDR-H1 is a CDR-H1 of SEQ ID NO: 1, with up to 1, 2, 3, 4, or 5 amino acid substitutions; the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 27, a CDR-H2 of SEQ ID NO: 2, a CDR-H1 of SEQ ID NO: 1, a CDR-L3 of SEQ ID NO: 6, a CDR-L2 of SEQ ID NO: 5, and a CDR-L1 of SEQ ID NO: 4. In some embodiments, the CDR-H3 has at least about 50%, 75%, 80%, 85%, 90%, or 95% identity with a CDR-H3 of SEQ ID NO: 27, the CDR-H2 has at least about 50%, 75%, 80%, 85%, 90%, or 95% identity with a CDR-H2 of SEQ ID NO: 2, the CDR-H1 has at least about 50%, 75%, 80%, 85%, 90%, or 95% identity with a CDR-H1 of SEQ ID NO: 1, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-H3 is a CDR-H3 of SEQ ID NO: 27, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; the CDR-H1 is a CDR-H1 of SEQ ID NO: 1, with up to 1, 2, 3, 4, or 5 amino acid substitutions; the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 28, a CDR-H2 of SEQ ID NO: 2, a CDR-H1 of SEQ ID NO: 1, a CDR-L3 of SEQ ID NO: 6, a CDR-L2 of SEQ ID NO: 5, and a CDR-L1 of SEQ ID NO: 4. In some embodiments, the CDR-H3 has at least about 50%, 75%, 80%, 85%, 90%, or 95% identity with a CDR-H3 of SEQ ID NO: 28, the CDR-H2 has at least about 50%, 75%, 80%, 85%, 90%, or 95% identity with a CDR-H2 of SEQ ID NO: 2, the CDR-H1 has at least about 50%, 75%, 80%, 85%, 90%, or 95% identity with a CDR-H1 of SEQ ID NO: 1, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-H3 is a CDR-H3 of SEQ ID NO: 28, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; the CDR-H1 is a CDR-H1 of SEQ ID NO: 1, with up to 1, 2, 3, 4, or 5 amino acid substitutions; the CDR-L3 is a CDR-L3 of SEQ ID NO: 6, with up to 1, 2, 3, 4, or 5 amino acid substitutions;

the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 29, a CDR-H2 of SEQ ID NO: 2, a CDR-H1 of SEQ ID NO: 1, a CDR-L3 of SEQ ID NO: 6, a CDR-L2 of SEQ ID NO: 5, and a CDR-L1 of SEQ ID NO: 4. In some embodiments, the CDR-H3 has at least about 50%, 75%, 80%, 85%, 90%, or 95% identity with a CDR-H3 of SEQ ID NO: 29, the CDR-H2 has at least about 50%, 75%, 80%, 85%, 90%, or 95% identity with a CDR-H2 of SEQ ID NO: 2, the CDR-H1 has at least about 50%, 75%, 80%, 85%, 90%, or 95% identity with a CDR-H1 of SEQ ID NO: 1, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-H3 is a CDR-H3 of SEQ ID NO: 29, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; the CDR-H1 is a CDR-H1 of SEQ ID NO: 1, with up to 1, 2, 3, 4, or 5 amino acid substitutions; the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 30, a CDR-H2 of SEQ ID NO: 2, a CDR-H1 of SEQ ID NO: 1, a CDR-L3 of SEQ ID NO: 6, a CDR-L2 of SEQ ID NO: 5, and a CDR-L1 of SEQ ID NO: 4. In some embodiments, the CDR-H3 has at least about 50%, 75%, 80%, 85%, 90%, or 95% identity with a CDR-H3 of SEQ ID NO: 30, the CDR-H2 has at least about 50%, 75%, 80%, 85%, 90%, or 95% identity with a CDR-H2 of SEQ ID NO: 2, the CDR-H1 has at least about 50%, 75%, 80%, 85%, 90%, or 95% identity with a CDR-H1 of SEQ ID NO: 1, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-H3 is a CDR-H3 of SEQ ID NO: 30, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; the CDR-H1 is a CDR-H1 of SEQ ID NO: 1, with up to 1, 2, 3, 4, or 5 amino acid substitutions; the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO: 1, a CDR-H2 of SEQ ID NO: 2, a CDR-H3 of SEQ ID NO: 24, a CDR-L1 of SEQ ID NO: 4, a CDR-L2 of SEQ ID NO: 5, and a CDR-L3 of SEQ ID NO: 6.

In some embodiments, an antibody provided herein comprises a CDR-H1 of SEQ ID NO: 1, a CDR-H2 of SEQ ID NO: 2, a CDR-H3 of SEQ ID NO: 25, a CDR-L1 of SEQ ID NO: 4, a CDR-L2 of SEQ ID NO: 5, and a CDR-L3 of SEQ ID NO: 6.

In some embodiments, an antibody provided herein comprises a CDR-H1 of SEQ ID NO: 1, a CDR-H2 of SEQ ID NO: 2, a CDR-H3 of SEQ ID NO: 26, a CDR-L1 of SEQ ID NO: 4, a CDR-L2 of SEQ ID NO: 5, and a CDR-L3 of SEQ ID NO: 6.

In some embodiments, an antibody provided herein comprises a CDR-H1 of SEQ ID NO: 1, a CDR-H2 of SEQ ID NO: 2, a CDR-H3 of SEQ ID NO: 27, a CDR-L1 of SEQ ID NO: 4, a CDR-L2 of SEQ ID NO: 5, and a CDR-L3 of SEQ ID NO: 6.

In some embodiments, an antibody provided herein comprises a CDR-H1 of SEQ ID NO: 1, a CDR-H2 of SEQ ID NO: 2, a CDR-H3 of SEQ ID NO: 28, a CDR-L1 of SEQ ID NO: 4, a CDR-L2 of SEQ ID NO: 5, and a CDR-L3 of SEQ ID NO: 6.

In some embodiments, an antibody provided herein comprises a CDR-H1 of SEQ ID NO: 1, a CDR-H2 of SEQ ID NO: 2, a CDR-H3 of SEQ ID NO: 29, a CDR-L1 of SEQ ID NO: 4, a CDR-L2 of SEQ ID NO: 5, and a CDR-L3 of SEQ ID NO: 6.

In some embodiments, an antibody provided herein comprises a CDR-H1 of SEQ ID NO: 1, a CDR-H2 of SEQ ID NO: 2, a CDR-H3 of SEQ ID NO: 30, a CDR-L1 of SEQ ID NO: 4, a CDR-L2 of SEQ ID NO: 5, and a CDR-L3 of SEQ ID NO: 6.

Epitopes

In certain embodiments, described herein are isolated antibodies that binds human fibrin or fibrinogen γC domain, wherein the antibody binds human fibrin at any one of amino acid residues Lys 411, Ile 412, Ile 413, Phe 415, Asn 416, Arg 417, Leu 418, Thr 419, Ile 420, and Gly 421. In certain embodiments, the antibody binds human fibrin at least two, three, four, five, six, seven, eight, nine, or all ten of amino acid residues Lys 411, Ile 412, Ile 413, Phe 415, Asn 416, Arg 417, Leu 418, Thr 419, Ile 420, and Gly 421. In certain embodiments, the isolated antibody binds human fibrin at amino acid residues Lys 411, Ile 412, Ile 413, Phe 415, Asn 416, Arg 417, Leu 418, Thr 419, Ile 420, and Gly 421. In certain embodiments the amino acid residue of the human fibrin or fibrinogen γC domain epitope bind the paratope of the antibody with a distance of less than 5 Angstroms or less, 4 Angstroms or less, 3 Angstroms or less, or 2 Angstroms or less.

Paratopes

In certain embodiments, the antibodies described herein comprise a VH region comprising a paratope that binds human fibrin or fibrinogen γC domain, wherein the paratope comprises any one of amino acid residues Ser 31, Tyr 32, Trp 33, His 35, Trp 47, Leu 50, Asp 52, Asp 54, Tyr 56, Ala 93, Ser 94, Ser 95, Lys 96 or Asp 96, Pro 97 or Ala 97, Gly 101, Gly102, and Trp 103. In certain embodiments, the antibody comprises a VH region comprising a paratope that comprises at least two, three, four, five, six, seven, eight, nine, ten, eleven, twelve, thirteen, fourteen, fifteen, sixteen, or all seventeen of amino acid residues Ser 31, Tyr 32, Trp 33, His 35, Trp 47, Leu 50, Asp 52, Asp 54, Tyr 56, Ala 93, Ser 94, Ser 95, Lys 96 or Asp 96, Pro 97 or Ala 97, Gly 101, Gly102, and Trp 103. In certain embodiments, the antibody comprises a VH region comprising a paratope that comprises amino acid residues Ser 31, Trp 33, His 35, Asp 52, Asp 54, Tyr 56, Ser 94, Gly 101, Gly102, and Trp 103. In certain embodiments, the antibody comprises a VH region comprising a paratope that comprises amino acid residues Ser 31, Trp 33, His 35, Asp 52, Asp 54, Tyr 56, Ala 93, Ser 94, Lys 96, Pro 97, Gly 101, Gly102, and Trp 103. In certain embodiments, the antibody comprises a VH region comprising a paratope that comprises amino acid residues Ser 31, Tyr 32, Trp 33, His 35, Trp 47, Asp 52, Asp 54, Tyr 56, Ser 94, Ser 95, Asp 96, Ala 97, Gly 101, Gly102, and Trp 103.

In certain embodiments, the antibody comprises a VL region comprising a paratope that comprises any one of amino acid residues His 27, Tyr 32, Tyr 36, Leu 46, Tyr 49, Gln 50, Ala 91 or Asn 91, Leu 92, Leu 94, and Leu 96. In certain embodiments, the antibody comprises a VL region comprising a paratope that comprises at least two, three, four, five, six, seven, eight, nine or all ten amino acid residues His 27, Tyr 32, Tyr 36, Leu 46, Tyr 49, Gln 50, Ala 91 or Asn 91, Leu 92, Leu 94, and Leu 96. In certain embodiments, the antibody comprises a VL region comprising a paratope that comprises the amino acid residues His 27, Tyr 32, Tyr 36, Leu 46, Gln 50, Leu 92, Leu 94, and Leu 96. In certain embodiments, the antibody comprises a VL region comprising a paratope that comprises the amino acid residues His 27, Tyr 32, Tyr 36, Leu 46, Gln 50, Asn 91, Leu 92, Leu 94, and Leu 96. In certain embodiments, the antibody comprises a VL region comprising a paratope that comprises the amino acid residues His 27, Tyr 32, Tyr 36, Leu 46, Tyr 49, Gln 50, Ala 91, Leu 92, Leu 94, and Leu 96.

In certain embodiments the paratope of the antibody binds the amino acid residues of the human fibrin or fibrinogen γC domain epitope with a distance of less than 5 Angstroms or less, 4 Angstroms or less, 3 Angstroms or less, or 2 Angstroms or less.

Fc Region

The structures of the Fc regions of various immunoglobulins, and the glycosylation sites contained therein, are known in the art. See Schroeder and Cavacini, J. Allergy Clin. Immunol., 2010, 125:S41-52, incorporated by reference in its entirety. The Fc region may be a naturally occurring Fc region, or an Fc region modified as described in the art or elsewhere in this disclosure.

Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, M I D, 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM, and several of these may be further divided into subclasses (isotypes), e.g., IgG1, $IgG_2$, IgG3, IgG4, $IgA_1$, and IgA2.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

Modifications in the CH2 domain can affect the binding of FcRs to the Fc. A number of amino acid modifications in the Fc region are known in the art for selectively altering the affinity of the Fc for different Fc gamma receptors. In some aspects, the Fc comprises one or more modifications to promote selective binding of Fc-gamma receptors.

Exemplary mutations that alter the binding of FcRs to the Fc are listed below:

S298A/E333A/K334A, S298A/E333A/K334A/K326A (Lu Y, Vernes J M, Chiang N, et al. J Immunol Methods. 2011 Feb. 28; 365(1-2):132-41);

F243L/R292P/Y300L/V305I/P396L, F243L/R292P/Y300L/L235V/P396L (Stavenhagen J B, Gorlatov S, Tuaillon N, et al. Cancer Res. 2007 Sep. 15; 67(18): 8882-90; Nordstrom J L, Gorlatov S, Zhang W, et al. Breast Cancer Res. 2011 Nov. 30; 13(6):R123);

F243L (Stewart R, Thom G, Levens M, et al. Protein Eng Des Sel. 2011 September; 24(9):671-8.), S298A/E333A/K334A (Shields R L, Namenuk A K, Hong K, et al. J Biol Chem. 2001 Mar. 2; 276(9):6591-604);

S239D/I332E/A330L, S239D/I332E (Lazar G A, Dang W, Karki S, et al. Proc Natl Acad Sci USA. 2006 Mar. 14; 103(11):4005-10);

S239D/S267E, S267E/L328F (Chu S Y, Vostiar I, Karki S, et al. Mol Immunol. 2008 September; 45(15):3926-33);

S239D/D265S/S298A/I332E, S239E/S298A/K326A/A327H, G237F/S298A/A330L/I 332E, S239D/I332E/S298A, S239D/K326E/A330L/I332E/S298A, G236A/S239D/D270L/I332E, S239E/S267E/H268D, L234F/S267E/N325L, G237F/V266L/S267D and other mutations listed in WO2011/120134 and WO2011/120135, herein incorporated by reference. *Therapeutic Antibody Engineering* (by William R. Strohl and Lila M. Strohl, Woodhead Publishing series in Biomedicine No 11, ISBN 1 907568 37 9, October 2012) lists mutations on page 283.

In some embodiments an antibody described herein includes modifications to improve its ability to mediate effector function. Such modifications are known in the art and include afucosylation, or engineering of the affinity of the Fc towards an activating receptor, mainly FCGR3a for ADCC, and towards C1q for CDC. The following Table B summarizes various designs reported in the literature for effector function engineering.

Methods of producing antibodies with little or no fucose on the Fc glycosylation site (Asn 297 EU numbering) without altering the amino acid sequence are well known in the art. The GlymaX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology. 2010 December; 20 (12):1607-18. Another approach to obtaining antibodies with lowered levels of fucosylation can be found in U.S. Pat. No. 8,409,572, which teaches selecting cell lines for antibody production for their ability to yield lower levels of fucosylation on antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

Thus, in one embodiment, an antibody described herein can include a dimeric Fc that comprises one or more amino acid modifications as noted in Table B that confer improved effector function. In another embodiment, the antibody can be afucosylated to improve effector function.

TABLE B

Table B: CH2 domains and effector function engineering

| Reference | Mutations | Effect |
|---|---|---|
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |

TABLE B-continued

Table B: CH2 domains and effector function engineering

| Reference | Mutations | Effect |
|---|---|---|
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Fc modifications reducing FcgR and/or complement binding and/or effector function are known in the art. Recent publications describe strategies that have been used to engineer antibodies with reduced or silenced effector activity (see Strohl, WR (2009), Curr Opin Biotech 20:685-691, and Strohl, WR and Strohl LM, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc. For example, US Patent Publication No. 2011/0212087 (Strohl), International Patent Publication No. WO 2006/105338 (Xencor), US Patent Publication No. 2012/0225058 (Xencor), US Patent Publication No. 2012/0251531 (Genentech), and Strop et al ((2012) J. Mol. Biol. 420: 204-219) describe specific modifications to reduce FcgR or complement binding to the Fc.

Specific, non-limiting examples of known amino acid modifications to reduce FcgR or complement binding to the Fc include those identified in the following Table C:

TABLE C

Table C: Modifications to reduce FcgR or complement binding to the Fc

| Company | Mutations |
|---|---|
| GSK | N297A |
| Ortho Biotech | L234A/L235A |
| Protein Design labs | IGG2 V234A/G237A |
| Wellcome Labs | IGG4 L235A/G237A/E318A |
| GSK | IGG4 S228P/L236E |
| Alexion | IGG2/IGG4combo |
| Merck | IGG2 H268Q/V309L/A330S/A331S |
| Bristol-Myers | C220S/C226S/C229S/P238S |
| Seattle Genetics | C226S/C229S/E3233P/L235V/L235A |
| Amgen | E. coli production, non glyco |
| Medimune | L234F/L235E/P331S |
| Trubion | Hinge mutant, possibly C226S/P230S |

Methods of producing antibodies with little or no fucose on the Fc glycosylation site (Asn 297 EU numbering) without altering the amino acid sequence are well known in the art. The GlymaxX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology. 2010 December; 20 (12):1607-18.) Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., *Arch. Biochem. Biophys.*, 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.*, 2004, 87: 614-622; Kanda et al., *Biotechnol. Bioeng.*, 2006, 94:680-688; and WO 2003/085107; each of which is incorporated by reference in its entirety). Another approach to obtaining antibodies with lowered levels of fucosylation can be found in U.S. Pat. No. 8,409,572, which teaches selecting cell lines for antibody production for their ability to yield lower levels of fucosylation on antibodies Examples of cell lines capable of producing defucosylated antibody include CHO-DG44 with stable overexpression of the bacterial oxidoreductase GDP-6-deoxy-D-lyxo-4-hexylose reductase (RID) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety).

Antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

In some aspects, an antibody provided herein comprises an IgG1 domain with reduced fucose content at position Asn 297 compared to a naturally occurring IgG1 domain. Such Fc domains are known to have improved ADCC. See Shields et al., J. Biol. Chem., 2002, 277:26733-26740, incorporated by reference in its entirety. In some aspects, such antibodies do not comprise any fucose at position Asn 297. The amount of fucose may be determined using any suitable method, for example as described in WO 2008/077546, incorporated by reference in its entirety.

In certain embodiments, an antibody provided herein comprises an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330, as described in Lazar et al., Proc. Natl. Acad. Sci. USA, 2006, 103:4005-4010, incorporated by reference in its entirety.

Other illustrative glycosylation variants which may be incorporated into the antibodies provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., J. Mol. Biol., 2004, 336:1239-1249; and Yamane-Ohnuki et al., *Biotech. Bioeng.*, 2004, 87: 614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which his incorporated by reference in its entirety.

In some embodiments, an antibody provided herein comprises one or more alterations that improves or diminishes C1q binding and/or CDC. See U.S. Pat. No. 6,194,551; WO 99/51642; and Idusogie et al., J. Immunol., 2000, 164:4178-4184; each of which is incorporated by reference in its entirety.

Binding

The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. In some embodiments, the affinity of a fibrin antibody for a non-target molecule is less than about 50% of the affinity for fibrin. In some embodiments, the affinity of a fibrin antibody for a non-target molecule is less than about 40% of the affinity for fibrin. In some embodiments, the affinity of a fibrin antibody for a non-target molecule is less than about 30% of the affinity for fibrin. In some embodiments, the affinity of a fibrin antibody for a non-target molecule is less than about 20% of the affinity for fibrin. In some embodiments, the affinity of a fibrin antibody for a non-target molecule is less than about 10% of the affinity for fibrin. In some embodiments, the affinity of a fibrin antibody for a non-target molecule is less than about 1% of the affinity for fibrin. In some embodiments, the affinity of a fibrin antibody for a non-target molecule is less than about 0.1% of the affinity for fibrin.

When used herein in the context of two or more antibodies, the term "competes with" or "cross-competes with" indicates that the two or more antibodies compete for binding to an antigen (e.g., fibrin). In one exemplary assay, fibrin is coated on a surface and contacted with a first fibrin antibody, after which a second fibrin antibody is added. In another exemplary assay, a first fibrin antibody is coated on a surface and contacted with fibrin, and then a second fibrin antibody is added. If the presence of the first fibrin antibody reduces binding of the second fibrin antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, at least 95%, or at least 99% as measured in a competitive binding assay. A skilled artisan can select the concentrations of the antibodies used in the competition assays based on the affinities of the antibodies for fibrin and the valency of the antibodies. The assays described in this definition are illustrative, and a skilled artisan can utilize any suitable assay to determine if antibodies compete with each other. Suitable assays are described, for example, in Cox et al., "Immunoassay Methods," in Assay Guidance Manual [Internet], Updated Dec. 24, 2014 (ncbi.nlm.nih.gov/books/NBK92434/; accessed Sep. 29, 2015); Silman et al., Cytometry, 2001, 44:30-37; and Finco et al., J. Pharm. Biomed. Anal., 2011, 54:351-358; each of which is incorporated by reference in its entirety.

A test antibody competes with a reference antibody if an excess of a test antibody (e.g., at least 2×, 5×, 10×, 20×, or 100×) inhibits or blocks binding of the reference antibody by, e.g., at least 50%, 60%, 70%, 75%, 80%, 85%, 90%, 95%, or 99% as measured in a competitive binding assay. Antibodies identified by competition assay (competing antibody) include antibodies binding to the same epitope as the reference antibody and antibodies binding to an adjacent epitope sufficiently proximal to the epitope bound by the reference antibody for steric hindrance to occur. For example, a second, competing antibody can be identified that competes for binding to fibrin with a first antibody described herein. In certain instances, the second antibody can block or inhibit binding of the first antibody by, e.g., at least 50%, 60%, 70%, 75%, 80%, 85%, 90%, 95%, or 99% as measured in a competitive binding assay. In certain instances, the second antibody can displace the first antibody by greater than 50%, 60%, 70%, 75%, 80%, 85%, 90%, 95%, or 99%.

In some embodiments, an anti-fibrin antibody does not substantially bind myeloid cells present outside of cancer tissue. In some embodiments, an anti-fibrin antibody does not substantially bind stimulatory myeloid cells present in cancer tissue.

In some embodiments, an anti-fibrin antibody binds to residues 7377-395 of the fibrin or fibrinogen γC domain (SEQ ID NO: 31) of human fibrin. The binding epitope includes the residues within the numerical range (e.g., residues 377-395 of fibrin), the beginning residue of each range (e.g., residues 377-394 of human fibrin) and the end residue of each range (e.g., residues 378-395 of human fibrin), or any combination thereof.

In some embodiments, an antibody provided herein binds human Fibrin with a $K_D$ of less than or equal to about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 1.95, 2, 2.5, 3, 3.5, 4, 4.5, 5, 6, 7, 8, 9, or $10 \times 10^{-6}$ M, as measured by Biacore assay. In some embodiments, the $K_D$ of the antibody provided herein is between about 0.001-0.01, 0.01-0.1, 0.01-0.05, 0.05-0.1, 0.1-0.5, 0.5-1, 0.25-0.75, 0.25-0.5, 0.5-0.75, 0.75-1, 0.75-2, 1.1-1.2, 1.2-1.3, 1.3-1.4, 1.4-1.5, 1.5-1.6, 1.6-1.7, 1.7-1.8, 1.8-1.9, 1.9-2, 1-2, 1-5, 2-7, 3-8, 3-5, 4-6, 5-7, 6-8, 7-9, 7-10, or $5-10 \times 10^{-6}$ M, as measured by Biacore assay. In some embodiments, an antibody provided herein binds human Fibrin with a $K_D$ of less than or equal to about $1 \times 10^{-5}$ M, $1 \times 10^{-6}$ M, $1 \times 10^{-7}$ M, $1 \times 10^{-8}$ M, or $1 \times 10^{-9}$ M.

In some embodiments, the antibody provided herein binds human fibrin with a $K_D$ of less than or equal to about 10, 9, 8, 7, 6, 5, 4.5, 4, 3.5, 3, 2.5, 2, 1.98, 1.95, 1.9, 1.85, 1.8, 1.75, 1.7, 1.65, 1.6, 1.55, 1.50, 1.45, 1.4, 1.3, 1.2, 1.1, 1, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.01, 0.005, 0.001, 0.0005, or $0.0001 \times 10^{-5}$ M, or less, as measured by Biacore assay. In some embodiments, the antibody provided herein binds human fibrin with a $K_D$ between 5-3, 4-2, 3-1, 1.9-1.8, 1.8-1.7, 1.7-1.6, 1.6-1.5, 1.9-1.5, 1.5-1, 1-0.8, 1-0.5, 0.9-0.6, 0.7-0.4, 0.6-0.2, 0.5-0.3, 0.3-0.2, 0.2-0.1, 0.1-0.01, 0.01-0.001, or $0.001-0.0001 \times 10^{-5}$ M as measured by Biacore assay. In some embodiments, the antibody provided herein binds human fibrin with a $K_d$ of less than or equal to about 10, 9.56, 9.5, 9.0, 8.88, 8.84, 8.5, 8, 7.5, 7.32, 7, 6.5, 6, 5.5, 5, 4.5, 4, 3.5, 3, 2.5, 2, 1.5, or $1 \times 10^{-4}$ (1/s), or less, as measured by Biacore assay. In some embodiments, the antibody provided herein binds human fibrin with a $K_d$ between 7-10, 7-8, 8-9, 9-10, 7-7.5, 7.5-8, 8.-8.5, 8.5-9, 9-9.5, or $9.5-10 \times 10^{-4}$(1/s) as measured by Biacore assay. In some embodiments, the antibody provided herein binds human fibrin with a $K_a$ of greater than or equal to about 4, 4.1, 4.2, 4.3, 4.4, 4.5, 4.6, 4.7, 4.8, 4.9, 45, 5.1, 5.2, 5.3, 5.4, 5.5, 5.6, 5.7, 5.8, 5.9, 6, 7, 8, 9, or $10 \times 10^5$ (1/Ms), or more, as measured by Biacore assay. In some embodiments, the antibody provided herein binds human FIBRIN with a $K_a$ between 4-7, 4-4.5, 4.5-5, 5-5.5, 5.5-6, 6-6.5, or 6.5-7, 7-8, 8-9, or $9-10 \times 10^5$ (1/Ms) as measured by Biacore assay.

Function

"Effector functions" refer to those biological activities mediated by the Fc region of an antibody, which activities may vary depending on the antibody isotype. Examples of antibody effector functions include receptor ligand blocking, agonism, or antagonism, C1q binding to activate complement dependent cytotoxicity (CDC), Fc receptor binding to activate antibody-dependent cellular cytotoxicity (ADCC), and antibody dependent cellular phagocytosis (ADCP). In some embodiments, the effector function of the fibrin antibody described herein is antagonism and blocks Mac-1 receptor binding to fibrin.

Pharmaceutical Compositions

The present application provides compositions comprising the antibodies including pharmaceutical compositions comprising any one or more of the antibodies described herein with one or more pharmaceutically acceptable excipients. In some embodiments the composition is sterile. The pharmaceutical compositions generally comprise an effective amount of an antibody.

These compositions can comprise, in addition to one or more of the antibodies disclosed herein, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

The anti-fibrin antibody that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

Methods

Methods of Preparation

Antibodies described herein can be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody) or an amino acid sequence comprising the VHH of a single domain antibody. In a further embodiment, one or more vectors (e.g., expression vectors) comprising such nucleic acid are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antigen-binding polypeptide construct, or (2) a first vector comprising a nucleic acid that encodes an amino acid sequence comprising the VL of the antigen-binding polypeptide construct and a second vector comprising a nucleic acid that encodes an amino acid sequence comprising the VH of the antigen-binding polypeptide construct. In one embodiment, the host cell is eukaryotic, e.g. a Chinese Hamster Ovary (CHO) cell, or human embryonic kidney (HEK) cell, or lymphoid cell (e.g., Y0, NS0, Sp20 cell). In one embodiment, a method of making an antibody is provided, wherein the method comprises culturing a host cell comprising nucleic acid encoding the antibody, as provided above, under conditions suitable for expression of the antibody, and optionally recovering the antibody from the host cell (or host cell culture medium).

For recombinant production of the antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

When a heteromultimer or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the heteromultimer or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" heteromultimer produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of antibody-encoding vectors include prokaryotic or eukaryotic cells described herein.

Recombinant host cells or host cells are cells that include an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome. Host cells can include CHO, derivatives of CHO, NS0, Sp20, CV-1, VERO-76, HeLa, HepG2, Per.C6, or BHK.

For example, antibody may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one embodiment, the antibodies described herein are produced in stable mammalian cells, by a method comprising: transfecting at least one stable mammalian cell with: nucleic acid encoding the antibody, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antibody in the expressed product.

In some embodiments, is the method of producing an antibody in stable mammalian cells as described herein wherein the expression product of the at least one stable mammalian cell comprises a larger percentage of the desired glycosylated antibody as compared to the monomeric heavy or light chain polypeptides, or other antibodies.

In some embodiments, is the method of producing a glycosylated antibody in stable mammalian cells described herein, said method comprising identifying and purifying the desired glycosylated antibody. In some embodiments, the said identification is by one or both of liquid chromatography and mass spectrometry.

If required, the antibodies can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, $Ni^{+2}$ affinity chromatography if a His-tag is employed or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, N Y, 1994, incorporated entirely by reference. The degree of purification necessary will vary depending on the use of the antibodies. In some instances, no purification is necessary.

In certain embodiments, the antibodies are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments, the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, antibodies described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alanine, fluoro-amino acids, designer amino acids such as methyl amino acids, C-methyl amino acids, N-methyl amino acids, and amino acid analogs in general. Furthermore, the amino acid can be D (dextrorotary) or L (levorotary).

Methods of Use

In an aspect, the present application provides methods of contacting fibrin with an anti-fibrin antibody, such as a human or humanized antibody, which results in inhibition of microglial adhesion to the fibrin or fibrinogen γC domain.

In an aspect, the present application provides methods of using the isolated anti-fibrin antibodies described herein for treatment of a degenerative disorder of the nervous system. In certain aspects, described herein is a method for treating a degenerative disorder of the nervous system, the method comprising administering to a mammalian subject a therapeutically effective amount of an anti-fibrin antibody or pharmaceutical composition comprising an anti-fibrin antibody described herein. In certain embodiments, the present application provides methods of treating a degenerative disorder of the nervous system selected from the group consisting of: multiple sclerosis, spinal cord injury, stroke, and Alzheimer's Disease.

In certain aspects, described herein are methods for treating a pathology associated with Mac-1 binding to fibrin or Mac-1 binding with fibrinogen, the method comprising administering to a mammalian subject a therapeutically effective amount an isolated anti-fibrin antibody or a pharmaceutical composition comprising an isolated anti-fibrin antibody described herein.

In certain aspects, described herein are methods of inhibiting microglia activation, the method comprising administering to a mammalian subject a therapeutically effective amount an isolated anti-fibrin antibody or a pharmaceutical composition comprising an isolated antibody described herein.

In certain aspects, described herein is a method of preventing a degenerative disorder of the nervous system, the method comprising administering to a mammalian subject a therapeutically effective amount an isolated anti-fibrin antibody or a pharmaceutical composition comprising an isolated anti-fibrin antibody described herein. In certain embodiments, the present application provides methods of preventing a degenerative disorder of the nervous system selected from the group consisting of: multiple sclerosis, spinal cord injury, stroke, and Alzheimer's Disease.

In certain aspects, described herein are methods of treating or preventing colitis, comprising administering to a mammalian subject a therapeutically effective amount an isolated anti-fibrin antibody or a pharmaceutical composition comprising an isolated anti-fibrin antibody described herein.

In certain aspects, described herein are methods of treating or preventing an inflammatory condition of the eye comprising administering to a mammalian subject a therapeutically effective amount an isolated anti-fibrin antibody or a pharmaceutical composition comprising an isolated anti-fibrin antibody described herein. In certain embodiments, the inflammatory condition of the eye is uveitis.

Methods of Administration

In some embodiments, the methods provided herein are useful for the treatment of a degenerative nervous system disorder in an individual. In an embodiment, the individual is a human and the antibody is a fibrin antibody described herein.

In some embodiments, an antibody is administered intravenously, intramuscularly, subcutaneously, topically, orally, transdermally, intraperitoneally, intraorbitally, intravitreally, by implantation, by inhalation, intrathecally, intraventricularly, or intranasally. An effective amount of an anti-fibrin antibody may be administered for the treatment of cancer. The appropriate dosage of the anti-fibrin antibody may be determined based on the type of cancer to be treated, the type of the anti-fibrin antibody, the severity and course of the cancer, the clinical condition of the individual, the individual's clinical history and response to the treatment, and the discretion of the attending physician.

In some embodiments, an antibody provided herein is administered with at least one additional therapeutic agent. Any suitable additional therapeutic or immunotherapeutic agent may be administered with an antibody provided herein. Additional therapeutic agents include agents that are used to treat or prevent a degenerative disorder of the nervous system selected from the group consisting of: multiple sclerosis, spinal cord injury, stroke, and Alzheimer's Disease.

The additional therapeutic agent can be administered by any suitable means. In some embodiments, an antibody provided herein and the additional therapeutic agent are included in the same pharmaceutical composition. In some embodiments, an antibody provided herein and the additional therapeutic agent are included in different pharmaceutical compositions.

In embodiments where an antibody provided herein and the additional therapeutic agent are included in different pharmaceutical compositions, administration of the antibody can occur prior to, simultaneously, and/or following, administration of the additional therapeutic agent. In some embodiments, administration of an antibody provided herein and the additional therapeutic agent occur within about one month of each other. In some embodiments, administration of an antibody provided herein and the additional therapeutic agent occur within about one week of each other. In some embodiments, administration of an antibody provided herein and the additional therapeutic agent occur within about one day of each other. In some embodiments, administration of an antibody provided herein and the additional therapeutic agent occur within about twelve hours of each other. In some embodiments, administration of an antibody provided herein and the additional therapeutic agent occur within about one hour of each other.

Kits and Articles of Manufacture

The present application provides kits comprising any one or more of the antibody compositions described herein. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B(1992).

Materials and Methods

Antigens were biotinylated using the EZ-Link Sulfo-NHS-Biotinylation Kit from Pierce. Goat F(ab')$_2$ anti-human kappa-FITC (LC-FITC), ExtrAvidin-PE (EA-PE) and Streptavidin-AF633 (SA-633) were obtained from Southern Biotech, Sigma, and Molecular Probes, respectively. Goat anti-human IgG-PE (Human-PE) was obtained from Southern Biotech. Anti-Mouse APC was obtained from Jackson ImmunoResearch.

Example 1: Humanization of Anti-Fibrin Antibodies

The process of humanization modifies binding domains from a non-human antibody increasing similarity to human binding domains. Typically, a non-human antibody is humanized to reduce immunogenicity to humans, while retaining the specificity and affinity of the parental non-human antibody. Generally, a humanized antibody comprises one or more variable domains in which CDRs, (or portions thereof) are derived from a non-human antibody, and FRs (or portions thereof) are derived from human antibody sequences. A humanized antibody will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity, affinity, stability, or developability profile.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

Humanization of 5B8

Humanization of a Fibrin antibody (5B8) was conducted by characterizing a panel of humanization designs produced in yeast. In brief, the designs were generated by grafting CDR mouse sequences into human framework sequences that had in silico been predicted to be the most compatible to the original mouse frameworks. The following combinations were produced in yeast and characterized for binding to human fibrinogen P2 peptide antigen: Based on 5B8, 27 antibodies representing combinations of 9 humanized $V_H$ and 3 humanized VK.

Antibody Optimization

Optimization of the humanized antibodies was performed by introducing diversities into the heavy chain and light chain variable regions as described below.

Library generation: Oligonucleotides were ordered from IDT which comprised either the CDRH1, CDRH2, or CDRH3 as well as a flanking region on either side of the CDR. Amino acid positions in the CDRs were variegated via NNK diversity introduced into the CDR oligos. The DNA of the HC (heavy chain) variable region was then DNase treated to create fragments of 50-200 bps in size. The CDRH1, CDRH2, and CDRH3 oligos were then recombined with the DNase treated HC variable region via overlap extension PCR to incorporate the CDR diversity oligos into the HC variable region sequence. The library was then created by transforming this diversified HC variable sequence and the heavy chain expression vector into yeast already containing the light chain plasmid of the parent. A similar process was performed to introduce diversity in the CDRL1, CDRL2 and CDRL3. Oligonucleotides were ordered from IDT with diversity in the CDRL1, CDRL2 and CDRL3, and incorporated into diversified light chain (LC) variable regions as described for the CDRH1, CDRH2, CDRH3 libraries. These diversified LC variable regions and the light chain expression vector were transformed into yeast already containing the heavy chain plasmid of the parent. An additional set of libraries were built focusing diversity exclusively within the CDRH3. Walking singlet diversity was introduced into the CDRH3 by overlap extension PCR between VH FR1 through FR3 and an oligonucleotide with diversity in the CDRH3.

Selections were performed by using FACS sorting for three rounds. Approximately $2 \times 10^7$ yeast were pelleted, washed three times with wash buffer, and incubated at 30° C. with either an affinity pressure using human fibrinogen P2 peptide antigen or with a poly-specificity depletion reagent (PSR) to remove non-specific antibodies from the selection. For this selection the affinity pressure was applied by preincubating the antigen with parental IgG and then applying that precomplexed mixture to the yeast library for a length of time which would allow the selection to reach an equilibrium. For the PSR depletion the libraries were incubated with a 1:10 dilution of biotinylated PSR reagent as previously described (see Y. Xu et al, PEDS 26.10, 663-70 (2013).) Yeast were then washed twice with wash buffer and stained with LC-FITC (diluted 1:100) and either SA-633 (diluted 1:500), EAPE (diluted 1:50), or anti-mouse APC (diluted 1:500) secondary reagents for 15 min at 4° C. After washing twice with wash buffer, the cell pellets were resuspended in 0.3 mL wash buffer and transferred to strainer-capped sort tubes. Sorting was performed using a FACS ARIA sorter (BD Biosciences) and sort gates were determined to select for antibodies with desired characteristics. Four selection rounds were completed. After the final round of sorting, yeast were plated and individual colonies were picked for characterization. FIG. 1 shows results of first three rounds of selection of a single antibody library form one parental antibody and increased affinity of antibodies to fibrin P2 gamma peptide after each round of maturation.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 3.5. Fab fragments were generated by papain digestion and purified over CaptureSelect (Life Technologies).

Figure 2A:
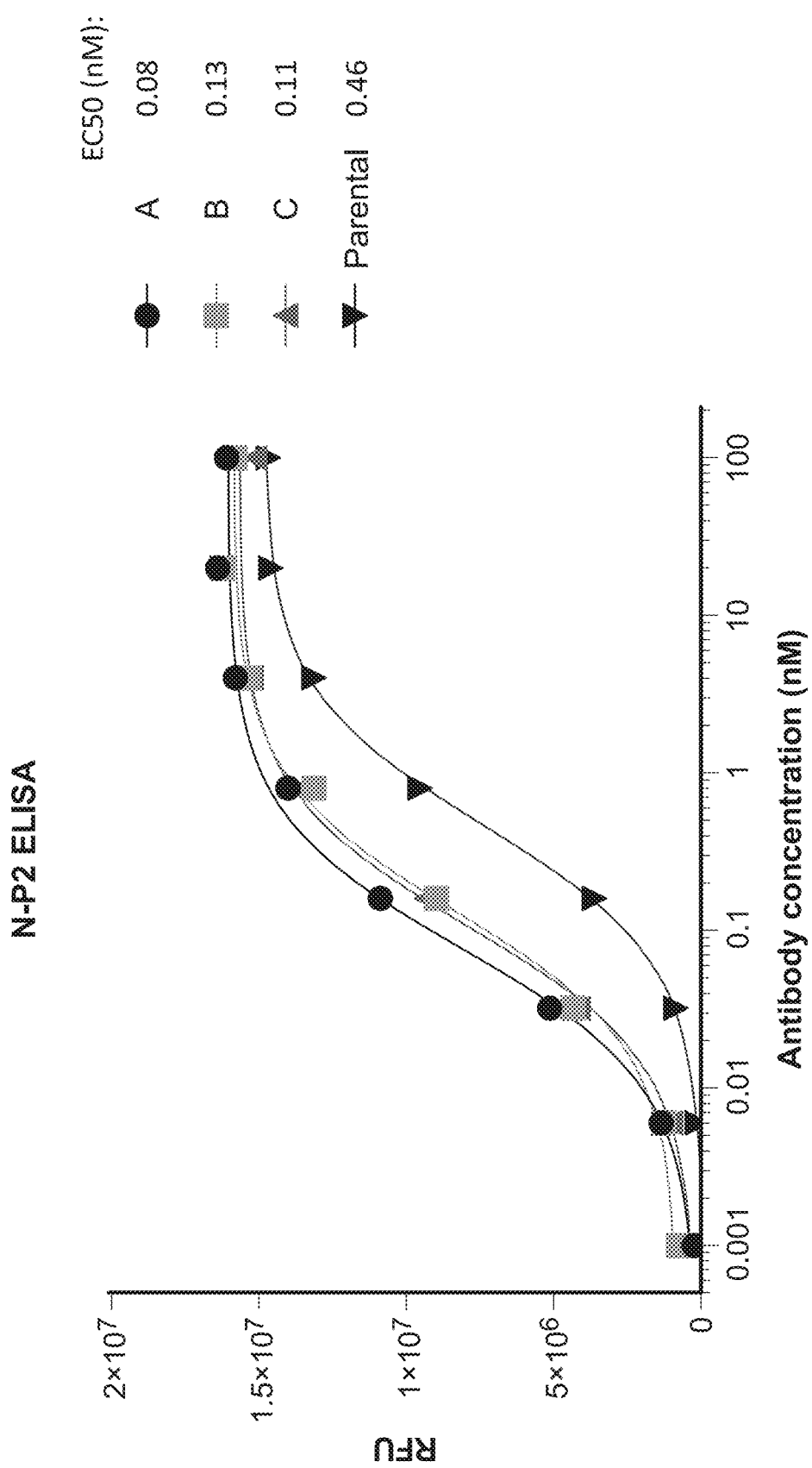
FIG. 2A is a graph showing the results of an enzyme-linked immunosorbant assay (ELISA) performed with the indicated humanized antibody variants and P2 peptide. A=clone 60143; B=clone 61278; C=clone 61278 (duplicate); D=parental antibody.
Figure 2B:
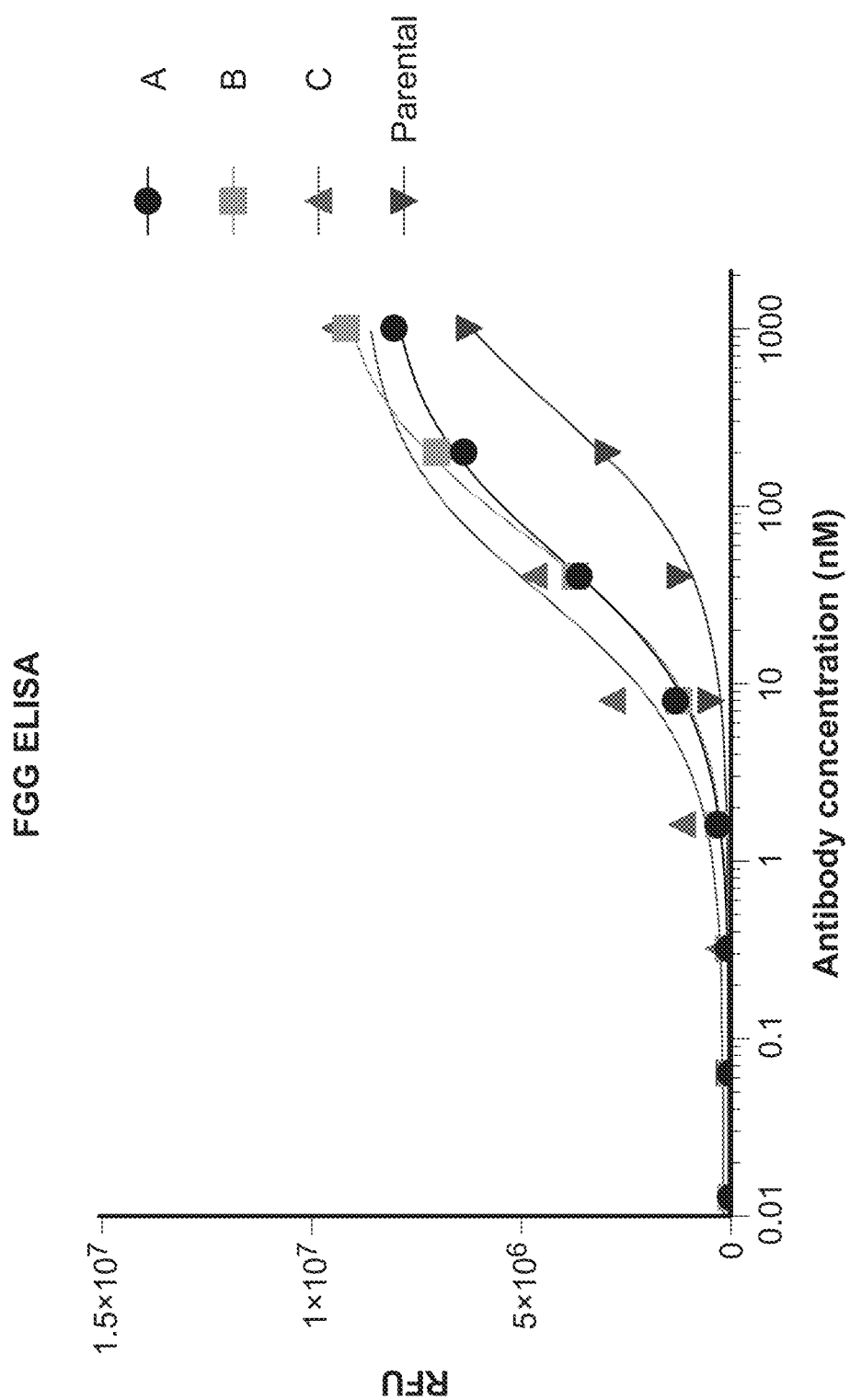
FIG. 2B is a graph showing the results of an enzyme-linked immunosorbant assay (ELISA) performed with the indicated humanized antibody variants and FGG (fibrinogen). A=clone 60143; B=clone 61278; C=clone 61278 (duplicate); D=parental antibody.
Figure 2C:
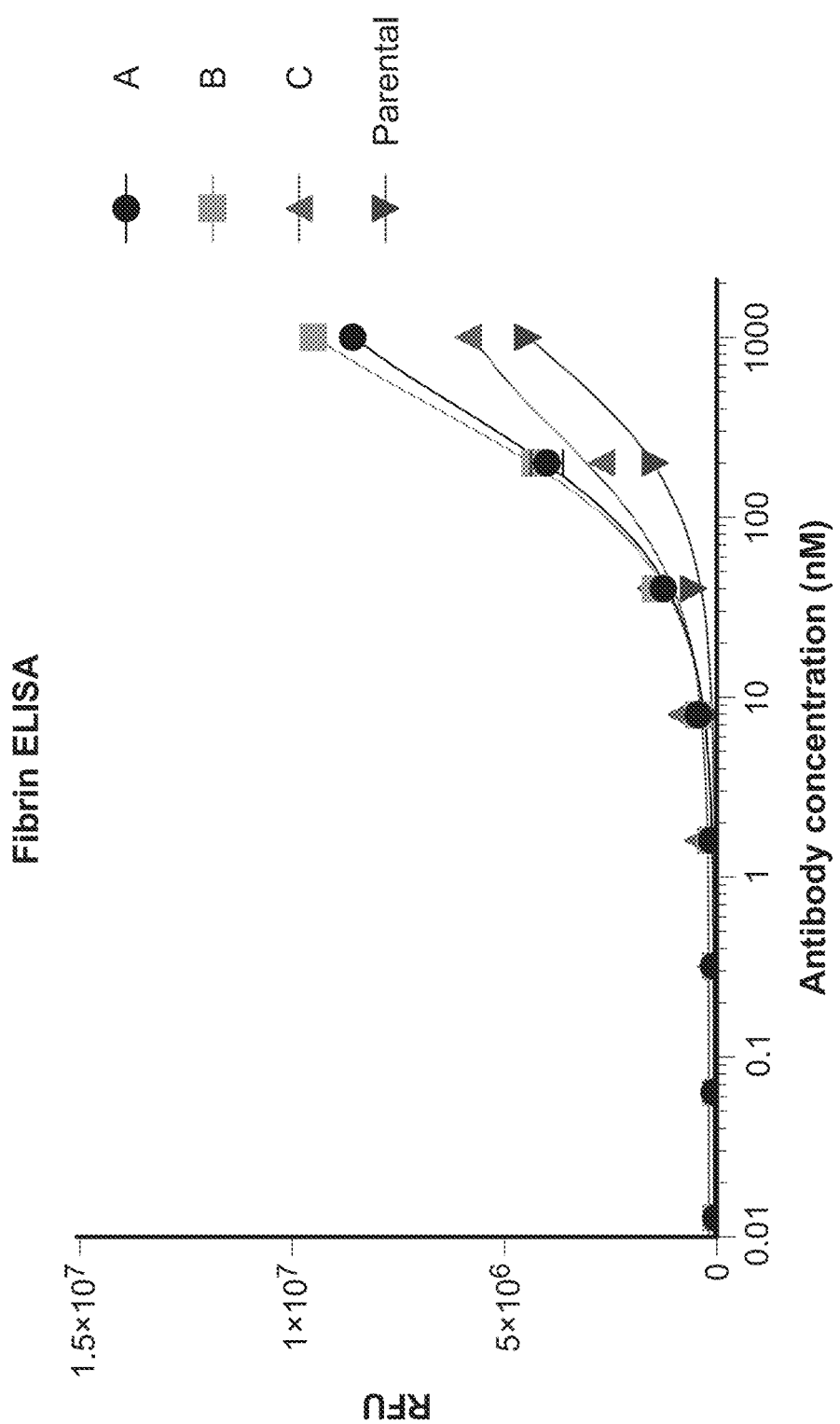
FIG. 2C is a graph showing the results of an enzyme-linked immunosorbant assay (ELISA) performed with the indicated humanized antibody variants and fibrin. A=clone 60143; B=clone 61278; C=clone 61278 (duplicate); D=parental antibody.

Example 2: Characterization and Affinity Maturation of Humanized Antibody Clones Enzyme-linked immunosorbant assays (ELISA) were performed with the select humanized antibody clones and the fibrin P2 peptide (FIG. 2A), fibrinogen (FIG. 2B) and Fibrin (FIG. 2C). A=clone 60143; B=clone 61278; C=clone 61278 (duplicate); D=parental antibody.

These results confirm that the affinity matured humanized antibody clones bind to fibrin P2 peptide and fibrin with improved affinity compared to the parental humanized antibody.

Figure 3A:
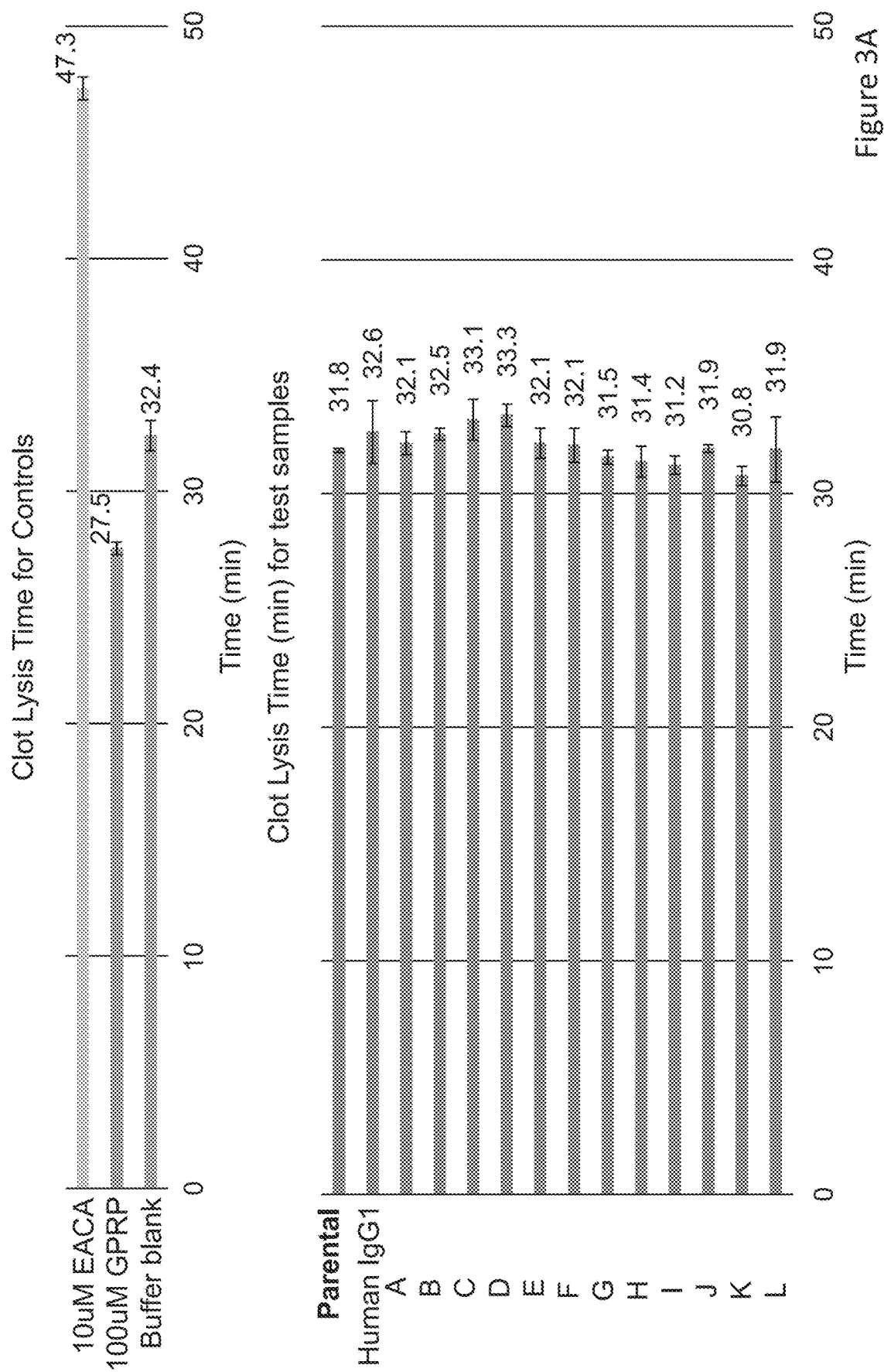
FIGS. 3A and 3B are graphs showing the results of an assay demonstrating clot lysis time of samples in the presence of variant humanized antibodies. A=clone 56666; B=clone 56657; C=clone 60143; D=clone 60181; E=clone 60175; F=clone 60163; G=clone 60173; H=clone 60184; I=clone 60141; J=clone 60179; K=clone 60140; L=clone 60183.
Figure 3B:
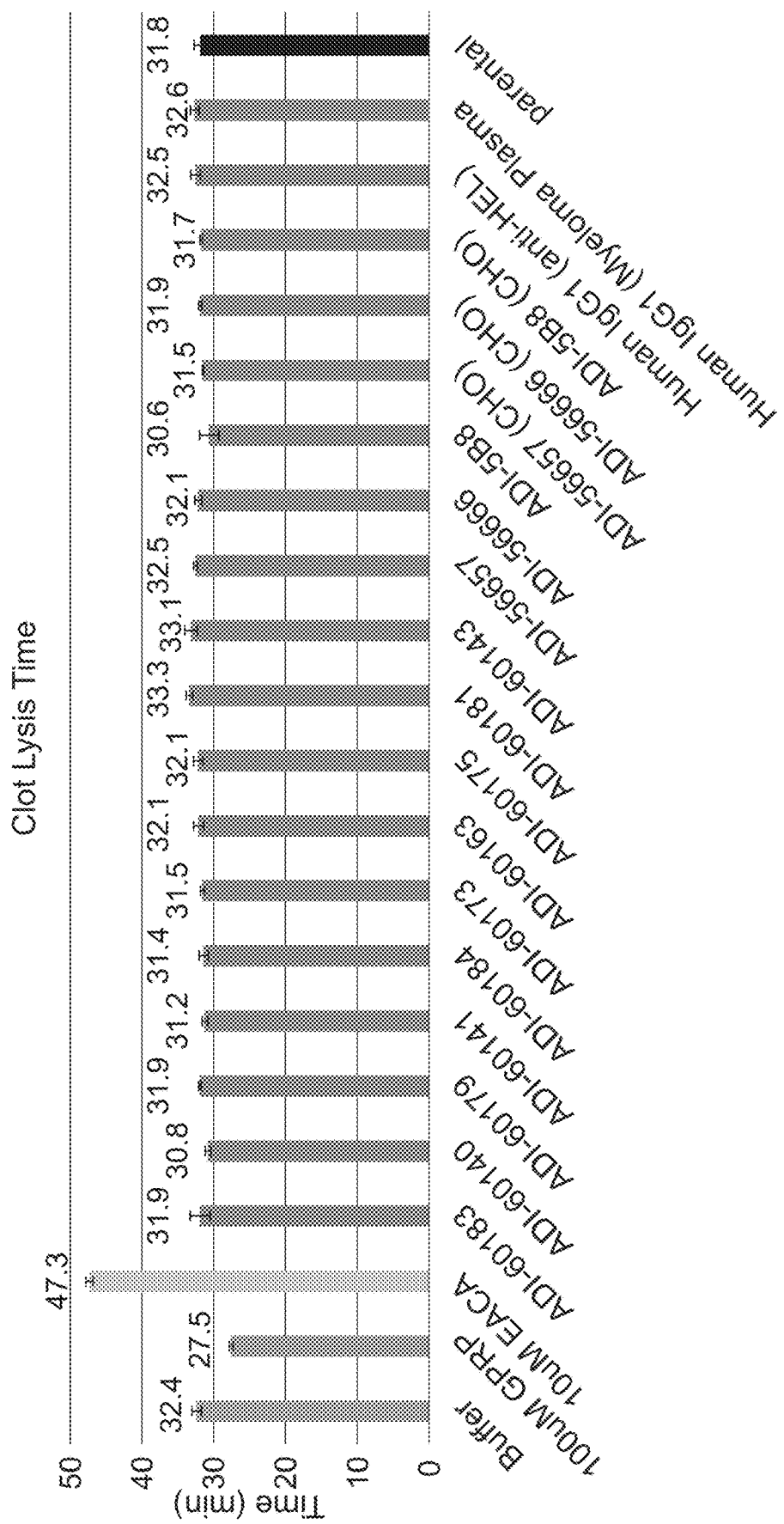
Figure 4A:
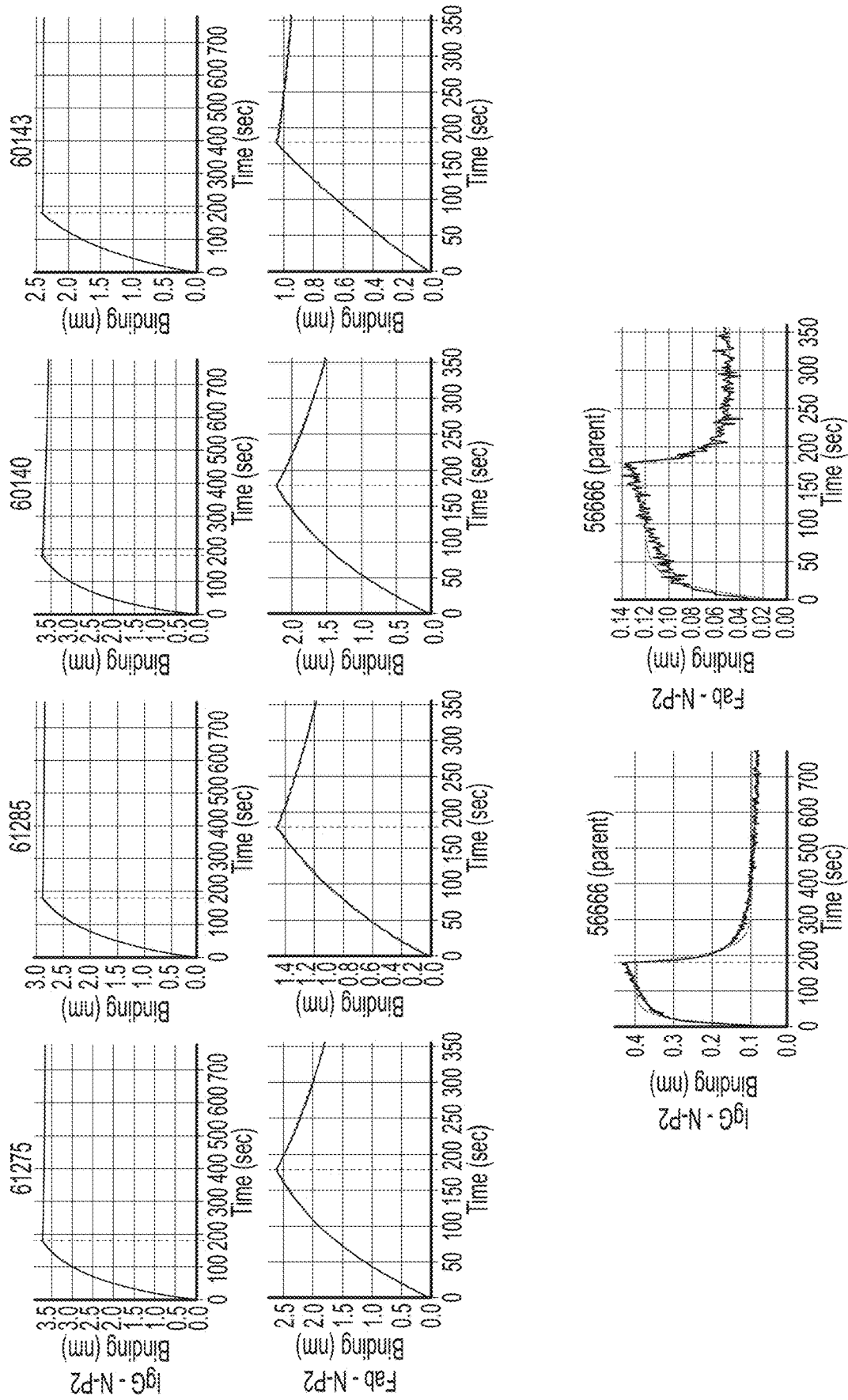
FIGS. 4A-4D are graphs showing the results of ForteBio $K_D$ measurements described herein with either N-terminally biotinylated fibrin P2 gamma peptide conjugated to IgG in solution (100 nM) or FAB (monovalent) in solution (100 nM). The antibody clones tested are indicated.
Figure 4A:
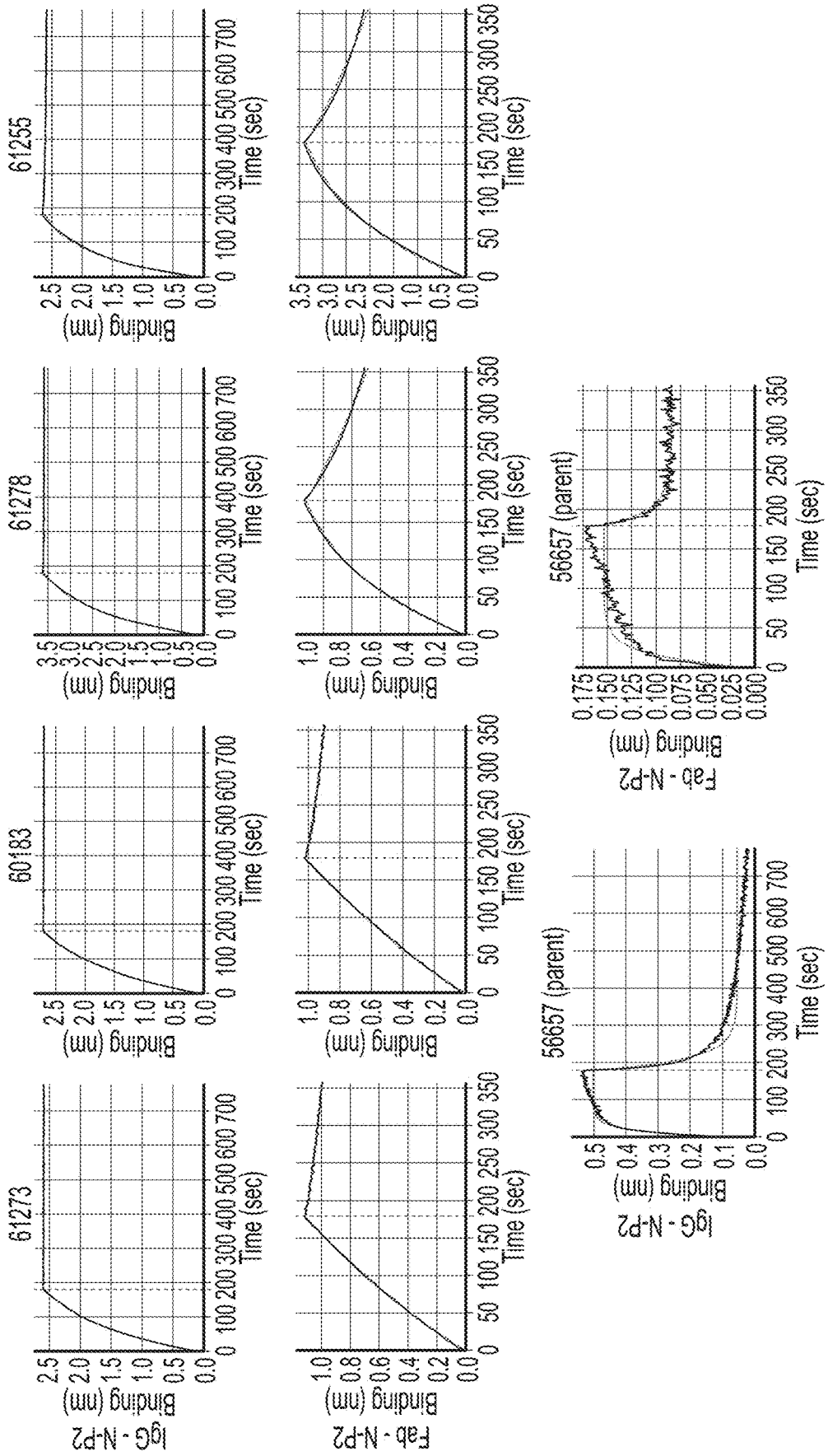
Figure 4B:
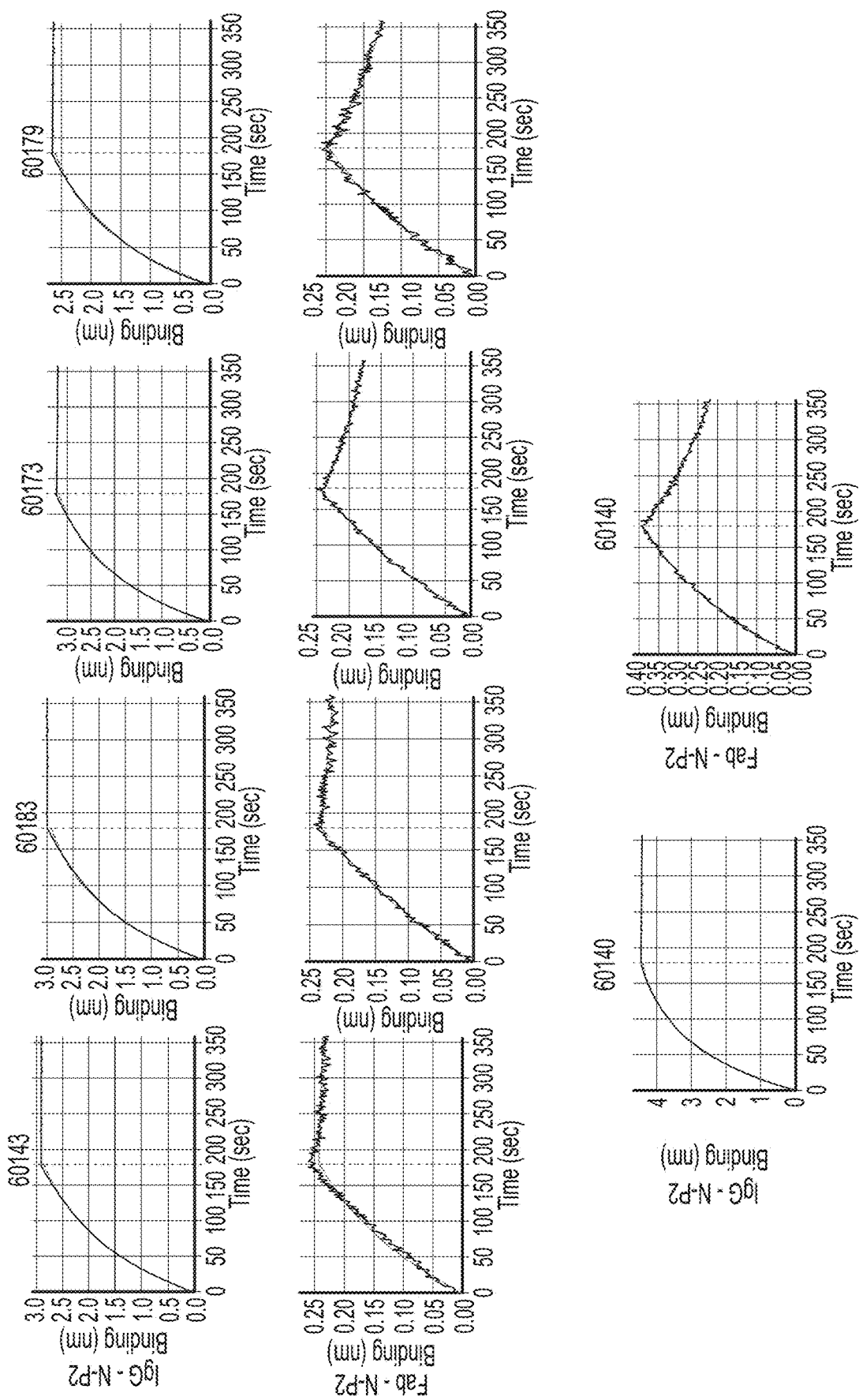
Figure 4B:
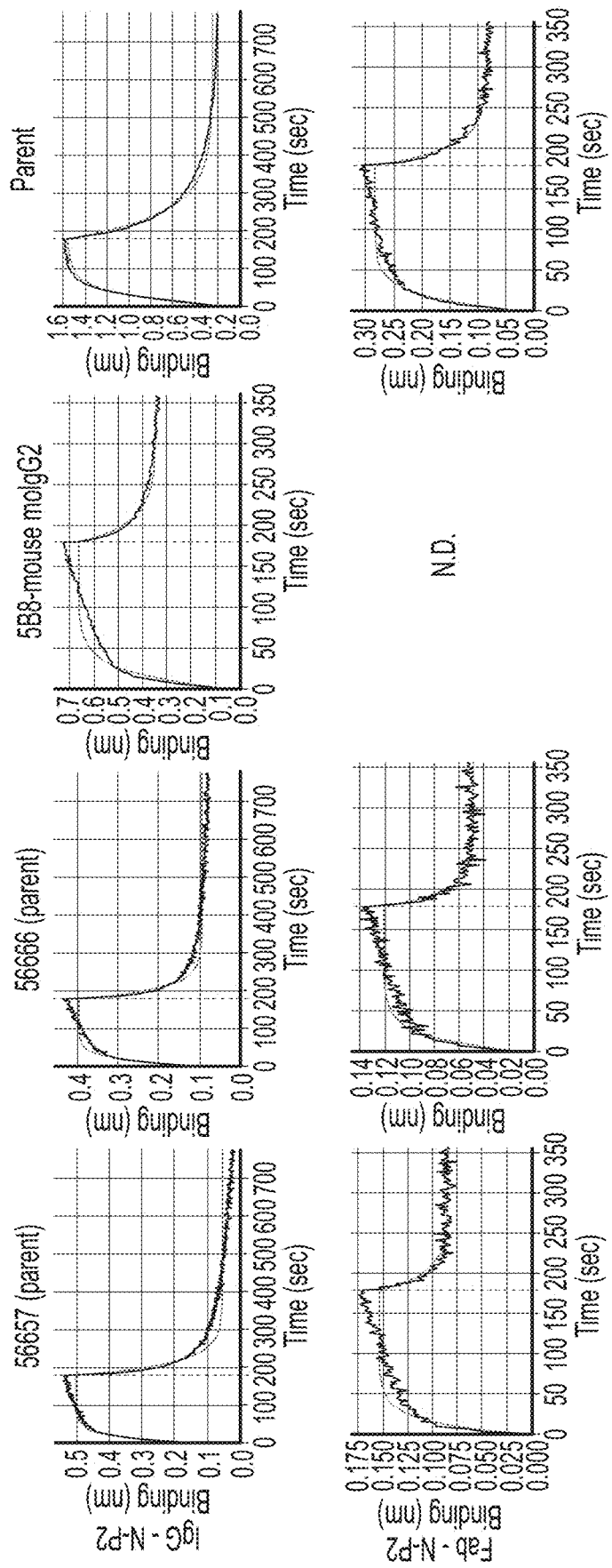
Figure 4C:
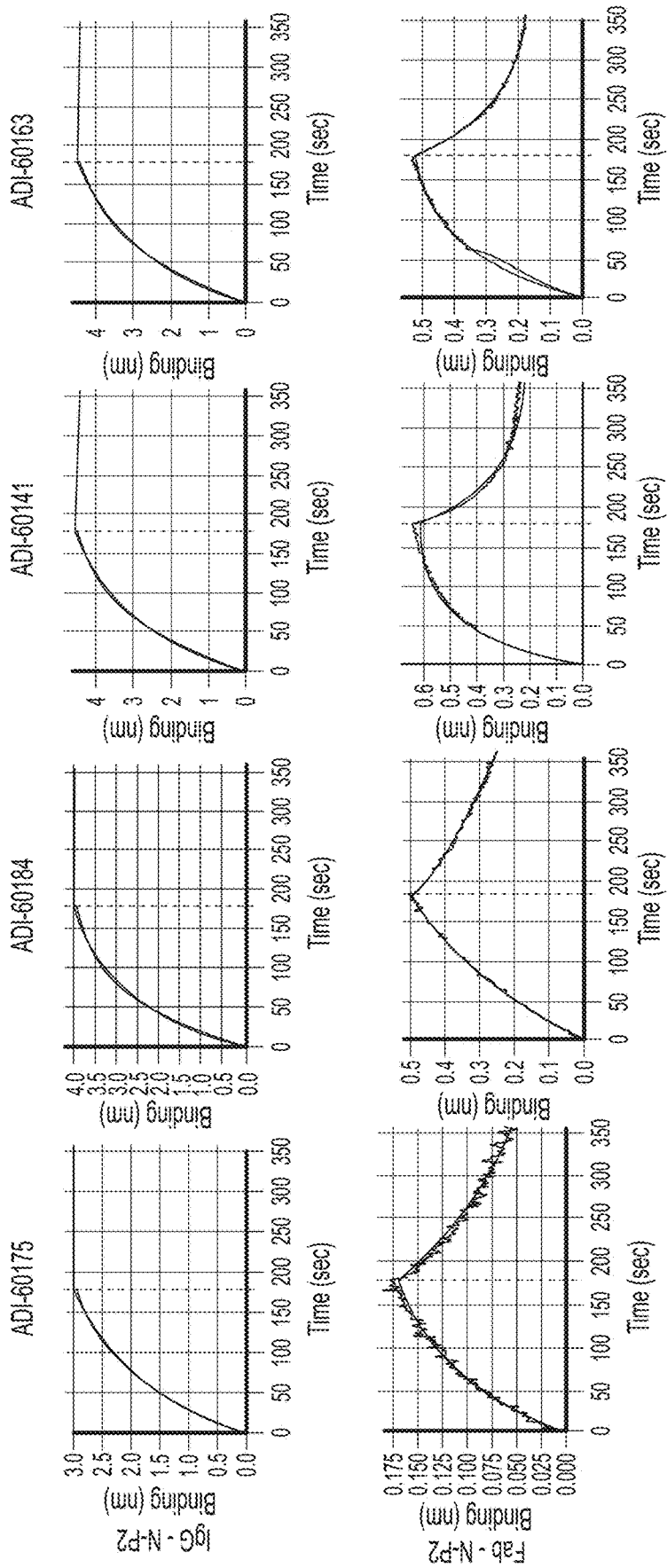
Figure 4D:
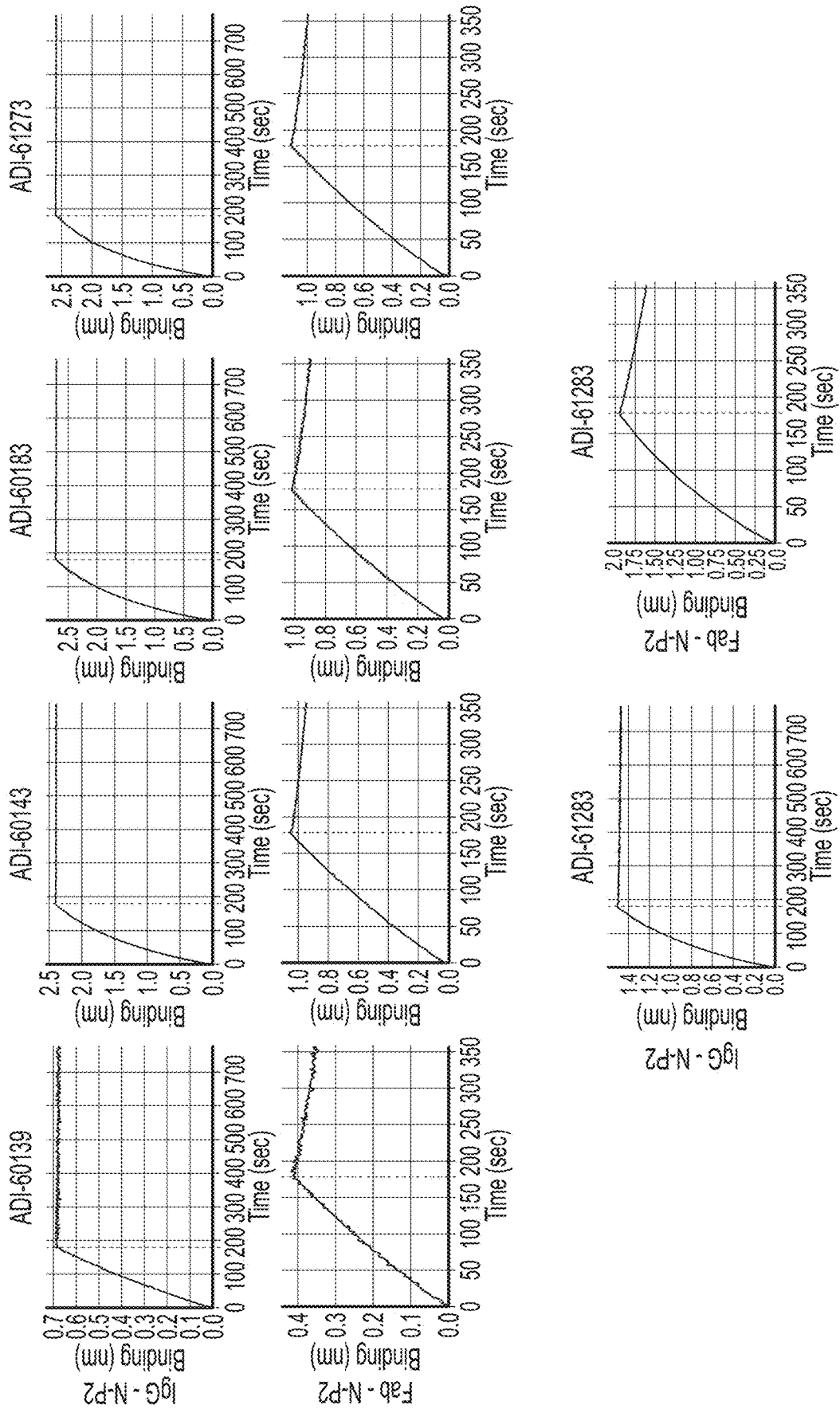
Figure 4D:
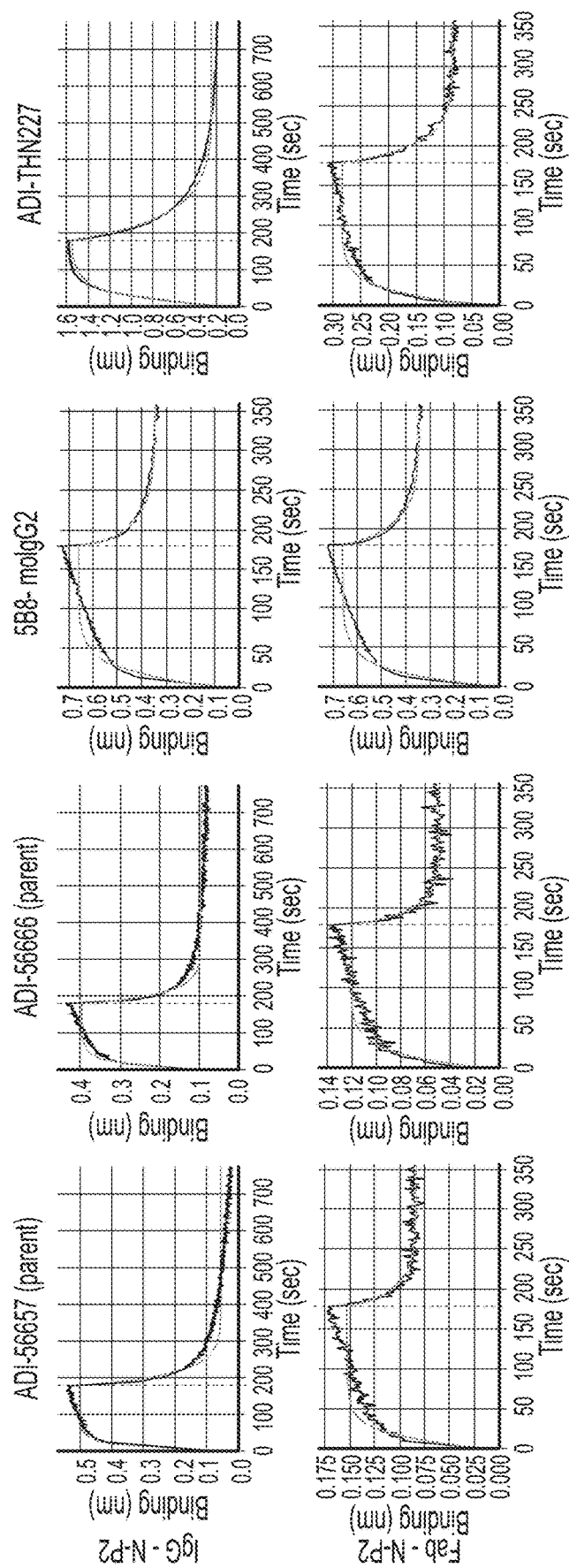

To evaluate if the affinity matured antibody clones affected fibrin polymerization or lysis, clot lysis assays were performed demonstrating clot lysis time of samples in the presence of variant humanized antibodies (FIG. 3). A=clone 56666; B=clone 56657; C=clone 60143; D=clone 60181; E=clone 60175; F=clone 60163; G=clone 60173; H=clone 60184; I=clone 60141; J=clone 60179; K=clone 60140; L=clone 60183. The clot lysis assay was performed by preparing two mixtures: mixture 1 comprising 133 nM antibody, 2 uM fibrinogen was prepared in 96 well plate, centrifuged at 55 rpm and incubated for 0.5 h at 37 degrees C., and mixture 2 comprising 20 nM plasminogen, 0.1 U thrombin, 4 mM $CaCl_2$ and 1 nM tPA was prepared and transferred to the plate. Clot lysis reactions were started immediately after Mixture 2 is transferred to the well. Progress of the reaction was measured at 350 nm. Each plate contained 4 controls: buffer blank without Thrombin-tPA-$CaCl_2$) mix, Buffer blank, 100 uM GPRP (polymerization inhibitor), and 10 uM EACA (lysis inhibitor).

The clot lysis time of all tested antibody clones was not significantly change compared to the parental humanized antibody or isotype control antibody (FIG. 3).

These results confirm that the affinity matured humanized antibody clones do not affect fibrin polymerization or fibrin lysis.

ForteBio $K_D$ Measurements

ForteBio affinity measurements were performed on an Octet RED384 generally as previously described (see Estep et al, High throughput solution-based measurement of antibody-antigen affinity and epitope binning. *Mabs* 5(2), 270-278 (2013)). Briefly, ForteBio affinity measurements were performed by loading IgGs on-line onto AHC sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. For monovalent affinity assessment Fabs were used instead of IgGs. For this assessment the unbiotinylated Fc fusion antigen was loaded on-line onto AHC or AMC sensors. Sensors were equilibrated off-line in assay buffer for 30 min and then monitored on-line for 60 seconds for baseline establishment. Sensors with loaded antigen were exposed to 100 nM Fab for 3 minutes, and afterwards they were transferred to assay buffer for 3 min for off-rate measurement. All kinetics were analyzed using the 1:1 binding model.

Figure 5:
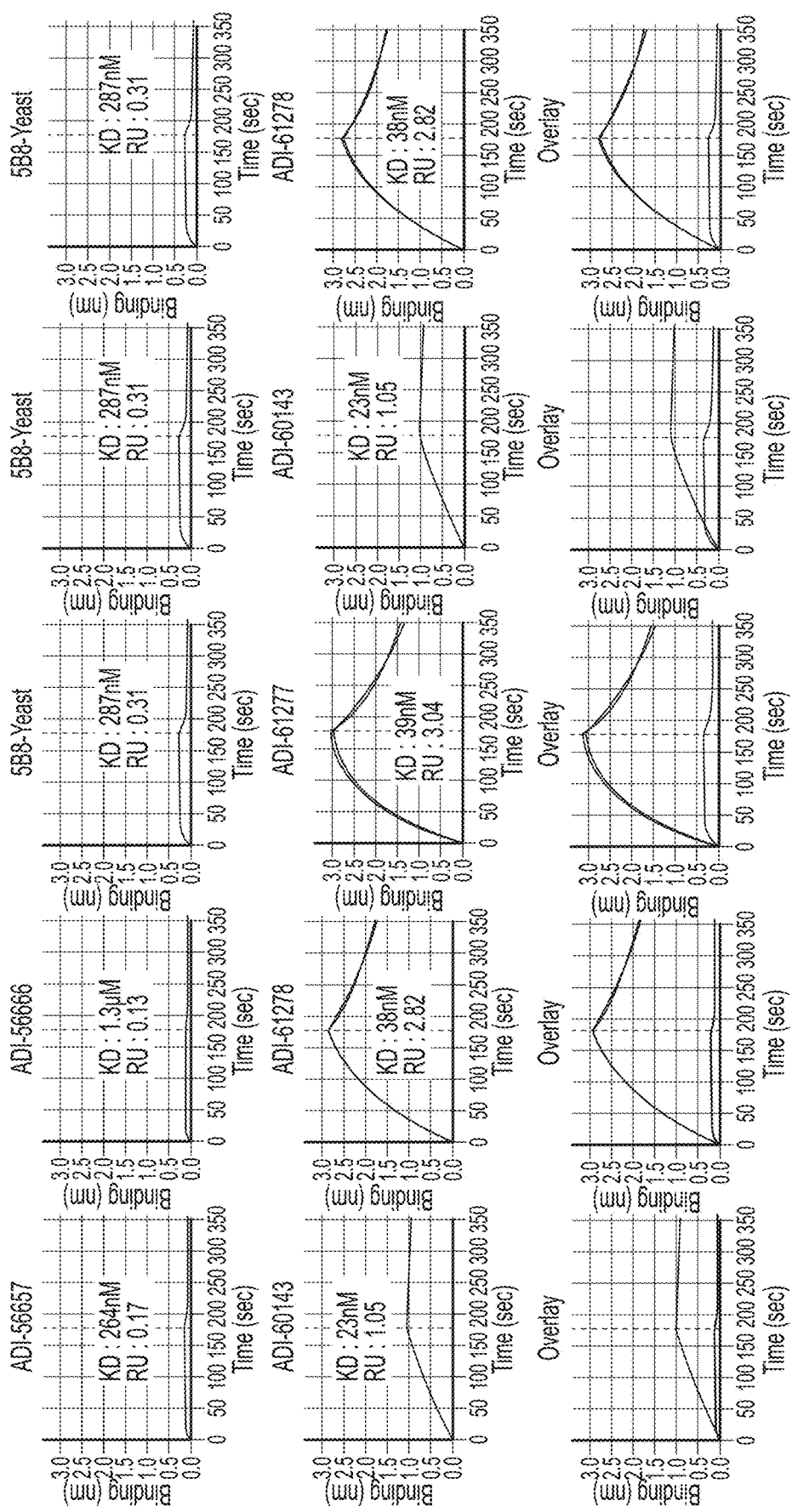
FIG. 5 are graphs showing results of octet Fab binding to N-terminally biotinylated Fibrin P2 gamma peptide on SA sensor with 100 mM Fab in solution. The antibody clones tested are indicated.

FIGS. 4A-4D shows results of ForteBio $K_D$ measurements with either N-terminally bioltinylated fibrin P2 peptide conjugated to IgG in solution (100 nM) or FAB (monovalent) in solution (100 nM). FIG. 5 shows results of octet Fab in solution (100 nM) binding to N-terminally bioltinylated fibrin P2 peptide.

These results show that the affinity matured humanized antibody clones have improved binding affinity to Fibrin P2 gamma peptide compared to the parental humanized antibodies.

PSR Binding Assay

The PSR assay was done as previously described (see Xu Y, et al. (2013) Addressing polyspecificity of antibodies selected from an in vitro yeast presentation system: A FACS-based, high-throughput selection and analytical tool. *Protein Eng Des Sel* 26(10):663-670). In short, soluble membrane proteins were prepared from CHO cells. The enriched membrane fraction was biotinylated using NHS-LCBiotin (Pierce, Thermo Fisher). This polyspecificity reagent was incubated with IgG-presenting yeast, followed by washing. Then secondary labeling mix (Extravidin-R-PE, anti-human LC-FITC, and propidium iodide) was added to the mixture. Samples were analyzed on a FACSCanto II analyzer (BD Biosciences) using an HTS sample injector. Flow cytometry data were analyzed for mean fluorescence intensity (MFI) in the R-PE channel to assess nonspecific binding. MFI values were normalized from 0 to 1 based on three reference antibodies exhibiting low, medium, and high PSR MFI values.

Dynamic Scanning Fluorimetry 10 uL of 20× Sypro Orange is added to 20 uL of 0.2-1 mg/mL mAb or Fab solution. A RT-PCR instrument (BioRad CFX96 RT PCR) is used to ramp the sample plate temperature from 40 to 95 C at 0.5 C increment, with 2 min equilibrate at each temperature. The negative of first derivative for the raw data is used to extract Tm.

AC-SINS

The AC-SINS assay was performed as described previously (see Liu Y, et al. (2014) High-throughput screening for developability during early-stage antibody discovery using self-interaction nanoparticle spectroscopy. *MAbs* 6(2):483-492). In short, gold nanoparticles (Ted Pella Inc.) were coated with 80% capturing anti-human goat IgG Fc (Jackson ImmunoResearch) and 20% with polyclonal goat nonspecific antibody (Jackson ImmunoResearch). The antibodies of interest were then incubated with the particles for 2 h and the wavelength shift was measured using Molecular Devices SpectraMax M2 with SoftMax Pro6 software. The self-interacting clones show a higher wavelength shift away from the PBS sample.

HIC (Hydrophobic Interaction Chromatography)

The methodology for this assay was described previously (see Estep P, et al. (2015) An alternative assay to hydrophobic interaction chromatography for high-throughput characterization of monoclonal antibodies. *MAbs* 7(3):553-561). In brief, 5 μg IgG samples (1 mg/mL) were spiked in with a mobile phase A solution (1.8 M ammonium sulfate and 0.1 M sodium phosphate at pH 6.5) to achieve a final ammonium sulfate concentration of about 1 M before analysis. A Sepax Proteomix HIC butyl-NP5 column was used with a linear gradient of mobile phase A and mobile phase B solution (0.1 M sodium phosphate, pH 6.5) over 20 min at a flow rate of 1 mL/min with UV absorbance monitoring at 280 nm.

Example 3: Therapeutic Treatment of Fibrinogen-Induced Encephalomyelitis (FIE)

Figure 6:
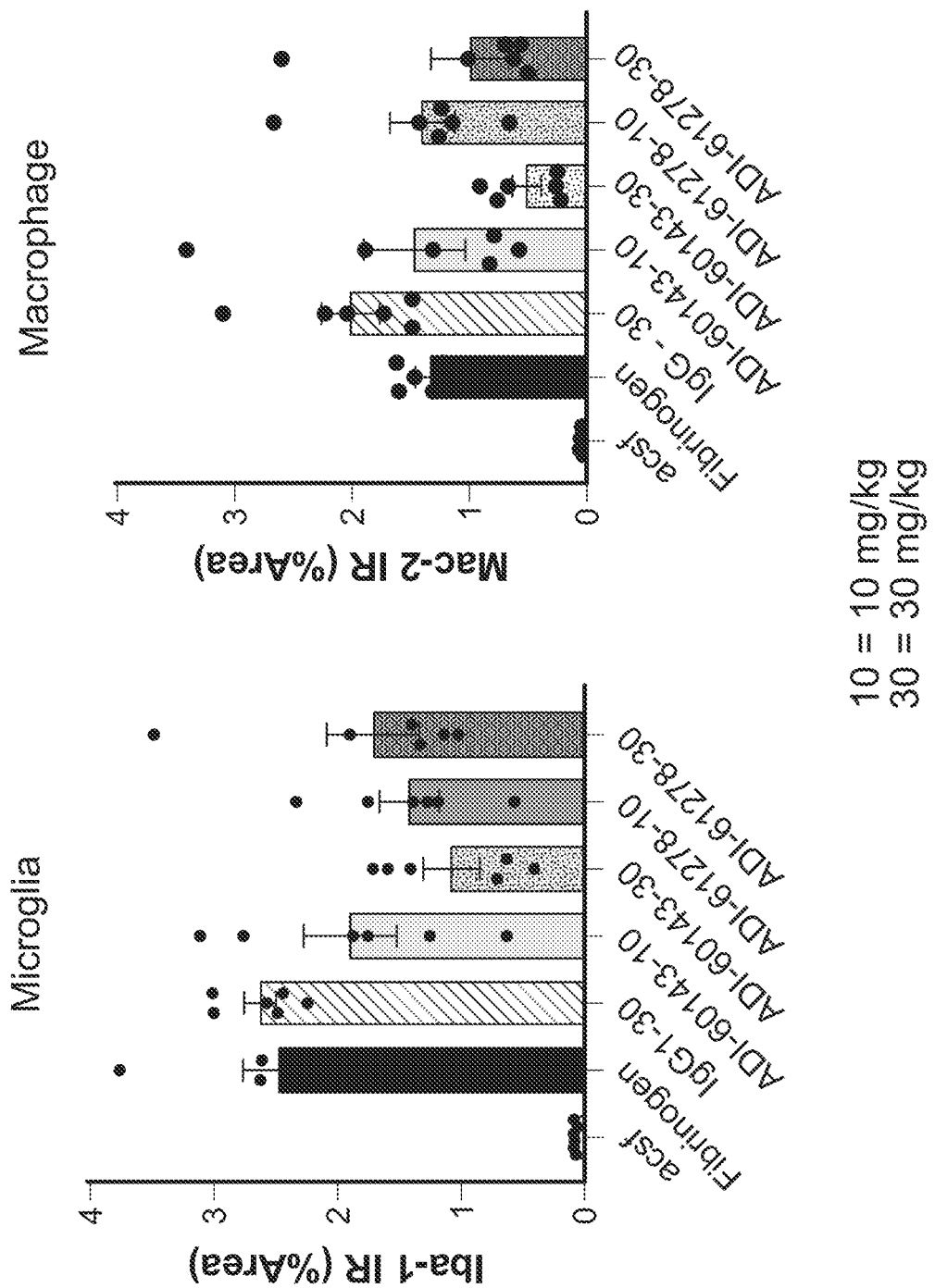
FIG. 6 are graphs showing staining of brain tissue sections from a fibrinogen induced encephalomyelitis (FIE) mouse model injected I.V with artificial cerebral spinal fluid (aCSF), fibrinogen alone, or fibrinogen and the indicated antibody clones at either 10 mg/Kg ("10") or 30 mg/Kg ("30"). Sections were stained with either Iba-1 (left) (microglial marker at 1:750 dilution) or Mac-2 (right) (macrophage infiltration marker at 1:750 dilution).

The ability of the humanized anti-fibrin antibodies to therapeutically inhibit microglia activation and macrophage infiltration (FIG. 6) in a fibrinogen-induced encephalomyelitis (FIE) mouse model was then assessed. To induced FIE, mice were anaesthetized with avertin and placed in a stereotactic apparatus. Plasminogen-free fibrinogen was dissolved in endotoxin-free distilled water, diluted to 5 mg/ml with ACSF (artificial cerebral spinal fluid). Fibrinogen (1 μl of 5 mg/ml) was injected at a rate of 0.3 μl/min with a 10-μl Hamilton syringe attached to a 33 gauge needle into the brain at coordinates: anteroposterior, −1.0 mm; mediolateral, −0.7 mm; dorsoventral, −1.325 mm from the bregma, according to Paxinos and Watson.

For prophylactic intracerebroventricular (i.c.v.) injections, 10 ug of antibodies were delivered (at a rate of 0.3 l/min) with a 10-μl syringe attached to a 33 gauge needle into the cerebral ventricle (anteroposterior, −2.0 mm; mediolateral, 0 mm, dorsoventral, −2.0 mm) 30 min before fibrinogen injection. For prophylactic intravenous (i.v.) injections, antibodies were injected retro-orbitally with a 0.3 mL 29 g insulin syringe 1 h before fibrinogen injection.

Stereotaxic fibrinogen was injected into the corpus callosum to induce encephalomyelitis. A total of 78 mice, separated into 13 groups: n=6 mice per group were then injected i.v. with anti-fibrin humanized antibodies at either 10 mg/kg or 30 mg/kg. Brain tissue harvesting and preparation was performed three days post-injection. Sample exclusion: 5 mice; found dead at day 1 post-surgery (C 10 mg/kg, n=1) and day 2 post-surgery (B 10 mg/kg, n=1; D 10 mg/kg, n=1). Wrong site injection (B 10 mg/kg, n=1; D 10 mg/kg, n=1). Blinding & Quantification: all FIE experiments, image collection and quantification performed in a blinded manner. Immunohistochemistry (IHC) and quantification was performed as follows: 73 mice samples were included for IHC and quantification. Coronal sections (30 um) were prepared on the Cryostat. Tissues were stained with Iba-1 (microglia marker, at a dilution of 1:750) and Mac-2 (macrophage infiltration marker, at a dilution of 1:750). The immunoreactivity of Iba-1 (Iba-1+ area) and Mac-2 (Mac-2+ area) was then calculated. A decrease in both microglia and macrophages were detected in tissues from mice treated with the affinity matured humanized anti-fibrin antibody clones at either 10 mg/kg or 30 mg/kg.

These results show the humanized antibody variants described herein can therapeutically reduce microglia and macrophage infiltration of mice with FIE.

Example 4: Prophylactic Treatment of Relapsing-Remitting Experimental Autoimmune Encephalomyelitis (EAE)

The ability of the humanized anti-fibrin antibodies to prophylactically treat Relapsing-Remitting EAE induced by the epitope of amino acids 139-151 of proteolipid protein (PLP) ('PLP139-151 EAE') was assessed. EAE was induced in 8-9 week old female SJL/J mice by subcutaneous immunization with 15 ug PLP139-151 in complete Freund's adjuvant supplemented with 400 ug of heat-inactivated *Mycobacterium tuberculosis* H37Ra (Day 0). 2 days after immunization, mice are injected with 5 ng pertussis toxin via IP administration. Antibodies were administered at 0.2, 1, or 5 mg/kg IP prophylactically twice per week starting on day 0. Dexamethasone (0.5 mg/kg) was administered IP daily as a positive control. Experimental Design: 6 groups: n=10 mice per group, a total of 60 mice. Dose regimen: Dexamethasone (5 mg/kg, daily), humanized anti-fibrin antibodies (A, B, C, D_5 mg/kg, every 3 days). EAE disability scores were monitored daily up to the end of the study. The study was terminated 3 days post peak-EAE at around day 14-16 of the study and spinal cords were collected for histopathological analysis.

Sample exclusion: 3 mice; found dead at day 12 (antibody B, n=1), day 15 (antibody C, n=1), or day 16 (antibody A, n=1). Blinding & Quantification: All EAE experiments (antibody treatment and clinical score) were performed in a blinded manner. 57 spinal cord samples were prepared for tissue processing.

Figure 7:
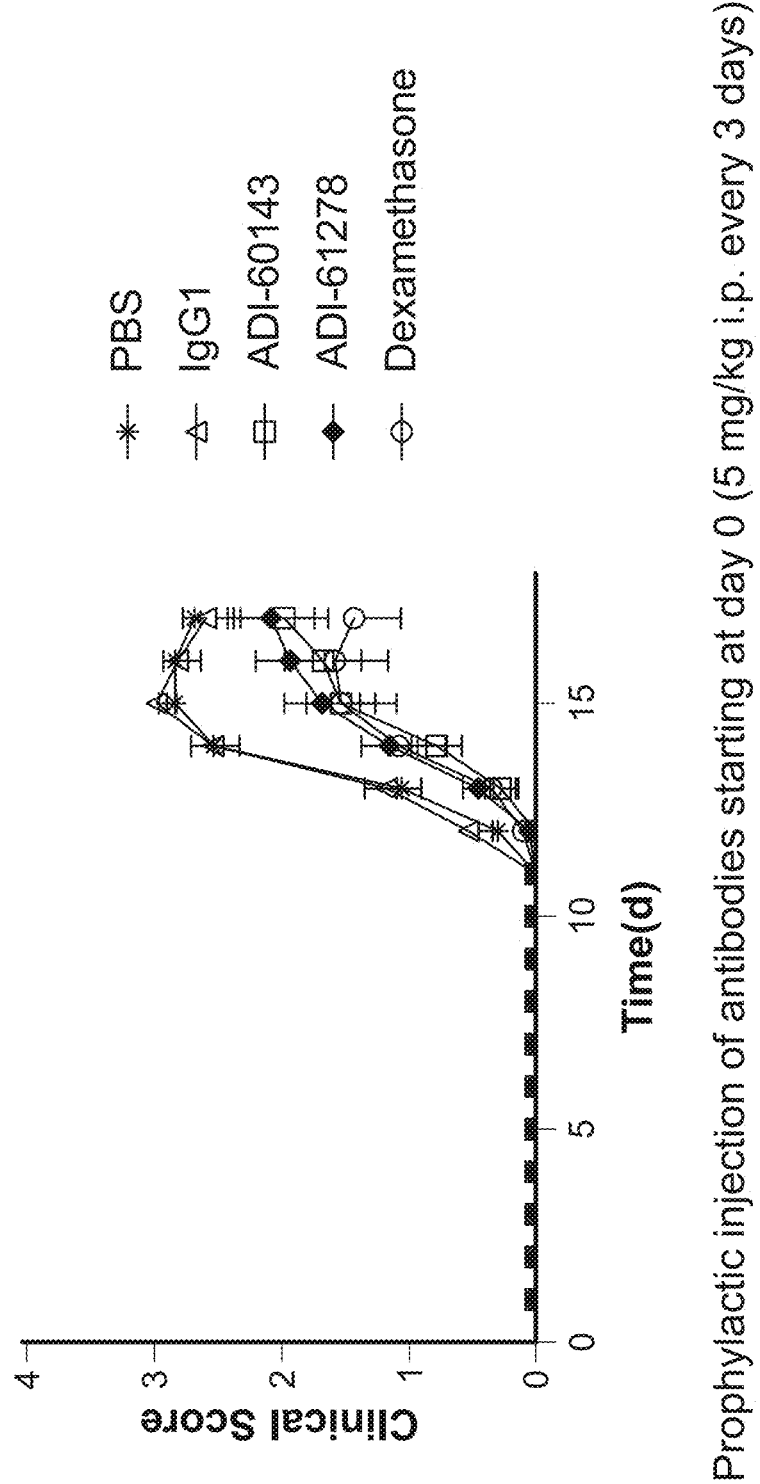
FIG. 7 is a graph showing clinical score of mice from an experimental autoimmune encephalomyelitis (EAE) model that were subjected to prophylactic injection of PBS alone, IgG1 alone, antibody clone 60143, antibody clone 61278, or dexamethasone. Antibodies were injected by intraperitoneal injection at 5 mg/kg every 3 days.
Figure 8:
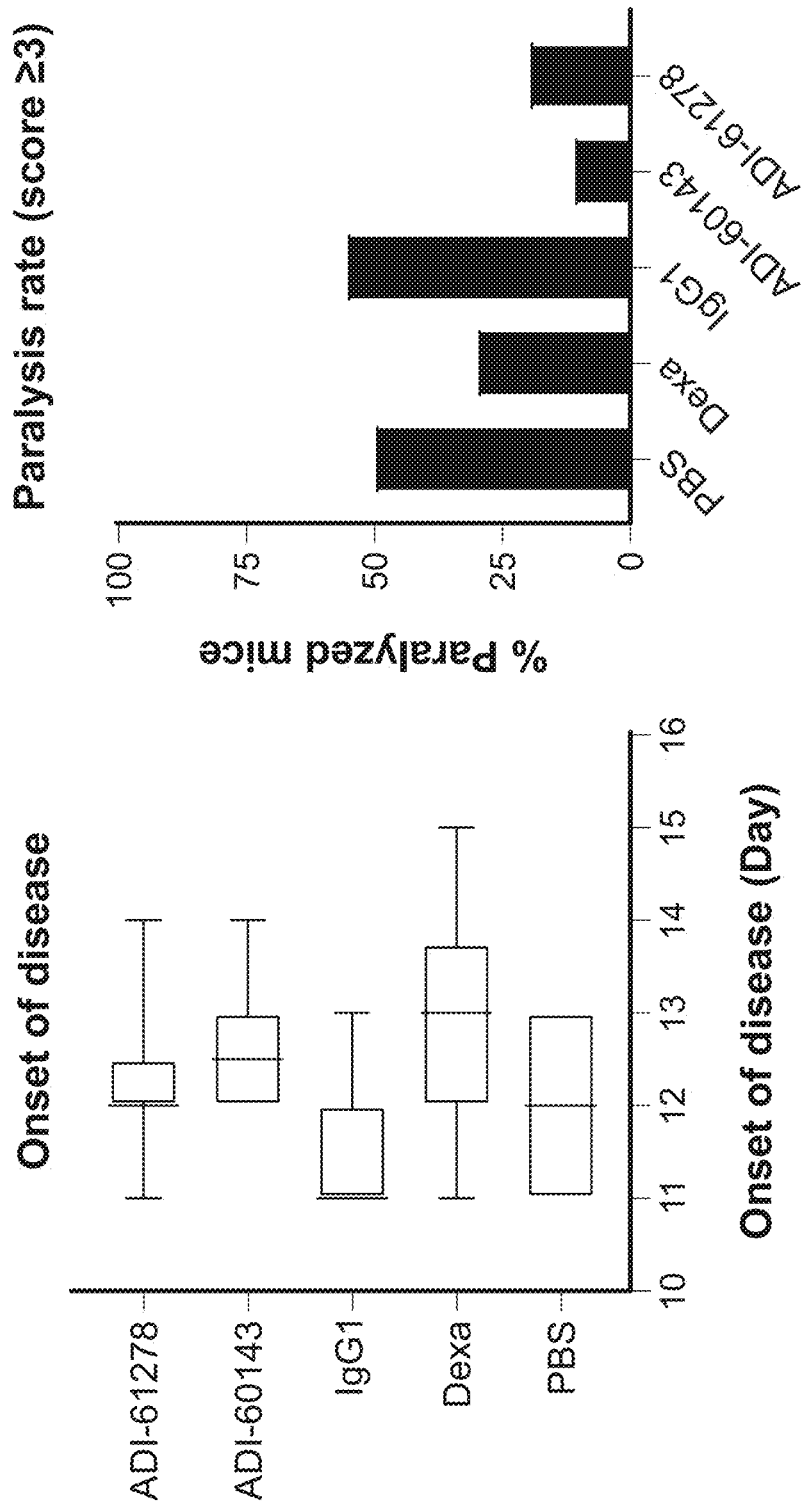
FIG. 8 shows graphs of onset of disease (left) and paralysis rate (right) of mice from an experimental autoimmune encephalomyelitis (EAE) model that were subjected to prophylactic injection of PBS alone, IgG1 alone, antibody clone 60143, antibody clone 61278, or dexamethasone. Antibodies were injected by intraperitoneal injection at 5 mg/kg every 3 days.
Figure 9:
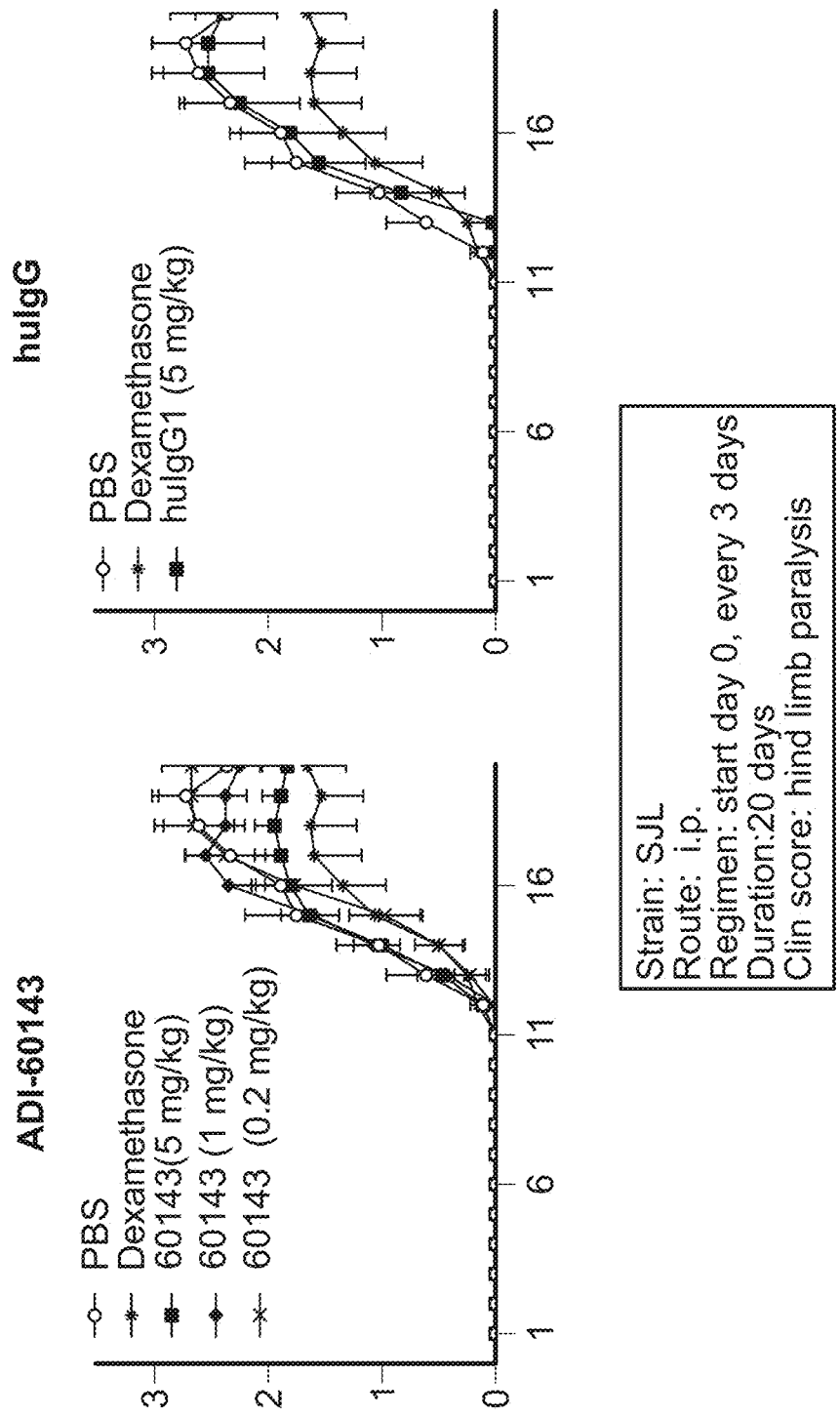
FIG. 9 are graphs showing clinical score of mice from an experimental autoimmune encephalomyelitis (EAE) model that were subjected to prophylactic injection of PBS alone, dexamethasone, antibody clone 60143 (left) or control antibody human IgG1 (right).
Figure 10:
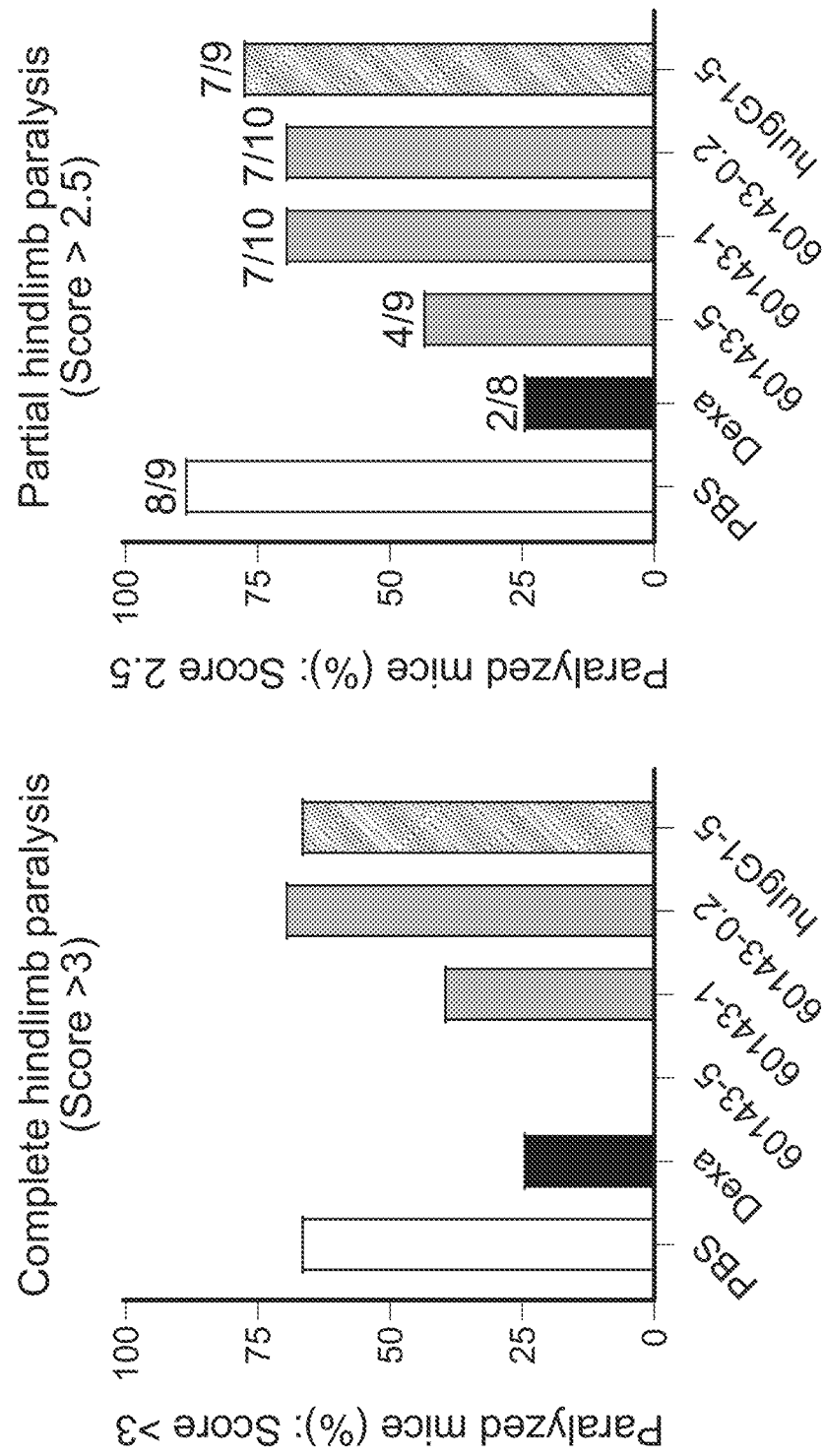
FIG. 10 are graphs showing proportion of paralyzed mice (complete paralysis—left) or (partial hindlimb paralysis—right) from an experimental autoimmune encephalomyelitis (EAE) model that were subjected to prophylactic injection of PBS alone, dexamethasone (dexa), antibody clone 6043 (at the indicated concentrations; 5=5 mg/kg, 1=1 mg/kg and 0.2=0.2 mg/kg) or control antibody human IgG1 (5 mg/kg).

Clinical score of PLP EAE was assessed in mice that were prophylactically injected with antibodies (5 mg/kg i.p. every 3 days) (FIG. 7). The clinical score of mice that had been injected with anti-fibrin humanized antibody was reduced compared to control mice injected with PBS or IgG1 alone. Time to onset of disease was also assessed (FIG. 8). The were no mice with paralysis that had been injected with anti-fibrin humanized antibody compared to control mice injected with PBS, IgG1, or dexamethasone alone which had between 25% and over 50% of mice with paralysis (FIG. 8). FIG. 9 shows clinical score of mice that were subjected to prophylactic injection of PBS alone, dexamethasone, antibody clone 6043 (left) or control antibody human IgG1 (right). FIG. 10 shows the proportion of paralyzed mice (complete paralysis—left) or (partial hindlimb paralysis—right) that were subjected to prophylactic injection of PBS alone, dexamethasone (dexa), antibody clone 6043 (at the indicated concentrations; 5=5 mg/kg, 1=1 mg/kg and 0.2=0.2 mg/kg) or control antibody human IgG1 (5 mg/kg).

These results show that the anti-fibrin humanized antibody is effective for prophylactic treatment of encephalomyelitis.

Figure 11:
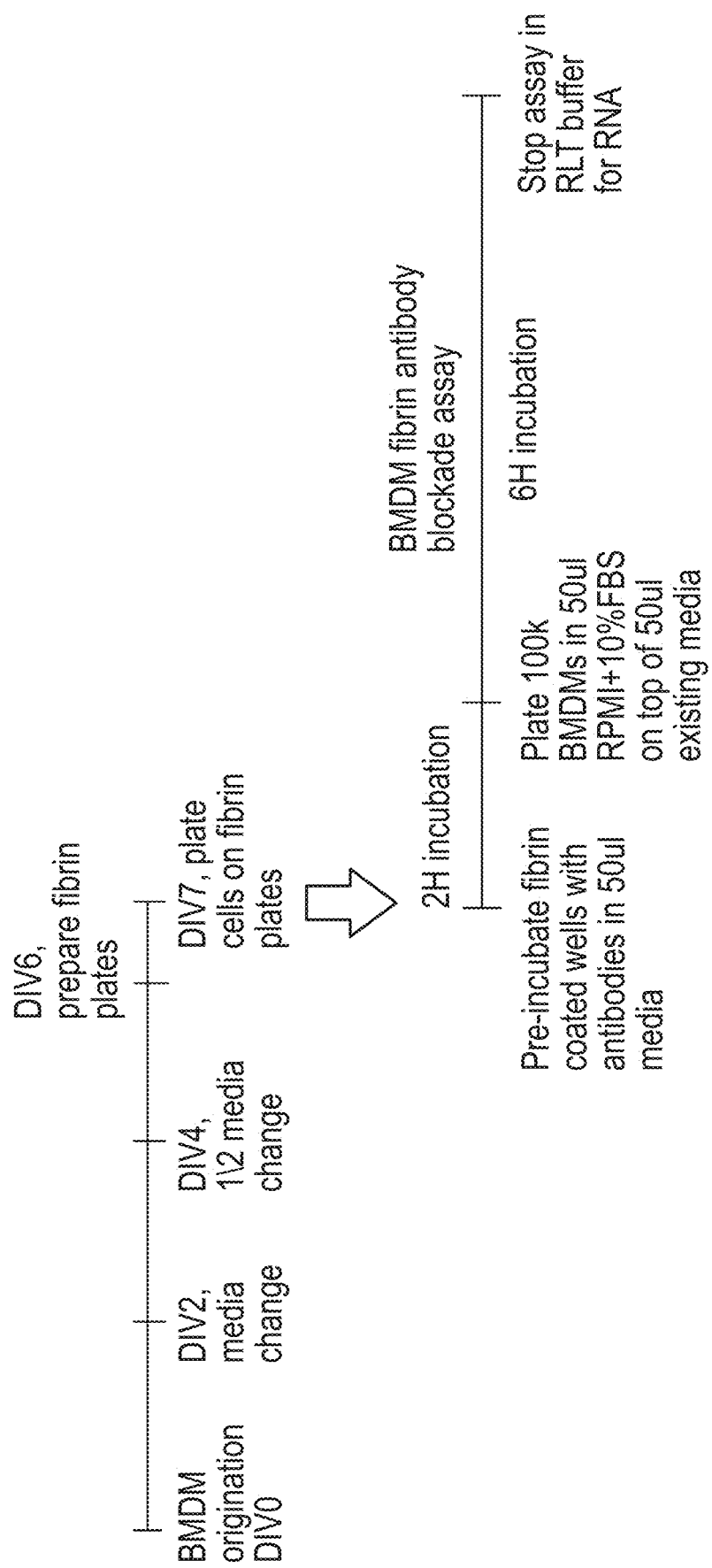
FIG. 11 is a diagram showing the gene expression assay workflow for the BMDM cell line.
Figure 12:
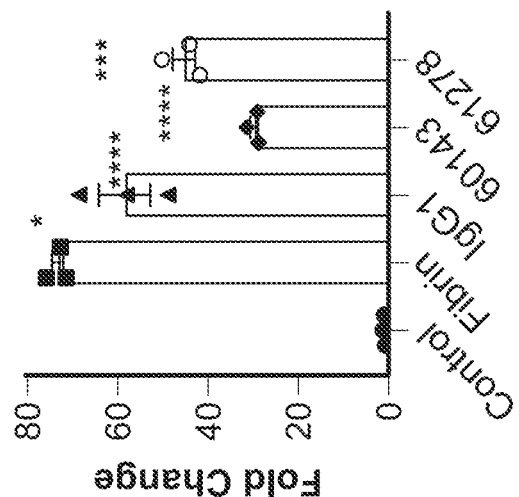
FIG. 12 are graphs showing interleukin (IL)-12b expression in BMDM cells after incubation with fibrinogen and fibrin, IgG1, antibody clone 60143 and antibody clone 61278 at either 50 ug/mL (left) or 10 ug/ml (right) antibody.
Figure 12:
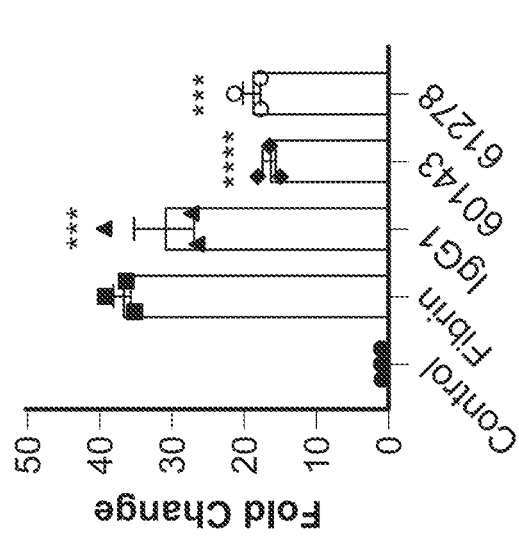
Figure 13:
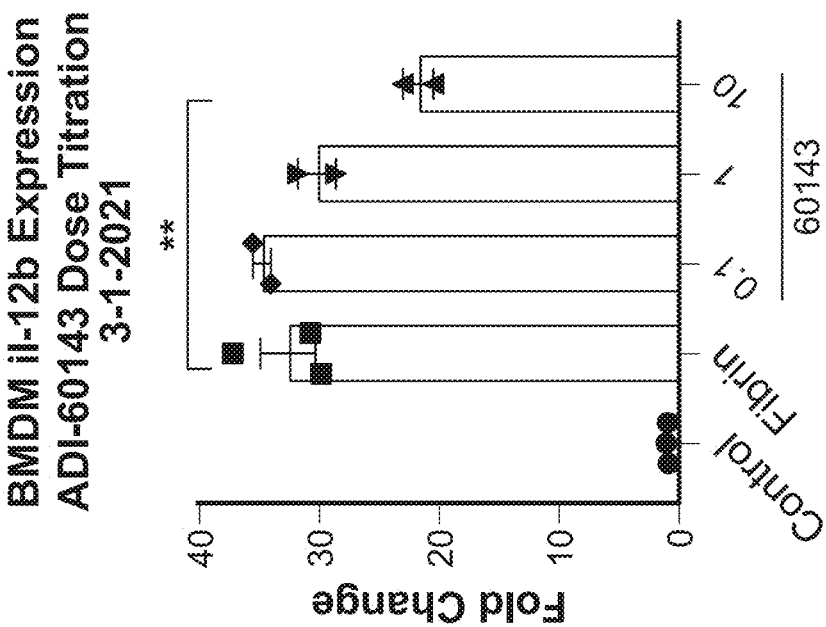
FIG. 13 are graphs showing interleukin (IL)-12b expression in BMDM cells after incubation with the indicated concentrations of fibrinogen and antibody clone 61278 (left) or antibody clone 60143 (right).
Figure 13:
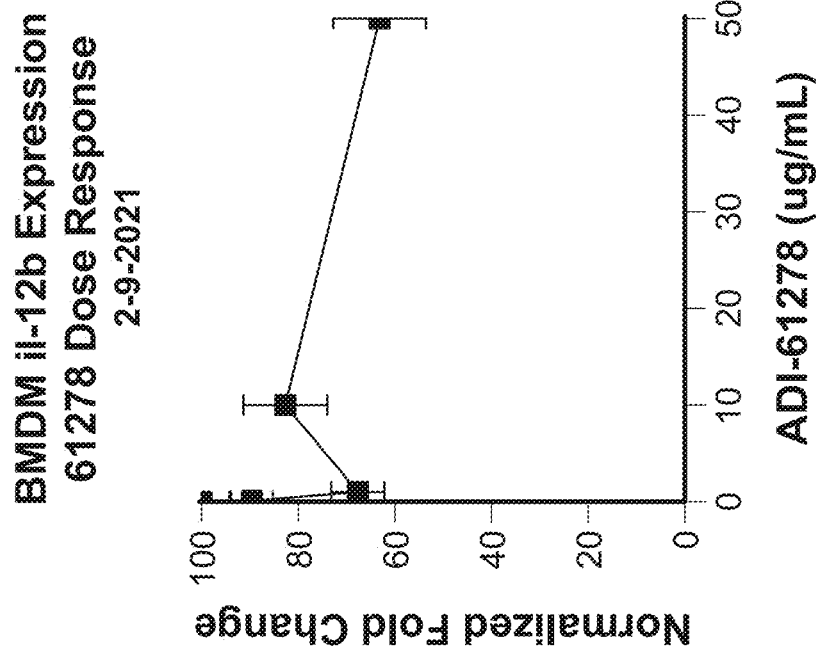

Example 5: Humanized Anti-Fibrin Antibodies Reduce Fibrin-Induced IL-12 Expression in BMDM Cells The ability of the affinity matured humanized anti-fibrin antibodies to alter gene expression of Interleukin (IL)-12b in bone marrow derived macrophage (BMDM) cell lines was assessed (FIGS. 11-13). Cell culture plates with fibrin-coated wells were pre-incubated with humanized anti-fibrin antibodies for 2 h prior to plating BMDM cells. The cells were incubated with the humanized anti-fibrin antibodies or isotype control, fibrinogen, thrombin and $CaCl_2$ for six hours and then cells were harvested and RNA isolated for gene expression analysis (FIG. 11). Cells incubated with 50 ug/mL isotype control exhibited over a 30 fold increase in IL-12b expression, whereas cells incubated with antibody clones 60143 and 61278 at a concentration of 50 ug/mL, exhibited between 15 and 20 fold increase in IL-12b expression (FIG. 10). In another experiment, cells incubated with 10 ug/mL isotype control exhibited about a 55 fold increase in IL-12b expression, whereas cells incubated with antibody clones 60143 and 61278 at a concentration of 10 ug/mL, exhibited between about 20 and 45 fold increase in IL-12b expression (FIG. 12). The fold change in IL-2b expression also was reduced as the concentration of antibody clone 60143 and 61278 were increased (FIG. 13).

These results confirm that fibrin induced IL-12b expression is reduced upon anti-fibrin antibody blockade in bone marrow derived macrophages.

Example 6: Treatment of Neurodegenerative Disease

The purified humanized antibody variants described herein are formulated into a pharmaceutical composition to be administered to patients for the treatment of a neurodegenerative disease (e.g., multiple sclerosis or Alzheimer's Disease). The pharmaceutical composition comprising a humanized antibody variant described herein is administered at a dose sufficient to effectively reduce the symptoms of the neurodegenerative disease. The pharmaceutical composition is well tolerated and does not induce significant harmful adverse effects in the patient.

Example 7: Humanized Antibody Variant for Treatment of Colitis

Figure 14:
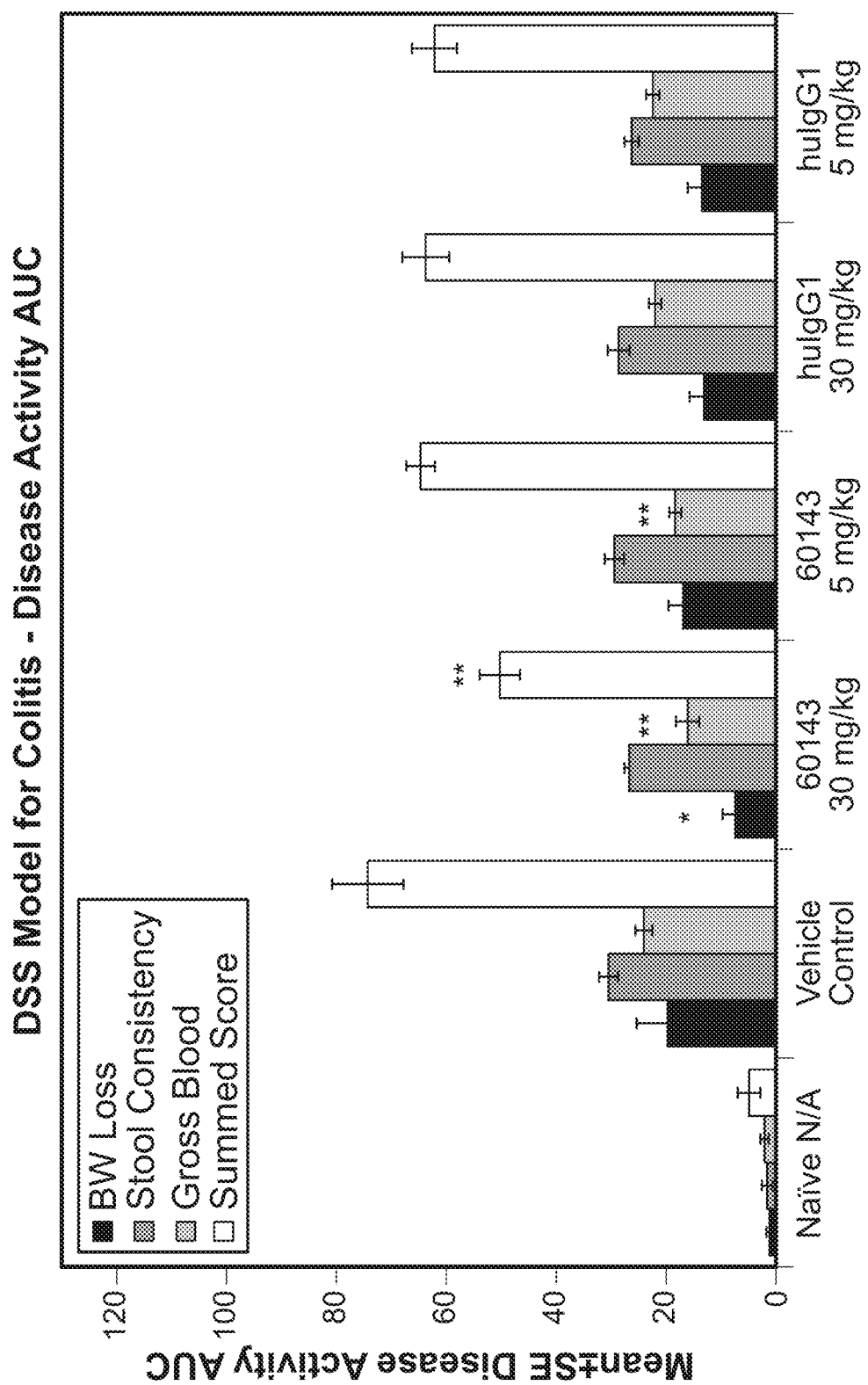
FIG. 14 is a graph showing reduced physiological symptoms of colitis in a dextran sodium sulfate (DSS)-induced mouse model of colitis in animals injected intravenously with 5 mg/kg or 30 mg/kg antibody clone 60143 or isotype control antibody human IgG1.

The humanized antibody variants were investigated the ability to treat colitis in a mouse model of colitis (FIG. 14). To initiate dextran sodium sulfate (DSS) induced colitis treatment, 8-10 week old female C57BL/6 mice were acclimated to the vivarium for at least 4 days, weighed, and randomized into treatment groups based on body weight. 2 types of studies were conducted: acute (7 days) and chronic (28 days).

The acute DSS study is performed by adding 2.5% DSS into drinking water for 7 days. Antibodies were administered IP every 2 days (Q2D) at 10 and 30 mg/kg. Mice were euthanized on day 7 with isoflurane anesthesia, exsanguination, followed by cervical dislocation. The colon were removed and analyzed for histopathology.

The chronic DSS study was performed by adding 2.0% DSS into drinking water for 1 week followed by replacing with 1 week of normal drinking water, followed by another week of 2% DSS and ending with another week of normal drinking water. Humanized antibody variants described herein were administered IV prophylactically starting on day 0 twice a week at 30 and 5 mg/kg. Mice were euthanized after 28 days with isoflurane anesthesia, exsanguination, followed by cervical dislocation. The colon was removed and analyzed for histopathology.

These results confirm that the humanized antibody variants described herein are effective for the treatment of colitis.

Example 8: Pharmacokinetics and Ex Vivo Biodistribution of Selected Anti-Fibrin Antibodies Materials and Methods

[125I]SIB-60143 and [125I]SIB-61278 Labelling Protocol

Four 125I-SIB productions were performed, employing 10 µL (35 MBq I-125) in each case. The smaller batches were labeled to increase overall efficiency and reproducibility. Two pairs of two reactions were combined and purified by HPLC. The yield of dried 125I-SIB in each case was 25 MBq.

The pH of 60143 and 61278 stock solution (0.5 mL of each) was reduced from 8.5 to 8.0 using 2 M HEPES. The pH adjusted solutions were each then added to the dried 125I-SIB and incubated for 1 hour at room temperature. Labelling efficiency was measured by iTLC and found to be 59% and 77% for 60143 and 61278, respectively. The reaction mixtures were then purified on NAP-5 columns, eluted with PBS.

Fractions 4-8 were combined giving 12.6 MBq of [125I] SIB-60143 and 18.0 MBq [125I]SIB-61278 each in 1.25 mL. The radiochemical purity was measured by iTLC and SEC-HPLC.

I-125 labelled proteins were diluted in phosphate buffered saline (PBS) to reach 1.33 mg/mL for the low dose stocks and 3.75 mg/mL for the high dose stock Animal Model Seventy-two female C57BL/6 mice were received from Charles River UK.

In Vivo High Dose Pilot Safety Study

Two female C57BL/6 mice were injected intravenously with 30 mg/kg of 60143 and two with 30 mg/kg of 61278. The animals were monitored continuously for the first (0 to 1 h post-injection) and fourth hour post-injection (4 to 5 h post-injection). Mice were checked daily for any adverse effects at 1 and 2 days post-injection, at which point they were euthanized.

In Vivo Study

For the pharmacokinetics analysis, sixty-eight female C57BL/6 mice (19.0±1.3 g) were injected with 10 or 30 mg/kg of [125I]SIB-60143 or [125I]SIB-61278 and sacrificed at various time points (5 min, 30 min, 1 hour, 4 hours, 1 day, 3 days, 7 days, and 14 days; n=2 per time point). Blood, plasma, protein-free plasma and protein activity were counted by gamma counter. Further details regarding the study design are provided in Table 1 below.

Thirty-two of these animals (18.6±1.3 g) were also included in the biodistribution study. All mice were injected with 10 or 30 mg/kg of [125I]SIB-60143 or [125I]SIB-61278 and sacrificed at various time points (1 day, 3 days, 7 days, and 14 days; n=2 per time point). Further details regarding the study design are provided in Table 2 below.

TABLE 1

| Study Design Summary for the PK analysis | |
| --- | --- |
| Time point | Samples |
| 5 min | Blood, plasma, protein-free plasma, protein |
| 30 min | Blood, plasma, protein-free plasma, protein |
| 1 hour | Blood, plasma, protein-free plasma, protein |
| 4 hours | Blood, plasma, protein-free plasma, protein |
| 1 day | Blood, plasma, protein-free plasma, protein |
| 3 days | Blood, plasma, protein-free plasma, protein |
| 7 days | Blood, plasma, protein-free plasma, protein |
| 14 days | Blood, plasma, protein-free plasma, protein |

TABLE 2

| Biodistribution Study Design Summary | | | | | |
| --- | --- | --- | --- | --- | --- |
| Group & Route | No. Animals | Tracer | Mass Dose (mg/kg) | Radioactivity Dose (MBq/animal) | Gamma counting time point |
| 1 IV | 16 | [125I]SIB-60143 | 9.8 ± 0.5 | 0.27 ± 0.02 | 24 hours |
| 2 IV | 16 | [125I]SIB-61278 | 9.8 ± 0.5 | 0.36 ± 0.02 | 72 hours |
| 3 IV | 16 | [125I]SIB-60143 | 29.6 ± 1.9 | 0.27 ± 0.02 | 168 hours |
| 4 IV | 17 | [125I]SIB-61278 | 29.3 ± 3.6 | 0.37 ± 0.05 | 336 hours |

All animals from group 1 and group 2 were injected awake on day 1. Biodistribution animals (1 day, 3 days, 7 days, and 14 days) from groups 3 and 4 were also injected awake on day 1. PK-only animals (5 min, 30 min, 1 hour, 4 hour) from groups 3 and 4 were injected awake on day 2. The same production of test article formulation was used for the different injection days.

Dose Administration

Each animal was weighed on the day of dose administration. The animals ranged in weight from 16.4 to 22.5 g. Single intravenous (IV) doses were administered by using a 0.5 mL syringe to provide the appropriate dosage of 10 mg/kg for groups 1 and 2 and 30 mg/kg for groups 3 and 4. The dosing syringe was weighed before and after injection to determine amount administered to each subject.

Ex Vivo Sample Preparation

Animals were sacrificed by cardiac puncture followed by exsanguination prior to organ resection. The following organs were collected for gamma counting: brain, heart, liver, kidneys, muscle, tail, stomach, large intestine, small intestine, cecum and spleen.

Analysis

Results are presented in units of percent injected dose (% ID) and percent injected dose per gram (% ID/g). The definition of these units can be found in the equations below:

The % ID for each analysed region from the ex vivo gamma counted data can be defined as stated in Equation 1:

$$\%ID = \frac{\text{Uptake}}{\text{Injected Dose}} * 100\%$$

Where Uptake=Radioactivity (MBq) in a particular gamma counting sample, decay-corrected to the time of injection. Injected dose=Radioactivity (MBq) injected into the subject The % ID/g for each analysed region from the ex vivo gamma counted data can be defined as stated in Equation 2:

$$\%\frac{ID}{g} = \frac{\frac{\text{Uptake}}{\text{Injected Dose}} * 100\%}{ROI \text{ weight}}$$

Where, Uptake=Radioactivity (MBq) in a particular gamma counting sample, decay-corrected to the time of injection. Injected dose=Radioactivity (MBq) injected into the subject.

Weight = Sample weight of the gamma counted tissue in g

Concentration values in units of µg/mL can be defined for the ex vivo gamma counting data according to Equation 3:

$$\frac{\mu g}{mL} = \frac{\%ID}{g} \times \frac{\frac{\text{Injected Dose } (\mu g)}{100 \%ID}}{\frac{1 \text{ mL}}{1 \text{ g}}}$$

Where, Injected Dose=Antibody mass (µg) injected into the subject. Assumption: tissue density of 1 g/mL.

Gamma Counting Analysis for Biodistribution

The activity of each collected tissue was measured in units of counts per minute (CPM). Triplicate aliquots of the radiotracer were also assayed in the gamma counter in order to calculate a factor for converting counts to mass of injected material (g/CPM). Values were corrected for background radiation and converted to percent injected dose (% ID) and percent injected dose per gram (% ID/g).

Gamma Counting Analysis for PK Study

The activity of each collected tissue was measured in units of counts per minute (CPM). Triplicate aliquots of the radiotracer were also assayed in the gamma counter in order to calculate a factor for converting counts to mass of injected material (g/CPM). Values were then corrected for background radiation and converted to percent injected dose (% ID) and percent injected dose per gram (% ID/g).

For the PK analysis, concentration (% ID/g) of radiotracer in blood from blood subsample gamma counting was pooled from 2 mice and calculated as follows:

$$\text{Mass(injectate in sample)}[g] = CPM(\text{sample}) \times \frac{\text{Mass(injectate in standard)}[g]}{CPM(\text{standard})}$$

$$\text{Injected Mass(pooled)}[g] = \frac{\text{Mass(injectate in Mouse 1)}[g] + \text{Mass(injectate in Mouse 2)}[g]}{2}$$

$$\% \text{ ID(sample)} = \frac{\text{Mass(injectate in sample)}[g]}{\text{Injected Mass(pooled)}[g]} \times 100$$

$$\% \text{ ID/ml(sample)} = \frac{\% \text{ ID(sample)}}{\text{Volume (sample)}[mL]}$$

Subsampled blood and plasma % ID values were also extrapolated to total (whole body) blood and plasma values, respectively. For extrapolation, the ratio of blood volume/body weight=0.072 mL/kg was used (Diehl et al., 2001). For calculating whole plasma, a haematocrit value of 0.387 was used.

Non-Compartmental Analysis

% ID/mL values were converted to units of µg/mL prior to non-compartmental analysis using the following equation:

$$\text{Concentration } (\mu g/mL) = \frac{\text{Mass (injectate in sample) } [g]}{\text{Volume (sample) } [g]} \times \frac{1 \times 10^6 \, [\mu g]}{1 \, [g]}$$

The regression was performed on µg/mL values with Python using Phoenix WinNonlin (Certara) rules to determine the terminal clearance rate $\lambda_z$. PK parameters were calculated as follows:

| | | |
|---|---|---|
| AUC | $AUC \, [\mu g \cdot h \cdot mL^{-1}]$ | $= \int_0^{tn} C(t)dt$ |
| AUC (0-24) | $AUC \, [\mu g \cdot h \cdot mL^{-1}]$ | $= \int_0^{24} C(t)dt$ |
| AUC (0-∞) ($AUC_{inf}$) | $AUC \, [\mu g \cdot h \cdot mL^{-1}]$ | $= \int_0^{tn} C(t)dt + \frac{C(tn)}{\lambda_z}$ |
| $AUC_{Tail}$ | $\frac{AUC_{Inf} - AUC}{AUC_{Inf}} \times 100$ | |
| Volume of Distribution | $V_D[mL] = \frac{\text{Dose } [\mu g]}{AUC_{Inf} \, [\mu g \cdot h \cdot mL^{-1}] \times \lambda_z}$ | |
| Clearance | $CL \, [mL \cdot h^{-1}] = \frac{\text{Dose } [\mu g]}{AUC_{Inf} \, [\mu g \cdot h \cdot mL^{-1}]}$ | |

Results

PK Analysis

Figures 15A, 15B:
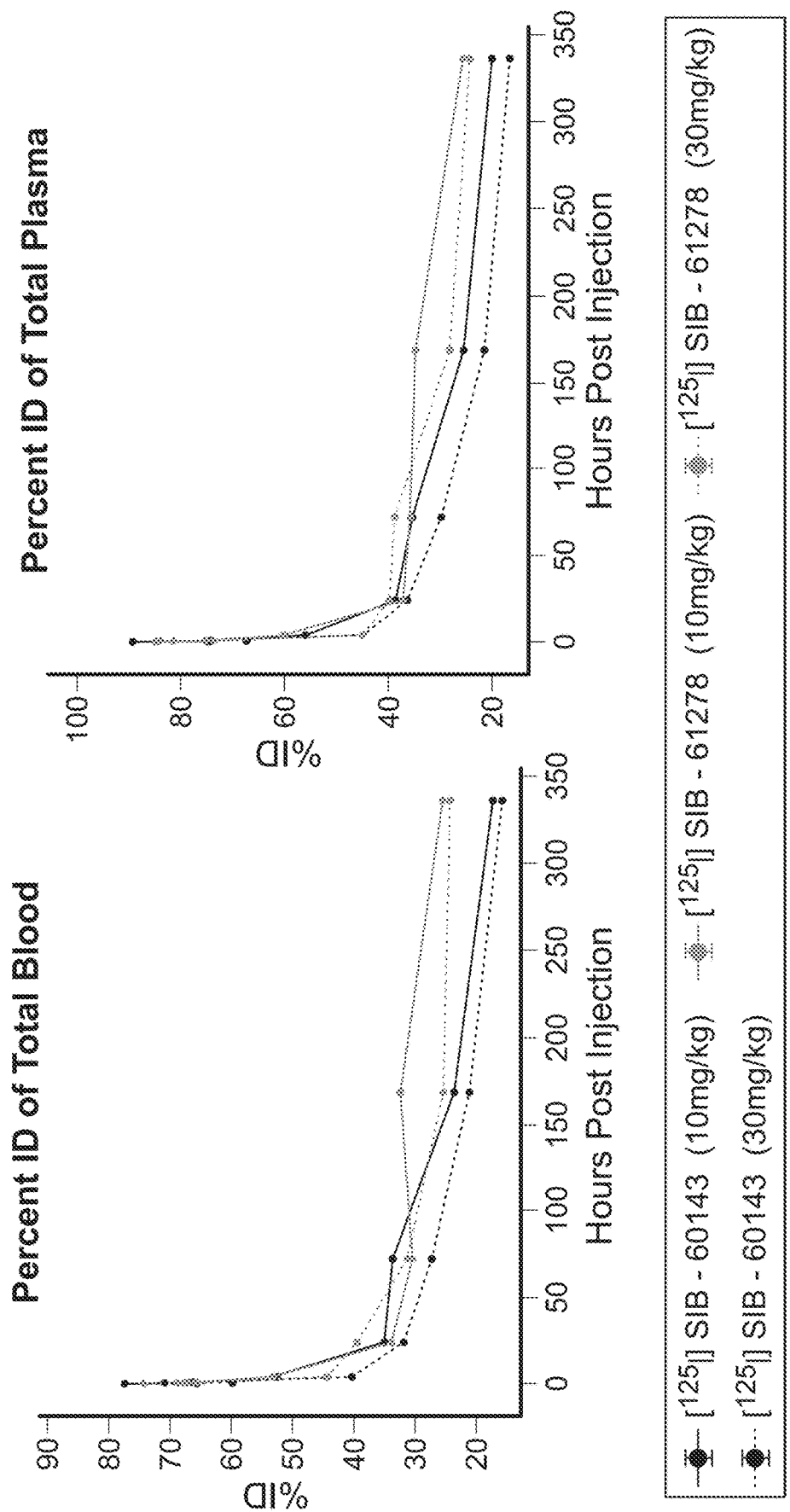
FIG. 15A and FIG. 15B shows uptake (% ID) of [$^{125}$I]SIB-60143 and [$^{125}$I]SIB-61278 injected at 10 mg/kg and 30 mg/kg in mice blood (A) and plasma (B), corrected for theoretical blood and plasma volumes.

A range of PK parameters was calculated for the radiolabeled antibodies [125I]SIB-60143 and [125I]SIB-61278 at 10 mg/kg and 30 mg/kg (FIG. 15A, FIG. 15B, and Table 3). There was no indication of instability in vivo with >95% of activity protein-bound (FIGS. 15A and 15B). About 50-70% of test article was removed from the blood and plasma after 24 hours post-injection for both antibodies at both dose levels. The elimination half-life of [125I]SIB-60143 in the blood and plasma at both doses was in the 275-375 hours range. The elimination half-life of [125I]SIB-61278 was longer than other antibodies at both dose levels; 550-600 hours in plasma and 775-825 hours in blood. The clearance values were similar when comparing the two dose levels for each antibody in blood and plasma independently.

TABLE 3

NCA analysis results of [$^{125}$I]SIB-60143 and [$^{125}$I]SIB-61278 at 10 mg/kg and 30 mg/kg

| | Regression range | [$^{125}$I]SIB-60143 (10 mg/kg) | | [$^{125}$I]SIB-60143 (30 mg/kg) | | [$^{125}$I]SIB-61278 (10 mg/kg) | | [$^{125}$I]SIB-61278 (30 mg/kg) | |
|---|---|---|---|---|---|---|---|---|---|
| | | Blood | Plasma | Blood | Plasma | Blood | Plasma | Blood | Plasma |
| $C_{max}$ (mg/mL) | N/A | 109 | 205 | 270 | 500 | 96 | 191 | 314 | 585 |
| $t_{1/2a}$ (h) | 5 min to 4 h | 7.7 | 6.8 | 6.2 | 6.0 | 7.6 | 6.5 | 5.3 | 4.1 |
| $t_{1/2}$ (h) | 24 h to 14 d | 291 | 316 | 350 | 309 | 820 | 557 | 789 | 597 |
| $\lambda_z$ (h$^{-1}$) | 24 h to 14 d | 0.0024 | 0.0022 | 0.0020 | 0.0022 | 0.0008 | 0.0012 | 0.0009 | 0.0012 |
| $t_{1/2}$ (h) | 3 d to 14 d | 281 | 325 | 398 | 371 | 876 | 503 | 732 | 398 |
| $\lambda_z$ (h$^{-1}$) | 3 d to 14 d | 0.0025 | 0.0021 | 0.0017 | 0.0019 | 0.0008 | 0.0014 | 0.0009 | 0.0017 |
| Vd (mL) | 24 h to 14 d | 3.64 | 2.11 | 4.27 | 2.36 | 3.80 | 2.02 | 4.30 | 2.32 |
| CL (mL/h) | 24 h to 14 d | 0.0087 | 0.0046 | 0.0084 | 0.0053 | 0.0032 | 0.0025 | 0.0038 | 0.0027 |
| AUC (mg/mL · h) | 5 min to 14 d | 12000 | 21000 | 32000 | 56000 | 14000 | 25000 | 39000 | 69000 |
| AUC$_\infty$ (mg/mL · h) | 3 d to 14 d | 22000 | 40000 | 66000 | 105000 | 56000 | 72000 | 149000 | 210000 |

Biodistribution

Figure 16B:
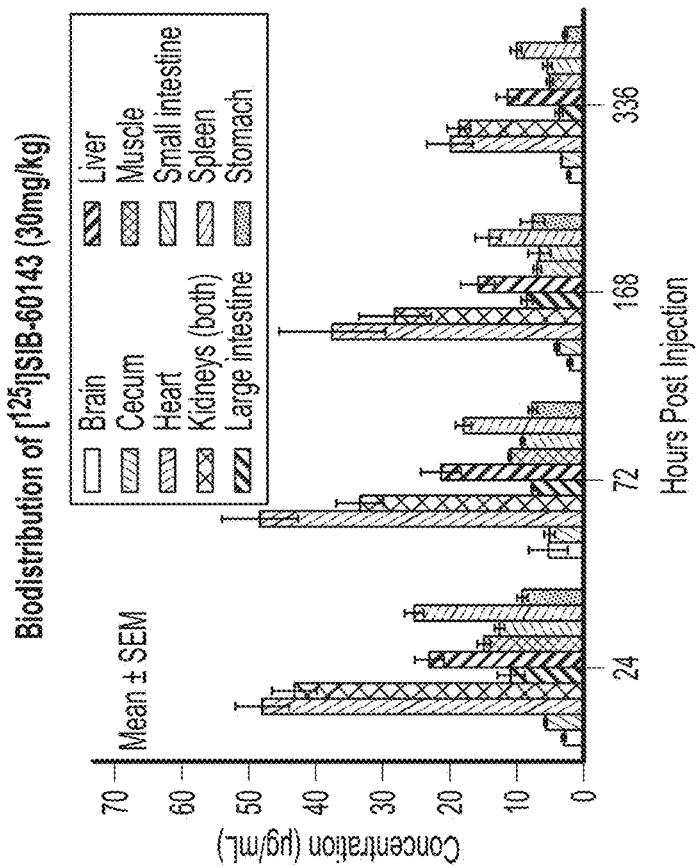
FIGS. 16A-16D show ex vivo biodistribution of [$^{125}$I]SIB-60143 (A and B) and [$^{125}$I]SIB-61278 (C and D) injected at 10 mg/kg (A and C) and 30 mg/kg (B and D) in mice over time.
Figure 16A:
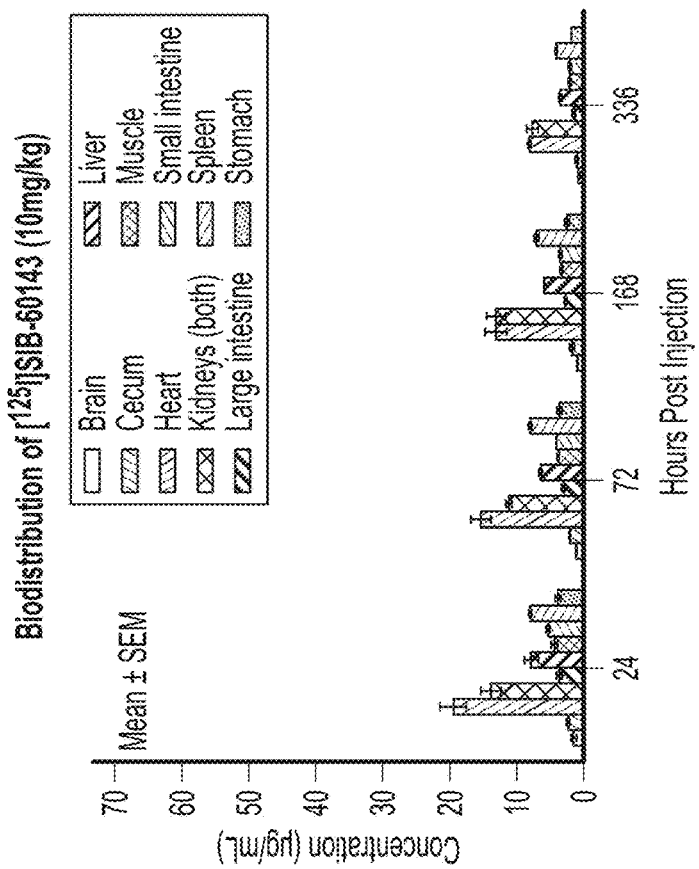
Figure 16D:
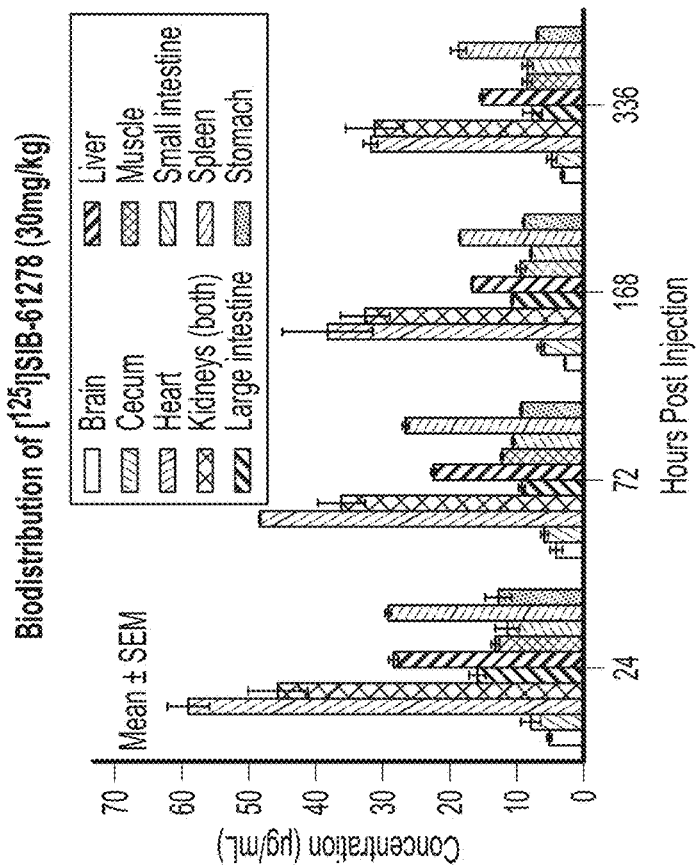
Figure 16C:
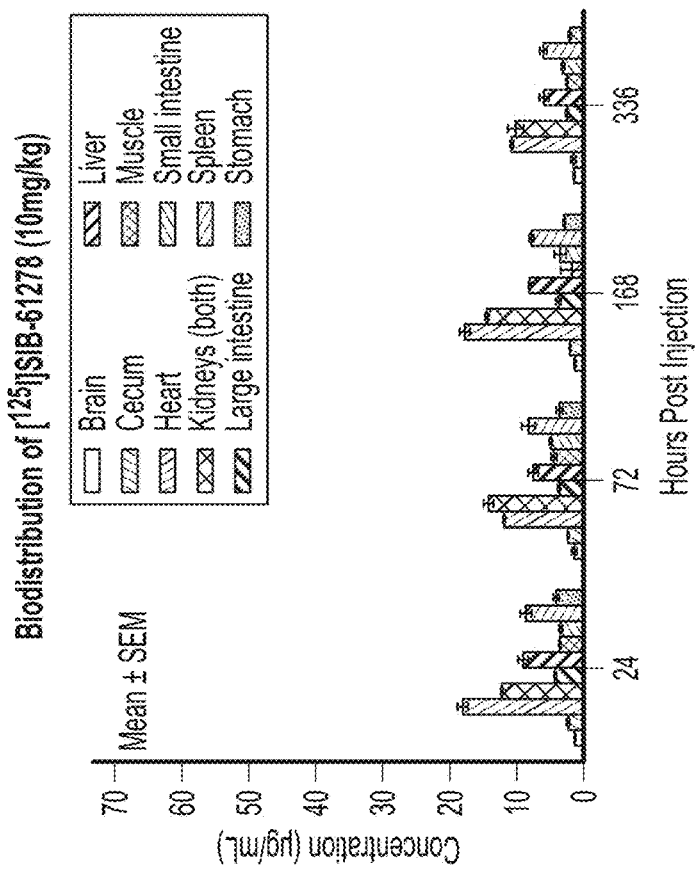

Ex vivo biodistribution of both antibodies was determined at 24, 72, 168 and 336 hours post-injection. FIG. 16A shows [$^{125}$I]SIB-60143 at 10 mg/kg in mice over time. FIG. 16B shows [$^{125}$I]SIB-60143 at 30 mg/kg in mice over time. FIG. 16C shows [$^{125}$I]SIB-61278 at 10 mg/kg in mice over time. FIG. 16D shows [$^{125}$I]SIB-61278 at 30 mg/kg in mice over time. The pattern of distribution was similar for both antibodies at both doses, with low brain concentration (between 0.39±<0.01 and 0.91±0.51% ID/g), and uptake in heart (between 3.50±0.03 and 10.69±2.02% ID/g), kidneys (between 3.28±0.01 and 8.40±1.37% ID/g), liver (between 1.85±0.01 and 5.12±0.85% ID/g) and spleen (between 1.77±0.05 and 5.27±0.55% ID/g). No difference of concentration was observed with increasing dose. The uptake of 61278 at 14 days was in higher in all organs than 60143, consistent with a longer elimination half-life.

50-70% of test article was removed from the blood and plasma after 24 hours post-injection for both antibodies at both dose levels. The elimination half-life of [$^{125}$I]SIB-60143 in blood and plasma at all dose ranges was in the 275-375 hours range. The elimination half-life of [$^{125}$I]SIB-61278 was longer than other antibodies at both dose levels; 550-600 hours in plasma and 775-825 hours in blood. The biodistribution data was comparable between both antibodies at both dose levels. The uptake of [$^{125}$I]SIB-61278 at 14 days was higher in all organs than [$^{125}$I]SIB-60143, consistent with a longer elimination half-life.

Example 9: Crystal Structure of the Fab of Antibody Clone 60143

The X-ray crystal structure of the Fab of antibody clone ABI-60143, comprising a heavy chain and light chain variable domain, in complex with fibrinogen gamma peptide P2 was solved at 1.5 Å resolution. The crystal described was grown using the hanging drop method of vapour diffusion in a 96 well plate with a precipitant solution containing 0.1 M sodium cacodylate pH 5.5 and 25% PEG 4000. The crystal was cryo-cooled without additional cryo-protectant by capturing it in a loop directly from the growth drop and plunging it into liquid nitrogen. A data set was collected at the Swiss Light Source (SLS), beamline X06DA (PXIII).

Data processing in MOSFLM (Battye et al., 2011) (CCP4) and AIMLESS (Evans & Murshudov, 2013) (CCP4) indicated that the most likely space group was P212121 with unit cell dimensions a=67.9 Å, b=73.3 Å, c=93.6 Å and a=R=7=90.0°, giving a total cell volume of 465741.4 Å3. Calculation of the Matthews coefficient (2.3 Å3/Da and 46.6% solvent content) indicated that there was most probably one complete Fab-ABI-60143-P2 complex per asymmetric unit. Models for use in molecular replacement (MR) were chosen by BLAST searching the sequences of the Fab heavy and light chains against the PDB. Models with highest sequence identity were 6ani (Fab heavy chain) and 3pp3 (Fab light chain). The large number of Fab crystal structures in the PDB has revealed a large variety in the elbow angles present between variable and constant domains. This variety in elbow angles can cause the overall tertiary structure of two otherwise highly homologous Fab fragments to be significantly different, which in turn causes MR to fail. For this reason, the hinge regions between the variable and constant domains of the heavy and light chains were removed. Four separate MR search ensembles were generated (VH, CH, VL and CL domains). Amino acid residues were trimmed from the CDRs of the heavy and light variable domain models after visual inspection in COOT to prevent any potential clashes in the interface with P2 that might also cause MR to fail. All four of the input search ensembles that were required to build a complete Fab were correctly located by MR using PHASER (McCoy et al., 2007) (CCP4). The MR output model was given 30 cycles of jelly body refinement using REFMAC5 (Vagin et al., 2004) (CCP4). The protein sequence was mutated to match that of Fab using CHAINSAW (Stein, 2008) (CCP4). The Fab ABI-60143 model was improved iteratively through successive cycles of model building and refinement until all of the ordered regions of protein visible in the electron density maps were complete. The P2 peptide chain was added to the model by hand in COOT and the complete complex model was refined in REFMAC5. The final protein model contained residues 410-421 from chain A (peptide P2), 1-127 and 134-214 from chain H (Fab heavy chain) and 1-213 from chain L (Fab light chain). Final Rwork=16.8%, Rfree=20.5%.

There was one copy each of Fab ADI-60143 and peptide P2 per asymmetric unit. The Fab ABI-60143 CDR canonical structures were analyzed in accordance with the PyIgClassify database (Adolf-Bryfogle et al., 2014). The heavy chain CDRs were classified as follows: H1-13-1 (CDR-length-cluster) and H2-10-1. CDR H3 was not classified. The light chain CDRs were classified as follows: L1-16-1, L2-8-1 and L3-9-cys7-1.

Each P2 peptide bound to a single Fab. The fold was similar, but not the same as that seen in published fibrinogen gamma chain crystal structures such as PDB ID: 1fzc.

TABLE 4

Fab ADI-60143 and peptide P2 interface analysis

| List of interface hydrogen bonds Monomer 1 | Length (Å) | Monomer 2 |
|---|---|---|
| A:LYS 411 [NZ] | 2.83 | H:ASP 54 [OD2] |
| A:LYS 411 [NZ] | 2.78 | H:ASP 52 [OD2] |
| A:LYS 411 [NZ] | 3.34 | H:ASP 54 [OD1] |
| A:ASN 416 [O] | 3.95 | H:SER 95 [OG] |
| A:ASN 416 [O] | 3.42 | H:LYS 96 [N] |
| A:ASN 416 [O] | 3.46 | H:LYS 96 [O] |
| A:ARG 417 [NE] | 3.43 | H:TRP 33 [NE1] |
| A:ARG 417 [NE] | 3.71 | H:SER 31 [O] |
| A:ARG 417 [NH1] | 3.50 | H:SER 31 [O] |
| A:ARG 417 [O] | 3.68 | H:SER 95 [OG] |
| A:ARG 417 [O] | 2.83 | H:HIS 35 [NE2] |
| A:LEU 418 [O] | 3.28 | L:ASN 91 [OD1] |
| A:THR 419 [O] | 2.94 | H:LYS 96 [N] |
| A:ILE 420 [N] | 3.58 | L:TYR 36 [OH] |
| A:ILE 420 [O] | 2.52 | L:TYR 36 [OH] |
| A:GLY 421 [N] | 3.02 | H:SER 94 [O] |
| A:GLY 421 [OXT] | 3.77 | H:GLY 102 [N] |
| A:GLY 421 [OXT] | 3.74 | H:GLY 101 [O] |

TABLE 5

Fab ADI-60143 Participating Interface residues

| Peptide P2 | Fab ADI-60143 |
|---|---|
| A:LYS 411 | H:SER 31 |
| A:ILE 412 | H:TRP 33 |
| A:ILE 413 | H:HIS 35 |
| A:PHE 415 | H:LEU 50 |
| A:ASN 416 | H:ASP 52 |
| A:ARG 417 | H:ASP 54 |
| A:LEU 418 | H:TYR 56 |
| A:THR 419 | H:ALA 93 |
| A:ILE 420 | H:SER 94 |
| A:GLY 421 | H:LYS 96 |
|  | H:PRO 97 |
|  | H:GLY 101 |
|  | H:GLY 102 |
|  | H:TRP 103 |
|  | L:HIS 27 |
|  | L:TYR 32 |
|  | L:TYR 36 |
|  | L:LEU 46 |
|  | L:ASN 91 |
|  | L:LEU 92 |
|  | L:LEU 94 |
|  | L:LEU 96 |

TABLE 6

Data collection, processing and refinement statistics

| | |
|---|---|
| Synchrotron, Beam line | SLS, PXIII |
| Date of data collection | 26 Aug. 2021 |
| Wavelength (Å) | 1.286281 |
| Detector type | DECTRIS PILATUS 2M-F |
| Transmission (%) | 100 |
| Temperature (K) | 100 |
| Exposure time (s) | 0.05 |
| Oscillation range per frame (°) | 0.10 |
| Overall rotation (°) | 180 |
| Resolution range (Å) (overall and last shell) | 46.81-1.50 (1.53-1.50) |
| Number of observed reflections (overall and last shell) | 462407 (14052) |
| Number of unique reflections (overall and last shell) | 75227 (3612) |
| Multiplicity (overall and last shell) | 6.1 (3.9) |
| Completeness (%) (overall and last shell) | 99.7 (97.7) |
| $R_{merge}$ (%) (overall and last shell) | 9.2 (104.7) |
| Mean I/sigma (overall and last shell) | 11.2 (1.1) |
| CC(½) (overall and last shell) | 0.998 (0.429) |
| Space group | P212121 |
| Unit cell parameters (Å), (°) | 67.89 73.28 93.62 90.00 90.00 90.00] |
| Refinement program | REFMAC5 |
| Resolution range (Å) | 46.81-1.50 |
| Number of reflections (working/test) | 71309/3845 |
| $R_{work}$ (%) | 16.8 |
| $R_{free}$ (%) | 20.5 |
| Protein residues modeled | 418 |
| Number of protein atoms modeled | 3320 |
| Number of water atoms modeled | 721 |
| RMSD Bond lengths (Å) | 0.012 |
| RMSD Bond angles (°) | 1.690 |
| Mean protein B value (Å2) | 16.4 |
| Mean water B value (Å2) | 29.1 |
| Ramachandran plot favored (%) | 97.85 |
| Ramachandran plot allowed (%) | 1.67 |
| Ramachandran plot outlier region (%) | 0.48 |

Example 10: Crystal Structure of the Fab of Antibody Clone ADI-61278

The X-ray crystal structure of Fab antibody clone ADI61278, comprising a heavy chain and light chain variable domain, in complex with fibrinogen gamma peptide P2 was solved at 1.8 Å resolution. The crystal described was grown using the hanging drop method of vapour diffusion in a 96 well plate with a precipitant solution containing 1% (w/v) Tryptone, 0.001 M sodium azide, 0.05 M sodium HEPES pH 7.0 and 20% PEG 3350. The crystal was cryo-cooled by brief transfer into a solution containing four parts precipitant solution and one part 100% (v/v) glycerol, before capturing it in a loop and plunging it into liquid nitrogen. A data set was collected at the Diamond Light Source (DLS), beamline i03.

Data processing in MOSFLM (Battye et al., 2011) (CCP4) and AIMLESS (Evans & Murshudov, 2013) (CCP4) indicated that the most likely space group was P21221 with unit cell dimensions a=47.0 Å, b=79.0 Å, c=144.3 Å and α=β=γ=90.0°, giving a total cell volume of 534840.2 Å3. Calculation of the Matthews coefficient (2.8 Å3/Da and 55.8% solvent content) indicated that there was most probably one complete Fab-ADI61278-P2 complex per asymmetric unit. The Fab-ADI61278 model was chosen for use in molecular replacement (MR). The large number of Fab crystal structures in the PDB has revealed a large variety in the elbow angles present between variable and constant domains. This variety in elbow angles can cause the overall tertiary structure of two otherwise highly homologous Fab fragments to be significantly different, which in turn causes MR to fail. For this reason, the hinge regions between the variable and constant domains of the heavy and light chains were removed. Two separate MR search ensembles were generated (VH-VL heterodimer and CH-CL heterodimer). Both of the input search ensembles that were required to build a complete Fab were correctly located by MR using PHASER (McCoy et al., 2007) (CCP4). The MR output model was given 30 cycles of jelly body refinement using REFMAC5 (Vagin et al., 2004) (CCP4). The protein sequence was mutated to match that of Fab-ADI61278 using CHAINSAW (Stein, 2008) (CCP4). The Fab ADI61278 model was improved iteratively through successive cycles of model building and refinement until all of the ordered regions of protein visible in the electron density maps were complete. The peptide P2 chain was added to the model by hand in COOT and the complete complex model was refined in REFMAC5. The final protein model contained residues 410-421 from chain A (peptide P2), 1-126 and 133-214 from chain H (Fab heavy chain) and 1-213 from chain L (Fab light chain). Final Rwork=19.1%, Rfree=24.0%.

There was one copy each of Fab ADI61278 and peptide P2 per asymmetric unit. The Fab ADI61278 CDR canonical structures were analysed in accordance with the PyIgClassify database (Adolf-Bryfogle et al., 2014). The heavy chain CDRs were classified as follows: H1-13-1 (CDR-length-cluster), H2-10-1 and H3-8-1. The light chain CDRs were classified as follows: L1-16-1, L2-8-1 and L3-9-cys7-1. Each P2 peptide bound to a single Fab. The fold is similar to, but not the same as that seen in published fibrinogen gamma chain crystal structures such as PDB ID: 1fzc.

TABLE 7

Fab ADI-61278 and peptide P2 interface analysis

| Monomer 1 | Length (Å) | Monomer 2 |
|---|---|---|
| A:LYS 411 [NZ] | 2.71 | H:ASP 54 [OD2] |
| A:LYS 411 [NZ] | 2.74 | H:ASP 52 [OD2] |
| A:LYS 411 [NZ] | 3.34 | H:ASP 54 [OD1] |
| A:ASN 416 [O] | 3.31 | H:ASP 96 [N] |
| A:ASN 416 [O] | 3.65 | H:ASP 96 [OD1] |
| A:ASN 416 [O] | 3.62 | H:ASP 96 [OD2] |
| A:ASN 416 [OD1] | 3.22 | L:GLN 50 [NE2] |
| A:ARG 417 [NE] | 3.25 | H:TRP 33 [NE1] |
| A:ARG 417 [NE] | 4.00 | H:ASP 96 [OD1] |
| A:ARG 417 [NH1] | 3.75 | H:TRP 33 [NE1] |
| A:ARG 417 [NH1] | 3.32 | H:SER 31 [O] |
| A:ARG 417 [NH2] | 3.08 | H:SER 31 [O] |
| A:ARG 417 [NH2] | 3.87 | H:SER 95 [OG] |
| A:ARG 417 [NH2] | 2.90 | H:ASP 96 [OD1] |
| A:ARG 417 [NH2] | 3.71 | H:ASP 96 [OD2] |
| A:ARG 417 [O] | 2.78 | H:HIS 35 [NE2] |
| A:THR 419 [O] | 3.13 | H:ASP 96 [N] |
| A:THR 419 [O] | 3.83 | H:HIS 35 [NE2] |
| A:ILE 420 [N] | 3.48 | L:TYR 36 [OH] |
| A:ILE 420 [O] | 2.57 | L:TYR 36 [OH] |
| A:GLY 421 [N] | 2.71 | H:SER 94 [O] |
| A:GLY 421 [O] | 3.64 | H:THR 98 [N] |
| A:GLY 421 [O] | 2.94 | H:GLY 101 [N] |
| A:GLY 421 [OXT] | 3.96 | H:ASP 96 [N] |
| A:GLY 421 [OXT] | 3.62 | H:SER 94 [O] |
| A:GLY 421 [OXT] | 3.58 | H:SER 95 [O] |
| A:GLY 421 [OXT] | 3.00 | H:THR 98 [N] |
| A:GLY 421 [OXT] | 3.89 | H:THR 98 [OG1] |
| A:GLY 421 [OXT] | 3.63 | H:GLY 101 [N] |
| A:GLY 421 [OXT] | 3.02 | H:ALA 97 [N] |

TABLE 8

List of participating interface residues

| Peptide P2 | Fab ADI-61278 |
|---|---|
| A:LYS 411 | H:SER 31 |
| A:ILE 413 | H:TYR 32 |
| A:PHE 415 | H:TRP 33 |
| A:ASN 416 | H:HIS 35 |
| A:ARG 417 | H:TRP 47 |
| A:LEU 418 | H:ASP 52 |
| A:THR 419 | H:ASP 54 |
| A:ILE 420 | H:TYR 56 |
| A:GLY 421 | H:SER 94 |

TABLE 8-continued

List of participating interface residues

| Peptide P2 | Fab ADI-61278 |
|---|---|
| | H:SER 95 |
| | H:ASP 96 |
| | H:ALA 97 |
| | H:THR 98 |
| | H:GLY 101 |
| | H:GLY 102 |
| | H:TRP 103 |
| | L:HIS 27 |
| | L:TYR 32 |
| | L:TYR 36 |
| | L:LEU 46 |
| | L:TYR 49 |
| | L:GLN 50 |
| | L:ALA 91 |
| | L:LEU 92 |
| | L:LEU 94 |
| | L:LEU 96 |

TABLE 9

Data collection, processing statistics and refinement statistics

| | |
|---|---|
| Synchrotron, Beam line | DLS, i03 |
| Date of data collection | 24 Sep. 2021 |
| Wavelength (Å) | 0.9763 |
| Detector type | DECTRIS EIGER2 XE 16M |
| Transmission (%) | 23.84 |
| Temperature (K) | 100 |
| Exposure time (s) | 0.004 |
| Oscillation range per frame (°) | 0.10 |
| Overall rotation (°) | 360 |
| Resolution range (Å) (overall and last shell) | 44.65-1.80 (1.84-1.80) |
| Number of observed reflections (overall and last shell) | 681993 (41185) |
| Number of unique reflections (overall and last shell) | 50679 (2967) |
| Multiplicity (overall and last shell) | 13.5 (13.9) |
| Completeness (%) (overall and last shell) | 100.0 (100.0) |
| $R_{merge}$ (%) (overall and last shell) | 9.5 (175.5) |
| Mean I/sigma (overall and last shell) | 14.7 (1.4) |
| CC(½) (overall and last shell) | 0.999 (0.669) |
| Space group | P21221 |
| Unit cell parameters (Å), (°) | 46.95 78.96 144.26 90.00 90.00 90.00 |
| Refinement program | REFMAC5 |
| Resolution range (Å) | 44.65-1.80 |
| Number of reflections (working/test) | 48037/2583 |
| $R_{work}$ (%) | 19.1 |
| $R_{free}$ (%) | 24.0 |
| Protein residues modeled | 419 |
| Number of protein atoms modeled | 3310 |
| Number of water atoms modeled | 421 |
| RMSD Bond lengths (Å) | 0.005 |
| RMSD Bond angles (°) | 1.300 |
| Mean protein B value (Å2) | 32.9 |
| Mean water B value (Å2) | 42.3 |
| Ramachandran plot favored (%) | 97.61 |
| Ramachandran plot allowed (%) | 2.15 |
| Ramachandran plot outlier region (%) | 0.24 |

Figure 17:
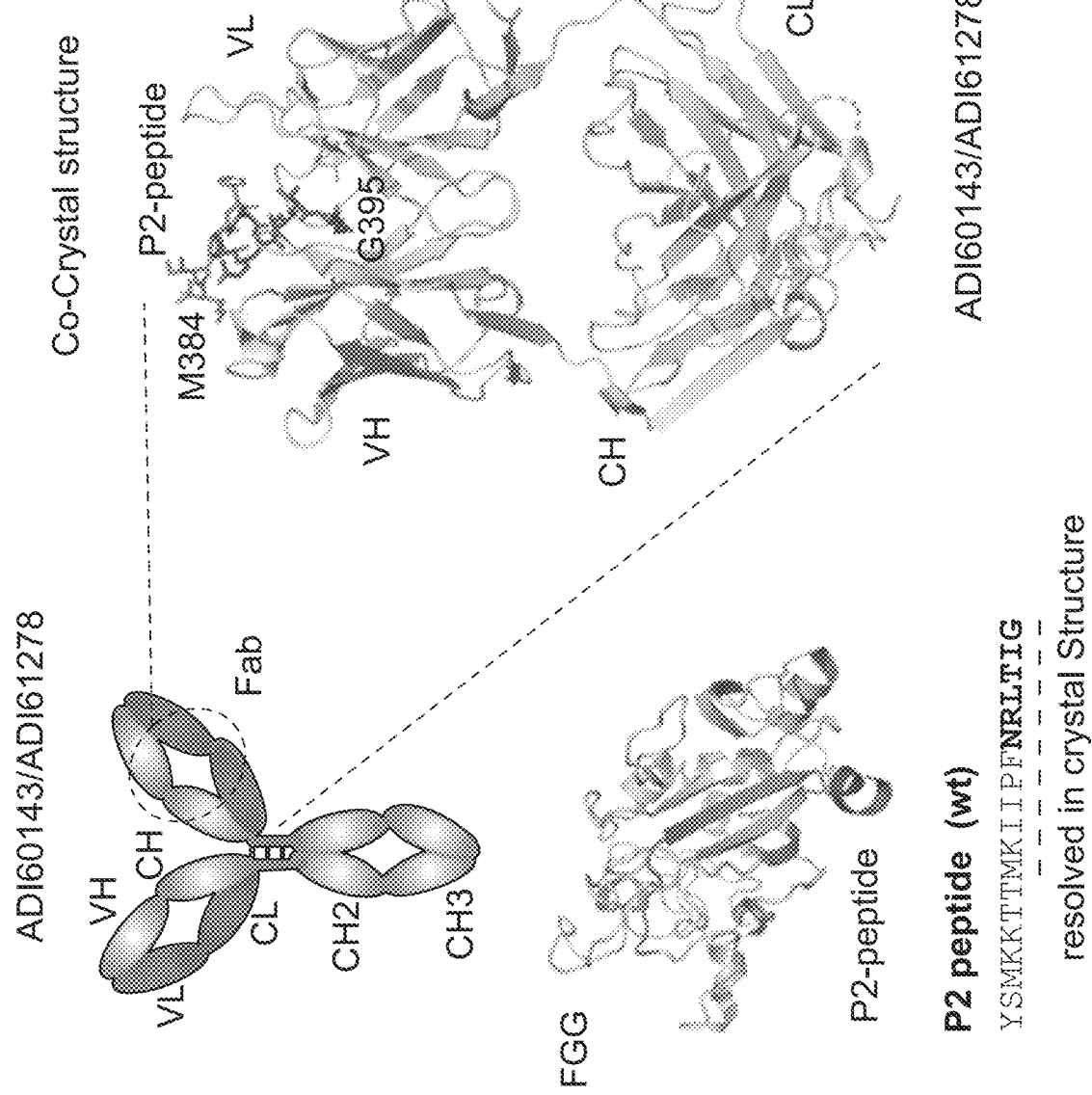
FIG. 17 is a diagram depicting the crystal structure of the Fab of antibody clone 60143 (ADI60143) and antibody clone 61278 (ADI61278) in complex with P2 peptide (co-crystal-right). The structure of Fibrinogen (FGG) and the location of P2-peptide are also shown (bottom left). Figure discloses SEQ ID NO: 241.
Figure 18:
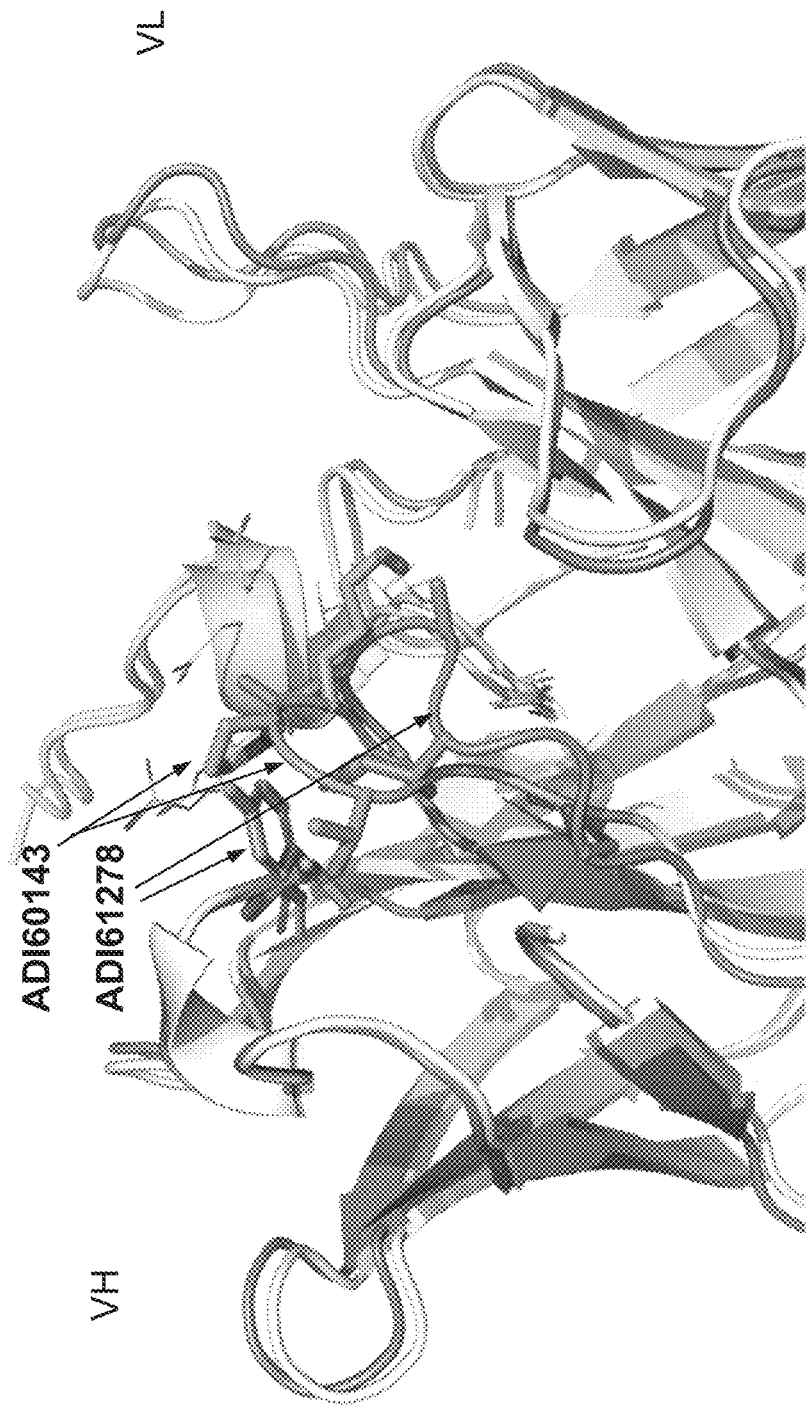
FIG. 18 is a diagram depicting the superimposed structures of the Fab of antibody clone 60143 (ADI60143) and antibody clone 61278 (ADI61278) in complex with P2 peptide. Figure discloses SEQ ID NOS 255, 2, 256-257, 2, and 258, respectively, in order of appearance.

Example 11: ADI-60143 and ADI-61278-Fabs Both Bind at the C-Terminus of P2-Peptide and Show Most Differences in the CDR-3 Regions The crystal structures of the FABs of antibody clones ADI-60143 and ADI-61278 described above were superimposed and the P2 peptide binding sites were compared as shown in FIGS. 17 and 18. These results show that ADI-60143 and ADI-61278-Fabs both bind at the C-terminus of P2-Peptide and also show most differences are located in the CDR-3 Regions of the two Fabs.

Figure 19:
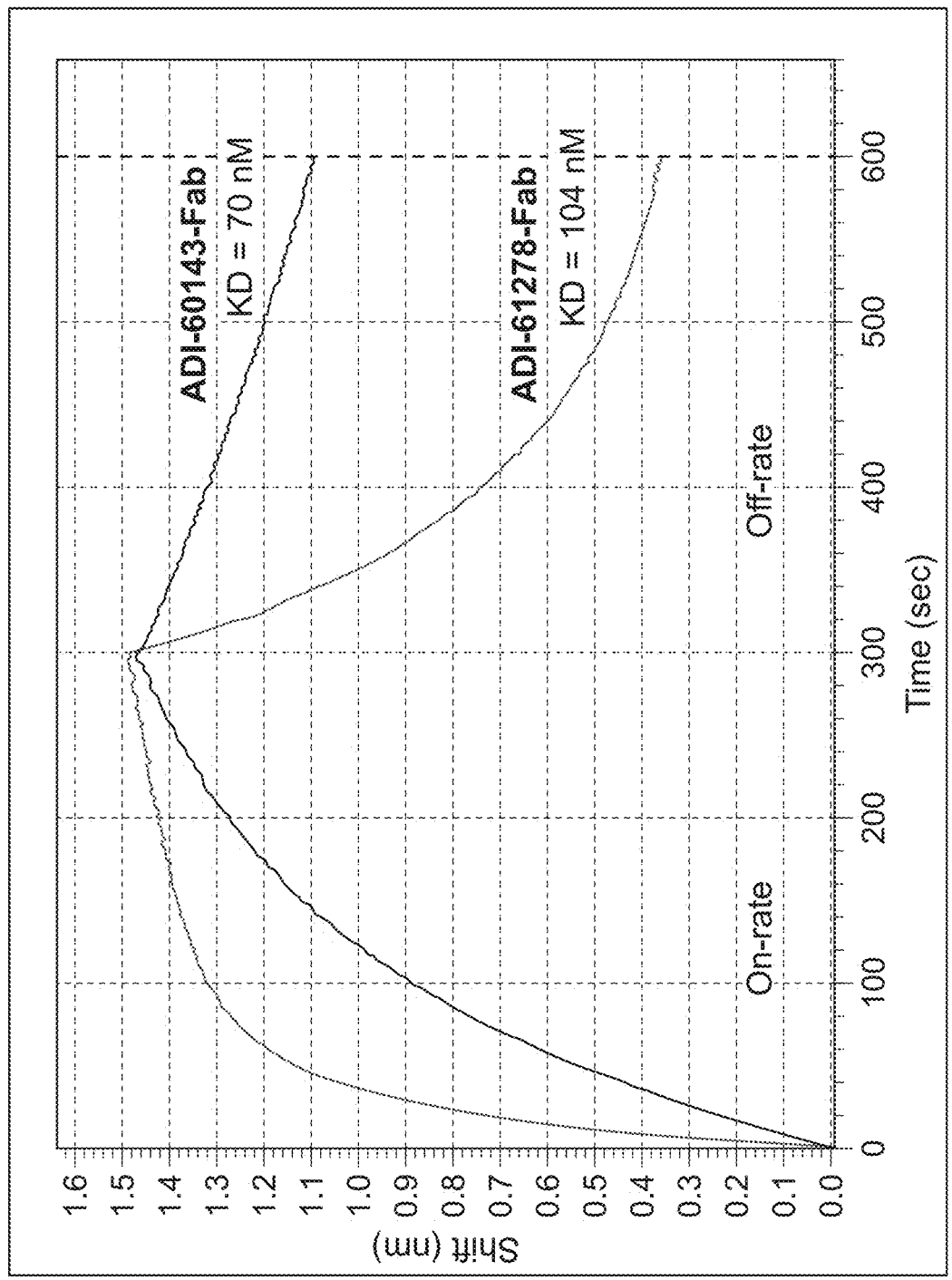
FIG. 19 is a graph depicting the binding affinity of antibody clone 60143 (ADI60143) and antibody clone 61278 (ADI61278). The binding of the ADI-60143 and ADI-61278 Fabs to P2 peptide was determined using Octet RED384.

The binding of the ADI-60143 and ADI-61278 Fabs to P2 peptide was determined as described in Example 2 using Octet RED384 (FIG. 19). Amino acid variations in CDR1 and CDR3 explain differences in binding on- and off-rates between ADI-60143 and ADI-61278-Fabs interacting with P2-peptide.

Figures 20A, 20B:
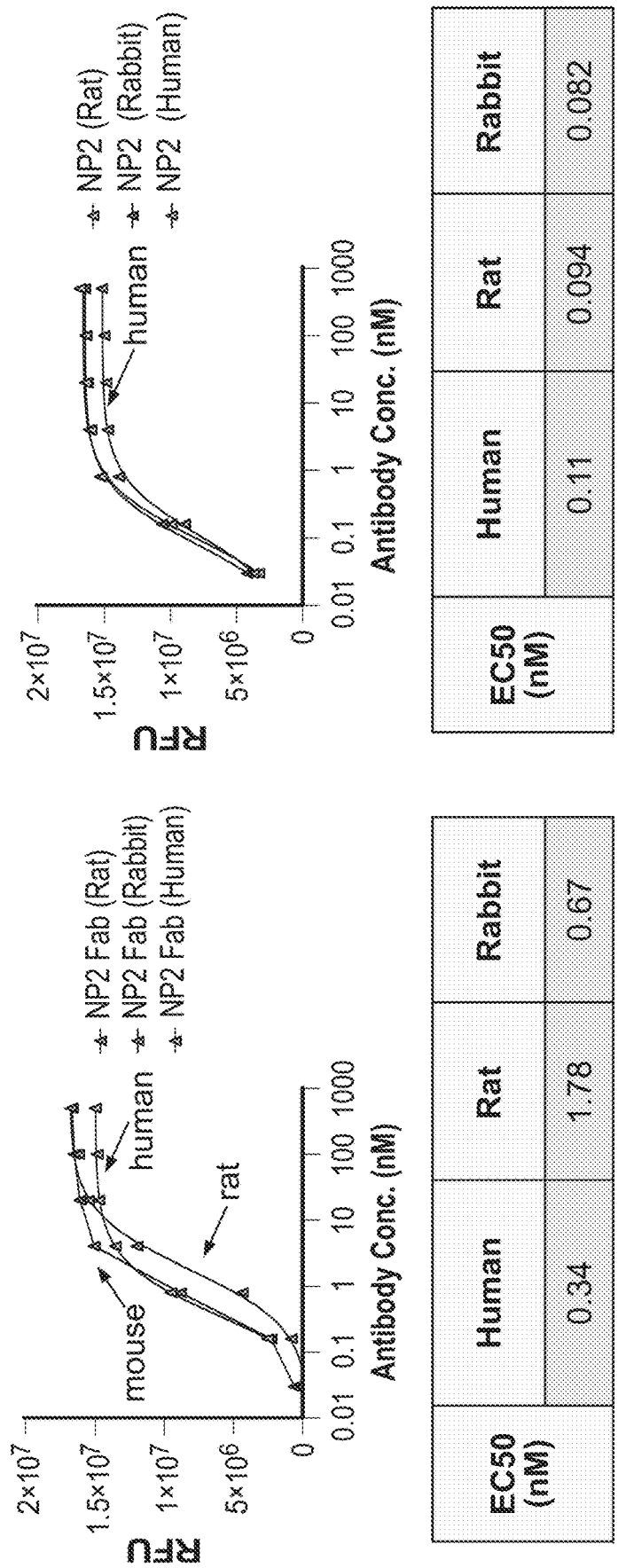
FIG. 20A is a graph depicting binding of ADI-60143 Fab to rat, mouse or human P2 peptide determined by ELISA.
FIG. 20B is a graph depicting binding of ADI-60143 IgG to rat, mouse or human P2 peptide determined by ELISA.
Figure 21:
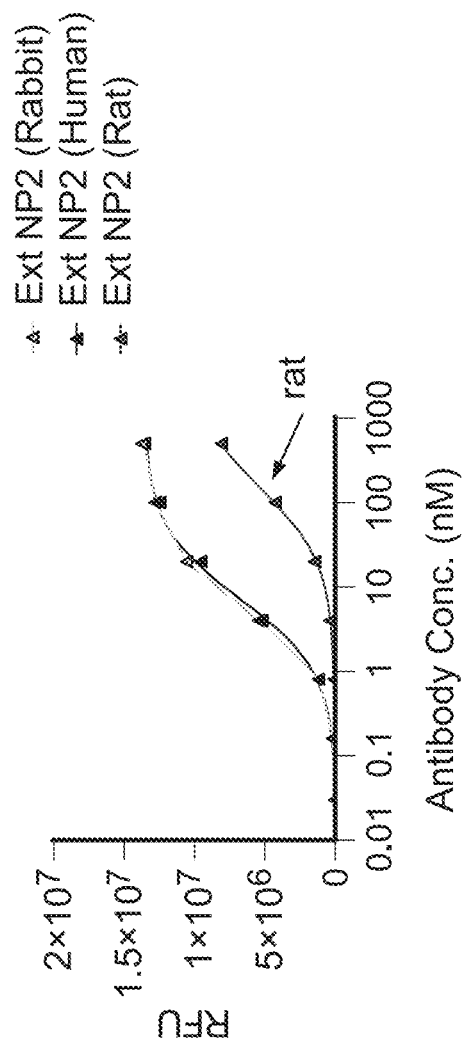
Figure 23:
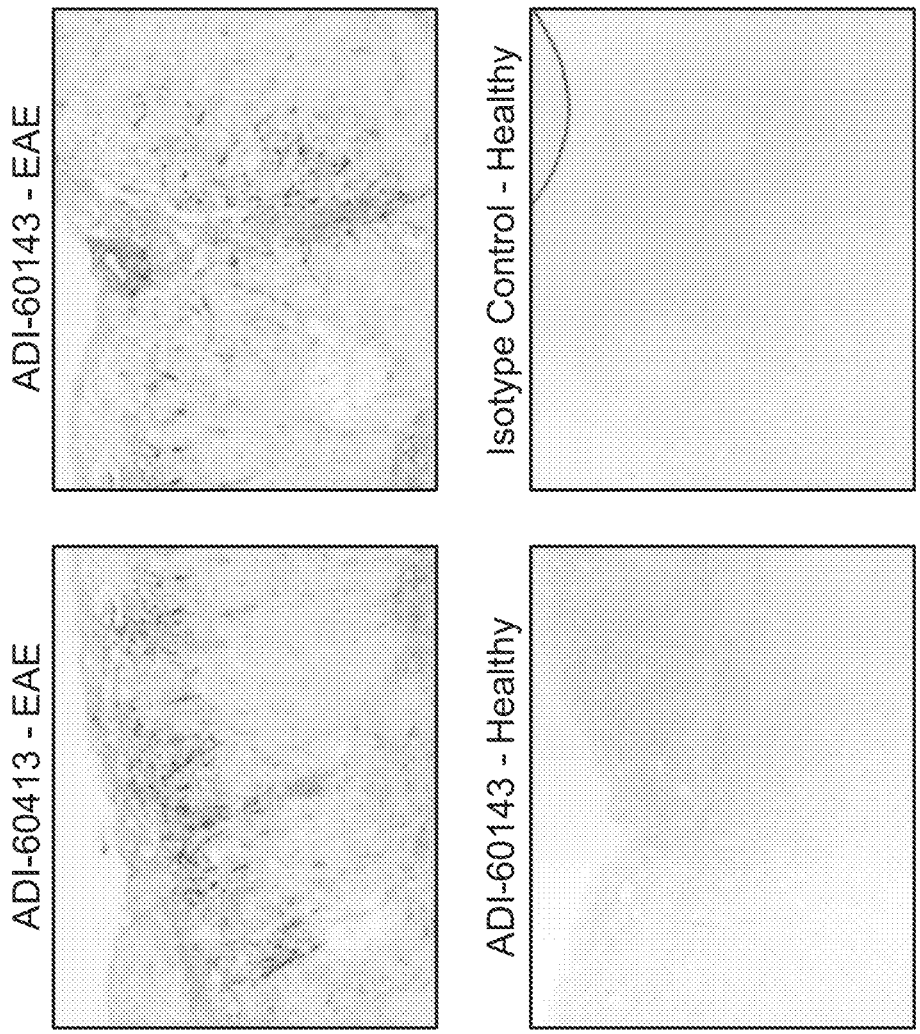
FIG. 23 are images showing tissue sections from spinal cords of healthy and EAE mice stained for ADI-60143.

Binding of ADI-60143 Fab and full length ADI-60143 IgG to rat, mouse or human P2 peptide and extended P2 peptide was also determined by ELISA (FIGS. 20 and 21). Similar binding profiles were observed for the three P2 peptides from the different species. However, the extended P2 peptide of the three species, did not bind well to ADI-60143 IgG (FIG. 21).

Example 12: Therapeutic Treatment with ADI-60143 Inhibits Microglia Activation and Macrophage Recruitment in Fibrin-Induced Encephalitis (FIE) PD Model In order to test the efficacy of the affinity matured antibody clones for inhibition of microglia activation and macrophage recruitment in treatment of neural degenerative disease and inflammation, a mouse model of fibrin-induced encephalitis (FIE) was used. Six mice per group, for a total of 78 mice, were administered fibrinogen by stereotaxic injection into the corpus callosum. Antibodies were administered by intravenous (IV.) injection. Four hrs after fibrinogen injection, mice were given an I.V. injection of the affinity matured anti-fibrin humanized antibodies (10 mg/kg or 30 mg/kg). Brain tissue was prepared at three days post-injection. 73 mice samples were included for immunohistochemistry and quantification. Coronal sections (30 um) were prepared on the Cryostat. Sections were incubated with anti-Iba-1 antibody (Microglia marker, 1:750) to detect microglial activation and anti-Mac-2 antibody (Macrophage infiltration marker, 1:750). Immunoreactivity of Iba-1 (Iba-1+ area) and Mac-2 (Mac-2+ area) was then calculated, and image collection and quantification was performed in a blinded manner.

As shown in FIGS. 22A-22C, there was a significant reduction in both microglia activation and macrophage recruitment in mice injected with 30 mg/kg ADI-60143. The reduction was also greater than what was measured in mice injected with the parental humanized 5B8 antibody (THN227), that had not undergone affinity maturation. These results confirm that the affinity matured antibody clone 60143 is therapeutically efficacious for the inhibition of microglia activation and macrophage recruitment for treatment of neural degenerative disease or conditions and/or neural inflammation.

Example 13: Antibody Clone ADI-60143 is Efficacious in a Preclinical Model of Multiple Sclerosis In order to test the therapeutic efficacy of the affinity matured antibody clones for treatment of multiple sclerosis (MS), a pre-clinical mouse of model of MS, experimental autoimmune encephalomyelitis (EAE) was used. EAE was induced by immunization of $PLP_{139-151}$/CFA (Hooke Kit™ $PLP_{139-151}$/CPA Emulsion, catalog number EK-0120, Hooke Laboratories, Lawrence MA) on day zero. EAE mice were therapeutically injected starting on day 2 and lasting through day 44 for dexamethasone and through day 33 for all other groups, with PBS alone, isotype control-human IgG1 (hu-IgG) alone, antibody clone 60143 (ABI-60143) or dexamethasone by intraperitoneal injection at 5 mg/kg, two times per week. Spinal cord tissue from the mice was harvested from mice with EAE at peak disease or heathy mice, and immunohistochemical (IHC) staining of the spinal cord tissue was performed to determine antibody drug distribution to the spinal tissue and demyelination.

For the IHC staining, freshly harvested, non-fixed tissue was placed in OCT compound inside a cryomold. The cryomold was placed in isopentane mixed with dry ice for freezing, and the frozen tissue kept at −80° C. Tissue sections were cut 10 μm thick in a cryostat and mounted on slides. Slides were stained by fixing immediately in ice-cold 4% para-formaldehyde in PBS for 10 minutes at 4° C. Slides were blocked in non-specific binding of primary antibodies to the tissue by incubating in blocking buffer (3% bovine serum albumin in PBS; Millipore Sigma, A9576) for 30 minutes at 25° C. To detect biotinylated antibody injected in tissue prior to sectioning, Cy3-conjugated streptavidin (1:100; SA1010, Thermo Fischer Scientific) was diluted in PBS, applied to tissue sections, and incubated for 30 minutes at 25° C. For fibrin staining, antibody (1:2000, rabbit polyclonal anti-fibrinogen) diluted in PBS was added to tissue sections and incubated for 60 minutes at 25° C. FITC donkey anti-rabbit IgG (1:500 in PBS, Jackson ImmunoResearch) was then added to each section, and incubated for 30 minutes at 25° C.

Figure 24B:
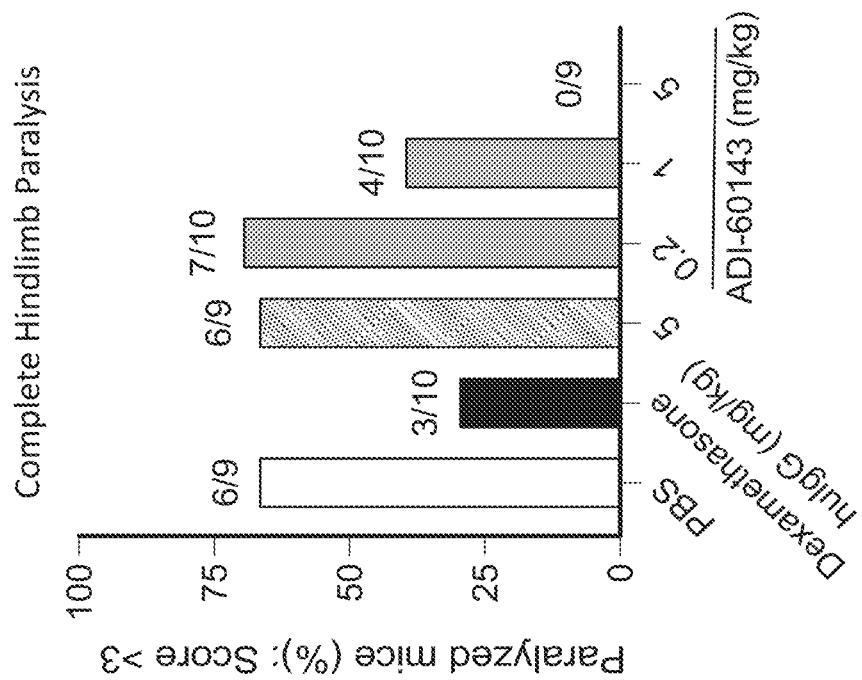
FIG. 24B is a graph depicting percent of EAE mice exhibiting complete hindlimb paralysis administered PBS, dexamethasone (DEXA), and 0.2, 1 or 5 mg/Kg antibody clone ADI-60143.
Figure 24A:
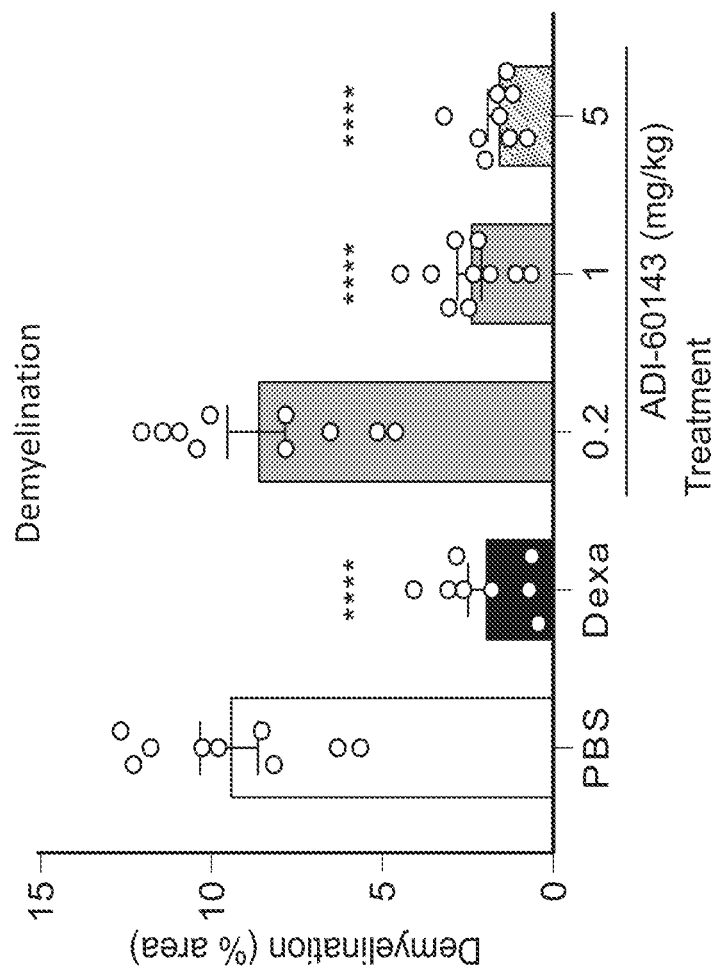
FIG. 24A is a graph depicting demyelination determined by MBP staining of tissue sections from spinal cords of EAE mice administered PBS, dexamethasone (DEXA), and 0.2, 1 or 5 mg/Kg antibody clone ADI-60143.

As shown in FIGS. 24A-24B, the affinity matured antibody (ABI-60143), was localized to the spinal cord in EAE mice at peak disease. This confirms that the affinity matured antibodies are well distributed to the diseased spinal tissue.

Percent demyelination of tissue sections was quantified by determination of the percent area lacking staining of myelin basic protein (MBP). As shown in FIG. 24A, the percent demyelination was significantly reduced in a dose dependent manner in mice administered antibody clone 60143.

The mice were also assessed for hind limb paralysis and clinical score. As shown in FIG. 24B, there was dose-dependent decrease in demyelination and complete hind limb paralysis in EAE mice administered the affinity matured antibody clone 60143.

EAE Clinical score was assessed by the criteria as shown in the Table below:

| Score | Clinical Observations |
|---|---|
| 0 | No obvious changes in motor functions of the mouse in comparison to non-immunized mice. When picked up by the tail, the tail has tension and is erect. Hind legs are usually spread apart. When the mouse is walking, there is no gait or head tilting. |
| 1 | Limp tail. When the mouse is picked up by the tail, instead of being erect, the whole tail drapes over your finger. |
| 2 | Limp tail and weakness of hind legs. When mouse is picked up by tail, legs are not spread apart, but held closer together. When the mouse is observed when walking, it has aberrant wobbly walk. |
| 3 | Limp tail and complete paralysis of hind legs (most common). OR Limp tail with paralysis of one front and one hind leg. OR ALL of: Severe head tilting, Walking only along the edges of the cage, Pushing against the cage wall, Spinning when picked up by the tail. |

-continued

| Score | Clinical Observations |
|---|---|
| 4 | Limp tail, complete hind leg and partial front leg paralysis. Mouse is minimally moving around the cage but appears alert and feeding. Usually, euthanasia is recommended after the mouse scores level 4 for 2 days. When the mouse is euthanized because of severe paralysis, score of 5 is entered for that mouse for the rest of the experiment. |
| 5 | Complete hind and complete front leg paralysis, no movement around the cage. OR Mouse is spontaneously rolling in the cage. OR Mouse is found dead due to paralysis. |

Figure 25:
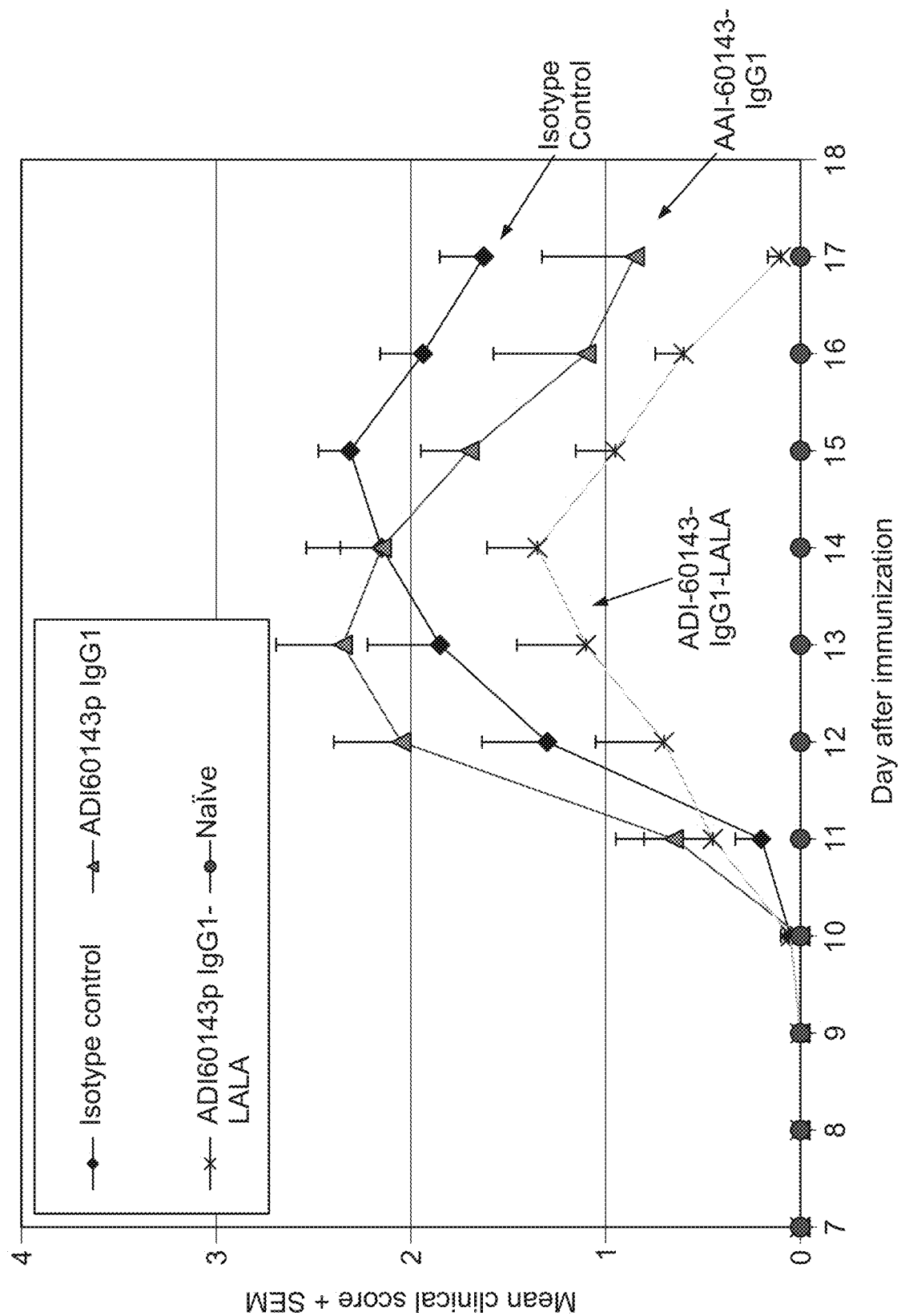
FIG. 25 is a graph depicting clinical score of EAE mice administered isotype control, antibody clone ADI-60143 IgG, and antibody clone ADI-60143—with Fc stabilization LALA mutations, and naïve mice with no EAE induction.

Both negative control groups (Vehicle and Isotype control) developed EAE as expected for this model. Mean maximum severity (MMS) of the first wave of EAE was 2.4 and 2.5 for the Vehicle and the Isotype control group, respectively. The incidence of relapses was 73% and 60% for the Vehicle and the Isotype control group, respectively. MMS of the relapse period was 2.3 and 1.9 for the Vehicle and the Isotype control group, respectively. Disease in these groups had typical course and severity for this model. As shown in FIG. 25, mice administered ABI-60143-LALA IgG (antibody clone 60143 comprising Fc stabilization LALA mutations) developed reduced disease, as demonstrated by a significantly reduced mean EAE clinical score, with no detectable disease at 17 days after immunization.

Figure 26B:
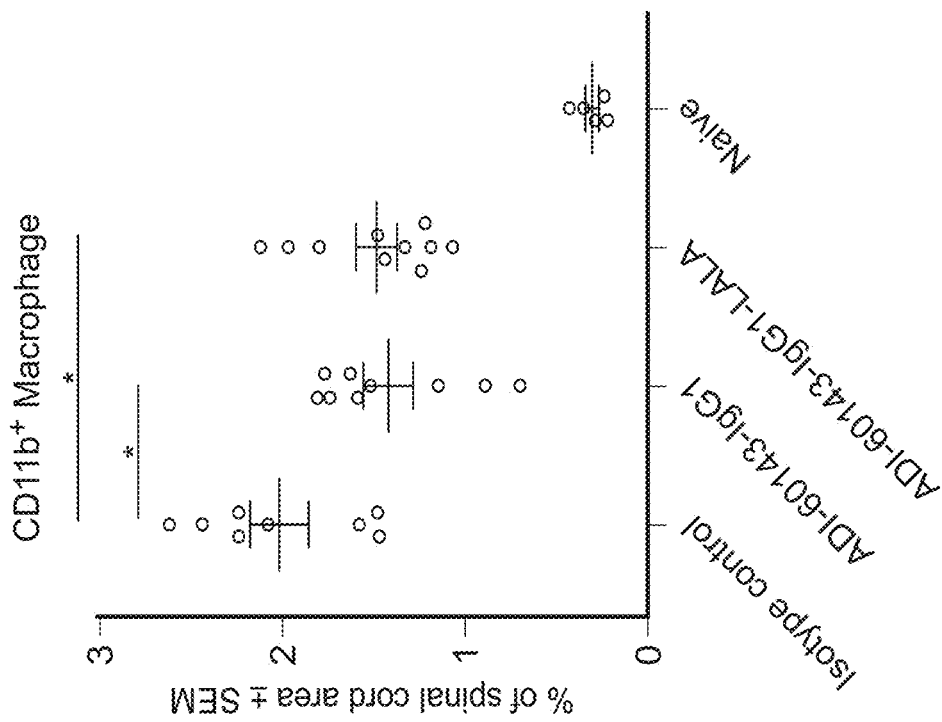
FIG. 26B is a graph depicting the percent CD11b+ area per tissue section of EAE mice administered isotype control, antibody clone ADI-60143 IgG, and antibody clone ADI-60143—with Fc stabilization LALA mutations, and naïve mice with no EAE induction.
Figure 26A:
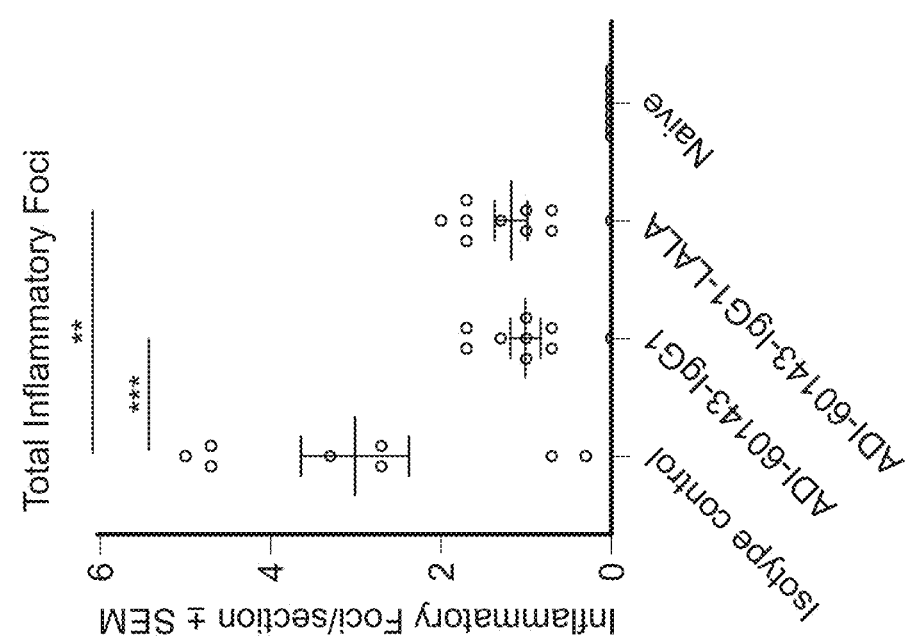
FIG. 26A is a graph depicting the average number of total inflammatory foci/spinal cord tissue section of EAE mice administered isotype control, antibody clone ADI-60143 IgG, and antibody clone ADI-60143—with Fc stabilization LALA mutations, and naïve mice with no EAE induction.

In order to confirm that the affinity matured antibodies reduced inflammation, segments from cervical, thoracic, and lumbar regions of spinal cord (3 segments) were prepared and stained with: H and E, and anti-CD4/anti-CD11b (dual-label) antibodies. Inflammatory foci of approximately 20 cells were counted in each H&E-stained section. When inflammatory infiltrates consisted of more than 20 cells, an estimate was made of how many foci of 20 cells were present. As shown in FIG. 26A, there was a significant reduction in the number of inflammatory foci in tissue sections from EAE mice administered antibody clone ABI-60143 IgG or ABI-60143-LALA IgG compared to isotype control. There was also a significant reduction in pro-inflammatory marker CD11b in tissue sections from EAE mice administered antibody clone ABI-60143 IgG or ABI-60143-LALA IgG compared to isotype control (FIG. 26B). These results confirm that the affinity matured antibodies ABI-60143 IgG and ABI-60143-LALA IgG are capable of reducing inflammation n a pre-clinical model of Multiple Sclerosis.

Taken together, these results confirm that the affinity matured humanized anti-fibrin antibody is therapeutically efficacious in a pre-clinical model of Multiple Sclerosis.

Example 14: Anti-Fibrin P2 Treatment Decreases Inflammation in Uveitis Model

Experimental autoimmune uveitis (EAU) is an organ specific autoimmune disease that targets the neural retina. This autoimmune response is induced when animals are immunized with retinal antigens (Interphotoreceptor Retinoid-Binding Protein [TRBP], in this case). In order to confirm the therapeutic role of anti-fibrin treatment in inflammatory eye conditions or diseases, the efficacy of the anti-fibrin affinity matured antibodies were tested in a rat experimental autoimmune uveitis (EAU) model after intravitreal administration of the anti-fibrin antibodies.

In this study, 52 Lewis rats were divided into six groups namely PBS (Group 1), Isotype control (Group 2), ABI-60143 low dose (Group 3), ABI-60143 high dose (Group 4), FTY-720 positive control (Group 5), and Naïve (Group 6). Animals from all groups, except Group 6, were immunized with an emulsion of RBP in Complete Freund's Adjuvant (CFA) on Day 0. Similarly, animals from Group 1-4 received a single intravitreal injection of sponsors test article once on Day 0. Animals in Group 5 received once daily oral administration of positive control FTY-720. After a period of 8-10 days, immunized animals developed uveitis in each eye. Clinical evaluations were performed for all the animals at baseline, day 4, 7, 11, and 14 to follow the extent of diseases developed. Clinical observations were performed as follows:
  Frequency: Once on each study day
  Procedure: Groups were randomized ahead of evaluations to keep the examiner masked.
  Animals were observed under a dissection microscope and scored on a scale of 0-4 based on their anterior clinical disease. Photographs of the anterior chamber were taken at the time of clinical evaluations.
Clinical Observation Scoring:
  0-0.5: No disease; eye is translucent. Some blood vessels in the iris may be dilated.
  1: Engorged blood vessels in iris; abnormal pupil contraction (or dilation).
  2: Slight haziness to the anterior chamber.
  3: Moderately opaque anterior chamber, but pupil still visible.
  4: Opaque anterior chamber and obscured pupil.

All animals were euthanized on day 14 and immediately following euthanasia, whole eyes (OU) were collected, Upon verification of death, both eyes of each animal were carefully removed. One eye was collected for histological analysis, and the other eye was collected for cytokine analysis. Eyes for cytokine analysis were hemisected and retina was collected. Each eye was carefully orientated for optimal microscopic examination prior to wax embedding. Sections (5 µm) were cut and stained with hematoxylin and eosin for histological examination and scoring according to the following scale summarized below and as described by Caspi, et al. (2012). Histological analysis was masked to the examiner.
Clinical Scoring/Uveitis grading was determined as follows:
  0: No disease, normal retinal architecture.
  0.5: Trace. <¼ Mild inflammatory cell infiltration of the retina with or without photoreceptor damage.
  1: ≥¼ Mild inflammation and/or photoreceptor outer segment damage.
  2: ≥¼ Mild to moderate inflammation and/or lesion extending to the outer nuclear layer.
  3: ≥¼ Moderate to marked inflammation and or lesion extending to the inner nuclear layer.
  4: ≥¼ Severe inflammation and/or full-thickness retinal damage.

Figure 27:
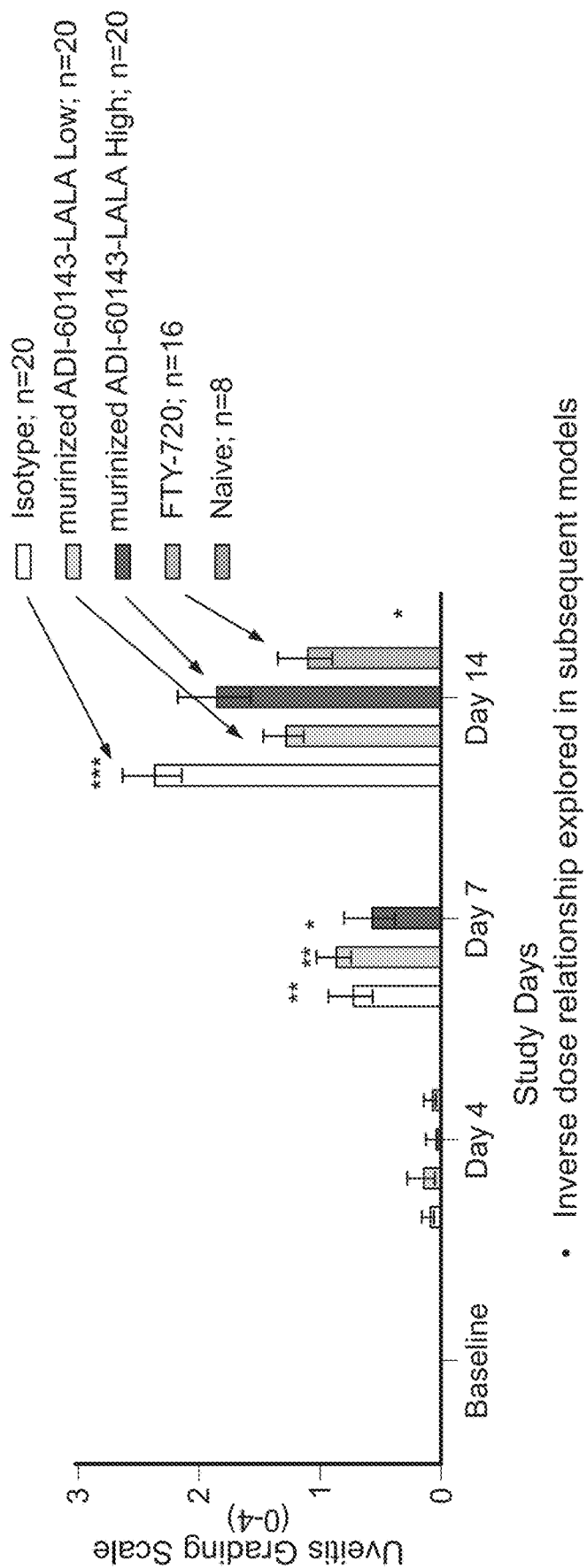
FIG. 27 is a graph depicting the uveitis clinical score of rats administered intravitreally isotype control, murinized antibody clone ADI-60143—with Fc stabilization LALA mutations (low dose=10 ug/eye; high dose=50 ug/eye), positive control FTY-720 (administered by oral gavage at a dose of 0.3 mg/kg) and naïve mice with no EAE induction.

As shown in FIG. 27, rats administered a low or high dose of the murinized ADI-60143-LALA Fc stabilized antibody clone exhibited a significantly reduced clinical uveitis score on day 14 of the study. These results confirm that the affinity matured anti-fibrin antibodies decreased inflammation in subjects with uveitis and are therapeutically effective in a pre-clinical model of eye conditions related to vascular defects of the eye, such as uveitis.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

INFORMAL SEQUENCE LISTING

| Description | Sequence | SEQ ID NO |
|---|---|---|
| 56666 CDR-H1 | YTFTSYWIH | SEQ ID NO: 1 |
| 56666 CDR-H2 | LIDPSDSYTNYNQKFRG | SEQ ID NO: 2 |
| 56666 CDR-H3 | ASSDPTGG | SEQ ID NO: 3 |
| 56666 CDR-L1 | RSSKSLLHSSGITYLS | SEQ ID NO: 4 |
| 56666 CDR-L2 | QMSNLAS | SEQ ID NO: 5 |
| 56666 CDR-L3 | AQNLELPLT | SEQ ID NO: 6 |
| 56666 VH | QVQLVQSGAEVKKPGASVKVSCKASGYTFTSYWIHWVRQAPGQGLEWMGLIDPSDSYTNYNQKFRGRVTMTVDTSTSTAYMELSSLRSEDTAVYYCASSDPTGGWGQGTTVTVSS | SEQ ID NO: 7 |
| 56666 CH | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | SEQ ID NO: 8 |
| 56666 CL | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 9 |
| 56666 VL | DIVMTQSPLSLPVTPGEPASISCRSSKSLLHSSGITYLSWYLQKPGQSPQLLIYQMSNLASGVPDRFSGSGSGTDFTLKISRVEAEDVGVYYCAQNLELPLTFGGGTKVEIK | SEQ ID NO: 10 |
| 56666 VH + CH | QVQLVQSGAEVKKPGASVKVSCKASGYTFTSYWIHWVRQAPGQGLEWMGLIDPSDSYTNYNQKFRGRVTMTVDTSTSTAYMELSSLRSEDTAVYYCASSDPTGGWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | SEQ ID NO: 11 |
| 56666 VL + CL | AEDVGVYYCAQNLELPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 12 |
| 61289 CDR-H1 | YTFTSSWIH | SEQ ID NO: 13 |
| 61289 CDR-H2 | LIDPSDSYTNYNQKFRG | SEQ ID NO: 14 |
| 61289 CDR-H3 | ASSDPHGG | SEQ ID NO: 15 |
| 61289 CDR-L1 | RSSKSLLHSSGITMLS | SEQ ID NO: 16 |
| 61289 CDR-L2 | QMSNLAS | SEQ ID NO: 17 |
| 61289 CDR-L3 | AQSLELPLT | SEQ ID NO: 18 |

-continued

| Description | Sequence | SEQ ID NO |
|---|---|---|
| 61289 VH | QVQLVQSGAEVKKPGASVKVSCKASGYTFTSSWIHWVRQAPGQGLEW MGLIDPSDSYTNYNQKFRGRVTMTVDTSTSTAYMELSSLRSEDTAVYYC ASSDPHGGWGQGTTVTVSS | SEQ ID NO: 19 |
| 61289 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 20 |
| 61289 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 21 |
| 61289 VL | DIVMTQSPLSLPVTPGEPASISCRSSKSLLHSSGITMLSWYLQKPGQSPQL LIYQMSNLASGVPDRFSGSGSGTDFTLKISRVEAEDVGVYYCAQSLELP LTFGGGTKVEIK | SEQ ID NO: 22 |
| 61289 VH + CH | QVQLVQSGAEVKKPGASVKVSCKASGYTFTSSWIHWVRQAPGQGLEW MGLIDPSDSYTNYNQKFRGRVTMTVDTSTSTAYMELSSLRSEDTAVYYC ASSDPHGGWGQGTTVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG | SEQ ID NO: 23 |
| 61289 VL + CL | DIVMTQSPLSLPVTPGEPASISCRSSKSLLHSSGITMLSWYLQKPGQSPQL LIYQMSNLASGVPDRFSGSGSGTDFTLKISRVEAEDVGVYYCAQSLELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 24 |
| 61275 CDR-H1 | YTFTSSWIH | SEQ ID NO: 25 |
| 61275 CDR-H2 | LIDPSDSYTNYNQKFRG | SEQ ID NO: 26 |
| 61275 CDR-H3 | ASSAPTGG | SEQ ID NO: 27 |
| 61275 CDR-L1 | RSSKSLLHSSGITYLS | SEQ ID NO: 28 |
| 61275 CDR-L2 | QMSNLAS | SEQ ID NO: 29 |
| 61275 CDR-L3 | AQALELPLT | SEQ ID NO: 30 |
| 61275 VH | QVQLVQSGAEVKKPGASVKVSCKASGYTFTSSWIHWVRQAPGQGLEW MGLIDPSDSYTNYNQKFRGRVTMTVDTSTSTAYMELSSLRSEDTAVYYC ASSAPTGGWGQGTTVTVSS | SEQ ID NO: 31 |
| 61275 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 32 |
| 61275 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 33 |
| 61275 VL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQALELP LTFGGGTKVEIK | SEQ ID NO: 34 |

| Description | Sequence | SEQ ID NO |
|---|---|---|
| 61275 VH + CH | QVQLVQSGAEVKKPGASVKVSCKASGYTFTSSWIHWVRQAPGQGLEW MGLIDPSDSYTNYNQKFRGRVTMTVDTSTSTAYMELSSLRSEDTAVYYC ASSAPTGGWGQGTTVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG | SEQ ID NO: 35 |
| 61275 VL + CL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQALELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 36 |
| 61278 CDR-H1 | YTFTSYWIH | SEQ ID NO: 37 |
| 61278 CDR-H2 | LIDPSDSYTNYNQKFRG | SEQ ID NO: 38 |
| 61278 CDR-H3 | ASSDATGG | SEQ ID NO: 39 |
| 61278 CDR-L1 | RSSKSLLHSSGITYLS | SEQ ID NO: 40 |
| 61278 CDR-L2 | QMSNLAS | SEQ ID NO: 41 |
| 61278 CDR-L3 | AQALELPLT | SEQ ID NO: 42 |
| 61278 VH | QVQLVQSGAEVKKPGASVKVSCKASGYTFTSYWIHWVRQAPGQGLEW MGLIDPSDSYTNYNQKFRGRVTMTVDTSTSTAYMELSSLRSEDTAVYYC ASSDATGGWGQGTTVTVSS | SEQ ID NO: 43 |
| 61278 CH | ASTKGPSVFPPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 44 |
| 61278 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 45 |
| 61278 VL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQALELP LTFGGGTKVEIK | SEQ ID NO: 46 |
| 61278 VH + CH | QVQLVQSGAEVKKPGASVKVSCKASGYTFTSYWIHWVRQAPGQGLEW MGLIDPSDSYTNYNQKFRGRVTMTVDTSTSTAYMELSSLRSEDTAVYYC ASSDATGGWGQGTTVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG | SEQ ID NO: 47 |
| 61278 VL + CL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQALELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 48 |

-continued

| Description | Sequence | SEQ ID NO |
|---|---|---|
| 61285 CDR-H1 | YTFTSSWIH | SEQ ID NO: 49 |
| 61285 CDR-H2 | LIDPSDSYTNYNQKFRG | SEQ ID NO: 50 |
| 61285 CDR-H3 | ASSDPHGG | SEQ ID NO: 51 |
| 61285 CDR-L1 | RSSKSLLHSSGITYLS | SEQ ID NO: 52 |
| 61285 CDR-L2 | QMSNLAS | SEQ ID NO: 53 |
| 61285 CDR-L3 | AQSLELPLT | SEQ ID NO: 54 |
| 61285 VH | QVQLVQSGAEVKKPGASVKVSCKASGYTFTSSWIHWVRQAPGQGLEWMGLIDPSDSYTNYNQKFRGRVTMTVDTSTSTAYMELSSLRSEDTAVYYCASSDPHGGWGQGTTVTVSS | SEQ ID NO: 55 |
| 61285 CH | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | SEQ ID NO: 56 |
| 61285 CL | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 57 |
| 61285 VL | DIVMTQSPLSLPVTPGEPASISCRSSKSLLHSSGITYLSWYLQKPGQSPQLLIYQMSNLASGVPDRFSGSGSGTDFTLKISRVEAEDVGVYYCAQSLELPLTFGGGTKVEIK | SEQ ID NO: 58 |
| 61285 VH + CH | QVQLVQSGAEVKKPGASVKVSCKASGYTFTSSWIHWVRQAPGQGLEWMGLIDPSDSYTNYNQKFRGRVTMTVDTSTSTAYMELSSLRSEDTAVYYCASSDPHGGWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | SEQ ID NO: 59 |
| 61285 VL + CL | DIVMTQSPLSLPVTPGEPASISCRSSKSLLHSSGITYLSWYLQKPGQSPQLLIYQMSNLASGVPDRFSGSGSGTDFTLKISRVEAEDVGVYYCAQSLELPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 60 |
| 61273 CDR-H1 | YTFTSTWIH | SEQ ID NO: 61 |
| 61273 CDR-H2 | LIDPSDSYTNYNQKFRG | SEQ ID NO: 62 |
| 61273 CDR-H3 | ASSKPTGG | SEQ ID NO: 63 |
| 61273 CDR-L1 | RSSKSLLHSSGITYIS | SEQ ID NO: 64 |
| 61273 CDR-L2 | QMSNLAS | SEQ ID NO: 65 |
| 61273 CDR-L3 | AQNLELPLT | SEQ ID NO: 66 |

| Description | Sequence | SEQ ID NO |
|---|---|---|
| 61273 VH | QVQLVQSGAEVKKPGASVKVSCKASGYTFTSTWIHWVRQAPGQGLEWMGLIDPSDSYTNYNQKFRGRVTMTVDTSTSTAYMELSSLRSEDTAVYYCASSKPTGGWGQGTTVTVSS | SEQ ID NO: 67 |
| 61273 CH | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | SEQ ID NO: 68 |
| 61273 CL | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 69 |
| 61273 VL | DIVMTQSPLSLPVTPGEPASISCRSSKSLLHSSGITYISWYLQKPGQSPQLLIYQMSNLASGVPDRFSGSGSGTDFTLKISRVEAEDVGVYYCAQNLELPLTFGGGTKVEIK | SEQ ID NO: 70 |
| 61273 VH + CH | QVQLVQSGAEVKKPGASVKVSCKASGYTFTSTWIHWVRQAPGQGLEWMGLIDPSDSYTNYNQKFRGRVTMTVDTSTSTAYMELSSLRSEDTAVYYCASSKPTGGWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | SEQ ID NO: 71 |
| 61273 VL + CL | DIVMTQSPLSLPVTPGEPASISCRSSKSLLHSSGITYISWYLQKPGQSPQLLIYQMSNLASGVPDRFSGSGSGTDFTLKISRVEAEDVGVYYCAQNLELPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 72 |
| 60183 CDR-H1 | YTFTSTWIH | SEQ ID NO: 73 |
| 60183 CDR-H2 | LIDPSDSYTNYNQKFRG | SEQ ID NO: 74 |
| 60183 CDR-H3 | ASSKPTGG | SEQ ID NO: 75 |
| 60183 CDR-L1 | RSSKSLLHSSGITYLS | SEQ ID NO: 76 |
| 60183 CDR-L2 | QMSNLAS | SEQ ID NO: 77 |
| 60183 CDR-L3 | AQNLELPLT | SEQ ID NO: 78 |
| 60183 VH | QVQLVQSGAEVKKPGASVKVSCKASGYTFTSTWIHWVRQAPGQGLEWMGLIDPSDSYTNYNQKFRGRVTMTVDTSTSTAYMELSSLRSEDTAVYYCASSKPTGGWGQGTTVTVSS | SEQ ID NO: 79 |
| 60183 CH | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | SEQ ID NO: 80 |
| 60183 CL | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 81 |
| 60183 VL | DIVMTQSPLSLPVTPGEPASISCRSSKSLLHSSGITYLSWYLQKPGQSPQLLIYQMSNLASGVPDRFSGSGSGTDFTLKISRVEAEDVGVYYCAQNLELPLTFGGGTKVEIK | SEQ ID NO: 82 |

| Description | Sequence | SEQ ID NO |
|---|---|---|
| 60183 VH + CH | QVQLVQSGAEVKKPGASVKVSCKASGYTFTSTWIHWVRQAPGQGLEW MGLIDPSDSYTNYNQKFRGRVTMTVDTSTSTAYMELSSLRSEDTAVYYC ASSKPTGGWGQGTTVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG | SEQ ID NO: 83 |
| 60183 VL + CL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQNLELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 84 |
| 61283 CDR-H1 | YTFTSAWIH | SEQ ID NO: 85 |
| 61283 CDR-H2 | LIDPSDSYTNYNQKFRG | SEQ ID NO: 86 |
| 61283 CDR-H3 | ASSDPYGG | SEQ ID NO: 87 |
| 61283 CDR-L1 | RSSKSLLHSSGITYLS | SEQ ID NO: 88 |
| 61283 CDR-L2 | QMSNKAS | SEQ ID NO: 89 |
| 61283 CDR-L3 | AQSLELPLT | SEQ ID NO: 90 |
| 61283 VH | QVQLVQSGAEVKKPGASVKVSCKASGYTFTSAWIHWVRQAPGQGLEW MGLIDPSDSYTNYNQKFRGRVTMTVDTSTSTAYMELSSLRSEDTAVYYC ASSDPYGGWGQGTTVTVSS | SEQ ID NO: 91 |
| 61283 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 92 |
| 61283 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 93 |
| 61283 VL | DIVMTQSPLSLPVTPGEPASISCRSSKSLLHSSGITYLSWYLQKPGQSPQL LIYQMSNKASGVPDRFSGSGSGTDFTLKISRVEAEDVGVYYCAQSLELP LTFGGGTKVEIK | SEQ ID NO: 94 |
| 61283 VH + CH | QVQLVQSGAEVKKPGASVKVSCKASGYTFTSAWIHWVRQAPGQGLEW MGLIDPSDSYTNYNQKFRGRVTMTVDTSTSTAYMELSSLRSEDTAVYYC ASSDPYGGWGQGTTVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG | SEQ ID NO: 95 |
| 61283 VL + CL | DIVMTQSPLSLPVTPGEPASISCRSSKSLLHSSGITYLSWYLQKPGQSPQL LIYQMSNKASGVPDRFSGSGSGTDFTLKISRVEAEDVGVYYCAQSLELP LTFGGGTKVEIKQVQLVQSGAEVKKPGASVKVSCKASGYTFTSAWIHW VRQAPGQGLEWMGLIDPSDSYTNYNQKFRGRVTMTVDTSTSTAYMELS SLRSEDTAVYYCASSDPYGGWGQGTTVTVSSASTKGPSVFPLAPSSKST SGGTAALGCLVKDYFPEPVTVSWNSGALTSGVHTFPAVLQSSGLYSLSS VVTVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIAV | SEQ ID NO: 96 |

| Description | Sequence | SEQ ID NO |
|---|---|---|
| | EWESNGQPENNYKTTPPVLDSDGSFFLYSKLTVDKSRWQQGNVFSCSV MHEALHNHYTQKSLSLSPG | |
| 61286 CDR-H1 | YTFTSTWIH | SEQ ID NO: 97 |
| 61286 CDR-H2 | LIDPSDSYTNYNQKFRG | SEQ ID NO: 98 |
| 61286 CDR-H3 | ASSDLTGG | SEQ ID NO: 99 |
| 61286 CDR-L1 | RSSKSLLHSSGITYLS | SEQ ID NO: 100 |
| 61286 CDR-L2 | QMSNLAS | SEQ ID NO: 101 |
| 61286 CDR-L3 | AQALELPLT | SEQ ID NO: 102 |
| 61286 VH | QVQLVQSGAEVKKPGASVKVSCKASGYTFTSTWIHWVRQAPGQGLEW MGLIDPSDSYTNYNQKFRGRVTMTVDTSTSTAYMELSSLRSEDTAVYYC ASSDLTGGWGQGTTVTVSS | SEQ ID NO: 103 |
| 61286 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 104 |
| 61286 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 105 |
| 61286 VL | DIVMTQSPLSLPVTPGEPASISCRSSKSLLHSSGITYLSWYLQKPGQSPQL LIYQMSNLASGVPDRFSGSGSGTDFSLKISRVEAEDVGVYYCAQALELP LTFGGGTKVEIK | SEQ ID NO: 106 |
| 61286 VH + CH | QVQLVQSGAEVKKPGASVKVSCKASGYTFTSTWIHWVRQAPGQGLEW MGLIDPSDSYTNYNQKFRGRVTMTVDTSTSTAYMELSSLRSEDTAVYYC ASSDLTGGWGQGTTVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG | SEQ ID NO: 107 |
| 61286 VL + CL | DIVMTQSPLSLPVTPGEPASISCRSSKSLLHSSGITYLSWYLQKPGQSPQL LIYQMSNLASGVPDRFSGSGSGTDFSLKISRVEAEDVGVYYCAQALELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 108 |
| 61279 CDR-H1 | YTFKSYWIH | SEQ ID NO: 109 |
| 61279 CDR-H2 | LIDPSDSYTNYNQIFRG | SEQ ID NO: 110 |
| 61279 CDR-H3 | ASSDATGG | SEQ ID NO: 111 |
| 61279 CDR-L1 | RSSKSLLHSSGITYLS | SEQ ID NO: 112 |
| 61279 CDR-L2 | QMSNLAS | SEQ ID NO: 113 |
| 61279 CDR-L3 | AQALELPLT | SEQ ID NO: 114 |

| Description | Sequence | SEQ ID NO |
|---|---|---|
| 61279 VH | QVQLVQSGAEVKKPGASVKVSCKASGYTFKSYWIHWVRQAPGQGLE WMGLIDPSDSYTNYNQIFRGRVTMTVDTSTSTAYMELSSLRSEDTAVYY CASSDATGGWGQGTTVTVSS | SEQ ID NO: 115 |
| 61279 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 116 |
| 61279 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 117 |
| 61279 VL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQALELP LTFGGGTKVEIK | SEQ ID NO: 118 |
| 61279 VH + CH | QVQLVQSGAEVKKPGASVKVSCKASGYTFKSYWIHWVRQAPGQGLE WMGLIDPSDSYTNYNQIFRGRVTMTVDTSTSTAYMELSSLRSEDTAVYY CASSDATGGWGQGTTVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG | SEQ ID NO: 119 |
| 61279 VL + CL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQALELP LTFGGGTKVEIK RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 120 |
| 56657 CDR-H1 | YTFTSTWIH | SEQ ID NO: 121 |
| 56657 CDR-H2 | LIDPSDSYTNYNQKFRG | SEQ ID NO: 122 |
| 56657 CDR-H3 | ASSKPTGG | SEQ ID NO: 123 |
| 56657 CDR-L1 | RSSKSLLHSSGITYLS | SEQ ID NO: 124 |
| 56657 CDR-L2 | QMSNLAS | SEQ ID NO: 125 |
| 56657 CDR-L3 | AQNLELPLT | SEQ ID NO: 126 |
| 56657 VH | QVQLVQSGAEVKKPGASVKVSCKASGYTFTSYWIHWVRQAPGQGLEW IGLIDPSDSYTNYNQKFRGRATLTVDTSTSTAYMELSSLRSEDTAVYYCA SSDPTGGWGQGTTVTVSS | SEQ ID NO: 127 |
| 56657 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 128 |
| 56657 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 129 |
| 56657 VL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQNLELP LTFGGGTKVEIK | SEQ ID NO: 130 |

| Description | Sequence | SEQ ID NO |
|---|---|---|
| 56657 VH + CH | QVQLVQSGAEVKKPGASVKVSCKASGYTFTSYWIHWVRQAPGQGLEW IGLIDPSDSYTNYNQKFRGRATLTVDTSTSTAYMELSSLRSEDTAVYYCA SSDPTGGWGQGTTVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKS LSLSPG | SEQ ID NO: 131 |
| 56657 VL + CL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQNLELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 132 |
| 61255 CDR-H1 | YTFTSYWIH | SEQ ID NO: 133 |
| 61255 CDR-H2 | LIDPSDSYTNYNQKFRG | SEQ ID NO: 134 |
| 61255 CDR-H3 | ASSDATGG | SEQ ID NO: 135 |
| 61255 CDR-L1 | RSSKSLLHSSGHTYLS | SEQ ID NO: 136 |
| 61255 CDR-L2 | QMSNLAS | SEQ ID NO: 137 |
| 61255 CDR-L3 | AQALELPLT | SEQ ID NO: 138 |
| 61255 VH | QVQLVQSGAEVKKPGASVKVSCKASGYTFTSYWIHWVRQAPGQGLEW IGLIDPSDSYTNYNQKFRGRATLTVDTSTSTAYMELSSLRSEDTAVYYCA SSDATGGWGQGTTVTVSS | SEQ ID NO: 139 |
| 61255 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 140 |
| 61255 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 141 |
| 61255 VL | DIVMTQSPLSLPVTPGEPASISCRSSKSLLHSSGHTYLSWYLQKPGQPPQ LLIYQMSNLASGVPDRFSGSGSGTDFTLKISRVEAEDVGVYYCAQALEL PLTFGGGTKVEIK | SEQ ID NO: 142 |
| 61255 VH + CH | QVQLVQSGAEVKKPGASVKVSCKASGYTFTSYWIHWVRQAPGQGLEW IGLIDPSDSYTNYNQKFRGRATLTVDTSTSTAYMELSSLRSEDTAVYYCA SSDATGGWGQGTTVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKS LSLSPG | SEQ ID NO: 143 |
| 61255 VL + CL | DIVMTQSPLSLPVTPGEPASISCRSSKSLLHSSGHTYLSWYLQKPGQPPQ LLIYQMSNLASGVPDRFSGSGSGTDFTLKISRVEAEDVGVYYCAQALEL PLTFGGGTKVEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC | SEQ ID NO: 144 |

-continued

| Description | Sequence | SEQ ID NO |
|---|---|---|
| 60140 CDR-H1 | YTFTSVWIH | SEQ ID NO: 145 |
| 60140 CDR-H2 | LIDPSDSYTNYNQKFRG | SEQ ID NO: 146 |
| 60140 CDR-H3 | ASSRPTGG | SEQ ID NO: 147 |
| 60140 CDR-L1 | RSSKSLLHSSGITYLS | SEQ ID NO: 148 |
| 60140 CDR-L2 | QMSNLAS | SEQ ID NO: 149 |
| 60140 CDR-L3 | AQNLELPLT | SEQ ID NO: 150 |
| 60140 VH | QVQLVQSGAEVKKPGASVKVSCKASGYTFTSVWIHWVRQAPGQGLEWIGLIDPSDSYTNYNQKFRGRATLTVDTSTSTAYMELSSLRSEDTAVYYCASSRPTGGWGQGTTVTVSS | SEQ ID NO: 151 |
| 60140 CH | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | SEQ ID NO: 152 |
| 60140 CL | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 153 |
| 60140 VL | DIVMTQSPLSLPVTPGEPASISCRSSKSLLHSSGITYLSWYLQKPGQSPQLLIYQMSNLASGVPDRFSGSGSGTDFTLKISRVEAEDVGVYYCAQNLELPLTFGGGTKVEIK | SEQ ID NO: 154 |
| 60140 VH + CH | QVQLVQSGAEVKKPGASVKVSCKASGYTFTSVWIHWVRQAPGQGLEWIGLIDPSDSYTNYNQKFRGRATLTVDTSTSTAYMELSSLRSEDTAVYYCASSRPTGGWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | SEQ ID NO: 155 |
| 60140 VL + CL | DIVMTQSPLSLPVTPGEPASISCRSSKSLLHSSGITYLSWYLQKPGQSPQLLIYQMSNLASGVPDRFSGSGSGTDFTLKISRVEAEDVGVYYCAQNLELPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 156 |
| 60143 CDR-H1 | YTFTSTWIH | SEQ ID NO: 157 |
| 60143 CDR-H2 | LIDPSDSYTNYNQKFRG | SEQ ID NO: 158 |
| 60143 CDR-H3 | ASSKPTGG | SEQ ID NO: 159 |
| 60143 CDR-L1 | RSSKSLLHSSGITYLS | SEQ ID NO: 160 |
| 60143 CDR-L2 | QMSNLAS | SEQ ID NO: 161 |
| 60143 CDR-L3 | AQNLELPLT | SEQ ID NO: 162 |

| Description | Sequence | SEQ ID NO |
|---|---|---|
| 60143 VH | QVQLVQSGAEVKKPGASVKVSCKASGYTFTSTWIHWVRQAPGQGLEW IGLIDPSDSYTNYNQKFRGRATLTVDTSTSTAYMELSSLRSEDTAVYYCA SSKPTGGWGQGTTVTVSS | SEQ ID NO: 163 |
| 60143 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 164 |
| 60143 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 165 |
| 60143 VL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQNLELP LTFGGGTKVEIK | SEQ ID NO: 166 |
| 60143 VH + CH | QVQLVQSGAEVKKPGASVKVSCKASGYTFTSTWIHWVRQAPGQGLEW IGLIDPSDSYTNYNQKFRGRATLTVDTSTSTAYMELSSLRSEDTAVYYCA SSKPTGGWGQGTTVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKS LSLSPG | SEQ ID NO: 167 |
| 60143 VL + CL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQNLELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 168 |
| 61264 CDR-H1 | YTFTSTWIH | SEQ ID NO: 169 |
| 61264 CDR-H2 | LIDPSDSYTNYNQKFVG | SEQ ID NO: 170 |
| 61264 CDR-H3 | ASSLPTGG | SEQ ID NO: 171 |
| 61264 CDR-L1 | RSSKSLLHSSGITYLS | SEQ ID NO: 172 |
| 61264 CDR-L2 | QMSNLAS | SEQ ID NO: 173 |
| 61264 CDR-L3 | AQQLELPLT | SEQ ID NO: 174 |
| 61264 VH | QVQLVQSGAEVKKPGASVKVSCKASGYTFTSTWIHWVRQAPGQGLEW IGLIDPSDSYTNYNQKFVGRATLTVDTSTSTAYMELSSLRSEDTAVYYCA SSLPTGGWGQGTTVTVSS | SEQ ID NO: 175 |
| 61264 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 176 |
| 61264 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 177 |
| 61264 VL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQQLELP LTFGGGTKVEIK | SEQ ID NO: 178 |

-continued

| Description | Sequence | SEQ ID NO |
|---|---|---|
| 61264 VH + CH | QVQLVQSGAEVKKPGASVKVSCKASGYTFTSTWIHWVRQAPGQGLEW IGLIDPSDSYTNYNQKFVGRATLTVDTSTSTAYMELSSLRSEDTAVYYCA SSLPTGGWGQGTTVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKS LSLSPG | SEQ ID NO: 179 |
| 61264 VL + CL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQQLELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 180 |
| 60130 CDR-H1 | YTFTSVWIH | SEQ ID NO: 181 |
| 60130 CDR-H2 | LIDPSDSYTNYNQKFR | SEQ ID NO: 182 |
| 60130 CDR-H3 | ASSQPTGG | SEQ ID NO: 183 |
| 60130 CDR-L1 | RSSKSLLHSSGITYLS | SEQ ID NO: 184 |
| 60130 CDR-L2 | QMSNLAS | SEQ ID NO: 185 |
| 60130 CDR-L3 | AQNLELPLT | SEQ ID NO: 186 |
| 60130 VH | QVQLVQSGAEVKKPGASVKVSCKASGYTFTSVWIHWVRQAPGQGLEW IGLIDPSDSYTNYNQKFRGRATLTVDTSTSTAYMELSSLRSEDTAVYYCA SSQPTGGWGQGTTVTVSS | SEQ ID NO: 187 |
| 60130 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 188 |
| 60130 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 189 |
| 60130 VL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQNLELP LTFGGGTKVEIK | SEQ ID NO: 190 |
| 60130 VH + CH | QVQLVQSGAEVKKPGASVKVSCKASGYTFTSVWIHWVRQAPGQGLEW IGLIDPSDSYTNYNQKFRGRATLTVDTSTSTAYMELSSLRSEDTAVYYCA SSQPTGGWGQGTTVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKS LSLSPG | SEQ ID NO: 191 |
| 60130 VL + CL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQNLELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 192 |
| 61286 CDR-H1 | YTFTSTWIH | SEQ ID NO: 193 |

| Description | Sequence | SEQ ID NO |
|---|---|---|
| 61286 CDR-H2 | LIDPSDSYTNYNQKFR | SEQ ID NO: 194 |
| 61286 CDR-H3 | ASSDLTGG | SEQ ID NO: 195 |
| 61286 CDR-L1 | RSSKSLLHSSGITYLS | SEQ ID NO: 196 |
| 61286 CDR-L2 | QMSNLAS | SEQ ID NO: 197 |
| 61286 CDR-L3 | AQALELPLT | SEQ ID NO: 198 |
| 61286 VH | QVQLVQSGAEVKKPGASVKVSCKASGYTFTSTWIHWVRQAPGQGLEW MGLIDPSDSYTNYNQKFRGRVTMTVDTSTSTAYMELSSLRSEDTAVYYC ASSDLTGGWGQGTTVTVSS | SEQ ID NO: 199 |
| 61286 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 200 |
| 61286 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 201 |
| 61286 VL | DIVMTQSPLSLPVTPGEPASISCRSSKSLLHSSGITYLSWYLQKPGQSPQL LIYQMSNLASGVPDRFSGSGSGTDFSLKISRVEAEDVGVYYCAQALELP LTFGGGTKVEIK | SEQ ID NO: 202 |
| 61286 VH + CH | QVQLVQSGAEVKKPGASVKVSCKASGYTFTSTWIHWVRQAPGQGLEW MGLIDPSDSYTNYNQKFRGRVTMTVDTSTSTAYMELSSLRSEDTAVYYC ASSDLTGGWGQGTTVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG | SEQ ID NO: 203 |
| 61286 VL + CL | DIVMTQSPLSLPVTPGEPASISCRSSKSLLHSSGITYLSWYLQKPGQSPQL LIYQMSNLASGVPDRFSGSGSGTDFSLKISRVEAEDVGVYYCAQALELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 204 |
| 61259 CDR-H1 | YRFTSYWIH | SEQ ID NO: 205 |
| 61259 CDR-H2 | LIDPSDSYTNYNQKFRG | SEQ ID NO: 206 |
| 61259 CDR-H3 | ASSDATGG | SEQ ID NO: 207 |
| 61259 CDR-L1 | VSSKSLLHSSGITYLS | SEQ ID NO: 208 |
| 61259 CDR-L2 | QMSNLGS | SEQ ID NO: 209 |
| 61259 CDR-L3 | AQALELPLT | SEQ ID NO: 210 |
| 61259 VH | QVQLVQSGAEVKKPGASVKVSCKASGYRFTSYWIHWVRQAPGQGLEW IGLIDPSDSYTNYNQKFRGRATLTVDTSTSTAYMELSSLRSEDTAVYYCA SSDATGGWGQGTTVTVSS | SEQ ID NO: 211 |
| 61259 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE | SEQ ID NO: 212 |

| Description | Sequence | SEQ ID NO |
|---|---|---|
| | PKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDW<br>LNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTV<br>DKSRWQQGNVFSCSVMHEALHNHYTQKSLSLSPG | |
| 61259 CL | RTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPV<br>TKSFNRGEC | SEQ ID NO: 213 |
| 61259 VL | DIVMTQSPLSLPVTPGEPASISCVSSKSLLHSSGITYLSWYLQKPGQSPQL<br>LIYQMSNLGSGVPDRFSGSGSGTDFTLKISRVEAEDVGVYYCAQALELP<br>LTFGGGTKVEIK | SEQ ID NO: 214 |
| 61259 VH + CH | QVQLVQSGAEVKKPGASVKVSCKASGYRFTSYWIHWVRQAPGQGLEW<br>IGLIDPSDSYTNYNQKFRGRATLTVDTSTSTAYMELSSLRSEDTAVYYCA<br>SSDATGGWGQGTTVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKS<br>LSLSPG | SEQ ID NO: 215 |
| 61259 VL + CL | DIVMTQSPLSLPVTPGEPASISCVSSKSLLHSSGITYLSWYLQKPGQSPQL<br>LIYQMSNLGSGVPDRFSGSGSGTDFTLKISRVEAEDVGVYYCAQALELP<br>LTFGGGTKVEIK<br>RTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPV<br>TKSFNRGEC | SEQ ID NO: 216 |
| 60136 CDR-H1 | YTHTSYWIH | SEQ ID NO: 217 |
| 60136 CDR-H2 | LIDPSDSYTNYNQKFR | SEQ ID NO: 218 |
| 60136 CDR-H3 | ASSRPTGG | SEQ ID NO: 219 |
| 60136 CDR-L1 | RSSKSLLHSSGITYLS | SEQ ID NO: 220 |
| 60136 CDR-L2 | QMSNLAS | SEQ ID NO: 221 |
| 60136 CDR-L3 | AQNLELPLT | SEQ ID NO: 222 |
| 60136 VH | QVQLVQSGAEVKKPGASVKVSCKASGYTHTSYWIHWVRQAPGQGLE<br>WIGLIDPSDSYTNYNQKFRGRATLTVDTSTSTAYMELSSLRSEDTAVYYC<br>ASSRPTGGWGQGTTVTVSS | SEQ ID NO: 223 |
| 60136 CH | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKVE<br>PKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDW<br>LNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTV<br>DKSRWQQGNVFSCSVMHEALHNHYTQKSLSLSPG | SEQ ID NO: 224 |
| 60136 CL | RTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPV<br>TKSFNRGEC | SEQ ID NO: 225 |
| 60136 VL | DIVMTQSPLSLPVTPGEPASISCRSSKSLLHSSGITYLSWYLQKPGQSPQL<br>LIYQMSNLASGVPDRFSGSGSGTDFTLKISRVEAEDVGVYYCAQNLELP<br>LTFGGGTKVEIK | SEQ ID NO: 226 |
| 60136 VH + CH | QVQLVQSGAEVKKPGASVKVSCKASGYTHTSYWIHWVRQAPGQGLE<br>WIGLIDPSDSYTNYNQKFRGRATLTVDTSTSTAYMELSSLRSEDTAVYYC<br>ASSRPTGGWGQGTTVTVSSASTKGPSVFPLAPSSKSTSGGTAALGCLVK<br>DYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREE | SEQ ID NO: 227 |

| Description | Sequence | SEQ ID NO |
|---|---|---|
| | QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG | |
| 60136 VL + CL | DIVMTQSPLSLPVTPGEPASISCRSSKSLLHSSGITYLSWYLQKPGQSPQL LIYQMSNLASGVPDRFSGSGSGTDFTLKISRVEAEDVGVYYCAQNLELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 228 |
| 61267 CDR-H1 | YTFTEYWIH | SEQ ID NO: 229 |
| 61267 CDR-H2 | LIDPSDSYTNYNQRFR | SEQ ID NO: 230 |
| 61267 CDR-H3 | ASSDATGG | SEQ ID NO: 231 |
| 61267 CDR-L1 | HSSKSLLHSSGITYLS | SEQ ID NO: 232 |
| 61267 CDR-L2 | QMSNLAS | SEQ ID NO: 233 |
| 61267 CDR-L3 | AQSLELPLT | SEQ ID NO: 234 |
| 61267 VH | QVQLVQSGAEVKKPGASVKASCKASGYTFTEYWIHWVRQAPGQGLEW IGLIDPSDSYTNYNQRFRGRATLTVDTSTSTAYMELSSLRSEDTAVYYCA SSDATGGWGQGTTVTVSS | SEQ ID NO: 235 |
| 61267 CH | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDW LNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTV DKSRWQQGNVFSCSVMHEALHNHYTQKSLSLSPG | SEQ ID NO: 236 |
| 61267 CL | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | SEQ ID NO: 237 |
| 61267 VL | DIVMTQSPLSLPVTPGEPASISCHSSKSLLHSSGITYLSWYLQKPGQSPQL LIYQMSNLASGVPDRFSGSGSGTDFTLKISRVEAEDVGVYYCAQSLELP LTFGGGTKVEIK | SEQ ID NO: 238 |
| 61267 VH + CH | QVQLVQSGAEVKKPGASVKASCKASGYTFTEYWIHWVRQAPGQGLEW IGLIDPSDSYTNYNQRFRGRATLTVDTSTSTAYMELSSLRSEDTAVYYCA SSDATGGWGQGTTVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQP REPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKS LSLSPG | SEQ ID NO: 239 |
| 61267 VL + CL | DIVMTQSPLSLPVTPGEPASISCHSSKSLLHSSGITYLSWYLQKPGQSPQL LIYQMSNLASGVPDRFSGSGSGTDFTLKISRVEAEDVGVYYCAQSLELP LTFGGGTKVEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | SEQ ID NO: 240 |
| Human fibrin γ377-395 (Human P2 peptide) | YSMKKTTMKIIPFNRLTIG | SEQ ID NO: 241 |
| 60143 Light Chain | ATGACTAGGCTGACCGTGCTGGCCCTGCTTGCCGGACTCTTGGCCTC CTCGAGAGCGGATATTGTGATGACTCAGAGCCCACTCTCCCTGCCCG TGACTCCTGGGGAACCCGCCTCGATCAGCTGTAGATCGTCCAAGTCA CTTCTCCACTCGTCCGGGATCACCTACCTGTCGTGGTATTTGCAAAG CCAGGACAGAGCCCGCAGCTCCTCATCTACCAAATGAGCAACCTGGC | SEQ ID NO: 242 |

-continued

| Description | Sequence | SEQ ID NO |
|---|---|---|
| | TTCCGGTGTCCCGGATCGGTTCTCGGGGTCCGGATCTGGCACCGACT<br>TCACGCTGAAAATTTCCCGCGTGGAAGCCGAGGACGTGGGAGTGTA<br>CTACTGCGCACAAAACCTGGAACTGCCCCTGACCTTCGGTGGCGGCA<br>CTAAGGTCGAAATCAAGCGGACCGTGGCAGCTCCGTCCGTGTTCATC<br>TTCCCGCCTTCCGACGAGCAGCTGAAGTCCGGAACCGCCTCCGTCGT<br>GTGCCTGCTCAACAACTTTTACCCTCGCGAGGCCAAGTCCAGTGGA<br>AGGTCGATAACGCGCTGCAGAGCGGAAATAGCCAGGAGAGCGTGAC<br>CGAGCAGGACTCCAAGGACTCAACCTACTCACTGAGCTCCACTCTGA<br>CCCTGTCAAAGGCGGACTACGAGAAGCACAAAGTGTACGCCTGCGA<br>AGTGACACATCAGGGCCTGTCCAGTCCCGTGACCAAGTCCTTCAACC<br>GGGGCGAATGCTAG | |
| 60143 Heavy Chain | ATGACCCGGCTGACCGTGCTGGCCCTCCTGGCTGGACTGCTGGCCTC<br>CTCAAGAGCCCAGGTCCAGCTGGTGCAATCCGGCGCCGAAGTCAAG<br>AAGCCAGGCGCAAGCGTGAAAGTGTCATGCAAAGCCTCCGGATACA<br>CCTTCACCTCCACCTGGATTCACTGGGTCAGACAGGCCCCCGGTCAA<br>GGACTGGAATGGATCGGCTGATCGACCCGTCGGACTCGTACACCAA<br>CTACAATCAGAAGTTTCGCGGTCGGGCTACTCTCACTGTGGATACCTC<br>GACCTCCACCGCTTACATGGAACTGTCATCGCTGCGGTCCGAGGATA<br>CCGCCGTGTACTATTGCGCGTCCTCCAAGCCGACTGGCGGATGGGGA<br>CAGGGAACTACTGTGACGGTGTCCTCCGCCTCGACCAAGGGCCCCTC<br>CGTGTTTCCACTGGCCCCCTCATCCAAGTCTACCAGCGGAGGAACCG<br>CAGCCCTAGGCTGTCTCGTGAAGGACTACTTCCCCGAGCCGGTCACT<br>GTCTCCTGGAACTCGGGAGCCCTCACTAGCGGTGTCCACACTTTCCC<br>GGCGGTGTTGCAAAGCTCCGGGCTGTACTCCCTGTCCTCGGTCGTCA<br>CCGTGCCGTCAAGCTCCCTCGGGACCCAGACATACATCTGTAACGTC<br>AACCATAAGCCATCCAACACCAAAGTGGACAAGAAAGTGGAGCCGA<br>AAAGCTGCGACAAGACTCACACTTGCCCTCCTTGCCCTGCACCCGAG<br>CTTCTCGGAGGTCCCAGCGTGTTCCTGTTCCCGCCGAAGCCCAAGGA<br>CACTCTGATGATTAGCCGCACTCCTGAGGTCACCTGTGTCGTGGTGG<br>ACGTGTCCCATGAGGACCCTGAAGTCAAGTTCAATTGGTACGTGGAC<br>GGCGTGGAGGTGCACAACGCCAAGACCAAGCCGAGGGAGGAGCAG<br>TACAACTCGACCTATCGCGTGGTGTCCGTGCTCACCGTGCTGCATCAG<br>GATTGGCTGAACGGGAAGGAGTATAAGTGCAAAGTGTCCAACAAGG<br>CTTTTGCCGGCCCCTATCGAAAAGACCATTAGCAAGGCCAAGGGGCAG<br>CCAAGGGAGCCTCAAGTGTACACCCTGCCGCCTTCGAGAGATGAACT<br>GACCAAGAACCAAGTGTCCCTCACGTGCCTCGTGAAGGGCTTCTACC<br>CCTCCGATATCGCGGTGGAATGGGAATCCAACGGACAGCCCGAAAAC<br>AACTACAAGACCACCCCTCCGGTGCTTGATAGCGACGGCTCGTTCTT<br>CCTGTACTCGAAGCTGACAGTGGACAAGTCACGGTGGCAGCAGGGC<br>AACGTGTTCTCATGCTCCGTGATGCACGAAGCGTTGCACAATCACTA<br>CACCCAGAAGTCGCTTAGCCTGAGCCCTGGATAG | SEQ ID NO: 243 |
| 60143-A234LA235L Light Chain | ATGACTAGGCTGACCGTGCTGGCCCTGCTTGCCGGACTCTTGGCCTC<br>CTCGAGAGCGGATATTGTGATGACTCAGAGCCCACTCTCCCTGCCCG<br>TGACTCCTGGGGAACCCGCCTCGATCAGCTGTAGATCGTCCAAGTCA<br>CTTCTCCACTCGTCCGGGATCACCTACCTGTCGTGGTATTTGCAAAAG<br>CCAGGACAGAGCCCGCAGCTCCTCATCTACCAAATGAGCAACCTGGC<br>TTCCGGTGTCCCGGATCGGTTCTCGGGGTCCGGATCTGGCACCGACT<br>TCACGCTGAAAATTTCCCGCGTGGAAGCCGAGGACGTGGGAGTGTA<br>CTACTGCGCACAAAACCTGGAACTGCCCCTGACCTTCGGTGGCGGCA<br>CTAAGGTCGAAATCAAGCGGACCGTGGCAGCTCCGTCCGTGTTCATC<br>TTCCCGCCTTCCGACGAGCAGCTGAAGTCCGGAACCGCCTCCGTCGT<br>GTGCCTGCTCAACAACTTTTACCCTCGCGAGGCCAAGTCCAGTGGA<br>AGGTCGATAACGCGCTGCAGAGCGGAAATAGCCAGGAGAGCGTGAC<br>CGAGCAGGACTCCAAGGACTCAACCTACTCACTGAGCTCCACTCTGA<br>CCCTGTCAAAGGCGGACTACGAGAAGCACAAAGTGTACGCCTGCGA<br>AGTGACACATCAGGGCCTGTCCAGTCCCGTGACCAAGTCCTTCAACC<br>GGGGCGAATGCTAG | SEQ ID NO: 244 |
| 60143-A234LA235L Heavy Chain | ATGACCCGGCTGACCGTGCTGGCCCTCCTGGCTGGACTGCTGGCCTC<br>CTCAAGAGCCCAGGTCCAGCTGGTGCAATCCGGCGCCGAAGTCAAG<br>AAGCCAGGCGCAAGCGTGAAAGTGTCATGCAAAGCCTCCGGATACA<br>CCTTCACCTCCACCTGGATTCACTGGGTCAGACAGGCCCCCGGTCAA<br>GGACTGGAATGGATCGGCTGATCGACCCGTCGGACTCGTACACCAA<br>CTACAATCAGAAGTTTCGCGGTCGGGCTACTCTCACTGTGGATACCTC<br>GACCTCCACCGCTTACATGGAACTGTCATCGCTGCGGTCCGAGGATA<br>CCGCCGTGTACTATTGCGCGTCCTCCAAGCCGACTGGCGGATGGGGA<br>CAGGGAACTACTGTGACGGTGTCCTCCGCCTCGACCAAGGGCCCCTC<br>CGTGTTTCCACTGGCCCCCTCATCCAAGTCTACCAGCGGAGGAACCG<br>CAGCCCTAGGCTGTCTCGTGAAGGACTACTTCCCCGAGCCGGTCACT<br>GTCTCCTGGAACTCGGGAGCCCTCACTAGCGGTGTCCACACTTTCCC<br>GGCGGTGTTGCAAAGCTCCGGGCTGTACTCCCTGTCCTCGGTCGTCA<br>CCGTGCCGTCAAGCTCCCTCGGGACCCAGACATACATCTGTAACGTC<br>AACCATAAGCCATCCAACACCAAAGTGGACAAGAAAGTGGAGCCGA<br>AAAGCTGCGACAAGACTCACACTTGCCCTCCTTGCCCTGCACCCGAG | SEQ ID NO: 245 |

| Description | Sequence | SEQ ID NO |
|---|---|---|
| | GCAGCAGGAGGTCCCAGCGTGTTCCTGTTCCCGCCGAAGCCCAAGG<br>ACACTCTGATGATTAGCCGCACTCCTGAGGTCACCTGTGTCGTGGTG<br>GACGTGTCCCATGAGGACCCTGAAGTCAAGTTCAATTGGTACGTGGA<br>CGGCGTGGAGGTGCACAACGCCAAGACCAAGCCGAGGGAGGAGCA<br>GTACAACTCGACCTATCGCGTGGTGTCCGTGCTCACCGTGCTGCATCA<br>GGATTGGCTGAACGGGAAGGAGTATAAGTGCAAAGTGTCCAACAAG<br>GCTTTGCCGGCCCCTATCGAAAAGACCATTAGCAAGGCCAAGGGGCA<br>GCCAAGGGAGCCTCAAGTGTACACCCTGCCGCCTTCGAGAGATGAA<br>CTGACCAAGAACCAAGTGTCCCTCACGTGCCTCGTGAAGGGCTTCTA<br>CCCCTCCGATATCGCGGTGGAATGGGAATCCAACGGACAGCCCGAAA<br>ACAACTACAAGACCACCCCTCCGGTGCTTGATAGCGACGGCTCGTTC<br>TTCCTGTACTCGAAGCTGACAGTGGACAAGTCACGGTGGCAGCAGG<br>GCAACGTGTTCTCATGCTCCGTGATGCACGAAGCGTTGCACAATCAC<br>TACACCCAGAAGTCGCTTAGCCTGAGCCCTGGATAG | |
| 5B8<br>Heavy Chain | QVQLQQPGAELVRPGTSVKLSCKASGYTFTSYWIHWVKQRPGQGLEWI<br>GLIDPSDSYTNYNQKFRGKATLTVDTSSSTAYMQLSSLTSEDSAVYYCAS<br>SDPTGCWGQGTTLTVSSAKTTPPSVYPLAPGCGDTTGSSVTSGCLVKGY<br>FPEPVTVTWNSGSLSSSVHTFPALLQSGLYTMSSSVTVPSSTWPSQTVTC<br>SVAHPASSTTVDKKLEPSGPISTINPCPPCKECHKCPAPNLEGGPSVFIFPP<br>NIKDVLMISLTPKVTCVVVDVSEDDPDVQISWFVNNVEVHTAQTQTHR<br>EDYNSTIRVVSTLPIQHQDWMSGKEFKCKVNNKDLPSPIERTISKIKGLV<br>RAPQVYTLPPPAEQLSRKDVSLTCLVVGFNPGDISVEWTSNGHTEENYK<br>DTAPVLDSDGSYFIYSKLNMKTSKWEKTDSFSCNVRHEGLKNYYLKKT<br>ISRSPGK | SEQ ID<br>NO: 246 |
| 5B8<br>Light Chain | RADAAPTVSIFPPSSEQLTSGGASVVCFLNNFYPKDINVKWKIDGSERQN<br>GVLNSWTDQDSKDSTYSMSSTLTLTKDEYERHNSYTCEATHKTSTSPIV<br>KSFNRNECDIVMTQAAFSNPITLGTSASMSCRSSKSLLHSSGITYLSWYL<br>QKPGQSPQLLIYQMSNLASGVPDRFSSSGSGTDFTLRISRVEAEDVGVY<br>YCAQNLELPLTFGAGTKLELK | SEQ ID<br>NO: 254 |
| THN227<br>Heavy Chain | QVQLVQSGAEVKKPGSSVKVSCKASGYTFTSYWIHWVRQAPGQGLEW<br>IGLIDPSDSYTNYNQKFRGRVTITRDTSTSTAYMELSSLRSEDTAVYYCA<br>SSDPTGGWGQGTTVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKRVEPKSCDKTHTCPPCPAPELLGGPSVFLFPPKPK<br>DTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQP<br>REPQVYTLPPSREEMTKNQVSLTCLVKGFYPSDIAVEWESNGQPENNYK<br>TTPPVLDSDGSFFLYSKLTVDKSRWQQGNVFSCSVMHEALHNHYTQKS<br>LSLSPGK | SEQ ID<br>NO: 247 |
| THN227<br>Light Chain | RTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPV<br>TKSFNRGECDIVMTQAAFSNPVTPGTPASISCRSSKSLLHSSGITYLSWY<br>LQKPGQSPQLLIYQMSNLASGVPDRESSSGSGTDFTLKISRVEAEDVGV<br>YYCAQNLELPLTFGQGTKLEIK | SEQ ID<br>NO: 248 |
| Mouse/Rat P2<br>peptide | YSMKETTMKIIPFNRLSIG | SEQ ID<br>NO: 249 |
| Rabbit P2<br>peptide | YSMKKTTMKIIPLNRLSIG | SEQ ID<br>NO: 250 |
| Human P2<br>peptide<br>extended | TTMKIIPFNRLTIGEGQQHHLGGAKQVRP | SEQ ID<br>NO: 251 |
| Rat P2 peptide<br>extended | TTMKIIPFNRLSIGDGQQHHMGGSKQVSV | SEQ ID<br>NO: 252 |
| Rabbit P2<br>peptide<br>extended | TTMKIIPLNRLSIGEGQQFHVGGAKQVRP | SEQ ID<br>NO: 253 |

SEQUENCE LISTING

Sequence total quantity: 258
SEQ ID NO: 1         moltype = AA   length = 9
FEATURE              Location/Qualifiers
REGION               1..9

-continued

```
                        note = Description of Artificial Sequence: Synthetic peptide
source                  1..9
                        mol_type = protein
                        organism = synthetic construct
SEQUENCE: 1
YTFTSYWIH                                                                        9

SEQ ID NO: 2            moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 2
LIDPSDSYTN YNQKFRG                                                              17

SEQ ID NO: 3            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 3
ASSDPTGG                                                                         8

SEQ ID NO: 4            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 4
RSSKSLLHSS GITYLS                                                               16

SEQ ID NO: 5            moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 5
QMSNLAS                                                                          7

SEQ ID NO: 6            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 6
AQNLELPLT                                                                        9

SEQ ID NO: 7            moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 7
QVQLVQSGAE VKKPGASVKV SCKASGYTFT SYWIHWVRQA PGQGLEWMGL IDPSDSYTNY                60
NQKFRGRVTM TVDTSTSTAY MELSSLRSED TAVYYCASSD PTGGWGQGTT VTVSS                    115

SEQ ID NO: 8            moltype = AA  length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 8
ASTKGPSVFP LAPSSKSTSG GTAALGCLVK DYFPEPVTVS WNSGALTSGV HTFPAVLQSS                60
```

```
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 9           moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 9
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 10          moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 10
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQNLELP LTFGGGTKVE IK           112

SEQ ID NO: 11          moltype = AA  length = 444
FEATURE                Location/Qualifiers
REGION                 1..444
                       note = Description of Artificial Sequence: Synthetic
                        polypeptide
source                 1..444
                       mol_type = protein
                       organism = synthetic construct
SEQUENCE: 11
QVQLVQSGAE VKKPGASVKV SCKASGYTFT SYWIHWVRQA PGQGLEWMGL IDPSDSYTNY    60
NQKFRGRVTM TVDTSTSTAY MELSSLRSED TAVYYCASSD PTGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 12          moltype = AA  length = 135
FEATURE                Location/Qualifiers
REGION                 1..135
                       note = Description of Artificial Sequence: Synthetic
                        polypeptide
source                 1..135
                       mol_type = protein
                       organism = synthetic construct
SEQUENCE: 12
AEDVGVYYCA QNLELPLTFG GGTKVEIKRT VAAPSVFIFP PSDEQLKSGT ASVVCLLNNF    60
YPREAKVQWK VDNALQSGNS QESVTEQDSK DSTYSLSSTL TLSKADYEKH KVYACEVTHQ   120
GLSSPVTKSF NRGEC                                                   135

SEQ ID NO: 13          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 13
YTFTSSWIH                                                            9

SEQ ID NO: 14          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 14
```

-continued

```
LIDPSDSYTN YNQKFRG                                                        17

SEQ ID NO: 15          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 15
ASSDPHGG                                                                   8

SEQ ID NO: 16          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 16
RSSKSLLHSS GITMLS                                                         16

SEQ ID NO: 17          moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 17
QMSNLAS                                                                    7

SEQ ID NO: 18          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 18
AQSLELPLT                                                                  9

SEQ ID NO: 19          moltype = AA   length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 19
QVQLVQSGAE VKKPGASVKV SCKASGYTFT SSWIHWVRQA PGQGLEWMGL IDPSDSYTNY         60
NQKFRGRVTM TVDTSTSTAY MELSSLRSED TAVYYCASSD PHGGWGQGTT VTVSS             115

SEQ ID NO: 20          moltype = AA   length = 329
FEATURE                Location/Qualifiers
REGION                 1..329
                       note = Description of Artificial Sequence: Synthetic
                        polypeptide
source                 1..329
                       mol_type = protein
                       organism = synthetic construct
SEQUENCE: 20
ASTKGPSVFP LAPSSKSTSG GTAALGCLVK DYFPEPVTVS WNSGALTSGV HTFPAVLQSS         60
GLYSLSSVVT VPSSSLGTQT YICNVNHKPS NTKVDKKVEP KSCDKTHTCP PCPAPELLGG        120
PSVFLFPPKP KDTLMISRTP EVTCVVVDVS HEDPEVKFNW YVDGVEVHNA KTKPREEQYN        180
STYRVVSVLT VLHQDWLNGK EYKCKVSNKA LPAPIEKTIS KAKGQPREPQ VYTLPPSRDE        240
LTKNQVSLTC LVKGFYPSDI AVEWESNGQP ENNYKTTPPV LDSDGSFFLY SKLTVDKSRW        300
QQGNVFSCSV MHEALHNHYT QKSLSLSPG                                          329

SEQ ID NO: 21          moltype = AA   length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 21
```

```
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 22           moltype = AA  length = 112
FEATURE                 Location/Qualifiers
REGION                  1..112
                        note = Description of Artificial Sequence: Synthetic
                          polypeptide
source                  1..112
                        mol_type = protein
                        organism = synthetic construct
SEQUENCE: 22
DIVMTQSPLS LPVTPGEPAS ISCRSSKSLL HSSGITMLSW YLQKPGQSPQ LLIYQMSNLA    60
SGVPDRFSGS GSGTDFTLKI SRVEAEDVGV YYCAQSLELP LTFGGGTKVE IK           112

SEQ ID NO: 23           moltype = AA  length = 444
FEATURE                 Location/Qualifiers
REGION                  1..444
                        note = Description of Artificial Sequence: Synthetic
                          polypeptide
source                  1..444
                        mol_type = protein
                        organism = synthetic construct
SEQUENCE: 23
QVQLVQSGAE VKKPGASVKV SCKASGYTFT SSWIHWVRQA PGQGLEWMGL IDPSDSYTNY    60
NQKFRGRVTM TVDTSTSTAY MELSSLRSED TAVYYCASSD PHGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 24           moltype = AA  length = 219
FEATURE                 Location/Qualifiers
REGION                  1..219
                        note = Description of Artificial Sequence: Synthetic
                          polypeptide
source                  1..219
                        mol_type = protein
                        organism = synthetic construct
SEQUENCE: 24
DIVMTQSPLS LPVTPGEPAS ISCRSSKSLL HSSGITMLSW YLQKPGQSPQ LLIYQMSNLA    60
SGVPDRFSGS GSGTDFTLKI SRVEAEDVGV YYCAQSLELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                         219

SEQ ID NO: 25           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 25
YTFTSSWIH                                                            9

SEQ ID NO: 26           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 26
LIDPSDSYTN YNQKFRG                                                  17

SEQ ID NO: 27           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 27
ASSAPTGG                                                             8

SEQ ID NO: 28           moltype = AA  length = 16
FEATURE                 Location/Qualifiers
```

```
REGION                  1..16
                        note = Description of Artificial Sequence: Synthetic peptide
source                  1..16
                        mol_type = protein
                        organism = synthetic construct
SEQUENCE: 28
RSSKSLLHSS GITYLS                                                              16

SEQ ID NO: 29           moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 29
QMSNLAS                                                                         7

SEQ ID NO: 30           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 30
AQALELPLT                                                                       9

SEQ ID NO: 31           moltype = AA   length = 115
FEATURE                 Location/Qualifiers
REGION                  1..115
                        note = Description of Artificial Sequence: Synthetic
                           polypeptide
source                  1..115
                        mol_type = protein
                        organism = synthetic construct
SEQUENCE: 31
QVQLVQSGAE VKKPGASVKV SCKASGYTFT SSWIHWVRQA PGQGLEWMGL IDPSDSYTNY     60
NQKFRGRVTM TVDTSTSTAY MELSSLRSED TAVYYCASSA PTGGWGQGTT VTVSS          115

SEQ ID NO: 32           moltype = AA   length = 329
FEATURE                 Location/Qualifiers
REGION                  1..329
                        note = Description of Artificial Sequence: Synthetic
                           polypeptide
source                  1..329
                        mol_type = protein
                        organism = synthetic construct
SEQUENCE: 32
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 33           moltype = AA   length = 107
FEATURE                 Location/Qualifiers
REGION                  1..107
                        note = Description of Artificial Sequence: Synthetic
                           polypeptide
source                  1..107
                        mol_type = protein
                        organism = synthetic construct
SEQUENCE: 33
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                  107

SEQ ID NO: 34           moltype = AA   length = 112
FEATURE                 Location/Qualifiers
REGION                  1..112
                        note = Description of Artificial Sequence: Synthetic
                           polypeptide
source                  1..112
                        mol_type = protein
                        organism = synthetic construct
SEQUENCE: 34
DIVMTQSPLS LPVTPGEPAS ISCRSSKSLL HSSGITYLSW YLQKPGQSPQ LLIYQMSNLA     60
SGVPDRFSGS GSGTDFTLKI SRVEAEDVGV YYCAQALELP LTFGGGTKVE IK            112
```

```
SEQ ID NO: 35          moltype = AA  length = 444
FEATURE                Location/Qualifiers
REGION                 1..444
                       note = Description of Artificial Sequence: Synthetic
                        polypeptide
source                 1..444
                       mol_type = protein
                       organism = synthetic construct
SEQUENCE: 35
QVQLVQSGAE VKKPGASVKV SCKASGYTFT SSWIHWVRQA PGQGLEWMGL IDPSDSYTNY   60
NQKFRGRVTM TVDTSTSTAY MELSSLRSED TAVYYCASSA PTGGWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                        444

SEQ ID NO: 36          moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 36
DIVMTQSPLS LPVTPGEPAS ISCRSSKSLL HSSGITYLSW YLQKPGQSPQ LLIYQMSNLA   60
SGVPDRFSGS GSGTDFTLKI SRVEAEDVGV YYCAQALELP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 37          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 37
YTFTSYWIH                                                            9

SEQ ID NO: 38          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 38
LIDPSDSYTN YNQKFRG                                                  17

SEQ ID NO: 39          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 39
ASSDATGG                                                             8

SEQ ID NO: 40          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 40
RSSKSLLHSS GITYLS                                                   16

SEQ ID NO: 41          moltype = AA  length = 7
FEATURE                Location/Qualifiers
REGION                 1..7
                       note = Description of Artificial Sequence: Synthetic peptide
source                 1..7
                       mol_type = protein
```

```
                                -continued
                       organism = synthetic construct
SEQUENCE: 41
QMSNLAS                                                                    7

SEQ ID NO: 42          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 42
AQALELPLT                                                                  9

SEQ ID NO: 43          moltype = AA   length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 43
QVQLVQSGAE VKKPGASVKV SCKASGYTFT SYWIHWVRQA PGQGLEWMGL IDPSDSYTNY          60
NQKFRGRVTM TVDTSTSTAY MELSSLRSED TAVYYCASSD ATGGWGQGTT VTVSS              115

SEQ ID NO: 44          moltype = AA   length = 329
FEATURE                Location/Qualifiers
REGION                 1..329
                       note = Description of Artificial Sequence: Synthetic
                        polypeptide
source                 1..329
                       mol_type = protein
                       organism = synthetic construct
SEQUENCE: 44
ASTKGPSVFP LAPSSKSTSG GTAALGCLVK DYFPEPVTVS WNSGALTSGV HTFPAVLQSS          60
GLYSLSSVVT VPSSSLGTQT YICNVNHKPS NTKVDKKVEP KSCDKTHTCP PCPAPELLGG         120
PSVFLFPPKP KDTLMISRTP EVTCVVVDVS HEDPEVKFNW YVDGVEVHNA KTKPREEQYN         180
STYRVVSVLT VLHQDWLNGK EYKCKVSNKA LPAPIEKTIS KAKGQPREPQ VYTLPPSRDE         240
LTKNQVSLTC LVKGFYPSDI AVEWESNGQP ENNYKTTPPV LDSDGSFFLY SKLTVDKSRW         300
QQGNVFSCSV MHEALHNHYT QKSLSLSPG                                           329

SEQ ID NO: 45          moltype = AA   length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 45
RTVAAPSVFI FPPSDEQLKS GTASVVCLLN NFYPREAKVQ WKVDNALQSG NSQESVTEQD          60
SKDSTYSLSS TLTLSKADYE KHKVYACEVT HQGLSSPVTK SFNRGEC                       107

SEQ ID NO: 46          moltype = AA   length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 46
DIVMTQSPLS LPVTPGEPAS ISCRSSKSLL HSSGITYLSW YLQKPGQSPQ LLIYQMSNLA          60
SGVPDRFSGS GSGTDFTLKI SRVEAEDVGV YYCAQALELP LTFGGGTKVE IK                 112

SEQ ID NO: 47          moltype = AA   length = 444
FEATURE                Location/Qualifiers
REGION                 1..444
                       note = Description of Artificial Sequence: Synthetic
                        polypeptide
source                 1..444
                       mol_type = protein
                       organism = synthetic construct
SEQUENCE: 47
QVQLVQSGAE VKKPGASVKV SCKASGYTFT SYWIHWVRQA PGQGLEWMGL IDPSDSYTNY          60
NQKFRGRVTM TVDTSTSTAY MELSSLRSED TAVYYCASSD ATGGWGQGTT VTVSSASTKG         120
PSVFPLAPSS KSTSGGTAAL GCLVKDYFPE PVTVSWNSGA LTSGVHTFPA VLQSSGLYSL         180
SSVVTVPSSS LGTQTYICNV NHKPSNTKVD KKVEPKSCDK THTCPPCPAP ELLGGPSVFL         240
```

```
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSRDELTKNQ    360
VSLTCLVKGF YPSDIAVEWE SNGQPENNYK TTPPVLDSDG SFFLYSKLTV DKSRWQQGNV    420
FSCSVMHEAL HNHYTQKSLS LSPG                                          444

SEQ ID NO: 48           moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 48
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQALELP LTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 49           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 49
YTFTSSWIH                                                             9

SEQ ID NO: 50           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 50
LIDPSDSYTN YNQKFRG                                                   17

SEQ ID NO: 51           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 51
ASSDPHGG                                                              8

SEQ ID NO: 52           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 52
RSSKSLLHSS GITYLS                                                    16

SEQ ID NO: 53           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 53
QMSNLAS                                                               7

SEQ ID NO: 54           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 54
AQSLELPLT                                                             9
```

```
SEQ ID NO: 55           moltype = AA   length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 55
QVQLVQSGAE VKKPGASVKV SCKASGYTFT SSWIHWVRQA PGQGLEWMGL IDPSDSYTNY    60
NQKFRGRVTM TVDTSTSTAY MELSSLRSED TAVYYCASSD PHGGWGQGTT VTVSS        115

SEQ ID NO: 56           moltype = AA   length = 329
FEATURE                 Location/Qualifiers
REGION                  1..329
                        note = Description of Artificial Sequence: Synthetic
                        polypeptide
source                  1..329
                        mol_type = protein
                        organism = synthetic construct
SEQUENCE: 56
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 57           moltype = AA   length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 57
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 58           moltype = AA   length = 112
FEATURE                 Location/Qualifiers
REGION                  1..112
                        note = Description of Artificial Sequence: Synthetic
                        polypeptide
source                  1..112
                        mol_type = protein
                        organism = synthetic construct
SEQUENCE: 58
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQSLELP LTFGGGTKVE IK           112

SEQ ID NO: 59           moltype = AA   length = 444
FEATURE                 Location/Qualifiers
REGION                  1..444
                        note = Description of Artificial Sequence: Synthetic
                        polypeptide
source                  1..444
                        mol_type = protein
                        organism = synthetic construct
SEQUENCE: 59
QVQLVQSGAE VKKPGASVKV SCKASGYTFT SSWIHWVRQA PGQGLEWMGL IDPSDSYTNY    60
NQKFRGRVTM TVDTSTSTAY MELSSLRSED TAVYYCASSD PHGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 60           moltype = AA   length = 219
FEATURE                 Location/Qualifiers
REGION                  1..219
                        note = Description of Artificial Sequence: Synthetic
                        polypeptide
source                  1..219
                        mol_type = protein
                        organism = synthetic construct
SEQUENCE: 60
```

```
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQSLELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 61              moltype = AA   length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 61
YTFTSTWIH                                                            9

SEQ ID NO: 62              moltype = AA   length = 17
FEATURE                    Location/Qualifiers
REGION                     1..17
                           note = Description of Artificial Sequence: Synthetic peptide
source                     1..17
                           mol_type = protein
                           organism = synthetic construct
SEQUENCE: 62
LIDPSDSYTN YNQKFRG                                                  17

SEQ ID NO: 63              moltype = AA   length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 63
ASSKPTGG                                                             8

SEQ ID NO: 64              moltype = AA   length = 16
FEATURE                    Location/Qualifiers
REGION                     1..16
                           note = Description of Artificial Sequence: Synthetic peptide
source                     1..16
                           mol_type = protein
                           organism = synthetic construct
SEQUENCE: 64
RSSKSLLHSS GITYIS                                                   16

SEQ ID NO: 65              moltype = AA   length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 65
QMSNLAS                                                              7

SEQ ID NO: 66              moltype = AA   length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 66
AQNLELPLT                                                            9

SEQ ID NO: 67              moltype = AA   length = 115
FEATURE                    Location/Qualifiers
REGION                     1..115
                           note = Description of Artificial Sequence: Synthetic
                            polypeptide
source                     1..115
                           mol_type = protein
                           organism = synthetic construct
SEQUENCE: 67
QVQLVQSGAE VKKPGASVKV SCKASGYTFT STWIHWVRQA PGQGLEWMGL IDPSDSYTNY    60
NQKFRGRVTM TVDTSTSTAY MELSSLRSED TAVYYCASSK PTGGWGQGTT VTVSS        115

SEQ ID NO: 68              moltype = AA   length = 329
FEATURE                    Location/Qualifiers
```

```
REGION                   1..329
                         note = Description of Artificial Sequence: Synthetic
                          polypeptide
source                   1..329
                         mol_type = protein
                         organism = synthetic construct
SEQUENCE: 68
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 69            moltype = AA   length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 69
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 70            moltype = AA   length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 70
DIVMTQSPLS LPVTPGEPAS ISCRSSKSLL HSSGITYISW YLQKPGQSPQ LLIYQMSNLA    60
SGVPDRFSGS GSGTDFTLKI SRVEAEDVGV YYCAQNLELP LTFGGGTKVE IK           112

SEQ ID NO: 71            moltype = AA   length = 444
FEATURE                  Location/Qualifiers
REGION                   1..444
                         note = Description of Artificial Sequence: Synthetic
                          polypeptide
source                   1..444
                         mol_type = protein
                         organism = synthetic construct
SEQUENCE: 71
QVQLVQSGAE VKKPGASVKV SCKASGYTFT STWIHWVRQA PGQGLEWMGL IDPSDSYTNY    60
NQKFRGRVTM TVDTSTSTAY MELSSLRSED TAVYYCASSK PTGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 72            moltype = AA   length = 219
FEATURE                  Location/Qualifiers
REGION                   1..219
                         note = Description of Artificial Sequence: Synthetic
                          polypeptide
source                   1..219
                         mol_type = protein
                         organism = synthetic construct
SEQUENCE: 72
DIVMTQSPLS LPVTPGEPAS ISCRSSKSLL HSSGITYISW YLQKPGQSPQ LLIYQMSNLA    60
SGVPDRFSGS GSGTDFTLKI SRVEAEDVGV YYCAQNLELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 73            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 73
YTFTSTWIH                                                            9
```

```
SEQ ID NO: 74          moltype = AA   length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 74
LIDPSDSYTN YNQKFRG                                                      17

SEQ ID NO: 75          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 75
ASSKPTGG                                                                8

SEQ ID NO: 76          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 76
RSSKSLLHSS GITYLS                                                       16

SEQ ID NO: 77          moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 77
QMSNLAS                                                                 7

SEQ ID NO: 78          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 78
AQNLELPLT                                                               9

SEQ ID NO: 79          moltype = AA   length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 79
QVQLVQSGAE VKKPGASVKV SCKASGYTFT STWIHWVRQA PGQGLEWMGL IDPSDSYTNY        60
NQKFRGRVTM TVDTSTSTAY MELSSLRSED TAVYYCASSK PTGGWGQGTT VTVSS            115

SEQ ID NO: 80          moltype = AA   length = 329
FEATURE                Location/Qualifiers
REGION                 1..329
                       note = Description of Artificial Sequence: Synthetic
                        polypeptide
source                 1..329
                       mol_type = protein
                       organism = synthetic construct
SEQUENCE: 80
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPELLGG       120
PSVFLFPPKP KDTLMISRTP EVTCVVVDVS HEDPEVKFNW YVDGVEVHNA KTKPREEQYN       180
STYRVVSVLT VLHQDWLNGK EYKCKVSNKA LPAPIEKTIS KAKGQPREPQ VYTLPPSRDE       240
LTKNQVSLTC LVKGFYPSDI AVEWESNGQP ENNYKTTPPV LDSDGSFFLY SKLTVDKSRW       300
QQGNVFSCSV MHEALHNHYT QKSLSLSPG                                        329
```

```
SEQ ID NO: 81            moltype = AA   length = 107
FEATURE                  Location/Qualifiers
REGION                   1..107
                         note = Description of Artificial Sequence: Synthetic
                         polypeptide
source                   1..107
                         mol_type = protein
                         organism = synthetic construct
SEQUENCE: 81
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                 107

SEQ ID NO: 82            moltype = AA   length = 112
FEATURE                  Location/Qualifiers
REGION                   1..112
                         note = Description of Artificial Sequence: Synthetic
                         polypeptide
source                   1..112
                         mol_type = protein
                         organism = synthetic construct
SEQUENCE: 82
DIVMTQSPLS LPVTPGEPAS ISCRSSKSLL HSSGITYLSW YLQKPGQSPQ LLIYQMSNLA     60
SGVPDRFSGS GSGTDFTLKI SRVEAEDVGV YYCAQNLELP LTFGGGTKVE IK            112

SEQ ID NO: 83            moltype = AA   length = 444
FEATURE                  Location/Qualifiers
REGION                   1..444
                         note = Description of Artificial Sequence: Synthetic
                         polypeptide
source                   1..444
                         mol_type = protein
                         organism = synthetic construct
SEQUENCE: 83
QVQLVQSGAE VKKPGASVKV SCKASGYTFT STWIHWVRQA PGQGLEWMGL IDPSDSYTNY     60
NQKFRGRVTM TVDTSTSTAY MELSSLRSED TAVYYCASSK PTGGWGQGTT VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP ELLGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSRDELTKNQ    360
VSLTCLVKGF YPSDIAVEWE SNGQPENNYK TTPPVLDSDG SFFLYSKLTV DKSRWQQGNV    420
FSCSVMHEAL HNHYTQKSLS LSPG                                          444

SEQ ID NO: 84            moltype = AA   length = 219
FEATURE                  Location/Qualifiers
REGION                   1..219
                         note = Description of Artificial Sequence: Synthetic
                         polypeptide
source                   1..219
                         mol_type = protein
                         organism = synthetic construct
SEQUENCE: 84
DIVMTQSPLS LPVTPGEPAS ISCRSSKSLL HSSGITYLSW YLQKPGQSPQ LLIYQMSNLA     60
SGVPDRFSGS GSGTDFTLKI SRVEAEDVGV YYCAQNLELP LTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 85            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 85
YTFTSAWIH                                                              9

SEQ ID NO: 86            moltype = AA   length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 86
LIDPSDSYTN YNQKFRG                                                    17

SEQ ID NO: 87            moltype = AA   length = 8
FEATURE                  Location/Qualifiers
REGION                   1..8
```

```
                        note = Description of Artificial Sequence: Synthetic peptide
source                  1..8
                        mol_type = protein
                        organism = synthetic construct
SEQUENCE: 87
ASSDPYGG                                                                          8

SEQ ID NO: 88           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 88
RSSKSLLHSS GITYLS                                                                16

SEQ ID NO: 89           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 89
QMSNKAS                                                                           7

SEQ ID NO: 90           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 90
AQSLELPLT                                                                         9

SEQ ID NO: 91           moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 91
QVQLVQSGAE VKKPGASVKV SCKASGYTFT SAWIHWVRQA PGQGLEWMGL IDPSDSYTNY    60
NQKFRGRVTM TVDTSTSTAY MELSSLRSED TAVYYCASSD PYGGWGQGTT VTVSS        115

SEQ ID NO: 92           moltype = AA  length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 92
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 93           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 93
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 94           moltype = AA  length = 112
FEATURE                 Location/Qualifiers
```

```
REGION                  1..112
                        note = Description of Artificial Sequence: Synthetic
                         polypeptide
source                  1..112
                        mol_type = protein
                        organism = synthetic construct
SEQUENCE: 94
DIVMTQSPLS LPVTPGEPAS ISCRSSKSLL HSSGITYLSW YLQKPGQSPQ LLIYQMSNKA   60
SGVPDRFSGS GSGTDFTLKI SRVEAEDVGV YYCAQSLELP LTFGGGTKVE IK          112

SEQ ID NO: 95           moltype = AA   length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 95
QVQLVQSGAE VKKPGASVKV SCKASGYTFT SAWIHWVRQA PGQGLEWMGL IDPSDSYTNY   60
NQKFRGRVTM TVDTSTSTAY MELSSLRSED TAVYYCASSD PYGGWGQTT  VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                        444

SEQ ID NO: 96           moltype = AA   length = 556
FEATURE                 Location/Qualifiers
REGION                  1..556
                        note = Description of Artificial Sequence: Synthetic
                         polypeptide
source                  1..556
                        mol_type = protein
                        organism = synthetic construct
SEQUENCE: 96
DIVMTQSPLS LPVTPGEPAS ISCRSSKSLL HSSGITYLSW YLQKPGQSPQ LLIYQMSNKA   60
SGVPDRFSGS GSGTDFTLKI SRVEAEDVGV YYCAQSLELP LTFGGGTKVE IKQVQLVQSG  120
AEVKKPGASV KVSCKASGYT FTSAWIHWVR QAPGQGLEWM GLIDPSDSYT NYNQKFRGRV  180
TMTVDTSTST AYMELSSLRS EDTAVYYCAS SDPYGGWGQG TTVTVSSAST KGPSVFPLAP  240
SSKSTSGGTA ALGCLVKDYF PEPVTVSWNS GALTSGVHTF PAVLQSSGLY SLSSVVTVPS  300
SSLGTQTYIC NVNHKPSNTK VDKKVEPKSC DKTHTCPPCP APELLGGPSV FLFPPKPKDT  360
LMISRTPEVT CVVVDVSHED PEVKFNWYVD GVEVHNAKTK PREEQYNSTY RVVSVLTVLH  420
QDWLNGKEYK CKVSNKALPA PIEKTISKAK GQPREPQVYT LPPSRDELTK NQVSLTCLVK  480
GFYPSDIAVE WESNGQPENN YKTTPPVLDS DGSFFLYSKL TVDKSRWQQG NVFSCSVMHE  540
ALHNHYTQKS LSLSPG                                                 556

SEQ ID NO: 97           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 97
YTFTSTWIH                                                           9

SEQ ID NO: 98           moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 98
LIDPSDSYTN YNQKFRG                                                 17

SEQ ID NO: 99           moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 99
ASSDLTGG                                                            8

SEQ ID NO: 100          moltype = AA   length = 16
```

```
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 100
RSSKSLLHSS GITYLS                                                         16

SEQ ID NO: 101          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 101
QMSNLAS                                                                   7

SEQ ID NO: 102          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 102
AQALELPLT                                                                 9

SEQ ID NO: 103          moltype = AA   length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 103
QVQLVQSGAE VKKPGASVKV SCKASGYTFT STWIHWVRQA PGQGLEWMGL IDPSDSYTNY          60
NQKFRGRVTM TVDTSTSTAY MELSSLRSED TAVYYCASSD LTGGWGQGTT VTVSS              115

SEQ ID NO: 104          moltype = AA   length = 329
FEATURE                 Location/Qualifiers
REGION                  1..329
                        note = Description of Artificial Sequence: Synthetic
                        polypeptide
source                  1..329
                        mol_type = protein
                        organism = synthetic construct
SEQUENCE: 104
ASTKGPSVFP LAPSSKSTSG GTAALGCLVK DYFPEPVTVS WNSGALTSGV HTFPAVLQSS          60
GLYSLSSVVT VPSSSLGTQT YICNVNHKPS NTKVDKKVEP KSCDKTHTCP PCPAPELLGG         120
PSVFLFPPKP KDTLMISRTP EVTCVVVDVS HEDPEVKFNW YVDGVEVHNA KTKPREEQYN         180
STYRVVSVLT VLHQDWLNGK EYKCKVSNKA LPAPIEKTIS KAKGQPREPQ VYTLPPSRDE         240
LTKNQVSLTC LVKGFYPSDI AVEWESNGQP ENNYKTTPPV LDSDGSFFLY SKLTVDKSRW         300
QQGNVFSCSV MHEALHNHYT QKSLSLSPG                                           329

SEQ ID NO: 105          moltype = AA   length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 105
RTVAAPSVFI FPPSDEQLKS GTASVVCLLN NFYPREAKVQ WKVDNALQSG NSQESVTEQD          60
SKDSTYSLSS TLTLSKADYE KHKVYACEVT HQGLSSPVTK SFNRGEC                       107

SEQ ID NO: 106          moltype = AA   length = 112
FEATURE                 Location/Qualifiers
REGION                  1..112
                        note = Description of Artificial Sequence: Synthetic
                        polypeptide
source                  1..112
                        mol_type = protein
                        organism = synthetic construct
SEQUENCE: 106
DIVMTQSPLS LPVTPGEPAS ISCRSSKSLL HSSGITYLSW YLQKPGQSPQ LLIYQMSNLA          60
```

```
SGVPDRFSGS GSGTDFSLKI SRVEAEDVGV YYCAQALELP LTFGGGTKVE IK          112

SEQ ID NO: 107            moltype = AA   length = 444
FEATURE                   Location/Qualifiers
REGION                    1..444
                          note = Description of Artificial Sequence: Synthetic
                            polypeptide
source                    1..444
                          mol_type = protein
                          organism = synthetic construct
SEQUENCE: 107
QVQLVQSGAE VKKPGASVKV SCKASGYTFT STWIHWVRQA PGQGLEWMGL IDPSDSYTNY   60
NQKFRGRVTM TVDTSTSTAY MELSSLRSED TAVYYCASSD LTGGWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 108            moltype = AA   length = 219
FEATURE                   Location/Qualifiers
REGION                    1..219
                          note = Description of Artificial Sequence: Synthetic
                            polypeptide
source                    1..219
                          mol_type = protein
                          organism = synthetic construct
SEQUENCE: 108
DIVMTQSPLS LPVTPGEPAS ISCRSSKSLL HSSGITYLSW YLQKPGQSPQ LLIYQMSNLA   60
SGVPDRFSGS GSGTDFSLKI SRVEAEDVGV YYCAQALELP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 109            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 109
YTFKSYWIH                                                            9

SEQ ID NO: 110            moltype = AA   length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 110
LIDPSDSYTN YNQIFRG                                                  17

SEQ ID NO: 111            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 111
ASSDATGG                                                             8

SEQ ID NO: 112            moltype = AA   length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 112
RSSKSLLHSS GITYLS                                                   16

SEQ ID NO: 113            moltype = AA   length = 7
FEATURE                   Location/Qualifiers
REGION                    1..7
                          note = Description of Artificial Sequence: Synthetic peptide
source                    1..7
```

```
                         mol_type = protein
                         organism = synthetic construct
SEQUENCE: 113
QMSNLAS                                                              7

SEQ ID NO: 114           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 114
AQALELPLT                                                            9

SEQ ID NO: 115           moltype = AA   length = 115
FEATURE                  Location/Qualifiers
REGION                   1..115
                         note = Description of Artificial Sequence: Synthetic
                         polypeptide
source                   1..115
                         mol_type = protein
                         organism = synthetic construct
SEQUENCE: 115
QVQLVQSGAE VKKPGASVKV SCKASGYTFK SYWIHWVRQA PGQGLEWMGL IDPSDSYTNY    60
NQIFRGRVTM TVDTSTSTAY MELSSLRSED TAVYYCASSD ATGGWGQGTT VTVSS        115

SEQ ID NO: 116           moltype = AA   length = 329
FEATURE                  Location/Qualifiers
REGION                   1..329
                         note = Description of Artificial Sequence: Synthetic
                         polypeptide
source                   1..329
                         mol_type = protein
                         organism = synthetic construct
SEQUENCE: 116
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 117           moltype = AA   length = 107
FEATURE                  Location/Qualifiers
REGION                   1..107
                         note = Description of Artificial Sequence: Synthetic
                         polypeptide
source                   1..107
                         mol_type = protein
                         organism = synthetic construct
SEQUENCE: 117
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 118           moltype = AA   length = 112
FEATURE                  Location/Qualifiers
REGION                   1..112
                         note = Description of Artificial Sequence: Synthetic
                         polypeptide
source                   1..112
                         mol_type = protein
                         organism = synthetic construct
SEQUENCE: 118
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQALELP LTFGGGTKVE IK           112

SEQ ID NO: 119           moltype = AA   length = 444
FEATURE                  Location/Qualifiers
REGION                   1..444
                         note = Description of Artificial Sequence: Synthetic
                         polypeptide
source                   1..444
                         mol_type = protein
                         organism = synthetic construct
SEQUENCE: 119
QVQLVQSGAE VKKPGASVKV SCKASGYTFK SYWIHWVRQA PGQGLEWMGL IDPSDSYTNY    60
NQIFRGRVTM TVDTSTSTAY MELSSLRSED TAVYYCASSD ATGGWGQGTT VTVSSASTKG   120
PSVFPLAPSS KSTSGGTAAL GCLVKDYFPE PVTVSWNSGA LTSGVHTFPA VLQSSGLYSL   180
```

```
SSVVTVPSSS LGTQTYICNV NHKPSNTKVD KKVEPKSCDK THTCPPCPAP ELLGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSRDELTKNQ    360
VSLTCLVKGF YPSDIAVEWE SNGQPENNYK TTPPVLDSDG SFFLYSKLTV DKSRWQQGNV    420
FSCSVMHEAL HNHYTQKSLS LSPG                                          444

SEQ ID NO: 120          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 120
DIVMTQSPLS LPVTPGEPAS ISCRSSKSLL HSSGITYLSW YLQKPGQSPQ LLIYQMSNLA     60
SGVPDRFSGS GSGTDFTLKI SRVEAEDVGV YYCAQALELP LTFGGGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 121          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 121
YTFTSTWIH                                                              9

SEQ ID NO: 122          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 122
LIDPSDSYTN YNQKFRG                                                    17

SEQ ID NO: 123          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 123
ASSKPTGG                                                               8

SEQ ID NO: 124          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 124
RSSKSLLHSS GITYLS                                                     16

SEQ ID NO: 125          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 125
QMSNLAS                                                                7

SEQ ID NO: 126          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 126
AQNLELPLT                                                              9
```

```
SEQ ID NO: 127         moltype = AA   length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 127
QVQLVQSGAE VKKPGASVKV SCKASGYTFT SYWIHWVRQA PGQGLEWIGL IDPSDSYTNY    60
NQKFRGRATL TVDTSTSTAY MELSSLRSED TAVYYCASSD PTGGWGQGTT VTVSS        115

SEQ ID NO: 128         moltype = AA   length = 329
FEATURE                Location/Qualifiers
REGION                 1..329
                       note = Description of Artificial Sequence: Synthetic
                        polypeptide
source                 1..329
                       mol_type = protein
                       organism = synthetic construct
SEQUENCE: 128
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 129         moltype = AA   length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 129
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 130         moltype = AA   length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 130
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQNLELP LTFGGGTKVE IK           112

SEQ ID NO: 131         moltype = AA   length = 444
FEATURE                Location/Qualifiers
REGION                 1..444
                       note = Description of Artificial Sequence: Synthetic
                        polypeptide
source                 1..444
                       mol_type = protein
                       organism = synthetic construct
SEQUENCE: 131
QVQLVQSGAE VKKPGASVKV SCKASGYTFT SYWIHWVRQA PGQGLEWIGL IDPSDSYTNY    60
NQKFRGRATL TVDTSTSTAY MELSSLRSED TAVYYCASSD PTGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                          444

SEQ ID NO: 132         moltype = AA   length = 219
FEATURE                Location/Qualifiers
REGION                 1..219
                       note = Description of Artificial Sequence: Synthetic
                        polypeptide
source                 1..219
                       mol_type = protein
                       organism = synthetic construct
```

```
SEQUENCE: 132
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQNLELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                         219

SEQ ID NO: 133          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 133
YTFTSYWIH                                                            9

SEQ ID NO: 134          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 134
LIDPSDSYTN YNQKFRG                                                  17

SEQ ID NO: 135          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 135
ASSDATGG                                                             8

SEQ ID NO: 136          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 136
RSSKSLLHSS GHTYLS                                                   16

SEQ ID NO: 137          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 137
QMSNLAS                                                              7

SEQ ID NO: 138          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 138
AQALELPLT                                                            9

SEQ ID NO: 139          moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 139
QVQLVQSGAE VKKPGASVKV SCKASGYTFT SYWIHWVRQA PGQGLEWIGL IDPSDSYTNY    60
NQKFRGRATL TVDTSTSTAY MELSSLRSED TAVYYCASSD ATGGWGQGTT VTVSS        115

SEQ ID NO: 140          moltype = AA  length = 329
```

```
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 140
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 141          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 141
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 142          moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 142
DIVMTQSPLS LPVTPGEPAS ISCRSSKSLL HSSGHTYLSW YLQKPGQPPQ LLIYQMSNLA    60
SGVPDRFSGS GSGTDFTLKI SRVEAEDVGV YYCAQALELP LTFGGGTKVE IK           112

SEQ ID NO: 143          moltype = AA   length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 143
QVQLVQSGAE VKKPGASVKV SCKASGYTFT SYWIHWVRQA PGQGLEWIGL IDPSDSYTNY    60
NQKFRGRATL TVDTSTSTAY MELSSLRSED TAVYYCASSD ATGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 144          moltype = AA   length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 144
DIVMTQSPLS LPVTPGEPAS ISCRSSKSLL HSSGHTYLSW YLQKPGQPPQ LLIYQMSNLA    60
SGVPDRFSGS GSGTDFTLKI SRVEAEDVGV YYCAQALELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 145          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 145
```

```
YTFTSVWIH                                                                    9

SEQ ID NO: 146         moltype = AA   length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 146
LIDPSDSYTN YNQKFRG                                                           17

SEQ ID NO: 147         moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 147
ASSRPTGG                                                                     8

SEQ ID NO: 148         moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 148
RSSKSLLHSS GITYLS                                                            16

SEQ ID NO: 149         moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 149
QMSNLAS                                                                      7

SEQ ID NO: 150         moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 150
AQNLELPLT                                                                    9

SEQ ID NO: 151         moltype = AA   length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 151
QVQLVQSGAE VKKPGASVKV SCKASGYTFT SVWIHWVRQA PGQGLEWIGL IDPSDSYTNY   60
NQKFRGRATL TVDTSTSTAY MELSSLRSED TAVYYCASSR PTGGWGQGTT VTVSS        115

SEQ ID NO: 152         moltype = AA   length = 329
FEATURE                Location/Qualifiers
REGION                 1..329
                       note = Description of Artificial Sequence: Synthetic
                        polypeptide
source                 1..329
                       mol_type = protein
                       organism = synthetic construct
SEQUENCE: 152
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329
```

```
SEQ ID NO: 153          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 153
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 154          moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 154
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQNLELP LTFGGGTKVE IK           112

SEQ ID NO: 155          moltype = AA   length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 155
QVQLVQSGAE VKKPGASVKV SCKASGYTFT SVWIHWVRQA PGQGLEWIGL IDPSDSYTNY    60
NQKFRGRATL TVDTSTSTAY MELSSLRSED TAVYYCASSR PTGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 156          moltype = AA   length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 156
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQNLELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 157          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 157
YTFTSTWIH                                                             9

SEQ ID NO: 158          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 158
LIDPSDSYTN YNQKFRG                                                   17

SEQ ID NO: 159          moltype = AA   length = 8
FEATURE                 Location/Qualifiers
```

```
REGION                  1..8
                        note = Description of Artificial Sequence: Synthetic peptide
source                  1..8
                        mol_type = protein
                        organism = synthetic construct
SEQUENCE: 159
ASSKPTGG                                                                        8

SEQ ID NO: 160          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 160
RSSKSLLHSS GITYLS                                                              16

SEQ ID NO: 161          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 161
QMSNLAS                                                                         7

SEQ ID NO: 162          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 162
AQNLELPLT                                                                       9

SEQ ID NO: 163          moltype = AA   length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 163
QVQLVQSGAE VKKPGASVKV SCKASGYTFT STWIHWVRQA PGQGLEWIGL IDPSDSYTNY    60
NQKFRGRATL TVDTSTSTAY MELSSLRSED TAVYYCASSK PTGGWGQGTT VTVSS        115

SEQ ID NO: 164          moltype = AA   length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 164
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 165          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 165
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 166          moltype = AA   length = 112
```

```
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 166
DIVMTQSPLS LPVTPGEPAS ISCRSSKSLL HSSGITYLSW YLQKPGQSPQ LLIYQMSNLA    60
SGVPDRFSGS GSTDFTLKI SRVEAEDVGV YYCAQNLELP LTFGGGTKVE IK            112

SEQ ID NO: 167          moltype = AA  length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 167
QVQLVQSGAE VKKPGASVKV SCKASGYTFT STWIHWVRQA PGQGLEWIGL IDPSDSYTNY    60
NQKFRGRATL TVDTSTSTAY MELSSLRSED TAVYYCASSK PTGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 168          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 168
DIVMTQSPLS LPVTPGEPAS ISCRSSKSLL HSSGITYLSW YLQKPGQSPQ LLIYQMSNLA    60
SGVPDRFSGS GSTDFTLKI SRVEAEDVGV YYCAQNLELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                         219

SEQ ID NO: 169          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 169
YTFTSTWIH                                                            9

SEQ ID NO: 170          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 170
LIDPSDSYTN YNQKFVG                                                  17

SEQ ID NO: 171          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 171
ASSLPTGG                                                             8

SEQ ID NO: 172          moltype = AA  length = 16
FEATURE                 Location/Qualifiers
REGION                  1..16
                        note = Description of Artificial Sequence: Synthetic peptide
source                  1..16
                        mol_type = protein
```

```
                        organism = synthetic construct
SEQUENCE: 172
RSSKSLLHSS GITYLS                                                        16

SEQ ID NO: 173          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 173
QMSNLAS                                                                   7

SEQ ID NO: 174          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 174
AQQLELPLT                                                                 9

SEQ ID NO: 175          moltype = AA   length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 175
QVQLVQSGAE VKKPGASVKV SCKASGYTFT STWIHWVRQA PGQGLEWIGL IDPSDSYTNY          60
NQKFVGRATL TVDTSTSTAY MELSSLRSED TAVYYCASSL PTGGWGQGTT VTVSS              115

SEQ ID NO: 176          moltype = AA   length = 329
FEATURE                 Location/Qualifiers
REGION                  1..329
                        note = Description of Artificial Sequence: Synthetic
                        polypeptide
source                  1..329
                        mol_type = protein
                        organism = synthetic construct
SEQUENCE: 176
ASTKGPSVFP LAPSSKSTSG GTAALGCLVK DYFPEPVTVS WNSGALTSGV HTFPAVLQSS          60
GLYSLSSVVT VPSSSLGTQT YICNVNHKPS NTKVDKKVEP KSCDKTHTCP PCPAPELLGG         120
PSVFLFPPKP KDTLMISRTP EVTCVVVDVS HEDPEVKFNW YVDGVEVHNA KTKPREEQYN         180
STYRVVSVLT VLHQDWLNGK EYKCKVSNKA LPAPIEKTIS KAKGQPREPQ VYTLPPSRDE         240
LTKNQVSLTC LVKGFYPSDI AVEWESNGQP ENNYKTTPPV LDSDGSFFLY SKLTVDKSRW         300
QQGNVFSCSV MHEALHNHYT QKSLSLSPG                                          329

SEQ ID NO: 177          moltype = AA   length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 177
RTVAAPSVFI FPPSDEQLKS GTASVVCLLN NFYPREAKVQ WKVDNALQSG NSQESVTEQD          60
SKDSTYSLSS TLTLSKADYE KHKVYACEVT HQGLSSPVTK SFNRGEC                      107

SEQ ID NO: 178          moltype = AA   length = 112
FEATURE                 Location/Qualifiers
REGION                  1..112
                        note = Description of Artificial Sequence: Synthetic
                        polypeptide
source                  1..112
                        mol_type = protein
                        organism = synthetic construct
SEQUENCE: 178
DIVMTQSPLS LPVTPGEPAS ISCRSSKSLL HSSGITYLSW YLQKPGQSPQ LLIYQMSNLA          60
SGVPDRFSGS GSGTDFTLKI SRVEAEDVGV YYCAQQLELP LTFGGGTKVE IK                112

SEQ ID NO: 179          moltype = AA   length = 444
FEATURE                 Location/Qualifiers
REGION                  1..444
```

```
                        note = Description of Artificial Sequence: Synthetic
                         polypeptide
source                  1..444
                        mol_type = protein
                        organism = synthetic construct
SEQUENCE: 179
QVQLVQSGAE VKKPGASVKV SCKASGYTFT STWIHWVRQA PGQGLEWIGL IDPSDSYTNY    60
NQKFVGRATL TVDTSTSTAY MELSSLRSED TAVYYCASSL PTGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 180          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 180
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQQLELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 181          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 181
YTFTSVWIH                                                             9

SEQ ID NO: 182          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 182
LIDPSDSYTN YNQKFR                                                    16

SEQ ID NO: 183          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 183
ASSQPTGG                                                              8

SEQ ID NO: 184          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 184
RSSKSLLHSS GITYLS                                                    16

SEQ ID NO: 185          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 185
QMSNLAS                                                               7
```

```
SEQ ID NO: 186          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 186
AQNLELPLT                                                                9

SEQ ID NO: 187          moltype = AA   length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 187
QVQLVQSGAE VKKPGASVKV SCKASGYTFT SVWIHWVRQA PGQGLEWIGL IDPSDSYTNY    60
NQKFRGRATL TVDTSTSTAY MELSSLRSED TAVYYCASSQ PTGGWGQGTT VTVSS         115

SEQ ID NO: 188          moltype = AA   length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 188
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 189          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 189
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                  107

SEQ ID NO: 190          moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 190
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQNLELP LTFGGGTKVE IK            112

SEQ ID NO: 191          moltype = AA   length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 191
QVQLVQSGAE VKKPGASVKV SCKASGYTFT SVWIHWVRQA PGQGLEWIGL IDPSDSYTNY    60
NQKFRGRATL TVDTSTSTAY MELSSLRSED TAVYYCASSQ PTGGWGQGTT VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KKVEPKSCDK THTCPPCPAP ELLGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALPAPI EKTISKAKGQ PREPQVYTLP PSRDELTKNQ    360
VSLTCLVKGF YPSDIAVEWE SNGQPENNYK TTPPVLDSDG SFFLYSKLTV DKSRWQQGNV    420
FSCSVMHEAL HNHYTQKSLS LSPG                                           444
```

```
SEQ ID NO: 192         moltype = AA   length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 192
DIVMTQSPLS LPVTPGEPAS ISCRSSKSLL HSSGITYLSW YLQKPGQSPQ LLIYQMSNLA   60
SGVPDRFSGS GSGTDFTLKI SRVEAEDVGV YYCAQNLELP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 193         moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 193
YTFTSTWIH                                                            9

SEQ ID NO: 194         moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 194
LIDPSDSYTN YNQKFR                                                   16

SEQ ID NO: 195         moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 195
ASSDLTGG                                                             8

SEQ ID NO: 196         moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 196
RSSKSLLHSS GITYLS                                                   16

SEQ ID NO: 197         moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 197
QMSNLAS                                                              7

SEQ ID NO: 198         moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 198
AQALELPLT                                                            9

SEQ ID NO: 199         moltype = AA   length = 115
FEATURE                Location/Qualifiers
REGION                 1..115
                       note = Description of Artificial Sequence: Synthetic
```

```
                          polypeptide
source                    1..115
                          mol_type = protein
                          organism = synthetic construct
SEQUENCE: 199
QVQLVQSGAE VKKPGASVKV SCKASGYTFT STWIHWVRQA PGQGLEWMGL IDPSDSYTNY    60
NQKFRGRVTM TVDTSTSTAY MELSSLRSED TAVYYCASSD LTGGWGQGTT VTVSS        115

SEQ ID NO: 200            moltype = AA   length = 329
FEATURE                   Location/Qualifiers
REGION                    1..329
                          note = Description of Artificial Sequence: Synthetic
                          polypeptide
source                    1..329
                          mol_type = protein
                          organism = synthetic construct
SEQUENCE: 200
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 201            moltype = AA   length = 107
FEATURE                   Location/Qualifiers
REGION                    1..107
                          note = Description of Artificial Sequence: Synthetic
                          polypeptide
source                    1..107
                          mol_type = protein
                          organism = synthetic construct
SEQUENCE: 201
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 202            moltype = AA   length = 112
FEATURE                   Location/Qualifiers
REGION                    1..112
                          note = Description of Artificial Sequence: Synthetic
                          polypeptide
source                    1..112
                          mol_type = protein
                          organism = synthetic construct
SEQUENCE: 202
DIVMTQSPLS LPVTPGEPAS ISCRSSKSLL HSSGITYLSW YLQKPGQSPQ LLIYQMSNLA    60
SGVPDRFSGS GSGTDFSLKI SRVEAEDVGV YYCAQALELP LTFGGGTKVE IK           112

SEQ ID NO: 203            moltype = AA   length = 444
FEATURE                   Location/Qualifiers
REGION                    1..444
                          note = Description of Artificial Sequence: Synthetic
                          polypeptide
source                    1..444
                          mol_type = protein
                          organism = synthetic construct
SEQUENCE: 203
QVQLVQSGAE VKKPGASVKV SCKASGYTFT STWIHWVRQA PGQGLEWMGL IDPSDSYTNY    60
NQKFRGRVTM TVDTSTSTAY MELSSLRSED TAVYYCASSD LTGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 204            moltype = AA   length = 219
FEATURE                   Location/Qualifiers
REGION                    1..219
                          note = Description of Artificial Sequence: Synthetic
                          polypeptide
source                    1..219
                          mol_type = protein
                          organism = synthetic construct
SEQUENCE: 204
DIVMTQSPLS LPVTPGEPAS ISCRSSKSLL HSSGITYLSW YLQKPGQSPQ LLIYQMSNLA    60
SGVPDRFSGS GSGTDFSLKI SRVEAEDVGV YYCAQALELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                         219
```

```
SEQ ID NO: 205           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 205
YRFTSYWIH                                                                        9

SEQ ID NO: 206           moltype = AA   length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 206
LIDPSDSYTN YNQKFRG                                                              17

SEQ ID NO: 207           moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 207
ASSDATGG                                                                         8

SEQ ID NO: 208           moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 208
VSSKSLLHSS GITYLS                                                               16

SEQ ID NO: 209           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 209
QMSNLGS                                                                          7

SEQ ID NO: 210           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 210
AQALELPLT                                                                        9

SEQ ID NO: 211           moltype = AA   length = 115
FEATURE                  Location/Qualifiers
REGION                   1..115
                         note = Description of Artificial Sequence: Synthetic
                         polypeptide
source                   1..115
                         mol_type = protein
                         organism = synthetic construct
SEQUENCE: 211
QVQLVQSGAE VKKPGASVKV SCKASGYRFT SYWIHWVRQA PGQGLEWIGL IDPSDSYTNY    60
NQKFRGRATL TVDTSTSTAY MELSSLRSED TAVYYCASSD ATGGWGQGTT VTVSS        115

SEQ ID NO: 212           moltype = AA   length = 329
FEATURE                  Location/Qualifiers
REGION                   1..329
                         note = Description of Artificial Sequence: Synthetic
                         polypeptide
source                   1..329
```

```
                           mol_type = protein
                           organism = synthetic construct
SEQUENCE: 212
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 213             moltype = AA   length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 213
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 214             moltype = AA   length = 112
FEATURE                    Location/Qualifiers
REGION                     1..112
                           note = Description of Artificial Sequence: Synthetic
                            polypeptide
source                     1..112
                           mol_type = protein
                           organism = synthetic construct
SEQUENCE: 214
DIVMTQSPLS LPVTPGEPAS ISCVSSKSLL HSSGITYLSW YLQKPGQSPQ LLIYQMSNLG    60
SGVPDRFSGS GSGTDFTLKI SRVEAEDVGV YYCAQALELP LTFGGGTKVE IK           112

SEQ ID NO: 215             moltype = AA   length = 444
FEATURE                    Location/Qualifiers
REGION                     1..444
                           note = Description of Artificial Sequence: Synthetic
                            polypeptide
source                     1..444
                           mol_type = protein
                           organism = synthetic construct
SEQUENCE: 215
QVQLVQSGAE VKKPGASVKV SCKASGYRFT SYWIHWVRQA PGQGLEWIGL IDPSDSYTNY    60
NQKFRGRATL TVDTSTSTAY MELSSLRSED TAVYYCASSD ATGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 216             moltype = AA   length = 219
FEATURE                    Location/Qualifiers
REGION                     1..219
                           note = Description of Artificial Sequence: Synthetic
                            polypeptide
source                     1..219
                           mol_type = protein
                           organism = synthetic construct
SEQUENCE: 216
DIVMTQSPLS LPVTPGEPAS ISCVSSKSLL HSSGITYLSW YLQKPGQSPQ LLIYQMSNLG    60
SGVPDRFSGS GSGTDFTLKI SRVEAEDVGV YYCAQALELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 217             moltype = AA   length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 217
YTHTSYWIH                                                            9

SEQ ID NO: 218             moltype = AA   length = 16
FEATURE                    Location/Qualifiers
REGION                     1..16
```

```
                        note = Description of Artificial Sequence: Synthetic peptide
source                  1..16
                        mol_type = protein
                        organism = synthetic construct
SEQUENCE: 218
LIDPSDSYTN YNQKFR                                                       16

SEQ ID NO: 219          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 219
ASSRPTGG                                                                 8

SEQ ID NO: 220          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 220
RSSKSLLHSS GITYLS                                                       16

SEQ ID NO: 221          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 221
QMSNLAS                                                                  7

SEQ ID NO: 222          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 222
AQNLELPLT                                                                9

SEQ ID NO: 223          moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 223
QVQLVQSGAE VKKPGASVKV SCKASGYTHT SYWIHWVRQA PGQGLEWIGL IDPSDSYTNY  60
NQKFRGRATL TVDTSTSTAY MELSSLRSED TAVYYCASSR PTGGWGQGTT VTVSS       115

SEQ ID NO: 224          moltype = AA  length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 224
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 225          moltype = AA  length = 107
FEATURE                 Location/Qualifiers
REGION                  1..107
                        note = Description of Artificial Sequence: Synthetic
```

```
                        polypeptide
source                  1..107
                        mol_type = protein
                        organism = synthetic construct
SEQUENCE: 225
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 226          moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 226
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQNLELP LTFGGGTKVE IK           112

SEQ ID NO: 227          moltype = AA   length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 227
QVQLVQSGAE VKKPGASVKV SCKASGYTHT SYWIHWVRQA PGQGLEWIGL IDPSDSYTNY    60
NQKFRGRATL TVDTSTSTAY MELSSLRSED TAVYYCASSR PTGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                         444

SEQ ID NO: 228          moltype = AA   length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 228
DIVMTQSPLS LPVTPGEPAS ISCRSSKSLL HSSGITYLSW YLQKPGQSPQ LLIYQMSNLA    60
SGVPDRFSGS GSGTDFTLKI SRVEAEDVGV YYCAQNLELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 229          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 229
YTFTEYWIH                                                             9

SEQ ID NO: 230          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 230
LIDPSDSYTN YNQRFR                                                    16

SEQ ID NO: 231          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
```

```
SEQUENCE: 231
ASSDATGG                                                                          8

SEQ ID NO: 232           moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 232
HSSKSLLHSS GITYLS                                                                16

SEQ ID NO: 233           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 233
QMSNLAS                                                                           7

SEQ ID NO: 234           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 234
AQSLELPLT                                                                         9

SEQ ID NO: 235           moltype = AA   length = 115
FEATURE                  Location/Qualifiers
REGION                   1..115
                         note = Description of Artificial Sequence: Synthetic
                         polypeptide
source                   1..115
                         mol_type = protein
                         organism = synthetic construct
SEQUENCE: 235
QVQLVQSGAE VKKPGASVKA SCKASGYTFT EYWIHWVRQA PGQGLEWIGL IDPSDSYTNY       60
NQRFRGRATL TVDTSTSTAY MELSSLRSED TAVYYCASSD ATGGWGQGTT VTVSS            115

SEQ ID NO: 236           moltype = AA   length = 329
FEATURE                  Location/Qualifiers
REGION                   1..329
                         note = Description of Artificial Sequence: Synthetic
                         polypeptide
source                   1..329
                         mol_type = protein
                         organism = synthetic construct
SEQUENCE: 236
ASTKGPSVFP LAPSSKSTSG GTAALGCLVK DYFPEPVTVS WNSGALTSGV HTFPAVLQSS       60
GLYSLSSVVT VPSSSLGTQT YICNVNHKPS NTKVDKKVEP KSCDKTHTCP PCPAPELLGG      120
PSVFLFPPKP KDTLMISRTP EVTCVVVDVS HEDPEVKFNW YVDGVEVHNA KTKPREEQYN      180
STYRVVSVLT VLHQDWLNGK EYKCKVSNKA LPAPIEKTIS KAKGQPREPQ VYTLPPSRDE      240
LTKNQVSLTC LVKGFYPSDI AVEWESNGQP ENNYKTTPPV LDSDGSFFLY SKLTVDKSRW      300
QQGNVFSCSV MHEALHNHYT QKSLSLSPG                                        329

SEQ ID NO: 237           moltype = AA   length = 107
FEATURE                  Location/Qualifiers
REGION                   1..107
                         note = Description of Artificial Sequence: Synthetic
                         polypeptide
source                   1..107
                         mol_type = protein
                         organism = synthetic construct
SEQUENCE: 237
RTVAAPSVFI FPPSDEQLKS GTASVVCLLN NFYPREAKVQ WKVDNALQSG NSQESVTEQD       60
SKDSTYSLSS TLTLSKADYE KHKVYACEVT HQGLSSPVTK SFNRGEC                    107

SEQ ID NO: 238           moltype = AA   length = 112
FEATURE                  Location/Qualifiers
REGION                   1..112
                         note = Description of Artificial Sequence: Synthetic
                         polypeptide
source                   1..112
```

```
SEQUENCE: 238
DIVMTQSPLS LPVTPGEPAS ISCHSSKSLL HSSGITYLSW YLQKPGQSPQ LLIYQMSNLA    60
SGVPDRFSGS GSGTDFTLKI SRVEAEDVGV YYCAQSLELP LTFGGGTKVE IK           112

SEQ ID NO: 239         moltype = AA   length = 444
FEATURE                Location/Qualifiers
REGION                 1..444
                       note = Description of Artificial Sequence: Synthetic
                         polypeptide
source                 1..444
                       mol_type = protein
                       organism = synthetic construct
SEQUENCE: 239
QVQLVQSGAE VKKPGASVKA SCKASGYTFT EYWIHWVRQA PGQGLEWIGL IDPSDSYTNY    60
NQRFRGRATL TVDTSTSTAY MELSSLRSED TAVYYCASSD ATGGWGQGTT VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPG                                          444

SEQ ID NO: 240         moltype = AA   length = 219
FEATURE                Location/Qualifiers
REGION                 1..219
                       note = Description of Artificial Sequence: Synthetic
                         polypeptide
source                 1..219
                       mol_type = protein
                       organism = synthetic construct
SEQUENCE: 240
DIVMTQSPLS LPVTPGEPAS ISCHSSKSLL HSSGITYLSW YLQKPGQSPQ LLIYQMSNLA    60
SGVPDRFSGS GSGTDFTLKI SRVEAEDVGV YYCAQSLELP LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 241         moltype = AA   length = 19
FEATURE                Location/Qualifiers
source                 1..19
                       mol_type = protein
                       organism = Homo sapiens
SEQUENCE: 241
YSMKKTTMKI IPFNRLTIG                                                 19

SEQ ID NO: 242         moltype = DNA   length = 717
FEATURE                Location/Qualifiers
misc_feature           1..717
                       note = Description of Artificial Sequence: Synthetic
                         polynucleotide
source                 1..717
                       mol_type = other DNA
                       organism = synthetic construct
SEQUENCE: 242
atgactaggc tgaccgtgct ggccctgctt gccggactct tggcctcctc gagagcggat    60
attgtgatga ctcagagccc actctccctg cccgtgactc ctggggaacc cgcctcgatc   120
agctgtagat cgtccaagtc acttctccac tcgtccggga tcacctacct gtcgtggtat   180
ttgcaaaagc caggacagag cccgcagctc ctcatctacc aaatgagcaa cctggcttcc   240
ggtgtcccgg atcggttctc ggggtccgga tctggcaccg acttcacgct gaaaatttcc   300
cgcgtggaag ccgaggacgt gggagtgtac tactgcgcac aaaacctgga actgcccctg   360
accttcggtg gcggcactaa ggtcgaaatc aagcggaccg tggcagctcc gtccgtgttc   420
atcttccgc cttccgacga gcagctgaag tccggaaccg cctccgtcgt gtgcctgctc    480
aacaactttt accctcgcga ggccaaggtc cagtggaagg tcgataacgc gctgcagagc   540
ggaaatagcc aggagagcgt gaccgagcag gactccaagg actcaaccta ctcactgagc   600
tccactctga ccctgtcaaa ggcggactac gagaagcaca agtgtacgc ctgcgaagtg    660
acacatcagg gcctgtccag tcccgtgacc aagtccttca ccggggcga atgctag       717

SEQ ID NO: 243         moltype = DNA   length = 1392
FEATURE                Location/Qualifiers
misc_feature           1..1392
                       note = Description of Artificial Sequence: Synthetic
                         polynucleotide
source                 1..1392
                       mol_type = other DNA
                       organism = synthetic construct
SEQUENCE: 243
atgacccggc tgaccgtgct ggccctcctg gctggactgc tggcctcctc aagagcccag    60
gtccagctgg tgcaatccgg cgccgaagtc aagaagccag cgcaagcgt gaaagtgtca   120
```

```
tgcaaagcct ccggatacac cttcacctcc acctggattc actgggtcag acaggccccc    180
ggtcaaggac tggaatggat cgggctgatc gacccgtcgg actcgtacac caactacaat    240
cagaagtttc gcggtcgggc tactctcact gtggatacct cgacctccac cgcttacatg    300
gaactgtcat cgctgcggtc cgaggatacc gccgtgtact attgcgcgtc ctccaagccg    360
actggcggat ggggacaggg aactactgtg acggtgtcct ccgcctcgac caagggcccc    420
tccgtgtttc cactggcccc ctcatccaag tctaccagcg gaggaaccgc agccctaggc    480
tgtctcgtga aggactactt ccccgagccg gtcactgtct cctggaactc gggagccctc    540
actagcggtg tccacacttt cccggcggtg ttgcaaagct ccgggctgta ctccctgtcc    600
tcggtcgtca ccgtgccgtc aagctccctc gggacccaga catacatctg taacgtcaac    660
cataagccat ccaacaccaa agtggacaag aaagtggagc gaaaagctg cgacaagact    720
cacacttgcc ctccttgccc tgcacccgag cttctcggag gtcccagcgt gttcctgttc    780
ccgccgaagc caaggacac tctgatgatt agccgcactc ctgaggtcac ctgtgtcgtg    840
gtggacgtgt cccatgagga ccctgaagtc aagttcaatt ggtacgtgga cggcgtggag    900
gtgcacaacg ccaagaccaa gccgagggag gagcagtaca actcgaccta tcgcgtggtg    960
tccgtgctca ccgtgctgca tcaggattgg ctgaacggga aggagtataa gtgcaaagtg   1020
tccaacaagg ctttgccggc ccctatcgaa aagaccatta gcaaggccaa ggggcagcca   1080
agggagcctc aagtgtacac cctgccgcct tcgagagatg aactgaccaa gaaccaagtg   1140
tccctcacgt gcctcgtgaa gggcttctac ccctccgata tcgcggtgga atgggaatcc   1200
aacggacagc ccgaaaacaa ctacaagacc acccctccgg tgcttgatag cgacggctcg   1260
ttcttcctgt actcgaagct gacagtggac aagtcacggt ggcagcaggg caacgtgttc   1320
tcatgctccg tgatgcacga agcgttgcac aatcactaca cccagaagtc gcttagcctg   1380
agccctggat ag                                                        1392

SEQ ID NO: 244        moltype = DNA   length = 717
FEATURE               Location/Qualifiers
misc_feature          1..717
                      note = Description of Artificial Sequence: Synthetic
                      polynucleotide
source                1..717
                      mol_type = other DNA
                      organism = synthetic construct
SEQUENCE: 244
atgactaggc tgaccgtgct ggccctgctt gccggactct tggcctcctc gagagcggat     60
attgtgatga ctcagagccc actctccctg cccgtgctg ctggggaacc cgcctcgatc    120
agctgtagat cgtccaagtc acttctccac tcgtccggga tcacctacct gtcgtggtat    180
ttgcaaaagc caggacagag cccgcagctc ctcatctacc aaatgagcaa cctggcttcc    240
ggtgtcccgg atcggttctc ggggtccgga tctggcaccg acttcacgct gaaaatttcc    300
cgcgtggaag ccgaggacgt gggagtgtac tactgcgcac aaaacctgga actgcccctg    360
accttcggtg gcggcactaa ggtcgaaatc aagcggaccg tggcagctcc gtccgtgttc    420
atcttcccgc cttccgacga gcagctgaag tccggaaccg cctccgtcgt gtgcctgctc    480
aacaactttt accctcgcga ggccaaggtc cagtggaagg tcgataacgc gctgcagagc    540
ggaaatagcc aggagagcgt gaccgagcag gactccaagg actcaaccta ctcactgagc    600
tccactctga ccctgtcaaa ggcggactac gagaagcaca aagtgtacgc ctgcgaagtg    660
acacatcagg gcctgtccag tcccgtgacc aagtccttca accggggcga atgctag       717

SEQ ID NO: 245        moltype = DNA   length = 1392
FEATURE               Location/Qualifiers
misc_feature          1..1392
                      note = Description of Artificial Sequence: Synthetic
                      polynucleotide
source                1..1392
                      mol_type = other DNA
                      organism = synthetic construct
SEQUENCE: 245
atgacccggc tgaccgtgct ggccctcctg gctggactgc tggcctcctc aagagcccag     60
gtccagctgg tgcaatccgg cgccgaagtc aagaagccag gcgcaagcgt gaaagtgtca    120
tgcaaagcct ccggatacac cttcacctcc acctggattc actgggtcag acaggccccc    180
ggtcaaggac tggaatggat cgggctgatc gacccgtcgg actcgtacac caactacaat    240
cagaagtttc gcggtcgggc tactctcact gtggatacct cgacctccac cgcttacatg    300
gaactgtcat cgctgcggtc cgaggatacc gccgtgtact attgcgcgtc ctccaagccg    360
actggcggat ggggacaggg aactactgtg acggtgtcct ccgcctcgac caagggcccc    420
tccgtgtttc cactggcccc ctcatccaag tctaccagcg gaggaaccgc agccctaggc    480
tgtctcgtga aggactactt ccccgagccg gtcactgtct cctggaactc gggagccctc    540
actagcggtg tccacacttt cccggcggtg ttgcaaagct ccgggctgta ctccctgtcc    600
tcggtcgtca ccgtgccgtc aagctccctc gggacccaga catacatctg taacgtcaac    660
cataagccat ccaacaccaa agtggacaag aaagtggagc gaaaagctg cgacaagact    720
cacacttgcc ctccttgccc tgcacccgag cagcaggag gtcccagcgt gttcctgttc    780
ccgccgaagc caaggacac tctgatgatt agccgcactc ctgaggtcac ctgtgtcgtg    840
gtggacgtgt cccatgagga ccctgaagtc aagttcaatt ggtacgtgga cggcgtggag    900
gtgcacaacg ccaagaccaa gccgagggag gagcagtaca actcgaccta tcgcgtggtg    960
tccgtgctca ccgtgctgca tcaggattgg ctgaacggga aggagtataa gtgcaaagtg   1020
tccaacaagg ctttgccggc ccctatcgaa aagaccatta gcaaggccaa ggggcagcca   1080
agggagcctc aagtgtacac cctgccgcct tcgagagatg aactgaccaa gaaccaagtg   1140
tccctcacgt gcctcgtgaa gggcttctac ccctccgata tcgcggtgga atgggaatcc   1200
aacggacagc ccgaaaacaa ctacaagacc acccctccgg tgcttgatag cgacggctcg   1260
ttcttcctgt actcgaagct gacagtggac aagtcacggt ggcagcaggg caacgtgttc   1320
tcatgctccg tgatgcacga agcgttgcac aatcactaca cccagaagtc gcttagcctg   1380
agccctggat ag                                                        1392
```

```
SEQ ID NO: 246          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 246
QVQLQQPGAE LVRPGTSVKL SCKASGYTFT SYWIHWVKQR PGQGLEWIGL IDPSDSYTNY   60
NQKFRGKATL TVDTSSSTAY MQLSSLTSED SAVYYCASSD PTGCWGQGTT LTVSSAKTTP  120
PSVYPLAPGC GDTTGSSVTS GCLVKGYFPE PVTVTWNSGS LSSSVHTFPA LLQSGLYTMS  180
SSVTVPSSTW PSQTVTCSVA HPASSTTVDK KLEPSGPIST INPCPPCKEC HKCPAPNLEG  240
GPSVFIFPPN IKDVLMISLT PKVTCVVVDV SEDDPDVQIS WFVNNVEVHT AQTQTHREDY  300
NSTIRVVSTL PIQHQDWMSG KEFKCKVNNK DLPSPIERTI SKIKGLVRAP QVYTLPPPAE  360
QLSRKDVSLT CLVVGFNPGD ISVEWTSNGH TEENYKDTAP VLDSDGSYFI YSKLNMKTSK  420
WEKTDSFSCN VRHEGLKNYY LKKTISRSPG K                                451

SEQ ID NO: 247          moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 247
QVQLVQSGAE VKKPGSSVKV SCKASGYTFT SYWIHWVRQA PGQGLEWIGL IDPSDSYTNY   60
NQKFRGRVTI TRDTSTSTAY MELSSLRSED TAVYYCASSD PTGGWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSREEMTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                       445

SEQ ID NO: 248          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 248
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGECDIV MTQAAFSNPV  120
TPGTPASISC RSSKSLLHSS GITYLSWYLQ KPGQSPQLLI YQMSNLASGV PDRFSSSGSG  180
TDFTLKISRV EAEDVGVYYC AQNLELPLTF GQGTKLEIK                         219

SEQ ID NO: 249          moltype = AA  length = 19
FEATURE                 Location/Qualifiers
REGION                  1..19
                        note = Description of Unknown: Mouse/Rat P2 peptide sequence
source                  1..19
                        mol_type = protein
                        organism = unidentified
SEQUENCE: 249
YSMKETTMKI IPFNRLSIG                                               19

SEQ ID NO: 250          moltype = AA  length = 19
FEATURE                 Location/Qualifiers
source                  1..19
                        mol_type = protein
                        organism = Oryctolagus sp.
SEQUENCE: 250
YSMKKTTMKI IPLNRLSIG                                               19

SEQ ID NO: 251          moltype = AA  length = 29
FEATURE                 Location/Qualifiers
source                  1..29
                        mol_type = protein
                        organism = Homo sapiens
SEQUENCE: 251
TTMKIIPFNR LTIGEGQQHH LGGAKQVRP                                    29

SEQ ID NO: 252          moltype = AA  length = 29
FEATURE                 Location/Qualifiers
source                  1..29
```

```
                         mol_type = protein
                         organism = Rattus sp.
SEQUENCE: 252
TTMKIIPFNR LSIGDGQQHH MGGSKQVSV                                  29

SEQ ID NO: 253           moltype = AA   length = 29
FEATURE                  Location/Qualifiers
source                   1..29
                         mol_type = protein
                         organism = Oryctolagus sp.
SEQUENCE: 253
TTMKIIPLNR LSIGEGQQFH VGGAKQVRP                                  29

SEQ ID NO: 254           moltype = AA   length = 219
FEATURE                  Location/Qualifiers
REGION                   1..219
                         note = Description of Artificial Sequence: Synthetic
                          polypeptide
source                   1..219
                         mol_type = protein
                         organism = synthetic construct
SEQUENCE: 254
RADAAPTVSI FPPSSEQLTS GGASVVCFLN NFYPKDINVK WKIDGSERQN GVLNSWTDQD  60
SKDSTYSMSS TLTLTKDEYE RHNSYTCEAT HKTSTSPIVK SFNRNECDIV MTQAAFSNPI 120
TLGTSASMSC RSSKSLLHSS GITYLSWYLQ KPGQSPQLLI YQMSNLASGV PDRFSSSGSG 180
TDFTLRISRV EAEDVGVYYC AQNLELPLTF GAGTKLELK                       219

SEQ ID NO: 255           moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 255
STWIH                                                             5

SEQ ID NO: 256           moltype = AA   length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 256
SKPTGG                                                            6

SEQ ID NO: 257           moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 257
SYWIH                                                             5

SEQ ID NO: 258           moltype = AA   length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 258
SDATGG                                                            6
```

The invention claimed is:

1. An isolated antibody that binds human fibrin γC or fibrinogen γC domain, comprising:

a. a variable heavy (VH) chain sequence comprising a CDR-H1 comprising an amino acid sequence as set forth in SEQ ID NO: 157; a CDR-H2 comprising an amino acid sequence as set forth in SEQ ID NO: 158; and a CDR-H3 comprising an amino acid sequence as set forth in SEQ ID NO: 159; and b. a variable light (VL) chain sequence comprising a CDR-L1 comprising an amino acid sequence as set forth in SEQ ID NO: 160; a CDR-L2 comprising an amino acid sequence as set forth in SEQ ID NO: 161; and a CDR-L3 comprising an amino acid sequence as set forth in SEQ ID NO: 162.

2. The isolated antibody of claim 1, wherein the VH sequence comprises an amino acid sequence at least 80% identical to the sequence as set forth in SEQ ID NO: 163.

3. The isolated antibody of claim 1, wherein the VL sequence comprises an amino acid sequence at least 80% identical to the sequence as set forth in SEQ ID NO: 166.

4. The isolated antibody of claim 1, wherein the VH sequence comprises an amino acid sequence at least 80% identical to the sequence as set forth in SEQ ID NO: 163; and the VL sequence comprises an amino acid sequence at least 80% identical to the sequence as set forth in SEQ ID NO: 166.

5. The isolated antibody of claim 1, wherein the antibody comprises a humanized, human, or chimeric antibody.

6. The isolated antibody of claim 5, wherein the antibody comprises a humanized antibody.

7. The isolated antibody of claim 1, wherein the antibody comprises a Fc region of a class selected from the group consisting of: IgG, IgA, IgD, IgE, and IgM.

8. The isolated antibody of claim 1, wherein the isolated antibody comprises an Fc region of the class IgG and of a subclass selected from the group consisting of: IgG1, IgG2, IgG3, and IgG4.

9. The isolated antibody of claim 1, wherein the isolated antibody comprises an Fc region, and wherein the Fc region comprises LALA mutations.

10. The isolated antibody of claim 1, wherein the isolated antibody comprises an Fc region, and wherein the Fc region binds an Fcγ Receptor selected from the group consisting of: FcγRI, FcγRIIa, FcγRIIb, FcγRIIc, FcγRIIIa, and FcγRIIIb.

11. The isolated antibody of claim 1, wherein the antibody comprises a monoclonal antibody.

12. The isolated antibody of claim 1, wherein the antibody binds an γ377-395 epitope of the fibrin γC or fibrinogen γC domain.

13. The isolated antibody of claim 1, wherein the antibody binds to a peptide comprising an amino acid sequence set forth in at least one of SEQ ID NOs: 241 and 249-253.

14. A polynucleotide encoding the antibody of claim 1.

15. A vector comprising the polynucleotide of claim 14.

16. A host cell comprising the polynucleotide of claim 14.

17. A method for treating uveitis or Alzheimer's disease, the method comprising administering to a mammalian subject in need thereof having uveitis or Alzheimer's disease, respectively, a therapeutically effective amount of the antibody of claim 1.

18. A method of inhibiting microglia activation, the method comprising administering to a mammalian subject in need thereof having uveitis or Alzheimer's disease a therapeutically effective amount of the antibody of claim 1.

19. The method of claim 17, wherein the method comprises administering to a mammalian subject in need thereof having uveitis.

20. The method of claim 19, wherein administering to the mammalian subject in need thereof having uveitis comprises intravitreal administration.

21. The method of claim 17, wherein the mammalian subject is a human.

* * * * *